United States Patent
Short et al.

(10) Patent No.: US 11,279,924 B2
(45) Date of Patent: Mar. 22, 2022

(54) CONDITIONALLY ACTIVE POLYPEPTIDES AND METHODS OF GENERATING THEM

(71) Applicant: BioAtla, LLC, San Diego, CA (US)

(72) Inventors: Jay M. Short, Del Mar, CA (US); Hwai Wen Chang, San Marcos, CA (US); Gerhard Frey, San Diego, CA (US)

(73) Assignee: BioAtla, Inc., San Diego, CA (US)

( * ) Notice: Subject to any disclaimer, the term of this patent is extended or adjusted under 35 U.S.C. 154(b) by 95 days.

(21) Appl. No.: 16/324,453

(22) PCT Filed: Aug. 22, 2017

(86) PCT No.: PCT/US2017/047950
§ 371 (c)(1),
(2) Date: Feb. 8, 2019

(87) PCT Pub. No.: WO2018/044619
PCT Pub. Date: Mar. 8, 2018

(65) Prior Publication Data
US 2020/0190503 A1 Jun. 18, 2020

Related U.S. Application Data

(60) Provisional application No. 62/382,023, filed on Aug. 31, 2016.

(51) Int. Cl.
*C40B 30/04* (2006.01)
*C12N 15/10* (2006.01)
(Continued)

(52) U.S. Cl.
CPC ............ *C12N 15/102* (2013.01); *C07K 14/76* (2013.01); *C07K 16/005* (2013.01); *C40B 30/04* (2013.01);
(Continued)

(58) Field of Classification Search
None
See application file for complete search history.

(56) References Cited

U.S. PATENT DOCUMENTS 6,329,178 B1   12/2001  Patel et al.
8,318,469 B2   11/2012  Rozzelle et al.
(Continued)

FOREIGN PATENT DOCUMENTS

EP      2275443 B1    12/2015
WO   WO03105757 A2   12/2003
(Continued)

OTHER PUBLICATIONS

International Search Report and Written Opinion; dated Nov. 8, 2017 for PCT Application No. PCT/US2017/047950.
(Continued)

*Primary Examiner* — Christian C Boesen
(74) *Attorney, Agent, or Firm* — Mendelsohn Dunleavy, P.C.

(57) ABSTRACT

A method of preparing a conditionally active polypeptide from a parent polypeptide, comprising steps of evolving a DNA encoding the parent polypeptide by increasing a net charge of the parent polypeptide using one or more techniques selected from increasing a total number of codons of charged amino acid residues in the DNA and decreasing a total number of codons of uncharged amino acid residues in the DNA to create mutant DNAs; expressing the mutant DNAs to obtain mutant polypeptides; and selecting the conditionally active polypeptide from the mutant polypeptides which exhibits a decrease in activity in a first assay at a first value of a condition compared to the same activity in a second assay at a second value of the same condition. The conditionally active polypeptide, pharmaceutical composi-
(Continued)

tions containing same, nanoparticle and drug conjugates thereof and uses thereof are also provided.

21 Claims, 29 Drawing Sheets

Specification includes a Sequence Listing.

(51) Int. Cl.
  *C07K 14/76* (2006.01)
  *C07K 16/00* (2006.01)
(52) U.S. Cl.
  CPC .... *C07K 2317/14* (2013.01); *C07K 2317/622* (2013.01)

(56) References Cited

U.S. PATENT DOCUMENTS

| | | |
|---|---|---|
| 8,536,301 B2 | 9/2013 | Cochran et al. |
| 8,709,755 B2 | 4/2014 | Short et al. |
| 8,921,086 B2 | 12/2014 | Hanzel et al. |
| 2006/0260711 A1 | 11/2006 | Fry et al. |
| 2009/0035836 A1 | 2/2009 | Datta et al. |
| 2012/0108445 A1* | 5/2012 | Lenz .................. C12Q 1/6886 506/7 |
| 2012/0258865 A1 | 10/2012 | Short et al. |
| 2014/0206596 A1 | 7/2014 | Shen et al. |

FOREIGN PATENT DOCUMENTS

| | | |
|---|---|---|
| WO | 2009125825 A1 | 10/2009 |
| WO | WO2012033953 A1 | 3/2012 |
| WO | WO2016033331 A1 | 3/2016 |
| WO | WO2017180842 A1 | 10/2017 |
| WO | WO2017197234 A1 | 11/2017 |

OTHER PUBLICATIONS

Wiedman, Gregory, William C. Wimley, and Kalina Hristova. "Testing the limits of rational design by engineering pH sensitivity into membrane active peptides." Biochimica et biophysica acta 1848.4 (2015): 951.
Donald, Jason E., Daniel W. Kulp, and William F. DeGrado. "Salt Bridges: Geometrically Specific, Designable Interactions." Proteins 79.3 (2011): 898-915.
Search Report and Written Opinion for corresponding Singaporean application No. 11201901411V; dated May 26, 2020; (8 pages).
Paladini, Rudolph D., et al. "Mutations in the Catalytic Domain of Human Matrix Metalloproteinase-1 (MMP-1) That Allow for Regulated Activity Through the Use of Ca2+. " Journal of Biological Chemistry 288.9 (2013): 6629-6639.
Notice of Reasons for Refusal for corresponding Japanese application No. 2019-531861; dated May 25, 2021 (9 pages) Machine Translation.
Decision of Rejection for corresponding Japanese application No. 2019-531861; dated Nov. 16, 2021 (7 pages).

* cited by examiner

CONDITIONALLY ACTIVE POLYPEPTIDES AND METHODS OF GENERATING THEM

FIELD OF THE DISCLOSURE

This disclosure relates to the field of providing improved polypeptides with desired activities. Specifically, this disclosure relates to conditionally active polypeptides and a method for generating the conditionally active polypeptides from a parent polypeptide, wherein the conditionally active polypeptides are more active under one condition than under another condition.

BACKGROUND OF THE DISCLOSURE

There is a considerable body of literature describing methods of evolving proteins for a variety of characteristics, especially enzymes or antibodies, to be active or stable at different conditions. For example, enzymes have been evolved to be stable at higher temperatures. In situations where there is an enzymatic activity improvement at the higher temperature, a substantial portion of the improvement can be attributed to the higher kinetic activity commonly described by the Q10 rule where it is estimated that in the case of an enzyme the turnover doubles for every increase of 10° C.

In addition, there exist natural mutations that destabilize proteins at their normal operating conditions, thus reducing the protein activity at the normal operating conditions. For instance, there are known temperature mutants that are active at a lower temperature, but typically at a reduced level compared to the wild type proteins from which they are derived.

It is desirable to generate polypeptides that are conditionally active, for example, less active or virtually inactive at one condition and more active at another condition. It is also desirable to generate polypeptides that are activated or inactivated in certain environments, or that are activated or inactivated over time. Besides temperature, other conditions under which the polypeptides can be evolved or improved for conditional activity include pH, osmotic pressure, osmolality, oxidative stress, and electrolyte concentration. In addition to the activity of polypeptides, it is often desirable to improve other properties during evolution include chemical resistance, and proteolytic resistance.

There are many known mutated polypeptides with improved properties where one or more amino acid substitutions have been made to achieve the improved properties. For example, U.S. Pat. No. 8,318,469 discloses mutant *Thermus brockianus* nucleic acid polymerases that have one of two mutations: G43D and F665Y. The mutant polymerases have a decreased 5'-3' exonuclease activity, as compared to the polymerase without the mutations. The 5'-3' exonuclease activity of DNA polymerase enzymes is often undesirable because this activity may digest nucleic acids, including primers, which have an unprotected 5' end.

U.S. Pat. No. 8,536,301 discloses mutant polypeptides that bind with high affinity to the cell surface receptors of fibronectin α5β1 or vitronectin αvβ3 and αvβ5 integrins. The mutant peptides are based on a molecular scaffold into which a sub-sequence containing the RGD integrin-binding motif has been inserted. The sub-sequence has the length of about 9-13 amino acids, with the RGD flanked by a variety of amino acids. The molecular scaffold is preferably based on a knottin, e.g., EETI, AgRP, and Agatoxin IVB, which peptides have a rigidly defined three-dimensional conformation.

U.S. Pat. No. 8,921,086 discloses mutant DNA polymerases with improved tolerance of nucleotide analogues into the active site region. The mutant polymerases may have amino acid substitutions at position 375 and position 512, relative to the wild-type DNA polymerase. The substitutions at position 375 include E375H, E375S, E375K, E375R, E375A, E375Q, E375W, E375Y, and E375F. The substitutions at position 52 include K512W, K512Y, K512F, K512L, K512H, K512D, and K512E.

U.S. Pat. No. 6,329,178 discloses a mutant DNA polymerase derived from a naturally occurring DNA polymerase by mutating one or more amino acids in its active site. The mutant DNA polymerase has an altered fidelity or altered enzymatic activity in comparison with the naturally occurring DNA polymerase. The naturally occurring DNA polymerase has an active site comprising an amino acid sequence motif: AspTyrSerGlnIleGluLeuArg or LeuLeuValAlaLeuAspTyrSerGlnIleGluLeuArg. The mutant DNA polymerase has either (a) two or more amino acid substitutions in the amino acid sequence motif, or (b) a substitution of an amino acid other than Glu in the amino acid sequence motif.

These mutant proteins have an altered property in comparison with the wild-type protein from which they are derived. However, the altered property of these mutant proteins does not vary as a condition changes.

Evolving a parent polypeptide to be inactive or virtually inactive (less than 50%, 30%, or 10% activity and especially 1% activity) at one condition, while maintaining activity equivalent or better at another condition, may require that one or more destabilizing mutation(s) co-exist with one or more activity-increasing mutation(s). There is a need to develop conditionally active polypeptides.

U.S. Pat. No. 8,709,755 discloses a method for generating a conditionally active antibody comprising steps of evolving the DNA encoding a wild-type antibody to generate mutant antibodies, subjecting the mutant antibodies and the wild-type antibody to an assay under a first condition and to an assay under second condition, and selecting a conditionally active antibody from the at least one mutant antibody which exhibits both (a) a decrease in binding activity to the antigen in the assay at the first condition compared to the binding activity of the wild-type antibody in the same assay at the first condition, and (b) an increase in binding activity to the antigen in the assay under the second condition compared to the activity of the wild-type antibody in the same assay at the second condition.

When used as therapeutic antibody, the conditionally active antibody preferably has a reduced activity at a normal physiological condition and an increased activity at an aberrant condition which may exist at a treatment site such as a tumor microenvironment. As a result of this preferential action, the conditionally active antibody may potentially cause less harm to normal tissues/organs where the normal physiological condition is present, thus producing less side-effects. This may allow more prolonged treatments and/or with higher doses of the conditionally active antibody to be used.

The present disclosure provides a new method for generating conditionally active polypeptides, taking advantage of directed mutagenesis for more efficiently production. The present disclosure also provides new conditionally active polypeptides produced by this method.

SUMMARY OF THE DISCLOSURE

In one aspect, the present invention provides a conditionally active polypeptide obtainable by increasing a net charge of a parent polypeptide, wherein said conditionally active polypeptide exhibits a decrease in activity in a first assay at a first value of a condition compared to the same activity in a second assay at a second value of the same condition. Charged amino acid residues may be selected from Aspartic acid, Glutamic acid, Arginine, Lysine, and, optionally, Histidine.

In each of the foregoing embodiments, the net charge may be increased through one or more techniques selected from increasing a total number of the charged amino acid residues in the polypeptide, decreasing a total number of uncharged amino acid residues in the polypeptide or a combination thereof. In each of the foregoing embodiments, the condition may be selected from pH, temperature, osmotic pressure, osmolality, oxidative stress, electrolyte concentration, concentration of a protein and combinations of two or more of these.

In each of the foregoing embodiments, the condition may be pH, and the conditionally active polypeptide may exhibit the decreased activity at a normal physiological pH and the increased activity at an aberrant pH that differs from the normal physiological pH.

In each of the foregoing embodiments, the conditional activity may be assayed in the presence in the presence of at least one species having a molecular weight of less than 900 a.m.u. and a pKa up to 2 units, or up to 3 units away from the pH at which the increased activity is desired. In the foregoing embodiments, the pKa of the species may be between the first value of the pH and the second value of the pH.

In each of the foregoing embodiments, the conditional activity may be assayed in the presence in the presence of at least one species selected from, histidine, histamine, hydrogenated adenosine diphosphate, hydrogen sulfide, hydrogenate adenosine triphosphate, citrate, acetate, lactate, bisulfide, ammonium, bicarbonate, dihydrogen phosphate and combinations thereof.

In each of the forgoing embodiments, the first assay and the second assay may be conducted in assay solutions in the absence of serum.

In each of the forgoing embodiments, the net charge may be increased by introducing one or more charged amino residues into the parent polypeptide through amino acid residue substitutions, amino acid insertions, or a combination thereof.

In each of the forgoing embodiments, the one or more charged amino residues may be introduced into an active site of the parent polypeptide. In each of the forgoing embodiments, the one or more charged amino residues may be introduced into a region outside of an active site of the parent polypeptide. In each of the forgoing embodiments, the conditionally active polypeptide may be a conditionally active antibody and the one or more charged amino acid residues may be introduced into at least one of complementarity determining regions of the conditionally active antibody.

In each of the forgoing embodiments, the one or more charged amino acid residues may be less than five charged amino acid residues, or less than four charged amino acid residues, or less than three charged amino acid residues, or less than two charged amino acid residues. In each of the forgoing embodiments, the one or more charged amino acid residues may be selected from Aspartic acid and Glutamic acid.

In each of the forgoing embodiments, the conditionally active polypeptide may be reversibly inactivated at the first value of the condition.

In each of the forgoing embodiments, the first and second assays may be conducted in the presence of a species selected from histidine, histamine, hydrogenated adenosine diphosphate, hydrogen sulfide, hydrogenate adenosine triphosphate, citrate, acetate, lactate, bicarbonate, bisulfide, ammonium, dihydrogen phosphate and combinations thereof.

In each of the forgoing embodiments, the first value of the condition may be a value of a normal physiological condition that is within a normal range of the physiological condition at a site of administration of the conditionally active polypeptide to a subject, or at a tissue or organ at a site of action of the conditionally active polypeptide of a subject, and the second value of the condition may be a value of an aberrant condition that deviates from the normal range of the physiological condition at the site of administration of the conditionally active polypeptide, or at the tissue or organ at the site of action of the conditionally active polypeptide.

In each of the forgoing embodiments, the conditionally active polypeptide may be a protein or protein fragment. In each of the forgoing embodiments, the conditionally active polypeptide may be an antibody, a single chain antibody, and an antibody fragment and the activity is a binding activity to an antigen, an Fc region of an antibody, or an enzyme and the activity is an enzymatic activity, or a receptor, a regulatory protein, a soluble protein, a cytokine and a fragment of a receptor, a regulatory protein, a stress protein, a vault-related protein, a neuron protein, a digestive tract protein, a growth factor, a mitochondrial protein, a cytosolic protein, an animal protein, a structural protein, and a plant protein.

In yet another aspect, the present invention provides a pharmaceutical composition comprising an effective amount of the conditionally active polypeptide of any one of the forgoing embodiments and a pharmaceutically acceptable carrier.

In each of the forgoing embodiments, the pharmaceutical composition may further comprise at least one anti-cancer agent. In each of the forgoing embodiments, the at least one anti-cancer agent may be a chemotherapeutic agent, a radiation therapeutic agent, a hormonal therapeutic agent, a toxin or an immunotherapeutic agent. In each of the forgoing embodiments, the at least one anti-cancer agent may be a toxin selected from a taxane, a maytansinoid, an auristatin, a calicheamicin, a duocramycin, a mmae, a soporific, a duomycin, an anthracycline, a CC-1065 analog, docetaxel, a cathepsin, ricin, gelonin, *Pseudomonas* exotoxin, diphtheria toxin, RNase, and a toxic radioisotope. In each of the forgoing embodiments the conditionally active polypeptide may be conjugated to the at least one anti-cancer agent, or at least four anti-cancer agent, or at least six anti-cancer agents.

In yet another aspect, the present invention provides a use of the conditionally active polypeptide of each of the forgoing embodiments for treatment of solid tumors, inflamed joints, or brain diseases or disorders, or removal of senescent cells from a subject.

In yet another aspect, the present invention provides a method of treatment of solid tumors, inflamed joints, or brain diseases or disorders comprising a step of administering a conditionally active polypeptide of each of the forgoing embodiments.

In another aspect, the present invention provides a nucleic acid molecule that encodes the conditionally active polypeptide of each of forgoing embodiments. In another aspect, the present invention provides an expression vector comprising the nucleic acid molecule of the forgoing embodiments or a host cell comprising such an expression vector.

In another aspect, the present invention provides a method for diagnosing the presence of cancer in a subject, comprising steps of (a) contacting cells or tissue of the subject with a detectably labeled conditionally active polypeptide of each of the forgoing embodiments, wherein the conditionally active polypeptide binds to a target on cancer cells; (b) determining whether the conditionally active polypeptide binds to the cell or tissue of the subject.

In each of the forgoing embodiments, the contacting of the cells or tissue with the conditionally active polypeptide may occur in vitro. In each of the forgoing embodiments, the contacting of the cells or tissue with the conditionally active polypeptide may occur within said subject.

In another aspect, the present invention provides a bispecific antibody comprising at least one binding domain that contains at least one of the conditionally active polypeptides of the forgoing embodiments. In another aspect, the present invention provides a chimeric protein containing two different binding or catalytic domains, wherein one or both of the domains comprise at least one of the conditionally active polypeptides of the forgoing embodiments. In another aspect, the present invention provides an oncolytic virus comprising at least one of the conditionally active polypeptides of the forgoing embodiments.

In yet another aspect, the present invention provides a method of preparing a conditionally active polypeptide from a parent polypeptide. In the method, a DNA encoding the parent polypeptide is evolved to increase the net charge of the polypeptide using one or more techniques selected from increasing a total number of codons of charged amino acid residues in the DNA, decreasing a total number of codons of uncharged amino acid residues in the DNA or a combination thereof to create mutant DNAs. The mutant DNAs are expressed to obtain mutant polypeptides; and the conditionally active polypeptide is selected from the mutant polypeptides. The selected conditionally active polypeptide exhibits a decrease in activity in a first assay at a first value of a condition compared to the same activity in a second assay at a second value of the same condition. The charged amino acid residues are selected from Aspartic acid, Glutamic acid, Arginine, Lysine, and Histidine.

In each of the foregoing embodiments, the evolving step may employ a site directed mutagenesis technique, optionally selected from oligonucleotide-mediated mutagenesis, PCR mutagenesis, and cassette mutagenesis. In each of the foregoing embodiments, the evolving step may employ codon substitution or codon insertion.

In each of the foregoing embodiments, the charged amino acid residues may be selected from Aspartic acid and Glutamic acid.

In each of the foregoing embodiments, the one or more codons may be introduced into a region of the DNA that encodes an active site of the parent polypeptide. In each of the foregoing embodiments, the parent polypeptide may be a parent antibody and the active site may be a complementarity determining region of the parent antibody.

In each of the foregoing embodiments, the one or more charged amino residues may be introduced into a region outside of an active site of the parent polypeptide.

In each of the foregoing embodiments, the region outside of the active site may be a constant region of an antibody, or a framework region of the antibody.

In each of the foregoing embodiments, the conditionally active polypeptide may be reversibly inactivated under the first value of the condition.

In each of the foregoing embodiments, the condition may be selected from pH, temperature, osmotic pressure, osmolality, oxidative stress, electrolyte concentration, and concentration of a protein.

In each of the foregoing embodiments, the first and second assays may be performed in assay solutions comprising a protein found in blood. In each of the foregoing embodiments, the blood protein may be albumin.

In each of the foregoing embodiments, the first and second assays may be performed in assay solutions in absence of serum.

In each of the foregoing embodiments, the value of the second condition may be a value of a normal physiological condition that is within a normal range of the physiological condition at a site of administration of the conditionally active polypeptide to a subject, or at a tissue or organ at a site of action of the conditionally active polypeptide of a subject, and the value of the first condition may be a value of an aberrant condition that deviates from the normal range of the physiological condition at the site of administration of the conditionally active polypeptide, or at the tissue or organ at the site of action of the conditionally active polypeptide.

In each of the foregoing embodiments, the condition may be pH and the first and second assays may be performed in assay media including at least one species having a molecular weight of less than 900 a.m.u. and a pKa up to 3 units away from the first value of pH.

In each of the foregoing embodiments, the condition may be pH and the first and second assays may be performed in assay media including at least one species having a molecular weight of less than 900 a.m.u. and a pKa between the second value of pH and the first value of pH.

In each of the foregoing embodiments, the first and second assays may be performed in assay media including a species selected from histidine, histamine, hydrogenated adenosine diphosphate, hydrogenate adenosine triphosphate, citrate, acetate, lactate, hydrogen sulfide, bisulfide, ammonium, bicarbonate, dihydrogen phosphate and a combination thereof.

In each of the foregoing embodiments, the selecting step may further comprise selecting the conditionally active polypeptide based on a property selected from affinity, expression level, and humanization.

In each of the foregoing embodiments, the expression step may employ phage display or a eukaryotic cell production host. In each of the foregoing embodiments, the expression step may be performed in the eukaryotic cell production host and the selected conditionally active polypeptide may be expressed in the same eukaryotic cell production host.

DEFINITIONS

Figure 1:
FIG. 1 shows the selectivity's at pH 6.0 over pH 7.4 of the conditionally active antibodies produced in Example 9.

In order to facilitate understanding of the examples provided herein, certain frequently occurring methods and/or terms will be defined herein. Definitions for the following terms are incorporated by reference from U.S. Pat. No. 8,709,755 B2: "agent", "ambiguous base requirement", "amino acid", "amplification", "chimeric property", "cognate", "comparison window", "conservative amino acid substitutions", "corresponds to", "degrading effective", "defined sequence framework", "defined sequence kernal", "digestion", "directional ligation", "DNA shuffling", "drug" or "drug molecule", "effective amount", "epitope", "enzyme", "evolution" or "evolving", "fragment" or "derivative" or "analog", "full range of single amino acid substitutions", "gene", "genetic instability", "heterologous", "homologous" or "homeologous", "industrial applications", "identical" or "identity", "areas of identity", "isolated", "isolated nucleic acid", "ligand", "ligation", "linker" or "spacer", "microenvironment", "molecular property to be evolved", "mutations", "N,N,G/T", "normal physiological conditions" or "wild type operating conditions", "nucleic acid molecule", "nucleic acid molecule", "nucleic acid sequence coding for" or a "DNA coding sequence of" or a "nucleotide sequence encoding", "nucleic acid encoding an enzyme (protein)" or "DNA encoding an enzyme (protein)" or "polynucleotide encoding an enzyme (protein)", "specific nucleic acid molecule species", "assembling a working nucleic acid sample into a nucleic acid library", "nucleic acid library", "construct", "oligonucleotide" (or synonymously an "oligo"), "homologous", "operably linked", "parental polynucleotide set", "patient" or "subject", "physiological conditions", "population", "pro-form", "pseudorandom", "quasi-repeated units", "random peptide library", "random peptide sequence", "receptor", "recombinant" enzymes, "synthetic" enzymes, "related polynucleotides", "reductive reassortment", "reference sequence", "repetitive Index (RI)", "restriction site", "selectable polynucleotide", "sequence identity", "similarity", "specifically bind", "specific hybridization", "specific polynucleotide", "stringent hybridization conditions", "substantially identical", "substantially pure enzyme", "substantially pure", "treating", "variable segment", and "variant".

As used herein in connection with a measured quantity, the term "about" refers to the normal variation in that measured quantity that would be expected by the skilled artisan making the measurement and exercising a level of care commensurate with the objective of the measurement and the precision of the measuring equipment used. Unless otherwise indicated, "about" refers to a variation of +/−10% of the value provided.

The term "activity" as used herein refers to any function that a protein can perform, including catalyzing reactions and binding to a partner. For enzymes, the activity may be an enzymatic activity. For antibodies, the activity may be a binding activity (i.e., binding activity) between an antibody and its antigen(s). For receptors or ligands, the activity may be binding activity between a receptor and its ligand.

The term "adoptive cell therapy" used herein refers to the transfer of immune cells with antitumour activity into cancer patients. Adoptive cell therapy is a treatment approach that involves the identification, in vitro, of lymphocytes with anti-tumor activity, the in vitro expansion of these cells to large numbers and their infusion into the cancer-bearing host. Of particular interest for the invention is autologous adoptive cell therapy, i.e. adoptive cell therapy in which the immune cells with antitumour activity to be transferred into cancer patients originate from the same patient.

The term "antibody", as used herein, refers to intact immunoglobulin molecules, as well as fragments of immunoglobulin molecules, such as Fab, Fab', (Fab')$_2$, Fv, and SCA fragments, that are capable of binding to an epitope of an antigen. These antibody fragments, which retain some ability to selectively bind to an antigen (e.g., a polypeptide antigen) of the antibody from which they are derived, can be made using well known methods in the art (see, e.g., Harlow and Lane, supra), and are described further, as follows. Antibodies can be used to isolate preparative quantities of the antigen by immunoaffinity chromatography. Various other uses of such antibodies are to diagnose and/or stage disease (e.g., neoplasia) and for therapeutic application to treat disease, such as for example: neoplasia, autoimmune disease, AIDS, cardiovascular disease, infections, and the like. Chimeric, human-like, humanized or fully human antibodies are particularly useful for administration to human patients.

An Fab fragment consists of a monovalent antigen-binding fragment of an antibody molecule, and can be produced by digestion of a whole antibody molecule with the enzyme papain, to yield a fragment consisting of an intact light chain and a portion of a heavy chain.

An Fab' fragment of an antibody molecule can be obtained by treating a whole antibody molecule with pepsin, followed by reduction, to yield a molecule consisting of an intact light chain and a portion of a heavy chain. Two Fab' fragments are obtained per antibody molecule treated in this manner.

An (Fab')2 fragment of an antibody can be obtained by treating a whole antibody molecule with the enzyme pepsin, without subsequent reduction. A (Fab')$_2$ fragment is a dimer of two Fab' fragments, held together by two disulfide bonds.

An Fv fragment is defined as a genetically engineered fragment containing the variable region of a light chain and the variable region of a heavy chain expressed as two chains.

A single chain antibody ("SCA" or scFv) is a genetically engineered single chain molecule containing the variable region of a light chain and the variable region of a heavy chain, linked by a suitable, flexible polypeptide liner, and which may include additional amino acid sequences at the amino- and/or carboxyl-termini. For example, a single chain antibody may include a tether segment for linking to the encoding polynucleotide. A functional single chain antibody generally contains a sufficient portion of the variable region of a light chain and a sufficient region of the variable region of a heavy chain so as to retain the property of a full-length antibody for binding to a specific target molecule or epitope.

The term "antibody-dependent cell-mediated cytotoxicity" or "ADCC" refers to a form of cytotoxicity in which secreted immunoglobulin bound onto Fc receptors (FcRs) present on certain cytotoxic cells (e.g., Natural Killer (NK) cells, neutrophils, and macrophages) that enables these cytotoxic effector cells to bind specifically to an antigen-bearing target cell and subsequently kill the target cell with cytotoxins. Ligand specific high-affinity IgG antibodies directed to the surface of target cells stimulate the cytotoxic cells and are required for such killing Lysis of the target cell is extracellular, requires direct cell-to-cell contact, and does not involve a complement.

The ability of any particular antibody to mediate lysis of the target cell by ADCC can be assayed. To assess ADCC activity, an antibody of interest is added to target cells displaying the target ligand in combination with immune effector cells, which may be activated by the antigen antibody complexes resulting in cytolysis of the target cell. Cytolysis is generally detected by the release of a label (e.g., radioactive substrates, fluorescent dyes or natural intracellular proteins) from the lysed cells. Useful effector cells for such assays include peripheral blood mononuclear cells (PBMC) and Natural Killer (NK) cells. Specific examples of in vitro ADCC assays are described in Bruggemann et al, 1987, *J. Exp. Med*, vol. 166, page 1351; Wilkinson et al, 2001, *J. Immunol. Methods*, vol. 258, page 183; Patel et al, 1995 *J. Immunol*. Methods, vol. 184, page 29. Alternatively, or additionally, ADCC activity of the antibody of interest may be assessed in vivo, e.g., in an animal model, such as that disclosed in Clynes et al, 1998, *PNAS USA*, vol. 95, p. 652.

The term "antigen" or "Ag" as used herein is defined as a molecule that is capable of triggering an immune response. This immune response may involve either antibody production, or the activation of specific immunologically-competent cells, or both. A person skilled in the art will understand that any macromolecule, including virtually all proteins or peptides, can serve as an antigen. It is readily apparent that an antigen can be generated, synthesized or can be derived from a biological sample. Such a biological sample can include, but is not limited to a tissue sample, a tumor sample, a cell or a biological fluid.

The term "antisense RNA" as used herein refers to an RNA molecule that is capable of forming a duplex with a second RNA molecule through complementary or partially complementary with the second RNA molecule. The antisense RNA molecule may be complementary to a translated or an untranslated region of the second RNA molecule. The antisense RNA need not be perfectly complementary to the second RNA molecule. Antisense RNA may or may not be the same length of the second RNA molecule; the antisense RNA molecule may be either longer or shorter than the second RNA molecule. If the second RNA molecule is an mRNA, the binding of the antisense RNA will prevent the mRNA completely or partially from being translated into a functional protein product.

The term "biosimilar" or "follow-on biologic" is used in a manner that is consistent with the working definition promulgated by the U.S. Food and Drug Administration (FDA), which defines a biosimilar to be a product that is "highly similar" to a reference product (despite minor differences in clinically inactive components). In practice there can be no clinically meaningful differences between the reference product and the biosimilar product in terms of safety, purity, and potency (Public Health Service (PHS) Act § 262). A biosimilar can also be one that satisfies one or more guidelines adopted May 30, 2012 by the Committee for Medicinal Products for Human Use (CHAT) of the European Medicines Agency and published by the European Union as "Guideline on similar biological medicinal products containing monoclonal antibodies non-clinical and clinical issues" (Document Reference EMA/CHMP/BMWP/403543/2010). For example, a "biosimilar antibody" refers to a subsequent version of an innovator's antibody (reference antibody) typically made by a different company. Differences between a biosimilar antibody and a reference antibody can include post-translational modification, e.g. by attaching to the antibody other biochemical groups such as a phosphate, various lipids and carbohydrates; by proteolytic cleavage following translation; by changing the chemical nature of an amino acid (e.g., formylation); or by many other mechanisms. Other post-translational modifications can be a consequence of manufacturing process operations for example, glycation may occur with exposure of the product to reducing sugars. In some cases, storage conditions may be permissive for certain degradation pathways such as oxidation, deamidation, or aggregation to occur. As all of these product-related variants may be included in a biosimilar antibody.

The terms "cancer" and "cancerous" refer to or describe the physiological condition in mammals that is typically characterized by unregulated cell growth/proliferation. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

The term "chimeric antigen receptor" or "CAR" or "CARs" as used herein refers to an engineered receptor, which graft antigen specificity onto a cytotoxic cell, for example T cells, NK cells and macrophages. The CARs of the invention may include at least one antigen specific targeting region (ASTR), an extracellular spacer domain (ESD), a transmembrane domain (TM), one or more co-stimulatory domains (CSD), and an intracellular signaling domain (ISD). In some embodiments, the ESD and/or CSD are optional. In one embodiment, the ASTR is bispecific and can recognize two different antigens or epitopes. After the ASTR binds specifically to a target antigen, the ISD activates intracellular signaling of the cytotoxic cell. For example, the ISD can redirect T cell specificity and cytotoxicity toward a selected target in a non-MHC-restricted manner, relying on the antigen-binding properties of CAR. The non-MHC-restricted antigen recognition gives cytotoxic cells expressing the CAR the ability to recognize an antigen independent of antigen processing, thus bypassing a major mechanism of tumor escape. Moreover, when expressed in T cells, CARs advantageously do not dimerize with endogenous T cell receptor (TCR) alpha and beta chains.

The term "complementarity determining region" or "CDR" as used herein refers to a region of an antibody in which amino acid residues involved in antigen binding are located. The CDRs have the highest variability in amino acid alignments of antibody variable domains. Databases such as the Kabat database can be used for CDR identification, the CDRs e.g. being defined as comprising amino acid residues 24-34 (L1), 50-56 (L2) and 89-97 (L3) of the light-chain variable domain and 31-35 (H1), 50-65 (H2) and 95-102 (H3) in the heavy-chain variable domain (Kabat et al., *The Journal of Immunology*, vol. 147, pp. 1709-1719, 1991, Sequences of Proteins of Immunological Interest, Fifth Edition, U.S. Department of Health and Human Services, NIH Publication No. 91-3242). Alternatively CDRs can be defined as those residues from a "hypervariable loop" (residues 26-33 (L1), 50-52 (L2) and 91-96 (L3) in the light-chain variable domain and 26-32 (H 1), 53-55 (H2) and 96-101 (H3) in the heavy-chain variable domain (Chothia and Lesk, *J. Mol. Biol* 1987; 196: 901-917). Typically, the numbering of amino acid residues in the variable domains is performed by the method described in Kabat et al., supra. Phrases such as "Kabat position", "Kabat residue", and "according to Kabat" herein refer to the numbering system described in Kabat et al. for the heavy chain variable domains or the light chain variable domains. Using the Kabat numbering system, the actual linear amino acid sequence of a variable domain may contain fewer or additional amino acids corresponding to a shortening of, or insertion into, a framework (FR) or CDR of the variable domain. For example, a heavy chain variable domain may include amino acid insertions (residue 52a, 52b and 52c according to Kabat) after residue 52 of CDR H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The term "conditionally active polypeptide" refers to a variant or mutant of a parent polypeptide which is more active than the parent polypeptide under at least one condition and less active than the parent polypeptide under a second condition, or refers to a variant or mutant of a parent polypeptide, wherein the variant or mutant polypeptide is at least 1.3 times more active under a first condition than under a second condition. This conditionally active polypeptide may exhibit activity in one or more selected locations of the body and/or exhibit increased or decreased activity at another location in the body. For example, in one aspect, an evolved conditionally active polypeptide is virtually inactive at body temperature, but is active at lower temperatures. Conditionally active polypeptides include conditionally active proteins, protein fragments, antibodies, antibody fragments, enzymes, enzyme fragments, receptors and fragments of receptors cytokines and fragments thereof, hormones and fragments thereof, ligands and fragments thereof, regulatory proteins and fragments thereof, and growth factors and fragments thereof. Each of the conditionally active polypeptides described herein is preferably a conditionally active biologic polypeptide.

The term "cytokine" or "cytokines" as used herein refers to a general class of biological molecules which effect/affect cells of the immune system. The definition is meant to include, but is not limited to, those biological molecules that act locally or at other locations away from the secretion site through blood circulation to regulate or modulate an individual's immune response. Exemplary cytokines include but are not limited to interferon-alpha (IFN-α), interferon-beta (IFN-β), and interferon-gamma (IFN-γ), interleukins (e.g., IL-1 to IL-29, in particular, IL-2, IL-5, IL-6, IL-7, IL-10, IL-12, IL-15 and IL-18), tumor necrosis factors (e.g., TNF-alpha and TNF-beta), erythropoietin (EPO), MIP3a, monocyte chemotactic protein (MCP)-1, intracellular adhesion molecule (ICAM), macrophage colony stimulating factor (M-CSF), granulocyte colony stimulating factor (G-CSF) and granulocyte-macrophage colony stimulating factor (GM-CSF).

As used herein, the term "electrolyte" is used to define a mineral in the blood or other body fluids that carries a charge. For example, in one aspect, a normal physiological condition and an aberrant condition can be different values of "electrolyte concentration". Exemplary electrolytes include, but are not limited to, ionized calcium, sodium, potassium, magnesium, chloride, citrate, lactate, bicarbonate, and phosphate.

The term "full length antibody" refers to an antibody which comprises an antigen-binding variable region ($V_H$ or $V_L$) as well as a light chain constant domain (CL) and heavy chain constant domains, CH1, CH2 and CH3. The constant domains may be native sequence constant domains (e.g. human native sequence constant domains) or amino acid sequence variants thereof. Depending on the amino acid sequence of the constant domain of their heavy chains, full length antibodies can be assigned to different "classes". There are five major classes of full length antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called alpha, delta, epsilon, gamma, and mu, respectively.

The term "growth factor" as used herein refers to a polypeptide molecule that is capable of effectuating differentiation of cells. Examples of growth factors include but not limited to epidermal growth factor (EGF), transforming growth factor-alpha (TGFα), transforming growth factor-beta (TGF-β), human endothelial cell growth factor (ECGF), granulocyte macrophage colony stimulating factor (GM-CSF), bone morphogenetic protein (BMP), nerve growth factor (NGF), vascular endothelial growth factor (NEGF), fibroblast growth factor (FGF), insulin-like growth factor (IGF), cartilage derived morphogenetic protein (CDMP), and platelet derived growth factor (PDGF).

The term "hormones" as used herein indicates a substance often identified as mediator, which is typically released by a cell or a gland in one part of an organism to act as a messenger to other parts of the organism. Exemplary hormones comprise endocrine hormones, which are released directly into the bloodstream, and exocrine hormones (or ectohormones), which are secreted directly into a duct, and, from the duct, they flow either into the bloodstream or from cell to cell by diffusion in a process known as paracrine signaling Vertebrate hormones can be categorized in three chemical classes: peptide hormones, lipid and phospholipid-derived hormones, and monoamines Peptide hormones consist of polypeptide chains Examples of peptide hormones include insulin and growth hormones. Lipid and phospholipid-derived hormones derive from lipids such as linoleic acid and arachidonic acid and phospholipids. The main classes are the steroid hormones that derive from cholesterol and the eicosanoids. Examples of steroid hormones are testosterone and cortisol. Monoamines derived from aromatic such as phenylalanine, tyrosine, and tryptophan by the action of aromatic amino acid decarboxylase enzymes. Examples of monoamines are thyroxine and adrenaline.

The term "immunomodulator" as used herein refers an agent whose action on the immune system leads to an immediate or delayed enhancement or reduction of the activity of at least one pathway involved in an immune response. Such response may be naturally occurring or artificially triggered as part of the innate or adaptive immune system, or both. Examples of immunomodulators include cytokines, stem cell growth factors, lymphotoxins, such as tumor necrosis factor (TNF), and hematopoietic factors, such as interleukins (e.g., interleukin-1 (IL-1), IL-2, IL-3, IL-6, IL-10, IL-12, IL-18, and IL-21), colony stimulating factors (e.g., granulocyte-colony stimulating factor (G-CSF) and granulocyte macrophage-colony stimulating factor (GM-CSF)), interferons (e.g., interferons-α, -β and -γ), the stem cell growth factor designated "S1 factor," erythropoietin and thrombopoietin. Examples of suitable immunomodulator moieties include IL-2, IL-6, IL-10, IL-12, IL-18, IL-21, interferons, TNFs (e.g., TNF-α), and the like.

An "individual" or "subject" is a mammal Mammals include, but are not limited to, domesticated animals (e.g., cows, sheep, cats, dogs, and horses), primates (e.g., humans and non-human primates such as monkeys), rabbits, and rodents (e.g., mice and rats).

The term "library" as used herein refers to a collection of proteins in a single pool. The library may be generated using DNA recombinant technology. For example, a collection of cDNAs or any other protein coding DNAs may be inserted in an expression vector to generate a protein library. A collection of cDNAs or protein coding DNAs may also be inserted into a phage genome to generate a bacteriophage display library of wild-type proteins. The collection of cDNAs may be produced from a selected cell population or a tissue sample, such as by the methods disclosed by Sambrook et al. (Molecular Cloning, Cold Spring Harbor Laboratory Press, 1989). cDNA collections from selected cell types are also commercially available from vendors such as Stratagene®. The library of wild-type proteins as used herein is not a collection of biological samples.

The term "ligand" as used herein refers to a molecule that is recognized by a particular receptor and specifically binds the receptor in one or more binding sites. Examples of ligands include, but not restricted to, agonists and antagonists for cell membrane receptors, toxins and venoms, viral epitopes, hormones, hormone receptors peptides, enzymes, enzyme substrates, co factors, drugs (e.g. opiates, steroids, etc.), lectins, sugars, polynucleotides, nucleic acids, oligosaccharides, proteins, and monoclonal antibodies. Typically, a ligand comprises two structural portions: a first portion that is involved in binding of the ligand to its receptor and a second portion that is not involved in such binding.

The term "receptor" as used herein refers to a molecule that has an affinity for a given ligand. Receptors can be naturally occurring or synthetic molecules. Receptors can be employed in an unaltered state or as aggregates with other species. Receptors can be attached, covalently or non-covalently, to a binding member, either directly or via a specific binding substance. Examples of receptors include, but are not limited to, antibodies, including monoclonal antibodies and antisera reactive with specific antigenic determinants (such as on viruses, cells, or other materials), cell membrane receptors, complex carbohydrates and glycoproteins, enzymes, and hormone receptors. The binding of a ligand to its receptor indicates a combination of the ligand and its receptor molecule through specific molecular recognition to form a complex, which can be detected by a variety of ligand receptor binding assays known to a skilled person.

The term "microRNA" or "miRNA" as used herein refers to the unprocessed or processed RNA transcript from a miRNA gene. The unprocessed microRNA gene transcript typically comprises an RNA transcript of about 70-100 nucleotides in length. The transcribed microRNA can be processed by digestion with an RNase (for example, Dicer, Argonaut, or RNase III) into an active 19-25 nucleotide RNA molecule. This active 19-25 nucleotide RNA molecule is also called the "processed" microRNA gene transcript or "mature" microRNA.

The term "multispecific antibody" as used herein refers to an antibody having binding specificities for at least two different epitopes. Exemplary multispecific antibodies may bind both a BBB-R and a brain antigen. Multispecific antibodies can be prepared as full-length antibodies or antibody fragments (e.g. F(ab')$_2$ bispecific antibodies). Engineered antibodies with two, three or more (e.g. four) functional antigen binding sites are also contemplated (see, e.g., US 2002/0004587 A1).

The term "mutagenic primer" as used herein refers to an oligonucleotide primer used in a linear cyclic amplification reaction (such as the polymerase chain reaction or PCR), wherein the primer does not precisely match the template DNA sequence. The mismatched nucleotides in the mutagenic primer are referred to as mutation sites with respect to the mutagenic primer. Thus, during the amplification reaction, the mismatched nucleotides of the primer are incorporated into the amplification product thereby resulting in the synthesis of a mutagenized DNA strand comprising the mutagenic primer. The mutagenic primers can thus introduce specific mutations to the template DNA sequence.

The term "nanoparticle" as used herein refers to a microscopic particle, whose size is in nanometers (nm) with a maximum linear dimension of less than about 1000 nm or less than about 500 nm, or less than about 200 nm, or less than about 100 nm, or less than about 50 nm. As used herein, the linear dimension refers to the distance between any two points on a nanoparticle as measured in a straight line. Nanoparticles of the present invention can be irregular, oblong, spindle, rod, discoid, pancake, cylindrical, red blood cell-like, spherical or substantially spherical in shape as long as their shape and size allow binding interactions. The nanoparticles of the present invention are preferably made from biocompatible materials (polymers or lipids).

The term "naturally-occurring" as used herein as applied to the object refers to the fact that an object can be found in nature. For example, a polypeptide or polynucleotide sequence that is present in an organism (including viruses) that can be isolated from a source in nature and which has not been intentionally modified by man in the laboratory is naturally occurring. A polypeptide excised from a larger polypeptide is not a naturally occurring polypeptide since the end groups of the excised polypeptide will be different in the excised form than in the larger naturally occurring polypeptide because these end groups will no longer be bound to adjacent polypeptides. Generally, the term naturally occurring refers to an object as present in a non-pathological (un-diseased) individual, such as would be typical for the species.

The term "net charge" of a polypeptide is the ratio between the total number of charged amino acid residues in the polypeptide and the total number of amino acid residues in the polypeptide. The charged amino acid residues include Aspartic acid, Glutamic acid, Arginine, Lysine, and, optionally, Histidine. The uncharged amino acid residues include the other 15 naturally occurring amino acids. The net charge of a polypeptide may be increased by either increasing the total number of charged amino acid residues in the polypeptide, decreasing the total number of uncharged amino acid residues in the polypeptide, or a combination thereof.

The term "oxidative stress" as used herein refers to an imbalance between the production of reactive oxygen radicals (e.g., superoxide anion ($O_2^-$), nitric oxide, hydroxy radical (OH), and hydrogen peroxide ($H_2O_2$)), generated, for example, as byproducts of metabolic processes that utilize molecular oxygen (see e.g., Coyle et al., Science 262:689-695 (1993)) and a biological system's ability to readily detoxify the reactive intermediates or easily repair the resulting damage. Oxidative stress may refer to a state of a cell or tissue of an animal, in vitro or in vivo. Disturbances in the normal redox state within a living cell can cause toxic effects through the production of peroxides and free radicals that damage all components of the cell, including proteins, lipids, and DNA.

In humans, oxidative stress is involved in many diseases, such as atherosclerosis, Parkinson's disease, Heart Failure, Myocardial Infarction, Alzheimer's disease, Fragile X Syndrome, and chronic fatigue syndrome, but short-term oxidative stress may also be important in prevention of aging by induction of mitohormesis. Reactive oxygen species can be beneficial, as they are used by the immune system as a way to attack and kill pathogens. Reactive oxygen species are also used in cell signaling. This is termed redox signaling.

In chemical terms, oxidative stress is a rise (becoming less negative) in the cellular reduction potential, or a decrease in the reducing capacity of the cellular redox couples, such as glutathione. The effects of oxidative stress depend upon the size of these changes, with a cell being able to overcome small perturbations and regain its original state. However, more severe oxidative stress can cause cell death and even moderate oxidation can trigger apoptosis, while more intense stresses may cause necrosis.

The terms "parent polypeptide" and "parent protein" as used herein refer to a polypeptide or protein that may be evolved to produce a conditionally active polypeptide or protein using the methods of the present invention. The parent polypeptide protein may be a wild-type protein or non-wild-type protein. For example, a therapeutic polypeptide or protein or a mutant or variant polypeptide or protein may be used as a parent polypeptide or protein. Examples of parent polypeptides and proteins include antibodies, antibody fragments, enzymes, enzyme fragments cytokines and fragments thereof, hormones and fragments thereof, ligands and fragments thereof, receptors and fragments thereof, regulatory proteins and fragments thereof, and growth factors and fragments thereof.

The term "pH-dependent" as used herein refers to a polypeptide having a property or activity that is different at different pH values.

The term "polypeptide" as used herein refers to a polymer in which the monomers are amino acids and are joined together through peptide or disulfide bonds. A polypeptide may be a full-length naturally-occurring amino acid chain or a fragment, mutant or variant thereof, such as a selected region of the amino acid chain that is of interest in a binding interaction. A polypeptide may also be a synthetic amino acid chain, or a combination of a naturally-occurring amino acid chain or fragment thereof and a synthetic amino acid chain. A fragment refers to an amino acid sequence that is a portion of a full-length protein, and will be typically between about 8 and about 500 amino acids in length, preferably about 8 to about 300 amino acids, more preferably about 8 to about 200 amino acids, and even more preferably about 10 to about 50 or 100 amino acids in length. Additionally, amino acids other than naturally-occurring amino acids, for example β-alanine, phenyl glycine and homoarginine, may be included in the polypeptides. Commonly-encountered amino acids which are not gene-encoded may also be included in the polypeptides. The amino acids may be either the D- or L-optical isomer. The D-isomers are preferred for use in a specific context, further described below. In addition, other peptidomimetics are also useful, e.g. in linker sequences of polypeptides (see Spatola, 1983, in Chemistry and Biochemistry of Amino Acids. Peptides and Proteins, Weinstein, ed., Marcel Dekker, New York, p. 267). In general, the term "protein" is not intended to convey any significant difference from the term "polypeptide" other than to include structures which comprise two or several polypeptide chains held together by covalent or non-covalent bonds.

The term "prodrug" as used herein refers to a precursor compound that will undergo metabolic activation in vivo to produce the active drug. A thorough discussion is provided in T. Higuchi and V. Stella, "Pro-drugs as Novel Delivery Systems," V. 14 of the A.C.S. Symposium Series, and in Edward B. Roche, ed., "Bioreversible Carriers in Drug Design," American Pharmaceutical Association and Pergamon Press (1987).

The term "recombinant antibody", as used herein, refers to an antibody (e.g. a chimeric, humanized, or human antibody or antigen-binding fragment thereof) that is expressed by a host cell comprising a nucleic acid encoding the antibody. Examples of "host cells" for producing recombinant antibodies include: (1) mammalian cells, for example, Chinese Hamster Ovary (CHO), COS, myeloma cells (including Y0 and NS0 cells), baby hamster kidney (BHK), Hela and Vero cells; (2) insect cells, for example, sf9, sf21 and Tn5; (3) plant cells, for example plants belonging to the genus *Nicotiana* (e.g. *Nicotiana tabacum*); (4) yeast cells, for example, those belonging to the genus *Saccharomyces* (e.g. *Saccharomyces cerevisiae*) or the genus *Aspergillus* (e.g. *Aspergillus niger*); (5) bacterial cells, for example *Escherichia. coli* cells or *Bacillus subtilis* cells, etc.

The term "regulatory protein" as used herein refers to any protein that increases or decreases the activity of another polypeptide or RNA molecule; increases or decreases the abundance of another polypeptide or RNA molecule; alters the interaction between another polypeptide or RNA molecule with other polypeptides, DNA or RNA molecules, or any other binding substrates; and/or alters the cellular location of another polypeptide or RNA molecule. The regulatory proteins when increase or decrease the transcription rates of a gene, they are often referred to as transcription factors that have effects on the promoter or enhancer regions of the gene. Examples of transcription factors include mammalian transcription factors such as NFkB, NF1, cyclic AMP responsive element binding protein (CREB), MyoDl, homeobox transcription factors, Sp1, the oncogenes and jun, Mep-1, GATA-1, Is1-1, LFB1, NFAT, Pit-1, OCA-B, Oct-1 and Oct-2, yeast A/a, cErb-A, myc, mad and max, p53, mdm1, and others as set forth in Latchman, 1998, Eukaryotic Transcription Factors, 3rd. Ed., Academic Press: New York. Fusion protein derivatives of these or other transcription factors, wherein at least the DNA binding motif of the fusion protein, which provides binding specificity, is fused to a small molecule regulator binding site may also be used.

The term "site directed mutagenesis" as used herein refers to a process in which a predetermined mutation is created at a defined site in a parent polypeptide. The defined site refers to sites chosen as desired according to need of research. The predetermined mutation may be substituting an amino acid residue at the defined site with a specific amino acid, inserting a specific amino acid residue at the defined site, or deleting a specific amino at the defined site.

The term "small interfering RNA" or "siRNA" as used herein refers to a RNA or RNA-like molecule that can interact and cause destruction of an mRNA molecule which shares sequence homology with the siRNA (Elbashir et al., Genes Dev, vol. 15, pp. 188-200, 2001). It is believed that the siRNA can be incorporated into a ribonucleoprotein complex known as the RNA-induced silencing complex (RISC). The RISC uses a siRNA sequence to identify mRNA molecules that are at least partially complementary to the incorporated siRNA strand, and then cleaves these target mRNA molecules or inhibits their translation. Typical siRNA is a double-stranded nucleic acid molecule with each strand having about 19 to about 28 nucleotides (i.e. about 19, 20, 21, 22, 23, 24, 25, 26, 27, or 28 nucleotides). siRNA may also be a single-stranded RNA, albeit less efficiently than double-stranded siRNA. The single-stranded siRNA has a length of about 19 to about 49 nucleotides. The single-stranded siRNA has a 5' phosphate or is phosphorylated in situ or in vivo at the 5' position. Single-stranded siRNAs can be synthesized chemically or by in vitro transcription or expressed endogenously from expression vectors or expression cassettes. 5' Phosphate groups may be added via a kinase, or may be the result of nuclease cleavage of an RNA.

The term, "small molecule" refers to molecules or ions that typically have a molecular weight of less than 900 a.m.u., or more preferably less than 500 a.m.u. or more preferably less than 200 a.m.u. or even more preferably less than 100 a.m.u. In the assays and environments of the present invention, small molecules may often be present as a mixture of the molecule and a deprotonated ion of the molecule, depending primarily on the pH of the assay or environment.

The term "therapeutic protein" as used herein refers to any protein and/or polypeptide that can be administered to a mammal to elicit a biological or medical response of a tissue, system, animal or human that is being sought, for instance, by a researcher or clinician. A therapeutic protein may elicit more than one biological or medical response.

Examples of therapeutic proteins include antibodies, enzymes, hormones, cytokines, regulatory proteins, and fragments thereof.

The term "therapeutically effective amount" as used herein means any amount which, as compared to a corresponding subject who has not received such amount, results in, but is not limited to, healing, prevention, or amelioration of a disease, disorder, or side effect, or a decrease in the rate of advancement of a disease or disorder. The term also includes within its scope amounts effective to enhance normal physiological function as well as amounts effective to cause a physiological function in a patient which enhances or aids in the therapeutic effect of a second pharmaceutical agent.

The term "tumor microenvironment" as used herein refers to a microenvironment in and surrounding a solid tumor to support the growth and metastasis of the tumor cells. The tumor microenvironment includes surrounding blood vessels, immune cells, fibroblasts, other cells, soluble factors, signaling molecules, an extracellular matrix, and mechanical cues that can promote neoplastic transformation, support tumor growth and invasion, protect the tumor from host immunity, foster therapeutic resistance, and provide niches for dormant metastases to thrive. The tumor and its surrounding microenvironment are closely related and interact constantly. Tumors can influence their microenvironment by releasing extracellular signals, promoting tumor angiogenesis and inducing peripheral immune tolerance, while the immune cells in the microenvironment can affect the growth and evolution of cancerous cells. See Swarts et al. "Tumor Microenvironment Complexity: Emerging Roles in Cancer Therapy," *Cancer Res*, vol., 72, pages 2473-2480, 2012; Weber et al., "The tumor microenvironment," *Surgical Oncology*, vol. 21, pages 172-177, 2012; Blagosklonny, "Antiangiogenic therapy and tumor progression," *Cancer Cell*, vol. 5, pages 13-17, 2004; Siemann, "Tumor microenvironment," Wiley, 2010; and Bagley, "The tumor microenvironment," Springer, 2010.

As used herein, the term "wild-type" means that the polynucleotide does not comprise any mutations. A "wild type protein", "wild-type protein", "wild-type biologic protein", or "wild type biologic protein", may refer to a protein which can be isolated from nature that will be active at a level of activity found in nature and will comprise the amino acid sequence found in nature. The terms "parent molecule" and "target protein" also encompass a wild-type protein.

DETAILED DESCRIPTION

A. Conditionally Active Polypeptides

The disclosure provides a conditionally active polypeptide and a method for generating the conditionally active polypeptide from a parent polypeptide. The conditionally active polypeptide has an increased net charge in comparison with the parent polypeptide. The net charge increase may be generated by introducing one or more charged amino acid residues into the parent polypeptide or by deleting one or more uncharged amino acid residues from the parent polypeptide, or both, thus increasing the net charge of the parent polypeptide. The charged amino acid residues are selected from Aspartic acid, Glutamic acid, Arginine, Lysine, and Histidine. In one aspect, the mutations may be substitutions that replace one or more uncharged amino acid residues in the parent polypeptide with one or more charged amino acid residues. In another aspect, the mutations may be insertions that insert one or more additional charged amino acid residues into the parent polypeptide. Combinations of such substitutions and insertions may also be employed. In another aspect, the mutations may be deletion of one or more uncharged amino acid residues from the parent polypeptide.

The charged amino acid residues introduced into the parent polypeptide are D (Aspartic acid or Asp), E (Glutamic acid or Glu), R (Arginine or Arg), K (Lysine or Lys), and H (Histidine or His). D and E are negatively charged amino acid residues. R, K, and H are positively charged amino acid residues. Aspartic acid, Glutamic Acid, Lysine and Arginine are typically charged at normal physiological pH. Histidine may also be charged at normal physiological pH.

Conditionally active polypeptides provided with the increased number of charged amino acid residues exhibit both (a) a decrease in activity in a first assay at a first value of a condition compared to the same activity of the parent polypeptide in the first assay, and (b) an increase in the same activity in a second assay at a second value of the same condition compared to the same activity of the parent polypeptide in the second assay.

In some embodiments, the conditionally active polypeptides exhibit a decrease in activity in a first assay at a first value of a condition compared to the same activity in a second assay at a second value of the same condition.

In one aspect, the conditionally active polypeptides may be light chain variable regions of antibodies against the Ax1 protein (SEQ ID NOS: 2-5), generated from the parent light chain variable region with SEQ ID NO: 1. In another aspect the conditionally active polypeptides may be heavy chain variable regions of antibodies against the Ax1 protein (SEQ ID NOS: 7-9), generated from the parent heavy chain variable region with SEQ ID NO: 6. In yet another aspect, conditionally active antibodies may contain both a light chain variable region selected from SEQ ID NOS: 2-5 and a heavy chain variable region selected from SEQ ID NOS: 7-9.

In another aspect, the conditionally active polypeptides are light chain variable regions of antibodies against the Ror2 protein (SEQ ID NOS: 11-13), generated from the parent light chain variable region with SEQ ID NO: 10. In another aspect, the conditionally active polypeptides are heavy chain variable regions of antibodies against the Ror2 protein (SEQ ID NOS: 15-18), generated from the parent heavy chain variable region with SEQ ID NO: 14. In yet another aspect, conditionally active antibodies may contain both a light chain variable region selected from SEQ ID NOS: 11-13 and a heavy chain variable region selected from SEQ ID NOS: 15-18.

The conditionally active antibodies against Ax1 or Ror2 are further described in Examples 15-22 of the present disclosure. These conditionally active light chain variable regions and heavy chain variable regions include amino acid substitutions where charged amino acid residues, especially E and D, have been introduced into the complementarity determining regions of the parent light chain variable region and parent heavy chain variable region.

The condition at which the assays are conducted is the same condition, though having different, first and second values or ranges. For example, the condition may be pH, such that the second, normal physiological pH (a normal physiological condition) is from 7.0 to 7.8, or 7.2-7.6, while first, aberrant pH (as an aberrant condition) is from 5.8 to 7.0, or from 6.2-6.8. The condition may also be, but is not limited to, temperature, concentrations of an electrolyte, concentrations of an organic molecule, or osmotic pressure.

In one aspect, the condition is pH and the conditionally active polypeptides have pH-dependent activity in the presence of a species having a pKa within 2 pH units, or 3 pH units of the pH at which the activity is desired. In another aspect, the present invention relates to conditionally active polypeptides having pH-dependent activity in the presence of a species having a pKa of from about 4 to about 10, or from about 4.5 to about 9.5 or from about 5 to about 9, or from about 5.5 to about 8, or from about 6.0 to about 7.0. In another aspect, the present invention relates to conditionally active polypeptides having pH-dependent activity in the presence of a species selected from bisulfide, bicarbonate, histidine, citrate, acetate, lactate and mixtures thereof.

Species present in the assay media that have a significant influence on the activity of the conditionally active polypeptide tend to be species that have at least two ionization states: an uncharged or less charged state and a charged or more charged state. As a result, the pKa of the species that influence the activity of the conditionally active polypeptide can play a role in determining the degree of influence that the species will have on a particular activity of a polypeptide and/or at a particular pH.

The pH-dependent conditionally active polypeptides have a higher activity at a first pH than at a second, different pH, both activities being measured in an assay in the presence of at the presence of one or more of the species listed above. To determine pH-dependence of a conditionally active polypeptide the same activity of the polypeptide is assayed in the same assay media at two different pH values.

The ratio of the activity at the first pH to the same activity at a second pH in the same assay media may be termed the selectivity of the pH-dependent conditionally active polypeptide. The pH-dependent conditionally active polypeptides have a selectivity of at least about 1.3, or at least about 1.5, or at least about 1.7, or at least about 2.0, or at least about 3.0, or at least about 4.0, or at least about 6.0, or at least about 8.0, or at least about 10.0, or at least about 20.0, or at least about 40.0, or at least about 60.0, or at least about 100.0.

It has also been observed that the pH-dependent conditionally active polypeptides typically have different activities in the presence of different species in the assay media. Species that have at least two ionization states: an uncharged or less charged state and a charged or more charged state may dissociate to a greater degree at a particular pH, dependent on the pKa value, to thereby increase the probability of interaction with charged amino acid residues present in the conditionally active polypeptide. This factor may be employed to enhance the selectivity and/or pH-dependent activity of the conditionally active polypeptide.

Without being bound by theory, it is believed that the charged amino acid residues introduced into the parent polypeptide change the activity of the conditionally active polypeptide at different pH by altering the charge on the conditionally active polypeptides as the pH in the assay media changes. For example, the negatively charged amino acid residues (e.g., E and D) in the conditionally active polypeptides are uncharged or less charged when the pH in the assay media is in an acidic pH range but negatively charged when the pH in the assay media is neutral or in a basic pH range. The change of the charge on the conditionally active polypeptides is believed to enable the polypeptides to interact with one of the species discussed above differently at different pH values. In one aspect, the conditionally active polypeptides are more likely to interact with charged species in the assay media at one pH but less likely to interact with the same charged species in the same assay media at another, different pH. This, in turn, is believed to influence the activity of the conditionally active polypeptides.

The nature of the charges on the conditionally active polypeptide may be one factor used to determine suitable species for influencing the activity of the conditionally active polypeptide. In some embodiments, the conditionally active polypeptide may have more positively charged amino acid residues: lysine, arginine and histidine, in comparison with the parent polypeptide. The conditionally active polypeptide can thus be selected to have the desired level interaction with a particular species present in the environment where the activity is desired and or to have the desired level of interaction with a particular species present in the environment where a reduced activity is desired. Similarly, the conditionally active polypeptide may have more negative charged amino acid residues: aspartate and glutamate, in comparison with the parent polypeptide.

The location of the charged amino acid residues on the pH-dependent conditionally active polypeptide may also have an influence on the activity. For example, the proximity of charged amino acid residues to a binding site of the conditionally active polypeptide may be used to influence the activity of the polypeptide.

In some embodiments, interaction of a charged environmental species to the conditionally active polypeptide may block or hinder the activity of the pH-dependent conditionally active polypeptide. For example, charged amino acids interacting with a charged environmental species may manifest allosteric effects on the binding site of the conditionally active polypeptide.

In other embodiments, it may be the case that the interaction of the charged environmental species with the conditionally active polypeptide may form salt bridges between different moieties on the polypeptide, especially the moieties that are charged or polarized. The formation of salt bridges is known to stabilize polypeptide structures (Donald, et al., "Salt Bridges: Geometrically Specific, Interactions," *Proteins*, 79(3): 898-915, 2011; Hendsch, et al., "Do salt bridges stabilize proteins? A continuum electrostatic analysis," *Protein Science*, 3:211-226, 1994). The salt bridges can stabilize or fix the protein structure which normally undergoes constant minor structural variation called "breathing" (Parak, "Proteins in action: the physics of structural fluctuations and conformational changes," *Curr Opin Struct Biol.*, 13(5):552-557, 2003). The protein structural "breathing" is important for protein function and its binding with its partner because the structural fluctuation permits the conditionally active protein to efficiently recognize and bind to its partner (Karplus, et al., "Molecular dynamics and protein functions," *PNAS*, vol. 102, pp. 6679-6685, 2015). By forming salt bridges, the binding site, especially the binding pocket, on the conditionally active polypeptide may be less accessible to its partner, possible because the salt bridges may directly block the partner from accessing the binding site. Even with salt bridges remote from the binding site, the allosteric effect may alter the conformation of the binding site to inhibit binding. Therefore, after the salt bridges stabilize (fix) the structure of the conditionally active polypeptide, the polypeptide may become less active in binding to its partner, leading to decreased activity.

Figure 6:
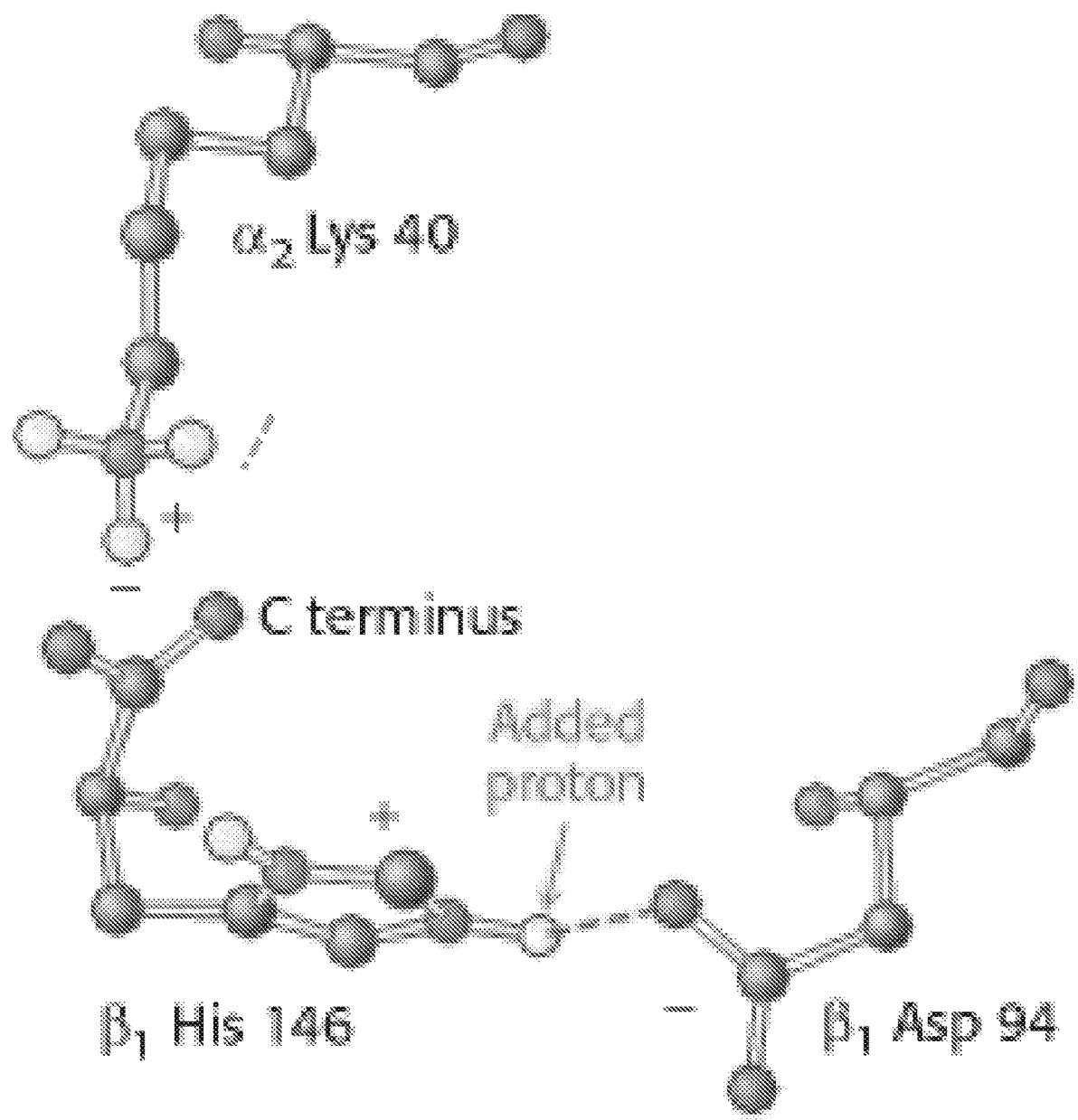
FIG. 6 is a diagram showing the formation of salt bridges in deoxyhemoglobin, where three amino acid residues form two salt bridges that stabilize the T quaternary structure of the deoxyhemoglobin, leading to lower affinity to oxygen.

One known example of polypeptide and how its structure is stabilized by salt bridges is hemoglobin. Structural and chemical studies have revealed that at least two sets of chemical groups are responsible for the salt bridges: the amino termini and the side chains of histidines β146 and α122, which have pKa values near pH 7. In deoxyhemoglobin, the terminal carboxylate group of β146 forms a salt bridge with a lysine residue in the a subunit of the other αβ dimer. This interaction locks the side chain of histidine β146 in a position where it can participate in a salt bridge with negatively charged aspartate 94 in the same chain, provided that the imidazole group of the histidine residue is protonated (FIG. 6). At high pH, the side chain of histidine β146 is not protonated and the salt bridges do not form. As the pH drops, however, the side chain of histidine β146 becomes protonated, the salt bridge between histidine β146 and aspartate β94 forms, which stabilizes the quaternary structure of deoxyhemoglobin, leading to a greater tendency for oxygen to be released at actively metabolizing tissues (with lower pH). The hemoglobin shows a pH-dependent binding activity for oxygen where at a low pH, the binding activity for oxygen is reduced because of the formation of salt bridges. On the other hand, at a high pH, the binding activity for oxygen is increased because of the absence of salt bridges.

Similarly, small molecules such as bicarbonate may reduce the binding activity of the conditionally active polypeptide to its partner by forming salt bridges in the conditionally active polypeptides. For example, at a pH lower than its pKa of 6.4, bicarbonate is protonated and thus not charged. The uncharged bicarbonate is not capable of forming salt bridges, thus has little effect on the binding of the conditionally active polypeptide with its partner. Hence, the conditionally active polypeptide has high binding activity with its partner at the low pH. On the other hand, at a high pH greater than the pKa of bicarbonate, bicarbonate is ionized by losing the proton, thus becoming negatively charged. The negatively charged bicarbonate will form salt bridges between positively charged moieties or polarized moieties on the conditionally active polypeptide to stabilize the structure of the conditionally active polypeptide. This will block or reduce the binding of the conditionally active polypeptide with its partner. Hence the conditionally active polypeptide has low activity at the high pH. The conditionally active polypeptide thus has a conditionally active activity at the presence of bicarbonate with higher binding activity at low pH than at high pH.

When a species such as bicarbonate is absent from the assay media, the conditionally active polypeptide may lose its conditional activity. This is likely due to the lack of salt bridges on the conditionally active polypeptide to stabilize (fix) the structure of the polypeptide. Thus, the partner will have similar access to the binding site on the conditionally active polypeptide at any pH, producing similar activity at the first pH and second pH.

In other embodiments, interactions between the small molecule or ion and the conditionally active polypeptide may alter the structure of the polypeptide in a manner that increases its activity. For example, the alteration in the structure may improve the binding affinity of the conditionally active polypeptide by altering a location, steric hindrance or binding energy for the binding site required for the binding affinity. In such cases, it may be desirable to select small molecules that bind to the conditionally active polypeptide at the pH where activity is desired.

It is to be understood that, though the salt bridges (ion bonds) are the strongest and most common manner for the compounds and ions to affect the activity of the conditionally active polypeptide, other interactions between such compounds and ions and the conditionally active polypeptide may also contribute to stabilize (fix) the structure of the conditionally active polypeptide. The other interactions include hydrogen bonds, hydrophobic interactions, and van der Waals interactions.

In some embodiments, to select a suitable compound or ion, the conditionally active polypeptide is compared with the parent polypeptide from which it is evolved to determine whether the conditionally active polypeptide has a higher proportion of negatively charged amino acid residues or positively charged amino acid residues. A compound with a suitable charge at the second pH respectively may then be chosen to influence the activity of the conditionally active polypeptide. For example, when the conditionally active polypeptide has a higher proportion of positively charged amino acid residues than the parent polypeptide, the suitable small molecule should typically be negatively charged at the second pH to interact with the conditionally active polypeptide. On the other hand, when the conditionally active polypeptide has a higher proportion of negatively charged amino acid residues than the parent polypeptide, the suitable small molecule should typically be positively charged at the second pH to interact with the conditionally active polypeptide.

In other embodiments, the activity of the conditionally active polypeptide is controlled by interaction of the small molecule or ion with a target polypeptide that is the binding partner of the conditionally active polypeptide. In this case the same principles as discussed above are also applicable except that the goal is to create interactions between the small molecule or ion and the target polypeptide. The target polypeptide can be, for example, an antigen for a conditionally active antibody, or a ligand for a conditionally active receptor.

A suitable small molecule may be any inorganic or organic molecule that transits from an uncharged or less charged state at the first pH to charged or more charged state at the second pH. Thus, the small molecule should typically have a pKa between the first pH and second pH. For example, bicarbonate has pKa at 6.4. Thus, at a higher pH such as pH 7.4, the negatively charged bicarbonate will bind to the charged amino acid residues in the conditionally active polypeptide and reduce the activity. On the other hand, at a lower pH such as pH 6.0, the less charged bicarbonate will not bind in the same quantity to the conditionally active polypeptide and thus allow a higher activity of the conditionally active polypeptide.

Bisulfide has a pKa 7.05. Thus, at a higher pH such as pH 7.4, the more negatively charged bisulfide will bind to the positively charged amino acid residues in the conditionally active polypeptide and reduce its activity. On the other hand, at a lower pH such as pH 6.2-6.8, the less charged hydrogen sulfide/bisulfide will not bind at the same level to the conditionally active polypeptide and thus allow a higher activity of the conditionally active polypeptide.

Small molecules with a pKa between the first and second pH are preferred for use in the present invention. Preferred species are selected from bisulfide, bicarbonate, histidine, histamine, citrate, acetate, and lactate. Each of these small molecules has a pKa between 6.2 and 7.0. Further, other small molecules such as tricine (pKa 8.05) and bicine (pKa 8.26) may also be used. Other suitable small molecules may be found in textbooks using the principles of the present application, such as CRC Handbook of Chemistry and Physics, 96th Edition, by CRC press, 2015; Chemical Properties Handbook, McGraw-Hill Education, 1998.

The concentration of the small molecules in the assay media or environment is preferably at or near the physiological concentration of the small molecules in a subject. For example, the physiological concentration of bicarbonate (in human serum) is in the range of 15 to 30 mM. Thus, the concentration of bicarbonate in the assay media may be from 10 mM to 40 mM, or from 15 mM to 30 mM, or from 20 mM to 25 mM, or about 20 mM. The physiological concentration of bisulfide is also low. The concentration of bisulfide in the assay media may be from 3 to 100 mM, or from 5 to 80 mM, or from 10 to 50 mM, or from 10 to 30 mM.

In the invention, conditionally active polypeptides are selected and employed at concentrations whereby the normal physiological concentration of a particular species in an environment will have a significant effect on the activity of the conditionally active polypeptides in the pH range of interest. Thus, in many therapeutic treatments, it may be advantageous to have a low activity for the conditionally active polypeptide around pH 7.2-7.4 of blood or human serum to allow delivery of the therapeutic treatment via the bloodstream while minimizing or preventing the conditionally active polypeptide from activation. As a result, for such treatments it will be advantageous to select small molecules having a pKa below pH 7.2-7.4 in order to ensure a sufficient amount of ionization of the small molecule at the bloodstream pH to have a significant effect on the activity of the conditionally active polypeptide. At the same time, the pKa of the small molecule should be at or above the pH at which the activity of the conditionally active polypeptide is desired in order to ensure activation of the conditionally active polypeptide by protonation of the small molecule to free up binding sites on the conditionally active polypeptide.

The small molecules preferably have a low molecular weight and/or a relatively small conformation to ensure maximum access to small pockets on the target polypeptide or conditionally active polypeptide by minimizing steric hindrance. For this reason, small molecules typically have a molecular weight of less than 900 a.m.u., or more preferably less than 500 a.m.u. or more preferably less than 200 a.m.u. or even more preferably less than 100 a.m.u. For example, bisulfide and bicarbonate both have low molecular weights and small structures that provide access to pockets on the target polypeptide or conditionally active polypeptide, as shown in Examples 13 and 14 below.

The small molecule may be present in the assays or environments at substantially the same concentration, e.g. about 20 μM for bicarbonate. In some embodiments, the small molecule may be present at different concentrations in different environments and thus it may be desirable to simulate this in the assays. For example, bisulfide has higher concentration in a tumor microenvironment than in human serum. Thus, one assay may simulate a tumor microenvironment with an acidic pH and higher concentration of bisulfide, while the second assay may simulate human serum with a neutral or slightly basic pH and lower concentration of bisulfide. The acidic pH may be in the range from 6.0 to 6.8 while the neutral or slightly basic pH may be around 7.4. The higher bisulfide for the first assay may be 30 μM while the lower bisulfide for the second buffer may be 10 μM or less, or 5 μM.

In some embodiments, the conditionally active polypeptide is pH-dependent when two or more different small molecules are present, for example, a combination of bicarbonate and histidine.

When the small molecule is absent, the conditionally active polypeptides may lose its pH-dependency. Thus, in the absence of the small molecule the conditionally active polypeptides may have similar activity between the first pH and the second pH in the absence of the small molecule.

In some embodiments, the first pH is an acidic pH while the second pH is a basic or neutral pH. In other embodiments, the first pH is a basic pH while the second pH is an acidic or neutral pH. For example, the first pH may be a pH in the range of from about 5.5 to 7.2, or from about 6.0 to 7.0, or from about 6.2 to 6.8. The second pH may be a pH in the range of from about 7.0 to 7.8, or from about 7.2 to 7.6.

Conditionally active polypeptides more active at an acidic pH and less active at a basic or neutral pH can target tumor microenvironment where the pH is acidic at from about 5.5 to 7.2, or from about 6.2 to 6.8.

In other embodiments, the first pH at which the pH-dependent polypeptides are more active may be a basic pH of, for example, 7.6-7.9, such as in synovial fluid, (See Jebens et al., "On the viscosity and pH of synovial fluid and pH of blood," Journal of Bone and Joint Surgery, vol. 41 B, pp. 388-400, 1959). The second pH may be the pH of blood of about 7.2-7.6, at which the conditionally active polypeptides are less active. These conditionally active polypeptides may be suitable for targeting the joint diseases, especially inflammation of joints.

In other embodiments, the conditionally active polypeptides may be designed to target the brain. There is a pH difference between the two sides of the blood brain barrier, with the pH on the brain side being about 0.2 pH unit lower than blood pH. Thus, the first pH of the brain at which the conditionally active polypeptides are more active may be about 7.0 to 7.2 (brain pH) while the second pH may be around 7.4 (blood pH).

The conditionally active polypeptide may be an enzyme, a cytokine, a receptor especially a cellular receptor, a regulatory polypeptide, a soluble polypeptide, an antibody, or hormone.

The conditionally active polypeptide may be a fragment of the parent polypeptide. For example, the conditionally active polypeptide may be an antibody fragment, a single chain antibody, a fragment of an enzyme, a fragment of a receptor, a fragment of a cytokine, or a fragment of a hormone. The antibody fragment may be an Fc fragment of antibody.

An Fc fragment may be used as the parent polypeptide for generating a conditionally active Fc fragment having higher binding activity to a complement at the first pH than the binding activity to the same complement at the second pH. The binding of the Fc fragment with the complement can be used to provide antibody-dependent cell mediated cytotoxicity. The first pH may be acidic in the range of 5.5 to 7.2 or 6.2 to 6.8, such as the pH in the tumor microenvironment, while the second pH is in the range of 7.2-7.6. The first pH is different from the pH in the lysosomes where the pH is typically around 4.0. Further, the lysosomes are a location where the Fc fragment, like any other polypeptides, is targeted for degradation. There is no complement in the lysosomes and no cell mediated cytotoxicity to be caused through lysosomes.

The conditionally active polypeptide may have two functional domains with at least one, preferably both of the functional domains having pH-dependent activities. These two functional domains may be evolved simultaneous and selection be made to identify both functional domains in the same mutant polypeptide. Alternatively, these two functional domains may be independently evolved and selected to identify the pH-dependent activities separately. If the two functional domains are not in the same mutant polypeptide, they may be fused into a chimeric polypeptide that has both of the separately identified functional domains.

The conditionally active polypeptides are reversibly or irreversibly inactivated at the first condition or normal physiological condition, but active at the second condition or aberrant conditions at the same or equivalent level as the first condition or normal physiological condition. These conditionally active polypeptides and methods of producing these polypeptides have been described in U.S. Pat. No. 8,709,755 B2. Conditionally active polypeptides are particularly valuable for development of novel therapeutics that are active for short or limited periods of time within the host. This is particularly valuable where extended action of the therapeutics at the given dose would be harmful to the host, but where limited activity is required to perform the desired therapy. Examples of beneficial applications include topical or systemic treatments at high dose, as well as localized treatments in high concentration. Inactivation under the first condition or normal physiological condition can be determined by a combination of the dosing and the rate of inactivation of the polypeptide. This condition based inactivation is especially important for enzyme therapeutics where catalytic activity cause substantial negative effects in a relatively short period of time.

The conditionally active polypeptides are reversibly or irreversibly activated or inactivated over time, or activated or inactivated only when they are in certain microenvironments in the body, including in specific organs in the body (such as tumor microenvironment, synovial fluid, the bladder or kidney). In some aspects, the conditionally active polypeptides are antibodies or antibody fragments against one or more target proteins (antigens) as described herein.

The conditionally active polypeptide may be an isolated polypeptide with a pH-dependent activity, where the activity at a first pH is at least about 1.3 fold of the activity at a second pH in the presence of a species selected from bicarbonate, histidine, histamine, bisulfide, citrate, lactate, and combinations thereof. The same activity is not pH-dependent in the absence of the small molecule. In some embodiments, the activity at the first pH that is at least about 1.5, or at least about 1.7, or at least about 2.0, or at least about 3.0, or at least about 4.0, or at least about 6.0, or at least about 8.0, or at least about 10.0, or at least about 20.0, or at least about 40.0, or at least about 60.0, or at least about 100.0 fold of the same activity at the second pH. The first pH may be an aberrant pH in the range of about 5.5-7.2, or about 6.2-6.8, while the second pH may be a normal physiological pH in the range of about 7.2-7.6.

With a conditionally active polypeptide selected, a nucleic acid, such as a DNA sequence, encoding the conditionally active polypeptide can be identified or synthesized. The nucleic acid may be used in a recombinant technique to produce the conditionally active polypeptide in large quantities. For example, the nucleic acid may be inserted into an expression vector, where the expression vector has a promoter operably linked to the nucleic acid to ensure high expression level for the conditionally active polypeptide. The expression vector may be introduced into a host cell, such as yeast, insect cell production host, or mammalian cell production host. Examples of host cells include 3T3 mouse fibroblast cells; BHK21 Syrian hamster fibroblast cells; MDCK, dog epithelial cells; Hela human epithelial cells; PtK1 rat kangaroo epithelial cells; SP2/0 mouse plasma cells; and NS0 mouse plasma cells; HEK 293 human embryonic kidney cells; COS monkey kidney cells; CHO, CHO-S Chinese hamster ovary cells; R1 mouse embryonic cells; E14.1 mouse embryonic cells; H1 human embryonic cells; H9 human embryonic cells; and PER C.6, human embryonic cells.

B. Engineering of Conditionally Active Polypeptides

The conditionally active polypeptides may be engineered by one or more protein engineering techniques described herein. Non-limiting examples of protein engineering techniques include conjugating the conditionally active polypeptides to nucleic acids, conjugating the conditionally active polypeptides to nanoparticles, engineering the conditionally active polypeptide in a chimeric antigen receptor, and engineering a masked conditionally active polypeptide.

The conditionally active polypeptides of the present invention may be conjugated to a nucleic acid molecule, e.g., a DNA or RNA molecule, through a linker. The conditionally active polypeptides can help to deliver the nucleic acid molecule to a target location of a subject which has a condition under which the conditionally active polypeptides are more active than other locations where the condition is not present. For example, the conditionally active polypeptides may be conditionally active antibodies that have higher a binding activity to their antigens under a condition in a tumor microenvironment than a condition at other locations such as in human serum. This effect can be used to deliver a nucleic acid molecule to the tumor microenvironment by conjugating the nucleic acid molecule to the conditionally active polypeptide and administering the conjugate to a subject.

In some embodiments, the nucleic acid molecule may be an agent for modulating the expression of a gene at the target location. Abnormal gene expression is associated with many diseases. Thus correcting the abnormal gene expression may contribute to control of or even curing of these diseases. For example, abnormal gene expression is characteristic of a majority of cancer cells, with some genes having an elevated expression level in cancer cells, such as many oncogenes (e.g., epidermal growth factor receptor 2 (HER2) is over expressed in breast cancer cells). Selective inhibition of constitutively elevated expression of the oncogenes provides an opportunity to inhibit proliferation of the cancer cells.

The nucleic acid molecules that can inhibit gene expression include antisense RNAs, small interfering RNAs (siRNAs), microRNAs, oligo DNAs, and oligonucleotide mimics with a non-charged achiral polyamide backbone to which the nucleobases are linked (Pooga et al., *Curr Cancer Drug Targets*, 1(3):231-9, 2001; Pandey et al., *Expert Opin Biol Ther.*, 9(8):975-89, 2009).

Antisense RNAs are short RNA molecules that can bind to specific complementary regions of an mRNA by base pairing to inhibit expression of the mRNA in a sequence-specific fashion. Antisense RNA may induce an RNaseH, which cleaves the mRNA at the site of binding with the antisense RNA, or can physically block translation or other steps in mRNA processing and protein synthesis.

Small interfering RNAs (siRNAs) are typically short double-stranded RNA segments with at least a portion of their sequence complementary to the mRNA sequences whose translation are to be blocked. siRNA functions through a posttranscriptional mechanism of gene silencing using chromatin remodeling, inhibition of protein translation, or direct mRNA degradation, which is ubiquitous in eukaryotic cells (Caplen, "Gene therapy progress and prospects. Downregulating gene expression: the impact of RNA interference," *Gene Ther.*, 11(16):1241-1248, 2004) and Bertrand et al., "Comparison of antisense oligonucleotides and siRNAs in cell culture and in vivo," *Biochem Biophys Res Commun.*, 296(4):1000-1004, 2002).

Particularly, through RISC, the siRNAs can initiate a potent cascade of sequence-specific degradation of the mRNAs that bear homology to the siRNAs (Fire et al., "Potent and specific genetic interference by doubles-stranded RNA in *Caenorhabditis elegans,*" *Nature* 391:806-811, 1998). When an siRNA is introduced into cells, it is processed by the RNase III enzyme called Dicer, which cleaves a long siRNA into short 21-23 nucleotide duplexes that have symmetric 2-3 nucleotide 3' overhangs and 5' phosphate and 3' hydroxyl groups (Tuschl et al., "Targeted mRNA degradation by double-stranded RNA in vitro," *Genes Dev.* 13:3191-3197, 1999; Hamilton and Baulcombe, "A species of small antisense RNA in posttranscriptional gene silencing in plants," *Science*, 286:950-952, 1999). Effective siRNAs thus require only a small segment of contiguous complementary sequence to pair with the mRNA in order to trigger siRNA-mediated silencing (Jackson and Linsley, "Noise amidst the silence: off-target effects of siRNAs?" *Trends Genet.*, 20:521-524, 2004). siRNAs do not integrate into the genome thus offer greater safety than plasmid or viral vehicles.

MicroRNAs (miRNAs) are a class of naturally occurring, small noncoding RNA molecules 21-25 nucleotides in length. MicroRNAs are partially complementary to mRNA molecules on which the microRNAs act. The main function of microRNAs is reducing gene expression via translational repression, mRNA cleavage, and deadenylation. A central online repository for miRNA species, sequence data, annotation, and target prediction is called miRBase, hosted by the Sanger Institute in the Great Britain. MicroRNA genes are transcribed by RNA polymerase II to produce pri-miRNAs that have a 5' cap and poly-A tail. In the nucleus, pri-miRNAs are processed to generate pre-miRNAs by a microprocessor complex, which consists of the RNAse III enzyme Drosha and the double-stranded RNA Pasha/DGCR8. These pre-miRNAs are exported by the karyopherin exportin (Exp5) and Ran-GTP complex into cytoplasm where Ran GTPase binds with Exp5 to form a nuclear heterotrimer with pre-miRNAs. These pre-miRNAs are additionally processed by the RNAse III enzyme Dicer to generate mature microRNA.

Another class of nucleic acids may be delivered by the conditionally active polypeptide are oligonucleotide mimics that comprise a non-charged achiral polyamide backbone to which the nucleobases are linked. The oligonucleotide mimic is often called a peptide nucleic acid (PNA). More specifically, PNA is DNA analogue in which an N-(2-aminoethyl) glycine polyamide replaces the phosphate-ribose ring backbone, and methylene-carbonyl linker connects natural as well as unnatural nucleo-bases to central amine of N-(2-aminoethyl) glycine. Despite the radical change to the backbone structure, PNA is capable of sequence specific binding to DNA and mRNA following the Watson-Crick base pairing rule.

PNA binds with higher affinity to complementary DNA/RNA than natural nucleic acids do, partly due to the lack of a negative charge on the backbone, and consequently reduced charge-charge repulsion, as well as favorable geometrical factors. The complex of PNA and DNA/mRNA is very stable in biological fluids, leading to inhibition of transcription and translation of target genes by specifically hybridizing to DNA or mRNA. Generally, PNAs are synthesized using well-known solid phase peptide synthesis protocols. See Kim et al., *J. Am. Chem. Soc.*, 115, 6477-6481, 1993; Hyrup et al., *J. Am. Chem. Soc.*, 116, 7964-7970; 1994; Egholm et al., *Nature*, 365, 566-568, 1993; Ducholm et al., *New J. Chem.*, 21, 19-31, 1997; Wittung et al., *J. Am. Chem. Soc.*, 118, 7049-7054; 1996; Leijon et al., *Biochemistry*, 33; 9820-9825, 1994, Orum et al., *BioTechnicques*, 19, 472-480, 1995; Tomac et al., *J. Am. Chem. Soc.*, 118, 5544-5552, 1996). In contrast to DNA, which depurinates on treatment with strong acids and hydrolyses in alkali hydroxides, PNAs are completely acid stable and sufficiently stable to weak bases.

Another class of nucleic acids that may be delivered by the conditionally active polypeptides are oligo DNAs. Oligo DNAs are short single-stranded segments of DNA that upon entry of cellular plasma can selectively inhibit the expression of a gene with a sequence complementary to the oligo DNAs. For antisense applications, oligo DNAs interact and form a duplex with the target mRNA or the pre-mRNA and inhibit its translation or processing, consequently inhibiting protein biosynthesis. For antigen applications, oligo DNAs must enter the cell nucleus, form a triplex with the double-stranded genomic DNA, and inhibit the transcription of the gene thus less mRNA is produced, leading to less gene product of protein being produced.

A further class of nucleic acids that may be delivered by the conditionally active polypeptides is spherical nucleic acids (SNAs, see Zhang, *J Am Chem Soc* 134(40):16488-16491, 2012). SNAs comprise densely functionalized and highly oriented nucleic acids covalently attached to the surface of a metallic, semiconducting, or insulating inorganic or polymeric core material. They can also be core-less, hollow structures composed almost entirely of nucleic acid molecules. Such spherical nucleic acids are capable of bypassing the natural defenses of a subject against exogenous nucleic acids. The spherical nucleic acids achieve protection and efficient delivery of nucleic acids utilizing unique properties arising from their densely packed, highly oriented nucleic acid shell. Such shells create areas of high local salt concentration, which when combined with steric inhibition, serve to reduce nuclease activity and protect the nucleic acids from enzymatic degradation. In addition, these spherical nucleic acids recruit scavenger proteins to their surfaces from the natural extracellular environment, which facilitate endocytosis.

After entry of cytoplasm, the spherical nucleic acids can inhibit the expression of target genes through either antisense or siRNA pathways. Consequently, spherical nucleic acids offer several advantages over viral vectors and many other synthetic systems, including low toxicity, low immunogenicity, resistance to enzymatic degradation, and more persistent gene knockdown. The conditionally active polypeptides, especially conditionally active antibodies, can deliver the spherical nucleic acids to a target location such as diseased or inflamed tissues (e.g., tumors and inflammatory joints).

The conditionally active polypeptides can also be conjugated to nanoparticles through a linker to help to deliver the nanoparticles to a target location having a condition under which the conditionally active polypeptide is more active. Nanoparticles are known vehicles for toxins, radioactive agents or other therapeutic agents, which are encapsulated in the nanoparticles.

The therapeutic agent encapsulated in the nanoparticles may be a protein that can dedifferentiate tumor cells, and thus possibly reverse the tumor cells back to normal cells (Friedmann-Morvinski and Verma, "Dedifferentiation and reprogramming: origins of cancer stem cells," *EMBO Reports,* 15(3):244-253, 2014). The nanoparticles may be linked to a conditionally active antibody to selectively deliver the linked nanoparticles and the encapsulated therapeutic agent to the environment where the conditionally active antibody is most active.

Several types of nanoparticles with different configurations may be used in the present invention. The nanoparticles may be made from a range of biocompatible materials including a biostable polymer, a biodegradable polymer, fullerenes, lipids, or a combination thereof. Biostable polymers refer to polymers that are not degraded in vivo. Biodegradable polymers refer to polymers that are capable of being degraded after delivery to a patient. For example, when the polymers are exposed to bodily fluids such blood, they can be gradually absorbed and/or eliminated by enzymes in the body. Methods of producing nanoparticles with various degradation rates are known to those skilled in the art, see for example U.S. Pat. Nos. 6,451,338, 6,168,804 and 6,258,378.

Exemplary nanoparticles of the invention include liposomes, polymersomes and polymer particles. Liposome refers to a compartment that is completely enclosed by a bilayer that are typically composed of phospholipids. Liposomes can be prepared according to standard techniques known to those skilled in the art. One technique is by suspending a suitable lipid, e.g., phosphatidyl choline, in an aqueous medium followed by sonication of the mixture. Another technique is by rapidly mixing a solution of lipid in ethanol water, for example, through injecting the lipid using a needle into an agitated ethanol-water solution. In some embodiments, liposomes can also comprise additionally or alternatively other amphiphilic substances, such as shingomyelin or lipids containing poly(ethylene glycol) (PEG).

Polymersomes comprise di- or tri-block copolymers that are modified to form bilayer structures similar to liposomes. Depending on the length and composition of the block copolymer, polymersomes can be substantially more robust than liposomes. In addition, the ability to control the chemistry of each block of the block copolymer permits tuning of the polymersome's composition to fit the desired application. For example, the membrane thickness of the polymersomes, i.e., the thickness of the bilayer structure, can be controlled by varying the chain length of the individual blocks in the block copolymer. Adjusting the glass transition temperatures of each block in the copolymer will affect the fluidity and therefore the permeability of the membrane of the polymersomes. Even the releasing mechanism of the encapsulated agent can be modified by altering the characteristics of the copolymers.

Polymersomes can be prepared by a process involving (i) dissolving the block copolymer in an organic solvent, (ii) applying the resultant solution to a vessel surface, and then (iii) removing the solvent, which leaves a film of the copolymer on the vessel wall. The film is then hydrated to form polymersomes. Alternatively, dissolving the block copolymer in a solvent and then adding a weak solvent for one of the blocks of the copolymer will also create polymersomes.

Therapeutic agents can be encapsulated in the polymersomes using several techniques. For example, a therapeutic agent may be mixed in water, which is then used to rehydrate the copolymer film. Another example is by osmotically driving the therapeutic agent into the core of preformed polymersomes, a process known as force loading. One more example is by using a double emulsion technique, which can generate polymersomes of relative monodispersivity and high loading efficiency. The double emulsion technique involves using microfluidic technology to generate double emulsions comprising water droplets surrounded by a layer of organic solvent. These droplet-in-a-drop structures are then dispersed in a continuous water phase. The block copolymer is dissolved in the organic solvent and self-assembles into proto-polymersomes on the concentric interfaces of the double emulsion. The final polymersomes are formed after completely evaporating the organic solvent from the shell of the proto-polymersomes. This technique allows fine control over the polymersome size. In addition, the ability to maintain complete separation of the internal fluids from the external fluid throughout the process allows extremely efficient encapsulation of the therapeutic agent.

Polymer particle refers to a solid or porous particle, in contrast to the shell structure of liposomes and polymersomes. Methods for adhering a therapeutic agent to the surface of, or integrating a bioactive agent into, the structure of a polymer particle are known to those skilled in the art.

Polymers that may be used to prepare nanoparticles of this invention include, but are not limited to, poly(N-acetylglucosamine) (Chitin), Chitosan, poly(3-hydroxyvalerate), poly (lactide-co-glycolide), poly(3-hydroxybutyrate), poly(4-hydroxybutyrate), poly(3-hydroxybutyrate-co-3-hydroxyvalerate), polyorthoester, polyanhydride, poly (glycolic acid), poly(glycolide), poly(L-lactic acid), poly(L-lactide), poly(D,L-lactic acid), poly(D,L-lactide), poly(L-lactide-co-D,L-lactide), poly(caprolactone), poly(L-lactide-co-caprolactone), poly(D,L-lactide-co-caprolactone), poly (glycolide-co-caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrin glue, fibrinogen, cellulose, starch, collagen and hyaluronic acid, elastin and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, acrylonitrile butadiene styrene (ABS) resins, polyamides (such as Nylon 66 and polycaprolactam), polycarbonates including tyrosine-based polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose.

In some embodiments, the nanoparticles may also provide tissue selectivity through coating, in addition to the selectivity derived from the conditionally active polypeptides. For example, the nanoparticles may be coated by electrostatically adsorbed poly(glutamic acid)-based peptide coatings to alter the exterior composition of the core particles. The negatively charged polyglutamic acid-based peptides containing the Arginine-Glycine-Aspartic Acid (ROD) ligand can increase in vitro gene delivery to endothelial cells compared to scrambled sequence coated particles that contained RDG instead of ROD. These peptides consist of three components: a stretch of poly (glutamic acid) that provides the negative charge, a linker of polyglycine, and a terminal sequence that varies in charge and has the potential to alter particle biophysical properties and tissue selectivity. The coatings as well as the particles themselves are biodegradable via their amide and ester linkages respectively. See Harris et al. ("Tissue-Specific Gene Delivery via Nanoparticle Coating," *Biomaterials*, vol. 31, pp. 998-1006, 2010).

T cells are used by the mammalian immune system for combating substances or cells having foreign antigens. On encountering a solid tumor, T cells often fail to mount an effective response. Even when the T cells reach tumor sites, they are faced with a barrage of immunosuppressive factors that enable the cancer cells to escape the immune system. CAR-T technology uses genetic engineering methods to reprogram natural circulating T cells by inserting a chimeric antigen receptor (CAR) into the T cells to produce highly specific CAR-T cells in which the CAR directs the engineered CAR-T cells to the target tissue by specifically binding to an antigen on the surface of the target tissue. Thus, the CAR-T cells can specifically target tumor cells, making the CAR-T cells much more effective than naturally circulating T cells. The CAR-T cells may also be engineered to target other target tissues such as inflamed joints and brain tissue.

Figure 5:
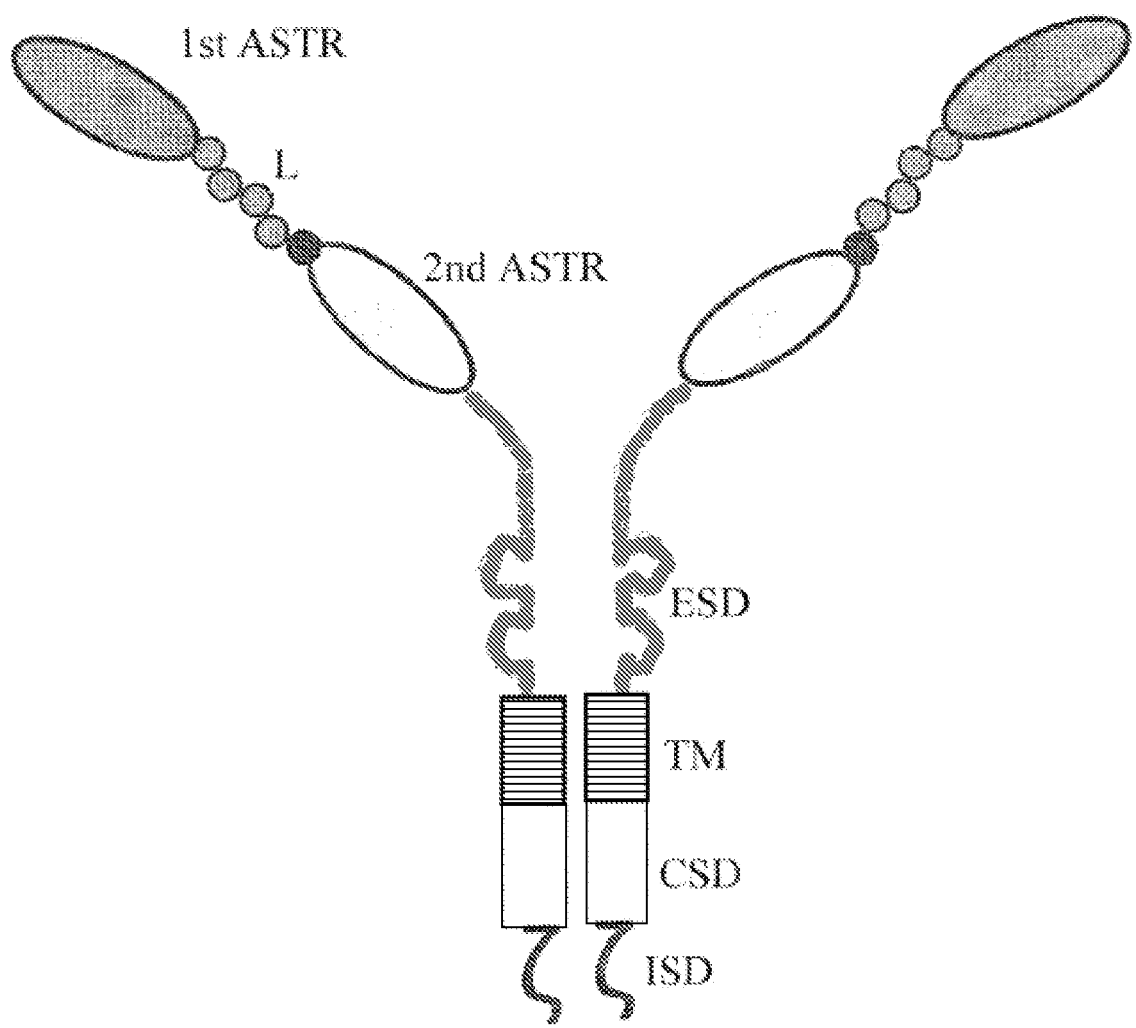
FIG. 5 is a diagram showing the structure of a chimeric antigen receptor (CAR).

The CARs of the invention include at least one antigen specific targeting region (ASTR), an extracellular spacer domain (ESD), a transmembrane domain (TM), one or more co-stimulatory domains (CSD), and an intracellular signaling domain (ISD), see FIG. 5 and Jensen et al., "Design and implementation of adoptive therapy with chimeric antigen receptor-modified T cells," *Immunol. Rev.*, vol. 257, pp. 127-144, 2014. After the ASTR binds specifically to a target antigen on a tumor or other targeted tissue, the ISD activates intracellular signaling in the CAR-T cells. For example, the ISD can redirect the CAR-T cell specificity and reactivity toward a selected target (e.g., tumor cells or other targeted cells) in a non-MHC-restricted manner, exploiting the antigen-binding properties of antibodies. The non-MHC-restricted antigen recognition gives the CAR-T cells the ability to recognize tumor cell and initiate antigen processing, thus bypassing a major mechanism of tumor escape from the surveillance of the immune system. In an embodiment, the ESD and/or CSD are optional. In another embodiment, the ASTR has a bispecificity, which allows it to specifically bind with two different antigens or epitopes.

The conditionally active polypeptide of the present invention may be engineered as the ASTR or portion thereof, in order to render the CARs more active at in a particular environment, such as a tumor microenvironment or synovial fluid, for binding to the target antigen than in blood or another part of the body where a different environment is present. Such CARs can preferentially deliver the T cells to the disease site thus dramatically reducing side-effects caused by T cells attacks on normal tissue. This allows higher doses of T cells to be used to increase therapeutic efficacy and improves the tolerance of a subject to the treatment.

These CARs are particularly valuable for development of novel therapeutics that are required for short or limited periods of time within a subject. Examples of beneficial applications include systemic treatments at high dosages, as well as localized treatments at high concentrations. See Maher, "Immunotherapy of Malignant Disease Using Chimeric Antigen Receptor Engrafted T Cells," *ISRN Oncology*, vol. 2012, article ID 278093, 2012.

The ASTR may comprise a conditionally active polypeptide, such as antibody, especially a single-chain antibody, or a fragment thereof that binds specifically to an antigen on tumors or other targeted tissues. Some examples of the polypeptides suitable for ASTRs include linked cytokines (which leads to recognition of cells bearing the cytokine receptor), affibodies, ligand binding domains from naturally occurring receptors, and soluble protein/peptide ligands for a receptor, for example on a tumor cell. In fact, almost any molecule that is capable of binding to a given antigen with high affinity can be used in the ASTR.

In some embodiments, the CAR of the invention includes at least two ASTRs which target at least two different antigens or two epitopes on the same antigen. In one embodiment, the CAR includes three or more ASTRs which target at least three or more different antigens or epitopes.

When a plurality of ASTRs is present in the CAR, the ASTRs may be arranged in tandem and may be separated by linker peptides (FIG. 5).

In yet another embodiment, an ASTR includes a diabody. In a diabody, the scFvs are created with linker peptides that are too short for the two variable regions to fold together, driving the scFvs to dimerize. Still shorter linkers (one or two amino acids) lead to the formation of trimers, the so-called triabodies or tribodies. Tetrabodies may also be used in the ASTR.

The antigens targeted by the CAR are present on the surface or inside of cells in a tissue that is targeted for removal, such as tumors, glandular (e.g. prostate) hyperplasia, warts, and unwanted fatty tissue. While the surface antigens are more efficiently recognized and bound by the ASTR of CARs, intracellular antigens may also be targeted by the CARs. In some embodiments, the target antigens are preferably specific for cancer, inflammatory disease, neuronal-disorders, diabetes, cardiovascular disease, or infectious diseases. Examples of target antigens include antigens expressed by various immune cells, carcinomas, sarcomas, lymphomas, leukemia, germ cell tumors, blastomas, and cells associated with various hematologic diseases, autoimmune diseases, and/or inflammatory diseases.

Antigens specific for cancer which may be targeted by the ASTR include one or more of 4-IBB, 5T4, adenocarcinoma antigen, alpha-fetoprotein, BAFF, B-lymphoma cell, C242 antigen, CA-125, carbonic anhydrase 9 (CA-IX), C-MET, CCR4, CD152, CD19, CD20, CD200, CD22, CD221, CD23 (IgE receptor), CD28, CD30 (TNFRSF8), CD33, CD4, CD40, CD44 v6, CD51, CD52, CD56, CD74, CD80, CEA, CTLA-4, DRS, EGFR, EpCAM, CD3, FAP, fibronectin extra domain-B, folate receptor 1, GD2, GD3 ganglioside, glycoprotein 75, GPNMB, HER2/neu, HGF, human scatter factor receptor kinase, IGF-1 receptor, IGF-I, IgG1, LI-CAM, IL-13, IL-6, insulin-like growth factor I receptor, integrin α5β1, integrin αvβ3, MORAb-009, MS4A1, MUC1, mucin CanAg, N-glycolylneuraminic acid, NPC-1C, PDGF-R a, PDL192, phosphatidylserine, prostatic carcinoma cells, RANKL, RON, ROR1, SCH 900105, SDC1, SLAMF7, TAG-72, tenascin C, TGF beta 2, TGF-β, TRAIL-R1, TRAIL-R2, tumor antigen CTAA16.88, VEGF-A, VEGFR-1, VEGFR2 or vimentin.

Antigens specific for inflammatory diseases which may be targeted by the ASTR include one or more of AOC3 (VAP-1), CAM-3001, CCL11 (eotaxin-1), CD125, CD147 (basigin), CD154 (CD40L), CD2, CD20, CD23 (IgE receptor), CD25 (a chain of IL-2 receptor), CD3, CD4, CD5, IFN-α, IFN-γ, IgE, IgE Fc region, IL-1, IL-12, IL-23, IL-13, IL-17, IL-17A, IL-22, IL-4, IL-5, IL-5, IL-6, IL-6 receptor, integrin a4, integrin α4β7, Lama glama, LFA-1 (CD1 1a), MEDI-528, myostatin, OX-40, rhuMAb β7, scleroscin, SOST, TGF beta 1, TNF-α or VEGF-A.

Antigens specific for neuronal disorders which may be targeted by the ASTR of the invention include one or more of beta amyloid or MABT5102A. Antigens specific for diabetes which may be targeted by the ASTR of the invention include one or more of L-Iβ or CD3. Antigens specific for cardiovascular diseases which may be targeted by the ASTR of the invention include one or more of C5, cardiac myosin, CD41 (integrin alpha-lib), fibrin II, beta chain, ITGB2 (CD 18) and sphingosine-1-phosphate.

Antigens specific for infectious diseases which may be targeted by the ASTR of the invention include one or more of anthrax toxin, CCR5, CD4, clumping factor A, cytomegalovirus, cytomegalovirus glycoprotein B, endotoxin, *Escherichia coli*, hepatitis B surface antigen, hepatitis B virus, HIV-1, Hsp90, Influenza A hemagglutinin, lipoteichoic acid, *Pseudomonas aeruginosa*, rabies virus glycoprotein, respiratory syncytial virus and TNF-a.

Further examples of target antigens include surface proteins found on cancer cells in a specific or amplified fashion, e.g. the IL-14 receptor, CD19, CD20 and CD40 for B-cell lymphoma, the Lewis Y and CEA antigens for a variety of carcinomas, the Tag72 antigen for breast and colorectal cancer, EGF-R for lung cancer, folate binding protein and the HER-2 protein which is often amplified in human breast and ovarian carcinomas, or viral proteins, e.g. gp120 and gp41 envelope proteins of HIV, envelope proteins from the Hepatitis B and C viruses, glycoprotein B and other envelope glycoproteins of human cytomegalovirus, and the envelope proteins from oncoviruses such as Kaposi's sarcoma-associated Herpes virus. Other potential target antigens include CD4, where the ligand is the HIV gp120 envelope glycoprotein, and other viral receptors, for example ICAM, which is the receptor for the human rhinovirus, and the related receptor molecule for poliovirus.

In another embodiment, the CAR may target antigens that engage cancer-treating cells, such as NK cells, to activate the cancer-treating cells by acting as immune effector cells. One example of this is a CAR that targets the CD16A antigen to engage NK cells to fight CD30-expressing malignancies. The bispecific, tetravalent AFM13 antibody is an example of an antibody that can deliver this effect. Further details of this type of embodiment can be found, for example, in Rothe, A., et al., "A phase 1 study of the bispecific anti-CD30/CD16A antibody construct AFM13 in patients with relapsed or refractory Hodgkin lymphoma," *Blood*, 25 Jun. 2015, Vl. 125, no. 26, pp. 4024-4031.

In some embodiments, the extracellular spacer domain and the transmembrane domain may be ubiquitylation-resistant, which can enhance CAR-T cell signaling and thus augment antitumor activity (Kunii et al., "Enhanced function of redirected human t cells expressing linker for activation oft cells that is resistant to ubiquitylation," *Human Gene Therapy*, vol. 24, pp. 27-37, 2013). Within this region, the extracellular spacer domain is outside of the CAR-T cells, and thus is exposed to different conditions and can potentially be made conditionally ubiquitylation-resistant.

C. Engineering Masked Conditionally Active Polypeptide

The conditionally active polypeptide, especially the conditionally active antibody, of the present invention may have its conditional activity masked, and/or have the activity of its conjugated agent masked by a masking moiety. The masked activity will become available once the masking moiety is removed or cleaved from the conditionally active polypeptide. Suitable masking technology is described, for example, in Desnoyers et al., "Tumor-Specific Activation of an EGFR-Targeting Probody Enhances Therapeutic Index," *Sci. Transl. Med.* 5, 207ra144, 2013.

In some embodiments, the conditionally active antibody is linked with a masking moiety, which masks the conditional activity and/or the activity of its conjugated agent. For example, when the conditionally active antibody is coupled to a masking moiety, such coupling or modification can effect a structural change which reduces or inhibits the ability of the conditionally active antibody to specifically bind with its antigen. Once the conditionally active antibody reaches the target tissue or microenvironment, the masking moiety is cleaved by an enzyme present in the target tissue or the microenvironment, thus releasing the masked activity. For example, the enzyme may be a protease commonly active in the tumor microenvironment, which can cleave the masking moiety to release the conditionally active antibody with activity within a tumor tissue.

In some embodiments, the activity is masked to be less than about 50% of the original activity, or less than about 30% of the original activity, or less than about 10% of the original activity, or less than about 5% of the original activity, or less than about 2% of the original activity, or less than about 1% of the original activity, or less than about 0.1% of the original activity, or less than about 0.01% of the original activity. In some embodiments, for example, in order to ensure adequate time for delivery, the masking effect is designed to last for at least 2, 4, 6, 8, 12, 28, 24, 30, 36, 48, 60, 72, 84, 96 hours, or 5, 10, 15, 30, 45, 60, 90, 120, 150, 180 days, or 1, 2, 3, 4, 5, 6, 7, 8, 9, 10, 11, 12 months or greater when measured in vivo or in a target displacement in vitro immunosorbent assay.

In certain embodiments, the masking moiety is structurally similar to the natural binding partner (antigen) of the conditionally active antibody. The masking moiety may be a modified natural binding partner of the conditionally active antibody, which contains amino acid changes that at least slightly decrease the affinity and/or avidity of binding to the conditionally active antibody. In some embodiments the masking moiety contains no or substantially no homology to the conditionally active antibody's natural binding partner. In other embodiments the masking moiety has a sequence identify of no more than 5%, 10%, 15%, 20%, 25%, 30%, 35%, 40%, 45%, 50%, 55%, 60%, 65%, 70%, 75%, or 80% to the natural binding partner of the conditionally active antibody.

The masking moiety can be provided in a variety of different forms. In certain embodiments, the masking moiety can be a known binding partner of the conditionally active antibody, provided that the masking moiety binds to the conditionally active antibody with less affinity and/or avidity than the target protein to which the conditionally active antibody is targeted following cleavage of the masking moiety so as to reduce interference of the masking moiety with the desired binding to the target. Thus, the masking moiety is preferably one that masks the conditionally active antibody from target binding before the masking moiety is cleaved, but does not substantially or significantly interfere with or compete for binding of the active molecule to the target when after the masking moiety has been cleaved from the antibody. In a specific embodiment, the conditionally active antibody and masking moiety do not contain the amino acid sequences of a naturally-occurring binding partner pair, such that at least one of the conditionally active antibody and masking moiety does not have the amino acid sequence of a member of a naturally occurring binding partner.

Alternatively, the masking moiety may not specifically bind to the conditionally active antibody, but rather interfere with conditionally active antibody-target binding through non-specific interactions such as steric hindrance. For example, the masking moiety may be positioned such that the structure or conformation of the antibody allows the masking moiety to mask the conditionally active antibody through, for example, a charge-based interaction, thereby interfering with target access to the conditionally active antibody.

In some embodiments, the masking moiety is coupled to the conditionally active antibody by covalent binding. In another embodiment, the conditionally active antibody is prevented from binding to its target by binding the masking moiety to an N-terminus of the conditionally active antibody. In yet another embodiment, the conditionally active antibody is coupled to the masking moiety by cysteine-cysteine disulfide bridges between the masking moiety and the conditionally active antibody.

In some embodiments, the conditionally active antibody is further coupled to a cleavable moiety (CM). The CM is capable of being cleaved by an enzyme, or the CM is capable of being reduced by a reducing agent, or the CM is capable of being photo lysed. In one embodiment, the amino acid sequence of the CM may overlap with or be included within the masking moiety. In another embodiment, the CM is between the conditionally active antibody and the masking moiety. It should be noted that all or a portion of the CM may facilitate masking of the conditionally active antibody before cleavage. When the CM is cleaved the conditionally active antibody becomes more active in binding to its antigen.

The CM may be a substrate for an enzyme that is co-localized with the target antigen at a treatment site in a subject. Alternatively, or in addition, the CM may have a cysteine-cysteine disulfide bond that is cleavable as a result of reduction of this disulfide bond. The CM may also be a photolabile substrate, activatable by a light source.

The enzymes that cleave the CM should be preferentially located in a desired target tissue of the conditionally active antibody where the conditionally active antibody is more active at the condition presented in the target tissue (aberrant condition), such as diseased tissue or tumor tissue. For example, there are known proteases with increased level in a number of cancers, e.g., solid tumors. See, e.g., La Rocca et al, (2004) *British J. of Cancer* 90(7): 1414-1421. Non-limiting examples of such diseases include: all types of cancers (breast, lung, colorectal, prostate, head and neck, pancreatic, etc.), rheumatoid arthritis, Crohn's disease, melanomas, SLE, cardiovascular damage, ischemia, etc. As such, a suitable CM may be selected which comprises a peptide substrate that is cleavable by a protease that is present in tumor tissue, particularly that is present at elevated levels in the tumor tissue as compared to non-cancerous tissues.

In some embodiments, the CM may be a substrate for an enzyme selected from legumain, plasmin, TMPRSS-3/4, MMP-9, MT1-MMP, cathepsin, caspase, human neutrophil elastase, beta-secretase, uPA and PSA. The enzyme that cleaves the CM is present at relatively higher levels in target tissue of a treatment site (for example diseased tissue or tumor tissue; for example for therapeutic treatment or diagnostic treatment) than in tissue of non-treatment sites (for example in healthy tissue). Therefore, besides the conditional activity of the antibody, which may be more active at the diseased tissue or tumor tissue, the enzyme presented at the diseased tissue or tumor tissue can cleave the CM, which further enhances the activity of the conditionally active antibody, or the activity of a conjugated agent. The unmodified or uncleaved CM can allow for efficient inhibition or masking of the activity of the conditionally active antibody, such that the conditionally active antibody is less active at normal tissue (normal physiological condition). The dual mechanism of suppressing the activity of conditionally active antibody at normal tissue (conditional activity and masking moiety) allows use of a much high dosage of the conditionally active antibody to be used without causing significant adverse effects.

In some embodiments, the CM may be a substrate of an enzyme selected from the enzymes listed in Table 1 below.

TABLE 1

Exemplary Enzymes/Proteases

| | | | |
|---|---|---|---|
| ADAM10 | Caspase 8 | Cathepsin S | MMP 8 |
| ADAM12 | Caspase 9 | FAP | MMP 9 |
| ADAM17 | Caspase 10 | Granzyme B | MMP-13 |
| ADAMTS | Caspase 11 | Guanidinobenzoatase (GB) | MMP 14 |
| ADAMTS5 | Caspase 12 | Hepsin | MT-SP1 |
| BACE | Caspase 13 | Human Neutrophil Elastase (HNE) | Neprilysin |
| Caspases | Caspase 14 | Legumain | NS3/4A |
| Caspase 1 | Cathepsins | Matriptase 2 | Plasmin |
| Caspase 2 | Cathepsin A | Meprin | PSA |
| Caspase 3 | Cathepsin B | MMP 1 | PSMA |
| Caspase 4 | Cathepsin D | MMP 2 | TACE |
| Caspase 5 | Cathepsin E | MMP 3 | TMPRSS 3/4 |
| Caspase 6 | Cathepsin K | MMP 7 | uPA |
| Caspase 7 | MT1-MMP | | |

Alternatively or in addition, the CM can include a disulfide bond of a cysteine pair, which is thus cleavable by a reducing agent such as a cellular reducing agent including glutathione (GSH), thioredoxins, NADPH, flavins, ascorbate, and the like, which can be present in large amounts in tissue of, or surrounding, a solid tumor.

In some embodiments, the conditionally active antibody contains both CM and a masking moiety. The activity of the conditionally active antibody is unmasked upon cleavage of the CM by an enzyme. In some embodiments, it may be desirable to insert one or more linkers, e.g., flexible linkers, between the antibody, the masking moiety and the CM, so as to provide for flexibility. For example, the masking moiety and/or CM may not contain a sufficient number of residues (e.g., Gly, Ser, Asp, Asn, especially Gly and Ser, particularly Gly) to provide the desired flexibility. As such, it may be beneficial to introduce one or more amino acids to provide for a flexible linker. For example, the masked conditionally active antibody may have the following structures (where the formula below represent an amino acid sequence in either N- to C-terminal direction or C- to N-terminal direction):

(MM)-L$_1$-(CM)-(AB)

(MM)-(CM)-L$_1$-(AB)

(MM)-L$_1$-(CM)-L$_2$-(AB)

Cyclo[L$_1$-(MM)-L$_2$-(CM)-L$_3$-(AB)]

wherein MM is the masking moiety and AB is the conditionally active antibody; L$_1$, L$_2$, and L$_3$ represent each independently and optionally present or absent, being the same or different flexible linkers that include at least one flexible amino acid (e.g., Gly); and cyclo where present, the entire structure is in the form of a cyclic structure due to the presence of a disulfide bond between a pair of cysteines at or near both N- and C-terminus of the structure.

Linkers suitable for use in the invention are generally ones that provide flexibility to the masking moiety to facilitate the inhibition of the activity of the conditionally active antibody. Such linkers are generally referred to as flexible linkers. Suitable linkers can be readily selected and can be of any of suitable different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids.

Exemplary flexible linkers include glycine polymers (G)$_n$, glycine-serine polymers (including, for example, (GS)$_n$, (GSGGS)$_n$ and (GGGS)$_n$, where n is an integer of at least one, glycine-alanine polymers, alanine-serine polymers, and other flexible linkers known in the art. Exemplary flexible linkers include, but are not limited to Gly-Gly-Ser-Gly, Gly-Gly-Ser-Gly-Gly, Gly-Ser-Gly-Ser-Gly, Gly-Ser-Gly-Gly-Gly, Gly-Gly-Gly-Ser-Gly, Gly-Ser-Ser-Ser-Gly, and the like.

Some of the techniques used for masking the activity of the conditionally active antibody are described in WO2010081173A2.

In some aspects, the conditionally active polypeptides are conditionally active antibodies, which may be engineered using a technique described herein. Non-limiting examples of antibody engineering techniques include antibody conjugation, engineering of multispecific antibodies, engineering a bi-specific conditionally active antibody against an immune effector-cell surface antigen and a target antigen, engineering of the Fc region of the antibodies.

The methods for conjugating the conditionally active antibodies have been described in WO 2015/175375. In one aspect, the conditionally active antibodies may be conjugated on the Fc region of the antibodies. The conjugating molecules, compounds or drugs described above may be conjugated to the Fc region, as described in U.S. Pat. No. 8,362,210. For example, the Fc region may be conjugated to a cytokine or a toxin to be delivered to the site where the conditionally active antibody displays preferential activity. Methods for conjugating polypeptides to the Fc region of antibodies are known in the art. See, e.g., U.S. Pat. Nos. 5,336,603, 5,622,929, 5,359,046, 5,349,053, 5,447,851, 5,723,125, 5,783,181, 5,908,626, 5,844,095, and 5,112,946; EP 307,434; EP 367,166; EP 394,827; WO 91/06570, WO 96/04388, WO 96/22024, WO 97/34631, and WO 99/04813; Ashkenazi et al., Proc. Natl. Acad. Sci. USA, vol. 88, pages 10535-10539, 1991; Traunecker et al., Nature, vol. 331, pages 84-86, 1988; Zheng et al., J. Immunol., vol. 154, pages 5590-5600, 1995; and Vil et al., Proc. Natl. Acad. Sci. USA, vol. 89, pages 11337-11341, 1992.

In one aspect, the conditionally active antibody may be covalently attached to the conjugated agent through an intermediate linker having at least two reactive groups, one to react with the conditionally active antibody and one to react with the conjugated agent. The linker, which may include any compatible organic compound, can be chosen such that the reaction with conditionally active antibody or conjugated agent does not adversely affect reactivity and/or selectivity of the conditionally active antibody. Furthermore, the attachment of linker to conjugated agent might not destroy the activity of the conjugated agent.

Suitable linkers for oxidized conditionally active antibodies include those containing a group selected from primary amines, secondary amines, hydrazine, hydrazide, hydroxylamines, phenylhydrazine, semicarbazide and thiosemicarbazide groups. Suitable linkers for reduced conditionally active antibodies include those having certain reactive groups capable of reaction with a sulfhydryl group of a reduced conditionally active antibody. Such reactive groups include, but are not limited to: reactive haloalkyl groups (including, for example, haloacetyl groups), p-mercuribenzoate groups and groups capable of Michael-type addition reactions (including, for example, maleimides and groups of the type described by Mitra and Lawton, J. Amer. Chem. Soc. Vol. 101, pages 3097-3110, 1979).

The methods for engineering multispecific conditionally active antibodies have been described in WO 2015/175375.

The conditionally active antibody may be engineered to generate a bi-specific conditionally active antibody against an immune effector-cell surface antigen and a target antigen. The bi-specific conditionally active antibodies of the invention can attract an immune effector cell to a disease site with the target antigen present. The bi-specific conditionally active antibody is an antibody that can specifically bind to two different antigens: the immune effector-cell surface antigen and the target antigen. The bi-specific antibody may be a full length antibody comprising two arms with one arm binding to the immune effector-cell surface antigen and the other arm binding to the target antigen. The bi-specific antibody may be an antibody fragment comprising only heavy chain variable domains ($V_H$) and light chain variable domains ($V_L$). In one embodiment, the antibody fragment includes at least two $V_H V_L$ units: one for binding to the immune effector-cell surface antigen and the other arm binding to the target antigen. In another embodiment, the antibody fragment includes at least two single variable domains ($V_H$ or $V_L$): one for binding to the immune effector-cell surface antigen and the other arm binding to the target antigen. In some embodiments, the bi-specific conditionally active antibody comprises two scFvs: one binding to the immune effector-cell surface antigen and the other binding to the target antigen.

The attracted immune effector cell, with its binding activity to both an immune effector-cell and a target antigen on diseased cells or diseased tissue, can attract the immune effector-cell to the diseased cells or diseased tissues containing the target antigen. The attracted immune effector-cell will then attack the diseased cells or diseased tissues, thus helping to cure the disease because the immune effector cell is capable of suppressing or even destroying the diseased cells or diseased tissue. For example, the immune effectors cell can destroy tumor cells or infected cells. The immune effector cells include natural killer cells (NK cells), macrophages, lymphokine-activated killer (LAK) cells and T-cells.

The bi-specific conditionally active antibody has two binding activities, one each to the immune effector-cell surface antigen and the target antigen. In one embodiment, both binding activities are conditional, meaning that the binding activities of the bi-specific conditionally active antibody to the immune effector-cell surface antigen and the target antigen are lower than the binding activities of a parent antibody under a normal physiological condition and higher than the parent antibody under an aberrant condition. In one embodiment, only one of two binding activities are conditional, meaning that either the binding activity of the bi-specific conditionally active antibody to the immune effector-cell surface antigen or the binding activity of the bi-specific conditionally active antibody to the target antigen is conditional. In this case one of the binding activity of the bi-specific conditionally active antibody to the immune effector-cell surface antigen or the binding activity of the bi-specific conditionally active antibody to the target antigen is lower than the corresponding activity of a parent antibody under a normal physiological condition and higher than the corresponding activity of the parent antibody under an aberrant condition.

The two arms (e.g., two $V_H V_L$ units or two scFvs) in the bi-specific conditionally active antibody may be joined by means of conventional methods. As is well known in the field, the minimum antibody fragment containing a complete antigen binding site has a dimer of one heavy and one light chain variable domain ($V_H$ and $V_L$) in non-covalent association. This configuration corresponds to the one found in native antibodies where three complementarity determining regions (CDRs) of each variable domain interact to define an antigen binding site on the surface of the $V_H$-$V_L$ dimer. Collectively, the six CDRs confer antigen binding specificity to the antibody. Frameworks (FRs) flanking the CDRs have a tertiary structure that is essentially conserved in native immunoglobulins of species as diverse as human and mouse. These FRs serve to hold the CDRs in their appropriate orientation. The constant domains are not required for binding function, but may aid in stabilizing $V_H$-$V_L$ interaction. Even a single variable domain (or half of an Fv comprising only three CDRs specific for an antigen) has the ability to recognize and bind antigen, although usually at a lower affinity than an entire binding site (Painter et al., "Contributions of heavy and light chains of rabbit immunoglobulin G to antibody activity. I. Binding studies on isolated heavy and light chains," *Biochemistry*, vol. 11 pages 1327-1337, 1972). Hence, said domain of the binding site of the bi-specific conditionally active antibody may be constructed as a pair of $V_H$-$V_L$, $V_H$-$V_H$ or $V_L$-$V_L$ domains of different immunoglobulins.

In some embodiments, the bi-specific conditionally active antibody may be constructed as a contiguous polypeptide chain by means of recombinant DNA techniques, e.g. in such a way that a nucleic acid molecule coding for bi-specific conditionally active antibody is expressed in order to construct a contiguous polypeptide chain (e.g., see Mack et al., "A small bispecific antibody construct expressed as a functional single-chain molecule with high tumor cell cytotoxicity," *Proc. Natl. Acad. Sci. USA*, vol. 92, pages 7021-7025, 2005). The order of $V_H$ and $V_L$ domains within the polypeptide chain is not critical for the present invention, as long as the $V_H$ and $V_L$ domains are arranged so that the antigen binding sites can properly fold to form one binding site for the immune effector-cell surface antigen and one binding site for the target antigen.

Some of the techniques described herein for engineering multi-specific conditionally active antibodies may be used in generating bi-specific conditionally active antibody against the immune effector cell surface antigen and target antigen.

The bi-specific antibodies may be configured as a single polypeptide chain, as described in WO 99/54440, Mack, *J. Immunol*. (1997), 158, 3965-3970, Mack, *PNAS*, (1995), 92, 7021-7025, Kufer, *Cancer Immunol. Immunother.*, (1997), 45, 193-197, Loffler, *Blood*, (2000), 95, 6, 2098-2103, Bruhl, *J. Immunol.*, (2001), 166, 2420-2426. A particularly preferred configuration for the bi-specific antibody is a polypeptide construct wherein the $V_H$ and $V_L$ regions are linked to each other by a linker-domain. The order of the $V_H$ and $V_L$ regions in the single polypeptide chain is not critical. In one embodiment, the single polypeptide chain is configured as $V_{H1}$-linker domain-$V_{L1}$-linker domain-$V_{H2}$-linker domain-$V_{L2}$. In another embodiment, the single polypeptide chain is configured as $V_{L1}$-linker domain-$V_{H1}$-linker domain-$V_{L2}$-linker domain-$V_{H2}$. In another embodiment, the single polypeptide chain is configured as $V_{H1}$-linker domain-$V_{H2}$-linker domain-$V_{L1}$-linker domain-$V_{L2}$. In another embodiment, the single polypeptide chain is configured as $V_{H1}$-linker domain-$V_{L2}$-linker domain-$V_{L1}$-linker domain-$V_{H2}$. The single polypeptide chain can fold into two arms with each capable of binding with the immune effector cell surface antigen or the target antigen.

The linker domain in the bi-specific conditionally active antibody is a peptide fragment long enough to allow inter-molecular association between these $V_H$ and $V_L$ domains. The design of linkers suitable for this purpose is described in the prior art, for example in EP 623 679 B1, U.S. Pat. No. 5,258,498, EP 573 551 B1 and U.S. Pat. No. 5,525,491. The linker domain is preferably a hydrophilic flexible linker of 1 to 25 amino acids selected from a Glycine, a Serine and/or a Glycine/Serine. In one embodiment, the linker domain is a 15 amino acid linker of sequence $(Gly_4Ser)_3$.

Additional linker domains comprise oligomerization domains. Oligomerization domains can facilitate the combination of two or several $V_H$ and $V_L$ domains thereof folding into the two arms with each capable of binding with the immune effector cell surface antigen or the target antigen. Non-limiting examples of oligomerization domains comprise leucine zippers (like jun-fos, GCN4, E/EBP; Kostelny, *J. Immunol.* 148 (1992), 1547-1553; Zeng, *Proc. Natl. Acad. Sci.* 94 (1997), 3673-3678, Williams, *Genes Dev.* 5 (1991), 1553-1563; Suter, "Phage Display of Peptides and Proteins", Chapter 11, (1996), Academic Press), antibody-derived oligomerization domains, like constant domains CH1 and CL (Mueller, *FEBS Letters* 422 (1998), 259-264) and/or tetramerization domains like GCN4-LI (Zerangue, *Proc. Natl. Acad. Sci.* 97 (2000), 3591-3595).

In some embodiments, knob-in-hole technology may be used to stabilize the folding of the single polypeptide chain bi-specific conditionally antibody. Knob-in-hole technology is described by Ridgway et al., ("Knobs-into-holes' engineering of antibody CH3 domains for heavy chain heterodimerization," *Protein Eng.* 1996 July; 9(7):617-21). This approach has been used for the packing of amino acid side chains between adjacent a-helices, where the side chains of residues in an a-helix are represented as spaced knobs on the surface of a cylinder alternating with holes in which knobs of an adjacent a-helix might fit (O'Shea et al., (1991) Science, 254, 539-544).

The immune effector-cell surface antigens should be specific to one or a class of immune effector cells. The surface antigens for many of the immune effector cells are known. The natural killer cells have surface antigens including CD56, CD8, CD16, KIR family receptors, NKp46, NKp30, CD244 (2B4), CD161, CD2, CD7, CD3, and killer cell immunoglobulin-like receptors (Angelis et al., "Expansion of CD56-negative, CD16-positive, KIR-expressing natural killer cells after T cell-depleted haploidentical hematopoietic stem cell transplantation," *Acta Haematol.* 2011; 126(1):13-20; Dalle et al., "Characterization of Cord Blood Natural Killer Cells: Implications for Transplantation and Neonatal Infections," *Pediatric Research* (2005) 57, 649-655; Agarwal et al., "Roles and Mechanism of Natural Killer Cells in Clinical and Experimental Transplantation," *Expert Rev. Clin. Immunol.* 2008; 4(1):79-91).

The macrophages have a surface antigen including CD11b, F4/80, CD68, CSF1R, MAC2, CD11c, LY6G, LY6C, IL-4Rα, CD163, CD14, CD11b, F4/80 (mice)/EMR1 (human), CD68 and MAC-1/MAC-3, PECAM-1 (CD31), CD62, CD64, CD45, Ym1, CD206, CD45RO, 25F9, S100A8/A9, and PM-2K (Murray et al., "Protective and pathogenic functions of macrophage subsets," *Nature Reviews Immunology,* 11, 723-737; Taylor et al., "Macrophage receptors and immune recognition," *Annu. Rev. Immunol.* 2005; 23:901-44; Pilling, et al., "Identification of Markers that Distinguish Monocyte-Derived Fibrocytes from Monocytes, Macrophages, and Fibroblasts," *PLoS ONE* 4(10): e7475. doi:10.1371/journal.pone.0007475, 2009).

The lymphokine-activated killer (LAK) cells have a surface antigen including T3, T4 T11, T8, T11, Leu7, Leu11 (Ferrini et al., "Surface markers of human lymphokine-activated killer cells and their precursors," Int J Cancer. 1987 Jan. 15; 39(1):18-24; Bagnasco et al., "Glycoproteic nature of surface molecules of effector cells with lymphokine-activated killer (LAK) activity," Int J Cancer. 1987 Jun. 15; 39(6):703-7; Kaufmann et al., "Interleukin 2 induces human acute lymphocytic leukemia cells to manifest lymphokine-activated-killer (LAK) cytotoxicity," The Journal of Immunology, Aug. 1, 1987, vol. 139 no. 3 977-982).

The T-cells, especially cytotoxic T-cells, have a surface antigen including CD2, CD3, CD4, CD5, CD6, CD8, CD28, T58, CD27, CD45, CD84, CD25, CD127, and CD196 (CCR6), CD197 (CCR7), CD62L, CD69, TCR, T10, T11, and CD45RO (Ledbetter et al., "Enhanced transmembrane signaling activity of monoclonal antibody heteroconjugates suggests molecular interactions between receptors on the T cell surface," *Mol. Immunol.* 1989 February; 26(2):137-45; Jondal et al., "SURFACE MARKERS ON HUMAN T AND B LYMPHOCYTES," *JOURNAL OF EXPERIMENTAL MEDICINE*, VOLUME 136, 1972, 207-215; Mingari et al., "Surface markers of human T lymphocytes," *Ric Clin Lab.* 1982 July-September; 12(3):439-448).

The bi-specific conditionally active antibody, after binding with an immune effector cell, can bring the immune effector cell to a cell or tissue where the target antigen is present, preferably on the surface. Once the bi-specific conditionally active antibody (with the immune effector cell) binds with the target antigen, the immune effector cell can attack the diseased cell or diseased tissue. The immune effector cells, such as natural killer cells, macrophages, LAK cells, T-cells (cytotoxic), are all capable of killing and/or destroying a diseased cell or tissue, for example, destroying tumor tissue.

The diseased cells or diseased tissue may be selected from cancer, inflammatory disease, neuronal-disorders, diabetes, cardiovascular disease, or infectious diseases. Examples of target antigens include antigens expressed by various immune cells, carcinomas, sarcomas, lymphomas, leukemia, germ cell tumors, blastomas, and cells associated with various hematologic diseases, autoimmune diseases, and/or inflammatory diseases.

The target antigens specific for a cancer which may be targeted by the bi-specific conditionally active antibody include one or more of 4-IBB, 5T4, adenocarcinoma antigen, alpha-fetoprotein, BAFF, B-lymphoma cell, C242 antigen, CA-125, carbonic anhydrase 9 (CA-IX), C-MET, CCR4, CD152, CD19, CD20, CD200, CD22, CD221, CD23 (IgE receptor), CD28, CD30 (TNFRSF8), CD33, CD4, CD40, CD44 v6, CD51, CD52, CD56, CD74, CD80, CEA, CNT0888, CTLA-4, DRS, EGFR, EpCAM, CD3, FAP, fibronectin extra domain-B, folate receptor 1, GD2, GD3 ganglioside, glycoprotein 75, GPNMB, HER2/neu, HGF, human scatter factor receptor kinase, IGF-1 receptor, IGF-I, IgG1, LI-CAM, IL-13, IL-6, insulin-like growth factor I receptor, integrin α5β1, integrin αvβ3, MORAb-009, MS4A1, MUC1, mucin CanAg, N-glycolylneuraminic acid, NPC-1C, PDGF-R a, PDL192, phosphatidylserine, prostatic carcinoma cells, RANKL, RON, ROR1, SCH 900105, SDC1, SLAMF7, TAG-72, tenascin C, TGF beta 2, TGF-β, TRAIL-R1, TRAIL-R2, tumor antigen CTAA16.88, VEGF-A, VEGFR-1, VEGFR2 or vimentin.

The types of cancers to be treated with the genetically engineered cytotoxic cells or pharmaceutical compositions of the invention include, carcinoma, blastoma, and sarcoma, and certain leukemia or lymphoid malignancies, benign and malignant tumors, and malignancies e.g., sarcomas, carcinomas, and melanomas. The cancers may be non-solid tumors (such as hematological tumors) or solid tumors. Adult tumors/cancers and pediatric tumors/cancers are also included.

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors that may be treated include sarcomas and carcinomas, including fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

Target antigens specific for inflammatory diseases which may be targeted by the bi-specific conditionally active antibody include one or more of AOC3 (VAP-1), CAM-3001, CCL11 (eotaxin-1), CD125, CD147 (basigin), CD154 (CD40L), CD2, CD20, CD23 (IgE receptor), CD25 (a chain of IL-2 receptor), CD3, CD4, CD5, IFN-α, IFN-γ, IgE, IgE Fc region, IL-1, IL-12, IL-23, IL-13, IL-17, IL-17A, IL-22, IL-4, IL-5, IL-5, IL-6, IL-6 receptor, integrin α4, integrin α4β7, LFA-1 (CD1 1a), MEDI-528, myostatin, OX-40, rhuMAb β7, sclerostin, SOST, TGF beta 1, TNF-α or VEGF-A.

Target antigens specific for neuronal disorders which may be targeted by the bi-specific conditionally active antibody of the invention include one or more of beta amyloid or MABT5102A. Antigens specific for diabetes which may be targeted by the bi-specific conditionally active antibody of the invention include one or more of L-Iβ or CD3. Antigens specific for cardiovascular diseases which may be targeted by the bi-specific conditionally active antibody of the invention include one or more of C5, cardiac myosin, CD41 (integrin alpha-lib), fibrin II, beta chain, ITGB2 (CD 18) and sphingosine-1-phosphate.

Target antigens specific for infectious diseases which may be targeted by the bi-specific conditionally active antibody of the invention include one or more of anthrax toxin, CCR5, CD4, clumping factor A, cytomegalovirus, cytomegalovirus glycoprotein B, endotoxin, *Escherichia coli*, hepatitis B surface antigen, hepatitis B virus, HIV-1, Hsp90, Influenza A hemagglutinin, lipoteichoic acid, *Pseudomonas aeruginosa*, rabies virus glycoprotein, respiratory syncytial virus and TNF-α.

Further examples of target antigens include surface proteins found on cancer cells in a specific or amplified fashion, e.g. the IL-14 receptor, CD19, CD20 and CD40 for B-cell lymphoma, the Lewis Y and CEA antigens for a variety of carcinomas, the Tag72 antigen for breast and colorectal cancer, EGF-R for lung cancer, folate binding protein and the HER-2 protein which is often amplified in human breast and ovarian carcinomas, or viral proteins, e.g. gp120 and gp41 envelope proteins of HIV, envelope proteins from the Hepatitis B and C viruses, glycoprotein B and other envelope glycoproteins of human cytomegalovirus, and the envelope proteins from oncoviruses such as Kaposi's sarcoma-associated Herpes virus. Other potential target antigens include CD4, where the ligand is the HIV gp120 envelope glycoprotein, and other viral receptors, for example ICAM, which is the receptor for the human rhinovirus, and the related receptor molecule for poliovirus.

Human immunodeficiency virus (HIV) cannot enter human cells unless it first binds to two key molecules on the cell surface, CD4 and a co-receptor. The co-receptor that is initially recognized is CCR5, later in the life cycle of the virus another chemokine receptor CXCR4 becomes the co-receptor for HIV-1 (D'Souza, *Nature Med.* 2, 1293 (1996); Premack, *Nature Med.* 2, 1174; Fauci, *Nature* 384, 529 (1996)). The HIV-1 strains that cause most transmissions of viruses by sexual contact are called M-tropic viruses. These HIV-1 strains (also known as non-syncytia inducing (NSI) primary viruses) can replicate in primary CD4+ T-cells and macrophages and use the chemokine receptor CCR5 (and, less often, CCR3) as their coreceptor. The T-tropic viruses (sometimes called syncytia inducing (SI) primary viruses) can also replicate in primary CD4+ T-cells but can in addition infect established CD4+ T-cell lines in vitro, which they do via the chemokine receptor CXCR4 (fusin). Many of these T-tropic strains can use CCR5 in addition to CXCR4, and some can enter macrophages via CCR5, at least under certain in vitro conditions (D'Souza, *Nature Med.* 2, 1293 (1996); Premack, *Nature Med.* 2, 1174; Fauci, *Nature* 384, 529 (1996)). Because M-tropic HIV-1 strains are implicated in about 90% of sexual transmissions of HIV, CCR5 is the predominant coreceptor for the virus in patients.

The numbers and identity of coreceptor molecules on target cells, and the ability of HIV-1 strains to likely enter cells via the different co-receptors, seem to be critical determinants of disease progression. High expression of CCR3 and CCR5 was also observed in T cells and B cells of lymph nodes derived from patients with Hodgkin's disease. Diabetes type I is considered to be a T-cell mediated autoimmune disease. The expression of CCR5 receptor in the pancreas was associated with the progression of type I diabetes in relevant animal models (Cameron (2000) *J. Immunol.* 165, 1102-1110). In one embodiment, the bi-specific conditionally active antibody binds to CCR5 as the target antigen, which may be used to suppress HIV infection of host cells as well as to slow the progression of other diseases.

Several antibodies specifically binding to (human) CCR5 are known in the art and comprise MC-1 (Mack (1998) *J. Exp. Med.* 187, 1215-1224 or MC-5 (Blanpain (2002) *Mol. Biol. Cell.* 13:723-37, Segerer (1999) *Kidney Int.* 56:52-64, Kraft (2001) *Biol. Chem.* 14; 276:34408-18). Therefore, it is preferred that the bi-specific conditionally active antibody comprises, for example, $V_L$ and $V_H$ domains of an antibody (i.e. an Ig-derived second domain) specific for CCR5, preferably the human CCR5, and $V_H$ and $V_L$ domains of an antibody specific for the CD3 antigen on T-cells.

In another embodiment, the present invention provides for a bi-specific conditionally active antibody against CD3 on T-cells and CD19 as the target antigen. CD19 has proved to be a very useful medical target. CD19 is expressed in the whole B cell lineage from the pro B cell to the mature B cell, as well as uniformly expressed on all lymphoma cells, and is absent from stem cells (Haagen, *Clin Exp Immunol* 90 (1992), 368-75; Uckun, *Proc. Natl. Acad. Sci. USA* 85 (1988), 8603-7). Combination therapy employing both an antibody directed against CD19 and an additional immunoregulatory antibody has been disclosed for the treatment of B cell malignancies (WO 02/04021, US2002006404, US2002028178) and autoimmune diseases (WO 02/22212, US2002058029). WO 00/67795 discloses the use of antibodies against CD19 for the treatment of indolent and aggressive forms of B-cell lymphomas, as well as acute and chronic forms of lymphatic leukemia's. WO 02/80987 discloses the therapeutic use of immunotoxins based on antibodies against the antigen CD19 for the treatment of such diseases as B cell non-Hodgkin's lymphoma, Hodgkin's lymphoma or B cell leukemia's (e.g. B cell acute lymphatic leukemia (B-ALL), (e.g. hairy cell lymphoma) B cell precursor acute lymphatic leukemia (pre-B-ALL), B cell chronic lymphatic leukemia (B-CLL)).

In a further embodiment, the present invention provides for bi-specific conditionally active antibody against CD3 on T-cells and CD20 as the target antigen. CD20 is one of the cell surface proteins present on B-lymphocytes. CD20 antigen is found in normal and malignant pre-B and mature B lymphocytes, including those in over 90% of B-cell non-Hodgkin's lymphomas (NHL). The antigen is absent in hematopoetic stem cells, activated B lymphocytes (plasma cells) and normal tissue. Several antibodies mostly of murine origin have been described: 1F5 (Press et al., 1987, Blood 69/2, 584-591), 2B8/C2B8, 2H7, 1H4 (Liu et al., 1987, *J Immunol.* 139, 3521-3526; Anderson et al., 1998, U.S. Pat. No. 5,736,137; Haisma et al., 1998, *Blood* 92, 184-190; Shan et al., 1999, *J. Immunol.* 162, 6589-6595).

CD20 has been described in immunotherapeutic strategies for the treatment of plasma cell malignancies using vaccination with DNA encoding scFv linked to a carrier protein (Treon et al., 2000, *Semin. Oncol.* 27(5), 598) and immunotherapeutic treatment using CD20 antibodies (IDEC-C2B8) have been shown to be effective in the treatment of non-Hodgkin's B-cell lymphoma.

In some embodiments, the bi-specific conditionally active antibody is a single polypeptide chain encoded by a polynucleotide molecule. The polynucleotide may be, e.g., DNA, cDNA, RNA or synthetically produced DNA or RNA or a recombinantly produced chimeric nucleic acid molecule comprising any of those polynucleotides either alone or in combination. The polynucleotide can be part of a vector, e.g., an expression vector, including plasmids, cosmids, viruses and bacteriophages, or any expression system used conventionally in genetic engineering. The vectors may comprise further genes, such as marker genes, that allow for the selection of the vector in a suitable host cell and under suitable conditions.

In one aspect, the polynucleotide is operatively linked to expression control sequences allowing expression in prokaryotic or eukaryotic cells. Expression vectors derived from viruses such as retroviruses, vaccinia virus, adeno-associated virus, herpes viruses, or bovine papilloma virus, may be used for delivery of the polynucleotides or vectors into mammalian cells. The vectors containing the polynucleotides of the invention can be transferred into the host cell by well-known methods, which vary depending on the type of cellular host. For example, calcium chloride transfection is commonly utilized for prokaryotic cells, whereas calcium phosphate treatment or electroporation may be used for other cellular hosts.

In another aspect, the conditionally active polypeptide may be engineered to produce bispecific conditionally active polypeptide. The methods for engineering bispecific conditionally active polypeptide are similar to the methods for engineering bispecific conditionally active antibodies as described in WO 2015/175375. For example, a bispecific conditionally active polypeptide may have two active sites, with each having a conditional activity, i.e., less active than the wild-type site under the normal physiological condition and more active than the wild-type site under the aberrant condition. These two conditionally active sites may be independently evolved and screened, followed by linking the two active sites into the same bispecific conditionally active polypeptide with a linker. In one aspect, the linkers used in the bispecific conditionally active antibody are suitable for generating the bispecific conditionally active polypeptide by linking two conditionally active sites in the conditionally active polypeptide.

The methods for engineering the Fc region of conditionally active antibodies have been described in WO 2015/175375. Methods for engineering conditionally active viral particles have also been described in WO 2015/175375.

In some aspects, the conditionally active polypeptide may be inserted into a viral particle that is an oncolytic virus, using the methods described in WO 2015/175375. Oncolytic viruses are viruses, which, when brought into contact with tumor cells, are capable of killing those tumor cells. The conditionally active polypeptide that is inserted into the oncolytic virus is more active in a tumor microenvironment but less active in other site of the subject. For example, the conditionally active polypeptide is more active at a pH in the tumor microenvironment (e.g., pH 6.2-6.8) but less active at a pH exist in other site of the subject (e.g., pH 7.2-7.6). The conditionally active polypeptide inserted into the oncolytic virus will enable the oncolytic virus to be delivered to tumors, where the oncolytic virus can target and kill the tumor cells.

Oncolytic viruses of interest include adenovirus; herpes simplex virus-1; vaccinia virus; parvovirus; reovirus; Newcastle disease virus; and the like. Vaccinia virus is of particular interest.

In one aspect, the oncolytic virus is selected from the group consisting of paramyxovirus, reovirus, herpesvirus, adenovirus, and Semliki Forest virus. In a further aspect, the paramyxovirus is selected from the group consisting of Newcastle Disease Virus (NDV), measles virus, and mumps virus. In another aspect, the NDV is from a strain selected from the group consisting of MTH68/H, PV-701, and 73-T.

In another aspect, the oncolytic virus is elected from herpesvirus, reovirus, E1B deleted adenovirus, Vesicular Stomatitis Virus, and Pox viruses. These oncolytic viruses have the potential to not only destroy tumor cells, but also release antigens from the destroyed tumor cells, thereby triggering an immune response.

Specific examples of oncolytic viruses include, without limitation, adenoviruses (e.g. Delta-24, Delta-24-RGD, ICOVIR-5, ICOVIR-7, Onyx-015, ColoAd1, H101, AD5/3-D24-GMCSF), reoviruses, herpes simplex virus (HSV;

OncoVEX GMCSF), Newcastle Disease virus, measles viruses, retroviruses (e.g. influenza viruses), poxviruses (e.g. vaccinia virus including Copenhagen, Western Reserve, Wyeth strains), myxoma viruses, rhabdoviruses (e.g. vesicular stomatitis virus (VSV)), picornaviruses (e.g. Seneca Valley virus; SW-001), coxsackievirus, and parvovirus.

In one aspect, the oncolytic virus is an adenovirus including members of any of the 57 human serotypes thereof (HAdV-1 to 57). In one embodiment, the adenovirus is an Ad5 serotype. In other aspects, the adenovirus is hybrid serotype which may or may not comprise an Ad5 component. Non-limiting examples of suitable adenoviruses include Delta-24, Delta-24-RGD, ICOVIR-5, ICOVIR-7, ONYX-015, ColoAd1, H101, and AD5/3-D24-GMCSF. ONYX-015 is a hybrid of virus serotype Ad2 and Ad5 with deletions in the E1B-55K and E3B regions to enhance cancer selectivity. HI 01 is a modified version of Onyx-015. ICOVIR-5 and ICOVIR-7 comprise an Rb-binding site deletion of E1 A and a replacement of the E1 A promoter by an E2F promoter. Colo Ad 1 is a chimeric Add1 1p/Ad3 serotype. AD5/3-D24-GMCSF (CGTG-102) is a serotype 5/3 capsid-modified adenovirus encoding GM-CSF (the Ad5 capsid protein knob is replaced with a knob domain from serotype 3).

In one particularly preferred embodiment, the oncolytic virus is Delta-24 or Delta-24-RGD adenovirus. Delta-24 is described in U.S. Patent Application Publication Nos. 2003/0138405 and 2006/0147420. The Delta-24 adenovirus is derived from adenovirus type 5 (Ad-5) and contains a 24-base-pair deletion within the CR2 portion of the E1 A gene. Delta-24-RGD further comprises an insertion of the RGD-4C sequence (which binds strongly to $\alpha v \beta 3$ and $\alpha v \beta 5$ integrins) into the HI loop of the fiber knob protein (Pasqualini R. et al., *Nat. Biotechnol.*, 15:542-546, 1997).

The oncolytic adenovirus may also be further modified to improve the ability of the oncolytic adenovirus to treat cancer. Such modifications of an oncolytic adenovirus have been described by Jiang et al. (*Curr. Gene Ther.*, 2009 Oct. 9(5):422-427), see also U.S. Patent Application No. 2006/0147420.

Oncolytic viruses with the conditionally active polypeptide may be administered locally or systemically. For example, without limitation, oncolytic viruses can be administered intravascularly (intraarterially or intravenously), intratumorally, intramuscularly, intradermally, intraperitoneally, subcutaneously, orally, parenterally, intranasally, intratracheally, percutaneously, intraspinally, ocularly, or intracranially.

The oncolytic viruses may be administered in a single administration or multiple administrations. The virus may be administered at dosage of at least $1 \times 10^5$ plaque forming units (PFU), at least $5 \times 10^5$ PFU, at least $1 \times 10^6$ PFU, at least $5 \times 10^6$ or at least $5 \times 10^6$ PFU, $1 \times 10^7$, at least $1 \times 10^7$ PFU, at least $1 \times 10^8$ or at least $1 \times 10^8$ PFU, at least $1 \times 10^8$ PFU, at least $5 \times 10^8$ PFU, at least $1 \times 10^9$ or at least $1 \times 10^9$ PFU, at least $5 \times 10^9$ or at least $5 \times 10^9$ PFU, at least $1 \times 10^{10}$ PFU or at least $1 \times 10^{10}$ PFU, at least $5 \times 10^{10}$ or at least $5 \times 10^{10}$ PFU, at least $1 \times 10^{11}$ PFU or at least $1 \times 10^{11}$ PFU, at least $1 \times 10^{12}$ PFU, or at least $1 \times 10^{13}$ PFU. For example, the oncolytic virus may be administered at a dosage of between about $10^8$-$10^{12}$ PFU, between about $10^8$-$10^{13}$ PFU, between about $10^9$-$10^{12}$ PFU, or between about $10^8$-$10^{12}$ PFU.

In certain aspects, the cancer to be treated with the oncolytic viruses includes any solid tumor, such as lung, ovary, breast, cervix, pancreas, stomach, colon, skin, larynx, bladder, and prostate cancer. In one aspect, the cancer is a cancer of the central nervous system. The cancer may be a neuroepithelial tumor such as an astrocytic tumor (e.g. astrocytoma, anaplastic astrocytoma, glioblastoma, gliosarcoma, pilocytic astrocytoma, giant cell astrocytoma, pleomorphic xanthoastrocytoma), an oligodendroglioma, an ependymoma, an oligoastrocytoma, a spongioblastoma, an astroblastoma, a choroid plexus papiloma, a choroid plexus carcinoma, a gangliocytoma, a ganglioglioma, a neurocytoma, a neuroepithelial tumor, a neuroblastoma, a pineal region tumor (such as a pineocytoma, a pineoblastoma, or a mixed pineocytoma/pineobastoma), a medulloepithelioma, a medulloblastoma, a neuroblastoma or ganglioneuroblastoma, a retinoblastoma, or an ependymoblastoma. The cancer may be a central nervous system neoplasm such as a tumor of the sellar region (such as a pituitary adenoma, a pituitary carcinoma, or a craniopharyngioma), a hematopoietic tumor (such as a primary malignant lymphoma, a plasmacytoma, or a granulocytic sarcoma), a germ cell tumor (such as a germinoma, an embryonal carcinoma, a yolk sac tumor, a choriocarcinoma, a teratoma or a mixed germ cell tumor), a meningioma, a mesenchymal tumor, melanocytoma, or a tumor of cranial or spinal nerves (such as a schwannoma, or a neurofibroma). The cancer may be a low-grade glioma (e.g. ependymoma, astrocytoma, oligodendroglioma or mixed glioma) or a high-grade (malignant) glioma (e.g. glioblastoma multiforme). The cancer may be a primary or metastatic brain tumor.

D. Generating the Conditionally Active Polypeptides

The method for generating the conditionally active polypeptide from a parent polypeptide comprises steps of evolving the DNA encoding the parent polypeptide to increase the net charge of the parent polypeptide using one or more techniques selected from increasing a total number of codons of charged amino acid residues in the DNA, decreasing a total number of codons of uncharged amino acid residues in the DNA and combinations thereof, to produce mutant DNAs; expressing the mutant DNAs to produce mutant polypeptides; and subjecting the mutant polypeptides and the parent polypeptide to a screening assay under the first condition which may be a normal physiological condition, and a screening assay under the second condition which may be an aberrant condition. Conditionally active polypeptides are selected from those mutant polypeptides which exhibit both (a) a decrease in activity in a first assay at a first value of a condition compared to the same activity of the parent polypeptide in the first assay, and (b) an increase in the same activity in a second assay at a second value of the same condition compared to the same activity of the parent polypeptide in the second assay. The decrease in activity in the first condition or normal physiological condition for the conditionally active polypeptide may be reversible or irreversible.

i. Parent Polypeptide

The parent polypeptide may be a wild-type polypeptide, a mutant polypeptide derived from a wild-type polypeptide, such as therapeutic polypeptide, a chimeric polypeptide derived from different wild-type polypeptides, or even a synthetic polypeptide. The parent polypeptide may be selected from antibodies, enzymes, cytokines, regulatory proteins, hormones, receptors, ligands, biosimilars, immunomodulators, growth factor, a stress protein, a vault-related protein, a neuron protein, a digestive tract protein, a growth factor, a mitochondrial protein, a cytosolic protein, an animal protein, a structural protein, a plant protein and fragments of these polypeptides.

In some embodiments, the parent polypeptide may be a fragment of a wild-type polypeptide, a fragment of a therapeutic polypeptide, or an antibody fragment. In some other embodiments, the parent polypeptide may be a polypeptide selected from mutant polypeptides generated by a mutagenesis process where the polypeptide is selected for having a desired property such as a high binding activity, a high expression level or humanization. The selected polypeptide, which in this case is not a wild-type polypeptide, may be used as the parent polypeptide to be evolved in the method disclosed herein.

The description of the suitable wild-type polypeptides and the ways that they may be evolved and selected for producing conditionally active polypeptides have been described in U.S. Pat. No. 8,709,755 B2.

In some embodiments, the parent polypeptide may be selected from a library of wild-type polypeptides or mutant polypeptides, such as a bacteriophage display library. In such embodiments, a large number of candidate polypeptides are expressed in a bacteriophage library, particularly by a surface display technique. The candidate polypeptides from the library are screened for a suitable parent polypeptide. A typical bacteriophage library may contain bacteriophages that express thousands or even millions of candidate polypeptides in a bacterial host. In one embodiment, the bacteriophage library may include a plurality of bacteriophages.

To construct a bacteriophage library, typically filamentous bacteriophages, such as the filamentous coliphage M13 are genetically modified by inserting oligonucleotides encoding the candidate polypeptides to the coding sequence of one of the bacteriophage coat proteins. The coat proteins of the bacteriophage are subsequently expressed with the candidate polypeptides such that the candidate polypeptides are displayed on the surface of bacteriophage particles. The displayed candidate polypeptides may then be screened for a suitable parent polypeptide.

One common technique for screening for a suitable parent polypeptide is by immobilizing the bacteriophage particles with a desired candidate polypeptide on a support. The support may be a plastic plate coated with "bait" that can bind with the desirable candidate polypeptide. Non-binding bacteriophage particles may be washed away from the plate. Bacteriophage particles binding to the plate (with desirable candidate) are eluted by washing and the eluted bacteriophage particles are amplified in bacteria. The sequence(s) encoding the candidate polypeptide in the selected bacteriophage particles may then be determined by sequencing. The relationship between the candidate polypeptide and bait may be, for example, a ligand-receptor or antigen-antibody relationship.

Another common technique of screening for a suitable parent polypeptide is by use of an enzymatic assay of individual bacteriophage clones for a desired enzymatic activity exhibited by the candidate polypeptides. Depending on the specific enzymatic activity, a person skilled in the art can design an appropriate assay to screen for the parent polypeptide with the desired level of enzymatic activity.

In some embodiments, the bacteriophage library is provided as an array, such that each bacteriophage clone occupies a specific location on the array. Such an array can be provided on a solid support, for example, a membrane, an agar plate or a microtiter plate, on which each bacteriophage clone of the library is placed or adhered thereto in a specific predetermined position on the solid support. In the case of agar plates, such plates preferably include bacterial growth media so as to support bacterial growth. When the array is provided on a membrane, for example, a nitrocellulose or a nylon membrane, a bacterial culture is applied onto the membrane and the membrane is soaked with a nutrient growth medium. In addition, the bacteriophage clones can also be provided on beads, in which case a single bacteriophage clone can be adhered to a single bead. Alternatively the bacteriophage clones can each be provided on an end of an optic fiber, in which case the fiber is used to optically communicate ultraviolet radiation from a light source.

A typical bacteriophage library may contain from $10^6$ to $10^{10}$ bacteriophages, each of which is distinguished by a coat protein (e.g. gp3 or gp8 in the case of phage M13) bearing a different candidate polypeptide. The bacterial hosts for the bacteriophage library may be selected from bacterial genera including, for example, *Salmonella, Staphylococcus, Streptococcus, Shigella, Listeria, Campylobacter, Klebsiella, Yersinia, Pseudomonas*, and *Escherichia*.

The oligonucleotides encoding the candidate polypeptides may be a collection of cDNAs that encode wild-type polypeptides. Methods are known for synthesizing cDNAs from a biological sample whereby a suitable parent polypeptide may be expressed. Any genetic information that manifests physiological activity through transcripts may be harvested as cDNAs. When producing cDNAs, it is essential to synthesize full-length cDNAs. There are several methods that may be used to synthesize full-length cDNAs. For example, suitable methods include a method utilizing a Cap binding protein of yeast or Hela cells for labeling the 5' Cap site (I. Edery et al., "An Efficient Strategy To Isolate Full-length cDNAs Based on a mRNA Cap Retention Procedure (CAPture)", *Mol. Cell. Biol.*, vol. 15, pages 3363-3371, 1995); and a method where phosphates of incomplete cDNAs without 5' Cap are removed by using alkaline phosphatase and then the whole cDNAs are treated with a de-capping enzyme of a tobacco mosaic virus so that only the full-length cDNAs have phosphates (K. Maruyama et al., "Oligocapping: a simple method to replace the cap structure of eukaryotic mRNAs with oligoribonucleotides", *Gene*, vol. 138, pages 171-174, 1995 and S. Kato et al., "Construction of a human full-length cDNA bank", *Gene*, vol. 150, pages 243-250, 1995).

In embodiments where the parent polypeptide is an antibody, the library of candidate antibodies may be produced using recombinant antibodies derived from a complete antibody repertoire of an organism. The genetic information representing the repertoire is assembled into a large collection of full antibodies that can be screened for a suitable parent antibody with the desired antigen binding activity and/or one or more other functional characteristics. In some embodiments, B-cells from an animal immunized with an antigen, such as immunized human, mouse, or rabbit are isolated. mRNAs from the isolated B-cells are collected and converted to cDNA, which are then sequenced. The most frequent cDNA fragments encoding a light chain and the most frequent cDNA fragments encoding a heavy chain are assembled into antibodies. In one embodiment, the 100 most frequent cDNA fragments encoding a light chain and the 100 most frequent cDNA fragments encoding a heavy chain are assembled to produce candidate antibodies. In another embodiment, the most frequent cDNA fragments only encode the variable regions of the heavy chain and the variable regions of the light chain are the assembled to produce antibody fragments contain only the variable regions but not the constant regions.

In some embodiments, cDNA fragments encoding the variable regions of IgG heavy chains are assembled with the most frequent variable regions of IgK or IgK light chains. The assembled antibodies contain a heavy chain variable region from IgG and a light chain variable region from IgK or IgK.

The cDNAs encoding the assembled antibodies are then cloned and expressed, preferably in a plate-based format. The binding activity of the expressed antibodies may be assayed with a bead-based ELISA assay and a suitable parent antibody may be selected based on the ELISA assay. The cDNAs encoding the assembled antibodies may also expressed in a bacteriophage display library, which may then be screened for one or more desirable parent antibodies by any one of the techniques disclosed herein.

In embodiments where the parent polypeptide is an antibody, the parent antibody preferably has at least one particular characteristic that make it easier to evolve the parent antibody into a conditionally active antibody. In certain embodiments, the parent antibody may have similar binding activity and/or characteristics under both the normal physiological condition and the aberrant condition. In such embodiments, the parent antibody is selected based on having the most similar binding activity and/or the most similar combination of one or more characteristics under both the normal physiological condition and the aberrant condition. For example, if the normal physiological condition and aberrant condition are pH 7.4 and pH 6.0 respectively, the parent antibody that has the most similar binding activity at pH 7.4 and 6.0 may be selected over an antibody having a less similar binding activity at pH 7.4 and 6.0.

ii. Evolving the Parent Polypeptides

In some aspects, the DNA encoding the parent polypeptide is mutated using one or more site directed mutagenesis techniques to introduce one or more charged amino acid residues into the parent polypeptide. In one aspect, the charged amino acid residues may be introduced at any location within the parent polypeptide. In another aspect, the charged amino acid residues are introduced into an active site of the parent polypeptide. The active site is a region within the parent polypeptide that is responsible for a particular property of the parent polypeptide. The property may be enzyme substrate specificity, enzyme product selectivity, a protein secretion property, ligand selectivity, ligand binding activity, protein stability, and antibody binding activity. Examples of an active site include a catalytic site of an enzyme, a binding site of a ligand or receptor, complementarity determining regions of an antibody, and an epitope of an antigen.

In one aspect, the charged amino acid residues are introduced into two or more complementarity determining regions of a parent antibody or a parent antibody variable region. In another aspect, the charged amino acid residues are introduced into two or more regions of a parent polypeptide that are involved in binding with a ligand, receptor, or hormone. In yet another aspect, the charged amino acid residues are introduced into two or more regions of a parent polypeptide that are involved in an catalytic activity, such as forming a catalytic pocket of an enzyme.

In another aspect, the charged amino acid residues may be introduced into a region outside of the active site of the parent polypeptide. For example, such region may be next to, surrounding, or even remote from the active site. In one aspect, the region is the constant region of a heavy chain or light chain of an antibody. The region may also be the framework region of the variable region of a heavy chain or light chain of an antibody.

To introduce one or more charged amino acid residues into the parent polypeptide, the DNA encoding the parent polypeptide is mutated either by substituting codons in the DNA with codons of charged amino acids, or by inserting codons of a charged amino acid into the DNA, thus producing mutant DNAs, which can be expressed to produce mutant polypeptides. The substitution or insertion of codons of charged amino acid residues may be accomplished using one or more site directed mutagenesis techniques described herein.

The codons of charged amino acid residues to be introduced into the DNA encoding the parent polypeptide are shown in Table 2.

TABLE 2

Codons for Charged Amino Acids

| Amino acid | Three-letter symbol | One-letter symbol | Codon |
|---|---|---|---|
| Aspartic acid | Asp | D | GAU, GAC |
| Glutamic acid | Glu | E | GAA, GAG |
| Arginine | Arg | R | CGU, CGC, CGA, CGG, AGA, AGG |
| Lysine | Lys | K | AAA, AAG |
| Histidine | His | H | CAU, CAC |

In one aspect, the mutant polypeptides have less than 6 mutations, or less than 5 mutations, or less than 4 mutations, or less than 3 mutations, or less than 2 mutations in comparison with the parent polypeptide. These numbers of mutations may be sufficient to produce a desirable conditionally active polypeptide.

In some aspects, the DNA encoding the parent polypeptide is mutated using one or more site directed mutagenesis techniques to delete one or more codons of uncharged amino acid residues. The deletion of one or more uncharged amino acid residues in the parent polypeptide increases the net charge of the parent polypeptide.

In another aspect, the parent polypeptide may be mutated by deleting a region that has no or very few charged amino acid residues, thereby increasing the net charge of the mutated polypeptide relative to the net charge of the parent polypeptide. For example, a full length antibody may have a constant region that has no or very few charged amino acid residues. By deleting the constant region and linking two variable regions of the antibody to form a single chain antibody, this may also result in an increase in the net charge of the mutant single chain antibody in comparison with the net charge of the parent antibody. In one example, the full length antibody is an IgG antibody and is converted to a single chain antibody with an increase in the net charge.

In some aspects, any site directed mutagenesis techniques may be used for mutating the DNA encoding the parent polypeptide, such as those described in U.S. Pat. Nos. 6,391,548, 7,132,265 and 6,713,285. In some embodiments, the site directed mutagenesis techniques that may be employed include oligonucleotide-mediated mutagenesis, PCR mutagenesis, and cassette mutagenesis of the DNA encoding the parent polypeptide.

Oligonucleotide-mediated mutagenesis is a suitable method for substitution or insertion of one or more codons into the DNA encoding the parent polypeptide. This technique has been described previously in Sambrook et al., Molecular Cloning: A Laboratory Manual, Cold Spring Harbor, 1989, second edition, chapter 15.51, "Oligonucleotide-mediated mutagenesis." Briefly, the DNA is altered by hybridizing an oligonucleotide primer carrying the desired mutation(s) to the DNA that has been reduced to a single-stranded form. After hybridization, a DNA polymerase is used to synthesize an entire second complementary strand of the DNA that will thus incorporate the oligonucleotide primer and produce a product containing the desired mutation(s).

Generally, oligonucleotides of at least 25 nucleotides in length are used. An optimal oligonucleotide will have 12 to 15 nucleotides that are completely complementary to the template on either side of the mutations(s). This ensures that the oligonucleotide will hybridize properly to the single-stranded DNA. The oligonucleotides are readily synthesized using techniques known in the art such as that described by Crea et al. (*Proc. Natl. Acad. Sci. USA,* 75: 5765, 1978).

In one aspect, the DNA encoding the parent polypeptide is within a cyclic DNA molecule, such as a plasmid or cosmid. The oligonucleotide is hybridized to the single-stranded cyclic DNA molecule under suitable hybridization conditions. A DNA polymerizing enzyme, usually the Klenow fragment of DNA polymerase I, is then added to synthesize the complementary strand of the single-stranded cyclic DNA molecule using the oligonucleotide as a primer for synthesis. A heteroduplex molecule is thus formed such that one strand of DNA has the mutation(s), and the other strand (the original strand) does not have the mutation(s). This heteroduplex molecule is then transformed into a suitable host cell, usually a prokaryote such as *E. coli* JM101. After the cells are grown, they are plated onto agarose plates and screened using the oligonucleotide primer radiolabeled with 32-phosphate to identify the bacterial colonies that contain the mutated DNA. The mutated DNA is then removed and placed in an appropriate expression vector for protein production.

This procedure may be modified such that a homoduplex molecule is created wherein both strands of the plasmid contain the mutation(s). The modifications are as follows: the oligonucleotide primer is annealed to the single-stranded cyclic DNA molecule as described above. A mixture of three deoxyribonucleotides, deoxyriboadenosine (dATP), deoxyriboguanosine (dGTP), and deoxyribothymidine (dTTP), is combined with a modified thio-deoxyribocytosine called dCTP-(aS). This mixture is added to the single-stranded cyclic DNA molecule-oligonucleotide hybridization complex. Upon addition of DNA polymerase to this mixture, a strand of DNA identical to the single-stranded cyclic DNA molecule except for the mutation(s) is generated. In addition, this new strand of DNA will contain dCTP-(aS) instead of dCTP, which serves to protect it from restriction endonuclease digestion. After the heteroduplex is nicked with an appropriate restriction enzyme, the single-stranded cyclic DNA molecule in the heteroduplex can be digested with ExoIII nuclease or another appropriate nuclease past the region that contains the site(s) to be mutagenized. The reaction is then stopped to produce a DNA molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as *E. coli* JM101, as described above.

Introduction of two or more mutations (insertion and/or substitution) into the DNA encoding the parent polypeptide may be accomplished in one of several ways. If the locations to be mutated are close together in the DNA molecule, they may be mutated simultaneously using one oligonucleotide primer with all of the desired mutations. If, however, the locations to be mutated are some distance from each other (e.g., separated by more than about 25 nucleotides), it is more difficult to generate a single oligonucleotide primer with all of the desired mutations. Instead, one of two alternative methods may be employed.

In one alternative, a separate oligonucleotide primer is used for each mutation. The oligonucleotide primers are then simultaneously annealed to the single-stranded cyclic DNA molecule, and the second complementary strand of DNA that is synthesized will contain all of the desired mutations from the separate oligonucleotide primers.

Another alternative involves two or more rounds of site directed mutagenesis to produce the desired DNA with all the mutations. The first round is as described for the single mutation: an oligonucleotide primer with the first desired mutation is used to generate the heteroduplex DNA molecule. The second round of mutagenesis utilizes the heteroduplex DNA molecule generated in the first round as the template, which already contains one mutation. A second oligonucleotide primer encoding the additional mutation is then annealed to this template to generate the second DNA molecule containing mutations from both the first and second rounds of mutagenesis. If desirable, the second DNA molecule can be used as a template in a third round of mutagenesis, and so on.

Another suitable site directed mutagenesis method is PCR mutagenesis, which can be used for making the insertion and/or substitution mutations in the parent polypeptide. As a cyclic amplification technique, PCR has been widely adopted in site-directed mutagenesis, in which mutagenic primers are used to introduce desired mutations, (see Allemandou et al., *J Biomed. Biotechnol.* S, 202-207, (2003); An et al., *Appl. Microbiol. Biotechnol. S* 68, 774-778, (2005); Jeltsch et al., *Methods Mol Biol. S* 182, 85-94 (2002); Hall, et al. *Protein Eng.* 4:601 (1991); Hemsley, et al. *Nucleic Acids Research* 17:6545-6551 (1989); Ho, et al. *Gene* 77:51-59 (1989); Hultman, et al. *Nucleic Acids Research* 18:5107-5112 (1990); Jones, et al. *Nature* 344:793-794 (1990); Jones, et al. *Biotechniques* 12:528-533 (1992); Landt, et al. *Gene* 96:125-128 (1990); Nassal, et al. *Nucleic Acids Research* 18:3077-3078 (1990); Nelson, et al. *Analytical Biochemistry* 180:147-151 (1989); Vallette, et al. *Nucleic Acids Research* 17:723-733 (1989); Watkins, et al. *Biotechniques* 15:700-704 (1993); Weiner, et al. *Gene* 126:35-41 (1993); and Yao, et al. *PCR Methods and Applications* 1:205-207 (1992)).

Specifically, a small amount of the DNA encoding the parent polypeptide is used as template DNA in a PCR. The mutagenic primers differ slightly in sequence from the corresponding region in the template DNA for generating relatively large quantities of a specific DNA fragment with the desired mutations only at the positions where the mutagenic primers differ from the template DNA. For introduction of a mutation into a circular DNA, one of the primers is designed to overlap the position of the mutation and contain the mutation; the sequence of the other primer may be identical to a stretch of sequence of the opposite strand of the circular DNA, but this sequence can be located anywhere along the circular DNA. It is preferred, however, that the sequence of the second primer is located within 200 nucleotides from that of the first, such that in the end the entire amplified region of DNA bounded by the primers can be easily sequenced for confirming the mutation(s). PCR amplification using the pair of primers results in a DNA fragment that differs at the position of the mutation in the mutagenic primer.

Mutations at separate positions can be introduced simultaneously by either using a second mutagenic primer, or performing a second round of PCR with a different mutagenic primers and ligating the two resulting PCR fragments simultaneously to a vector in a three (or more)-part ligation.

In a specific example of PCR mutagenesis, template plasmid DNA (1)(g) is linearized by digestion with a restriction endonuclease that has a unique recognition site in the plasmid DNA outside of the region to be amplified. Of this material, 100 ng is added to a PCR mixture containing PCR buffer, which contains the four deoxynucleotide tri-phosphates and is included in the GeneAmp® kits (obtained from Perkin-Elmer Cetus, Norwalk, Conn. and Emeryville, Calif.), and 25 pmole of each oligonucleotide primer, to a final volume of 50)(1. The reaction mixture is overlaid with 35)(1 mineral oil. The reaction is denatured for 5 minutes at 100° C., placed briefly on ice, and then 1 µl *Thermus aquaticus* (Taq) DNA polymerase (5 units/µ1, purchased from Perkin-Elmer Cetus, Norwalk, Conn. and Emeryville, Calif.) is added below the mineral oil layer. The reaction mixture is then inserted into a DNA Thermal Cycler (purchased from Perkin-Elmer Cetus) programmed as follows: 2 min. 55° C., 30 sec. 72° C., then 19 cycles of the following: 30 sec. 94° C. 30 sec. 55° C., and 30 sec. 72° C. At the end of the process, the reaction vial is removed from the thermal cycler and the aqueous phase transferred to a new vial, extracted with phenol/chloroform (50:50:vol.), and ethanol precipitated, and the DNA is recovered by standard procedures. This material is subsequently subjected to the appropriate treatments for insertion into a vector.

Cassette mutagenesis is another site directed mutagenesis technique that may be used to introduce insertions and/or substitutions into the DNA encoding the parent polypeptide. This technique has been described by Wells et al. (*Gene*, 34:315, (1985)). There must be a unique restriction endonuclease site on each side of the mutation(s). If no such restriction sites exist, they may be generated using the above-described oligonucleotide-mediated mutagenesis technique to introduce them at appropriate locations in the DNA. The DNA encoding the parent polypeptide is cut at these restriction sites. A separate double-stranded DNA fragment having the same sequence of the DNA between the restriction sites but containing the desired mutation(s) is synthesized using standard chemical synthesis procedures. This synthesized DNA fragment containing the mutation(s) is referred to as the cassette. This cassette is designed to have 3' and 5' ends that are compatible with the ends of the restriction endonuclease-treated DNA, such that it can be directly ligated to the restriction endonuclease-treated DNA. The ligated DNA now contains the desired mutations.

Using one or more site directed mutagenesis techniques the DNA encoding the parent polypeptide is mutated to introduce one or more codons of charged amino acid residues. The mutant DNAs thus generated encode mutant polypeptides that have charged amino acid residues corresponding to the introduced codons. As a result, the mutant polypeptides may have an increased total number of charged amino acid residues in comparison with the parent polypeptide.

iii. Expression of Mutant Polypeptides

After the mutant DNAs are generated using one or more site directed mutagenesis techniques, the mutant DNAs are expressed to produce the mutant polypeptides. Suitable methods of expressing the mutant DNAs to produce mutant polypeptides have been described in U.S. Pat. No. 8,709,755 B2.

In one aspect, the mutant DNAs may be expressed using peptide display method for efficient screening for the conditionally active polypeptides. Such methods are further described in PCT patent publication Nos. WO 91/17271, WO 91/18980, WO 91/19818 and WO 93/08278.

WO 93/08278 describes a recombinant DNA method for the display of peptide ligands that involves the production of a library of fusion proteins with each fusion protein composed of a first polypeptide portion, typically comprising a variable sequence, that is available for potential binding to a macromolecule, and a second polypeptide portion that binds to DNA, such as the DNA vector encoding the individual fusion protein. When transformed host cells are cultured under conditions that allow for expression of the fusion protein, the fusion protein binds to the DNA vector encoding it. Upon lysis of the host cell, the fusion protein/vector DNA complexes can be screened against an immobilized macromolecule in the same way as bacteriophage particles are screened in the phage-based display system, with the replication and sequencing of the DNA vectors in the selected fusion protein/vector DNA complexes serving as the basis for identification of the selected polypeptide sequence(s).

The peptide display method includes methods for in vitro and in vivo display of single-chain antibodies, such as nascent scFv on polysomes or scFv displayed on phage, which enable large-scale screening of scFv libraries having broad diversity of variable region sequences and binding specificities.

Other methods of expressing the mutant polypeptides use cell-free enzymatic machinery to accomplish the in vitro synthesis of the mutant polypeptides. These methods which rely upon in vitro translation, generally comprising stabilized polysome complexes, are described further in PCT patent publication Nos. WO 88/08453, WO 90/05785, WO 90/07003, WO 91/02076, WO 91/05058, and WO 92/02536.

A method of affinity enrichment allows a very large library of mutant polypeptides to be screened and the mutant DNA encoding the desired polypeptide(s) to be selected. The mutant DNA can then be isolated and shuffled to recombine combinatorially the amino acid sequence of the selected polypeptide(s) (or predetermined portions thereof) or single-chain antibodies (or just VH, VL, or CDR portions thereof). Using these methods, one can identify a mutant polypeptide or single-chain antibody as having a desired binding affinity for a molecule and can exploit the process of shuffling to converge rapidly to a desired high-affinity mutant polypeptide or scFv.

iv. Screening of Conditionally Active Polypeptides

The methods of screening the mutant polypeptides for selection of the conditionally active polypeptide have been described in U.S. Pat. No. 8,709,755 B2, with these methods hereby incorporated by reference herein.

v. Assay Conditions for Screening and Selecting the Conditionally Active Polypeptides The first condition and second condition, or the normal physiological condition and the aberrant condition, for the assays used in the screening step may be conducted using a condition selected from temperature, pH, osmotic pressure, osmolality, oxidative stress, electrolyte concentration, concentration of a protein, as well as combinations of two or more such conditions. For example, the normal physiological condition for temperature may be a normal human body temperature of 37.0° C., while the aberrant condition for temperature may be a temperature different from the temperature of 37.0° C., such as a temperature in tumor microenvironment which may be 1-2° C. higher than the normal physiological temperature. In another example, the normal physiological condition and the aberrant condition may also be a normal physiological pH in the range of 7.2-7.8, or 7.2-7.6 and an aberrant pH such as in the range of 5.5-7.2, 6-7, or 6.2-6.8 presented in a tumor microenvironment.

The assays under both first condition and second condition, or the normal physiological condition and the aberrant condition, may be performed in an assay media. The assay media may be a solution, which may contain, for example, a buffer as well as other components. Common buffers that can be used in the assay media include citrate buffers such as sodium citrate, phosphate buffers, bicarbonate buffers such as the Krebs buffer, phosphate buffered saline (PBS) buffer, Hank's buffer, Tris buffer, HEPES buffer, etc. Other buffers known to a person skilled in the art to be suitable for the assays may be used. These buffers may be used to mimic a characteristic or component of the composition of a bodily fluid, of a human or animal such as blood plasma or lymphatic fluid.

The assay solutions useful in the methods of the invention may contain at least one component selected from inorganic compounds, ions and organic molecules, preferably ones that are commonly found in a bodily fluid of a mammal such as a human or animal. Examples of such components include nutritional components and metabolites, as well as any other components that may be found in a bodily fluid. The present invention contemplates that this component may or may not be part of the buffer system. For example, the assay solutions may be PBS buffer with added bicarbonate ion where bicarbonate is not part of PBS buffer. Alternatively, bicarbonate ion is a component in Krebs buffer.

The component may be present in both assay solutions (for the first and second conditions) at substantially the same concentration, while the two assay solutions different in other aspect such as pH, temperature, electrolyte concentrations, or osmotic pressure. Thus, the component is used as a constant, rather than the difference between the two conditions of the first and second conditions, or the normal physiological condition and aberrant condition.

In some embodiments, the component is present in both assay solutions at a concentration that is close to or the same as the normal physiological concentration of the component is mammals, especially in human.

The inorganic compounds or ions may be selected from one or more of boric acid, calcium chloride, calcium nitrate, di-ammonium phosphate, magnesium sulfate, mono-ammonium phosphate, mono-potassium phosphate, potassium chloride, potassium sulfate, copper sulfate, iron sulfate, manganese sulfate, zinc sulfate, magnesium sulfate, calcium nitrate, chelates of calcium, copper, iron, manganese and zinc, ammonium molybdate, ammonium sulphate, calcium carbonate, magnesium phosphate, potassium bicarbonate, potassium nitrate, hydrochloric acid, carbon dioxide, sulfuric acid, phosphoric acid, carbonic acid, uric acid, hydrogen chloride, urea, phosphorus ion, sulfuric ion, chloride ion, magnesium ion, sodium ion, potassium ion, ammonium ion, iron ion, zinc ion and copper ion.

Examples of normal physiological concentrations of some of the inorganic compounds include: uric acid in a concentration range of 2-7.0 mg/dL, calcium ion in a concentration range of 8.2-11.6 mg/dL, chloride ion in a concentration range of 355-381 mg/dL, iron ion in a concentration range of 0.028-0.210 mg/dL, potassium ion in a concentration range of 12.1-25.4 mg/dL, sodium ion in a concentration range of 300-330 mg/dL, carbonic acid in a concentration range of 15-30 mM, citrate ion at about 80 µM, histidine ion in the range of 0.05-2.6 mM, histamine in the range of 0.3-1 µM, HAPT ion (hydrogenated adenosine triphosphate) in the range of 1-20 µM, and HADP ion in the range of 1-20 µM.

In some embodiments, the ion present in the assay solutions for both the first condition and second conditions, or the normal physiological condition and aberrant condition, is selected from hydroxide ion, halide ion (chloride, bromide, iodide), oxyhalide ion, sulfate ion, magnesium ion, calcium ion, bisulfate ion, carbonate ion, bicarbonate ion, sulfonate ion, oxyhalide ion, nitrate ion, nitrite ion, phosphate ion, hydrogen phosphate ion, dihydrogen phosphate ion, persulfate ion, monopersulfate ion, borate ion, ammonium ion, or organic ion, such as carboxylate ion, phenolate ion, sulfonate ion (organosulfate such as methyl sulfate), vanadate ion, tungstate ion, borate ion, organoboronate ion, citrate ion, oxalate ion, acetate ion, pentaborate ion, histidine ion, and phenolate ion.

The organic compounds present in the assay solutions for both the first condition and second conditions, or the normal physiological condition and aberrant condition, may be selected from, for example, amino acids such as Histidine, Alanine, Isoleucine, Arginine, Leucine, Asparagine, Lysine, Aspartic acid, Methionine, Cysteine, Phenylalanine, Glutamic acid, Threonine, Glutamine, Tryptophan, Glycine, Valine, Pyrrolysine, Proline, Selenocysteine, Serine, Tyrosine and mixtures thereof.

Examples of a normal physiological concentration of some of the amino acids include: Alanine at 3.97±0.70 mg/dL, Arginine at 2.34±0.62 mg/dL, Glutamic acid at 3.41±1.39 mg/dL, Glutamine at 5.78±1.55 mg/dL, Glycine at 1.77±0.26 mg/dL, Histidine at 1.42±0.18 mg/dL, Isoleucine at 1.60±0.31 mg/dL, Leucine at 1.91±0.34 mg/dL, Lysine at 2.95±0.42 mg/dL, Methionine at 0.85±0.46 mg/dL, Phenylalanine at 1.38±0.32 mg/dL, Threonine at 2.02±6.45 mg/dL, Tryptophane at 1.08±0.21 mg/dL, Tyrosine at 1.48±0.37 mg/dL and Valine at 2.83±0.34 mg/dL.

The organic compounds present in the assay solutions for both the first condition and second conditions, or the normal physiological condition and aberrant condition, may be selected from non-protein nitrogen-containing compounds such as creatine, creatinine, guanidino acetic acid, uric acid, allantoin, adenosine, urea, ammonia and choline. Examples of normal physiological concentrations of some of these compounds include: creatine at 1.07±0.76 mg/dL, creatinine at from 0.9 to 1.65 mg/dL, guanidino acetic acid at 0.26±0.24 mg/dL, uric acid at 4.0±2.9 mg/dL, allantoin at from 0.3 to 0.6 mg/dL, adenosine at 1.09±0.385 mg/dL, urea 27.1±4.5 mg/dL and choline at from 0.3 to 1.5 mg/dL.

The organic compounds present in the assay solutions for both the first condition and second conditions, or the normal physiological condition and aberrant condition, may be selected from organic acids such as citric acid, α-ketoglutaric acid, succinic acid, malic acid, fumaric acid, acetoacetic acid, β-hydroxybutyric acid, lactic acid, pyruvic acid, α-ketonic acid, acetic acid, and volatile fatty acids. Examples of normal physiological concentrations of some of these organic acids include: citric acid at 2.5±1.9 mg/dL, α-ketoglutaric acid at 0.8 mg/dL, succinic acid at 0.5 mg/dL, malic acid at 0.46±0.24 mg/dL, acetoacetic acid at from 0.8 to 2.8 mg/dL, β-hydroxybutyric acid at 0.5±0.3 mg/dL, lactic acid at from 8 to 17 mg/dL, pyruvic acid at 1.0±0.77 mg/dL, α-ketonic acids at from 0.6 to 2.1 mg/dL, volatile fatty acids at 1.8 mg/dL.

The organic compounds present in the assay solutions for both the first condition and second conditions, or the normal physiological condition and aberrant condition, may be selected from sugars (carbohydrates) such as glucose, pentose, hexose, xylose, ribose, mannose and galactose, as well as disaccharides including lactose, GlcNAcβ1-3Gal, Galα1-4Gal, Manα1-2Man, GalNAcβ1-3Gal and O-, N-, C-, or S-glycosides. Examples of normal physiological concentrations of some of these sugars include: glucose at 83±4 mg/dL, polysaccharides at 102±73 mg/dL (as hexose), glucosamine at 77±63 mg/dL, hexuronates at from 0.4 to 1.4 mg/dL (as glucuronic acid) and pentose at 2 0.55±0.37 mg/dL.

The organic compounds present in the assay solutions for both the first condition and second conditions, or the normal physiological condition and aberrant condition, may be selected from fats or their derivatives such as cholesterol, lecithin, cephalin, sphingomyelin and bile acid. Examples of normal physiological concentrations of some of these compounds include: free cholesterol at from 40 to 70 mg/dL, lecithin at from 100 to 200 mg/dL, cephalin at from 0 to 30 mg/dL, sphingomyelin at from 10 to 30 mg/dL and bile acids at from 02. To 0.3 mg/dL (as cholic acid).

The organic compounds present in the assay solutions for both the first condition and second conditions, or the normal physiological condition and aberrant condition, may be selected from proteins such as fibrinogen, antihaemophilic globulin, immune γ-globulin, immune euglobulins, isoagglutinins, β-pseudoglobulin, glycoproteins, lipoproteins and albumin. For example, the normal physiological concentration of mammal serum albumin is 3.5-5.0 g/dL. In one embodiment, the albumin is bovine serum albumin.

In some aspects, the assay solution may include a blood protein, such as those found in the blood of the subject. A person skilled in the art can determine suitable blood proteins in a particular subject from a blood sample. For example, suitable human blood proteins may include albumin and hemoglobin.

The organic compounds present in the assay solutions for both the first condition and second conditions, or the normal physiological condition and aberrant condition, may be selected from vitamins such as Vitamin A, Carotene, Vitamin E, Ascorbic acid, Thiamine, Inositol, Folic acid, Biotin, Pantothenic acid, Riboflavin. Examples of normal physiological concentrations of some of these vitamins include: Vitamin A at from 0.019 to 0.036 mg/dL, Vitamin E at from 0.90 to 1.59 mg/dL, Inositol at from 0.42 to 0.76 mg/dL, Folic acid at from 0.00162 to 0.00195 mg/dL and biotin from 0.00095 to 0.00166 mg/dL.

The concentration of the inorganic compound, ion, or organic molecule in the assay solutions (for both assays under the first condition and second conditions, or the normal physiological condition and aberrant condition) may be within the normal range of physiological concentration of the inorganic compound, ion, or organic molecule in human or animal blood serum. However, the concentrations outside of the normal physiological range may also be used. For example, the normal range in human serum for magnesium ion is 1.7-2.2 mg/dL, and calcium is 8.5 to 10.2 mg/dL. The concentration for magnesium ion in the assay solutions may be from about 0.17 mg/dL to about 11 mg/dL. The concentration for calcium ion in the assay solutions may be from about 0.85 mg/dL to about 51 mg/dL. As a general rule, the concentration of the inorganic compound, ion, or organic molecule in the assay solutions may be as low as 5%, or 10%, or 20%, or 30%, or 40%, or 50%, or 60%, or 70%, or 80% of the normal physiological concentration of the inorganic compound, ion, or organic molecule in human serum, or as high as 1.5 times, or 2 times, or 3 times, or 4 times or 5 times, or 7 times or 9 times or 10 times or even 20 times the normal physiological concentration of the inorganic compound, ion, or organic molecule in human serum. Different components of the assay solutions may be used at different concentration levels relative to their respective normal physiological concentrations.

The assays under the first and second conditions, or the normal physiological condition and aberrant condition, are used to measure the activity of the mutant polypeptides. During the assays both the mutant polypeptide and its binding partner are present in the assay solutions. The relationship between the mutant polypeptide and its binding partner may be, for example, antibody-antigen, ligand-receptor, enzyme-substrate, or hormone-receptor. In order for a mutant polypeptide to manifest its activity, the mutant polypeptide should be able to come into contact with and bind to its binding partner. The activity of the mutant polypeptide on its binding partner is then manifested and measured after the binding between the mutant polypeptide and its binding partner.

In some embodiments, the ions used in the assay may function in forming a bridge between the mutant polypeptide being screened and its binding partner, particularly those including charged amino acid residues. The ion may thus be capable of binding to both the mutant polypeptide and its binding partner through hydrogen bonds and/or ionic bonds. This may assist the binding between the mutant polypeptide and its binding partner by allowing the ion to reach a site that may be hard to reach by a large molecule (mutant polypeptide or its binding partner). In some cases, the ion in the assay solutions may increase the probability of the mutant polypeptide and its binding partner binding to one another. Further, the ion may additionally or alternatively assist the binding between the mutant polypeptide and its binding partner by binding to a larger molecule (mutant polypeptide or its binding partner). This binding may alter the conformation of the large molecule and/or cause the larger molecule to remain in a particular conformation that facilitates binding with its binding partner.

It has been observed that the ions can assist the binding between the mutant polypeptide and its binding partner, possibly by forming ionic bonds with the mutant polypeptide and its binding partner. Thus, the screening may be much more efficient and more hits (candidate conditionally active polypeptides) can be identified in comparison with the same assays without the ion. Suitable ions may be selected from magnesium ion, sulfate ion, bisulfate ion, carbonate ion, citrate ion, HAPT ion, HADP ion, bicarbonate ion, nitrate ion, nitrite ion, phosphate ion, hydrogen phosphate ion, dihydrogen phosphate ion, persulfate ion, monopersulfate ion, borate ion, lactate ion, citrate ion, histidine ion, histamine ion, and ammonium ion.

It has been found that the ions function to assist the binding between the mutant polypeptide and its binding partner at a pH near a pKa of the ion. Such ions are preferably relatively small in relation to the size of the mutant polypeptides.

In one embodiment, when the aberrant condition is a pH that is different from the normal physiological pH under the normal physiological condition, the ions suitable for increasing the number of hits for candidate conditionally active polypeptides may be selected from ions having a pKa that is close to the aberrant pH to be tested in the assay. For example, the pKa of the ion may be up to 3 pH units away from the aberrant pH, up to 2 pH units away from the aberrant pH, up to 1 pH unit away from the aberrant pH, up to 0.8 pH unit away from the aberrant pH, up to 0.6 pH unit away from the aberrant pH, up to 0.5 pH unit away from the aberrant pH, up to 0.4 pH unit away from the aberrant pH, up to 0.3 pH unit away from the aberrant pH, up to 0.2 pH unit away from the aberrant pH, or up to 0.1 pH unit away from the aberrant pH.

Exemplary pKa's of ions useful in the present invention, which pKa's may vary slightly at different temperatures, are as follows: ammonium ion having a pKa at about 9.24, dihydrogen phosphate having a pKa at about at 7.2, acetic acid having a pKa at about 4.76, histidine having a pKa at about 6.04, bicarbonate ion having a pKa at about 6.4, citrate having a pKa at 6.4, lactate ion having a pKa at about 3.86, histamine having a pKa at about 6.9, HATP having a pKa at 6.95 (HATP$^{3-}$⇔ATP$^{4-}$+H$^+$) and HADP having a pKa at 6.88 (HADP$^{3-}$⇔ADP$^{4-}$+H$^+$).

In one embodiment, the conditionally active polypeptides are assayed and selected in the presence bisulfide. Bisulfide has a pKa of 7.05. In some embodiments, different concentrations of bisulfide may be used in the assays representing the normal and aberrant physiological conditions. Alternatively, the assay media for both the normal physiological condition and aberrant condition have approximately the same concentration of bisulfide and also some difference in the value of the particular condition, for example, the assay may be conducted at different pH's. The concentration of bisulfide to be used in the assay may be from 1 mM to 100 mM. Preferably, the assay medium has a bisulfide concentration of from 2 to 50 mM, or from 3 to 35 mM, or from 5 to 20 mM. Assays conducted in the presence of bisulfide are known.

In certain embodiments, once the pH for the aberrant condition (i.e., aberrant pH) is known, the ion suitable for increasing the hits for candidate conditionally active polypeptides may be selected from ions that have a pKa that is at or near the aberrant pH, for example, the candidate ions may have a pKa up to 3 pH units way from the aberrant pH, up to 2 pH units way from the aberrant pH, up to 1 pH unit away from the aberrant pH, up to 0.8 pH unit away from the aberrant pH, up to 0.6 pH unit away from the aberrant pH, up to 0.5 pH unit away from the aberrant pH, up to 0.4 pH unit away from the aberrant pH, up to 0.3 pH unit away from the aberrant pH, up to 0.2 pH unit away from the aberrant pH, or up to 0.1 pH unit away from the aberrant pH.

As stated above, the ion is most effective at assisting the binding between the mutant polypeptide and its binding partner at a pH that is at or close to the pKa of the ion. For example, it has been found that in an assay solution with a pH 7.2-7.6, the bicarbonate ion (having pKa about 6.4) is not very effective in assisting the binding between the mutant polypeptide and its binding partner. As the pH in the assay solution decreased to 6.7 and further to around 6.0, the bicarbonate ion became increasingly effective in assisting the binding between the mutant polypeptide and its binding partner. As a result, more hits could be identified in the assay at pH 6.0 in comparison with assay at pH 7.2-7.6. Similarly, histidine is not very effective in assisting the binding between the mutant polypeptide and its binding partner at pH 7.4. As the pH of the assay solution is decreased to 6.7 and further to around 6.0, histidine becomes increasingly effective in assisting the binding between the mutant polypeptide and its binding partner also allowing more hits to be identified at pHs in a range of about 6.2-6.4, for example.

The present invention surprisingly found that, when the pHs of the assay solutions for the normal physiological condition (i.e., a normal physiological pH) and aberrant condition (i.e., an aberrant pH) are different, an ion with pKa in the range of from about the middle point of the normal physiological pH and the aberrant pH to about the aberrant pH can greatly assist the binding between the mutant polypeptide being screened and its binding partner. As a result, the screening assay is much more efficient in founding more hits or candidate conditionally polypeptides with high activity at the aberrant condition.

In some embodiments, the pKa may even be at least one pH unit away from the aberrant pH. When the aberrant pH is an acidic pH, the pKa of a suitable ion may be in the range of from (aberrant pH−1) to the middle point between the aberrant pH and the normal physiological pH. When the aberrant pH is a basic pH, the pKa of a suitable ion may be in the range of from (aberrant pH+1) to the middle point between the aberrant pH and the normal physiological pH. The ions may be selected from those described in this application. However, many more ions that have not been explicitly described in the application may also be used. It is understood that, once the aberrant pH and the normal physiological pH are selected for the screening assays, a person skilled in the art can use the guiding principles of the invention to select any ion with a suitable pKa for increasing the efficiency of screening in identifying more hits with high activity at the aberrant condition.

For example, when the aberrant pH is 8.4 and the normal physiological pH is 7.4 for an exemplary screening, any ion with a pKa in the range of about 7.9 (the middle point) to 9.4 (i.e., 8.4+1) may be used in the screening. Some ions with a pKa in this range include ions derived from tricine (pKa 8.05), hydrazine (pKa 8.1), bicine (pKa 8.26), N-(2-Hydroxyethyl) piperazine-N'-(4-butanesulfonic acid) (pKa 8.3), N-Tris[hydroxymethyl]methyl-3-aminopropanesulfonic acid (pKa 8.4), taurine (pKa 9.06). For another example, when the aberrant pH is 6 and the normal physiological pH is 7.4 for an exemplary screening, any ion with a pKa in the range of about 5 (i.e., 6-1) to 6.7 (the middle point) may be used in the screening. Some ions with a pKa in this range include ions derived from malate (pKa 5.13), pyridine (pKa 5.23), piperazine (pKa 5.33), cacodylate (pKa 6.27), succinate (pKa 5.64), 2-(N-morpholino)ethanesulfonic acid (pKa 6.10), citrate (pKa 6.4), histidine (pKa 6.04) and bis-tris (6.46). A person skilled in the art will be able to consult a vast number of chemical manuals and text books to identify the known chemical compounds that can be converted to ions with a pKa falling in the ranges, including both inorganic chemical compounds and organic chemical compounds. Among the chemical compounds with a suitable pKa, the ones with a smaller molecular weight may be preferred.

Consequently, the present invention unexpectedly found that production of conditionally active polypeptides eventually identified not only depends on generating the right polypeptide mutants from a wild-type polypeptide, but also depend on using an ion with a suitable pKa in the assay solutions. The invention contemplates that in addition to generating a large library of mutant polypeptides (e.g., through CPE and CPS), efforts should also be made to find a suitable ion (with proper pKa) for use in the assay solutions, because the ion can facilitate efficiently selecting the mutants with high activity from the large library. It is further contemplated that, without the suitable ion, the screening is less efficient and the probability of finding the mutants with high activity is decreased. Consequently, it may require multiple rounds of screening to achieve the same number of mutants with high activity without the suitable ion.

The ion in the assay solutions may be formed in situ from a component of the assay solution or be directly included in the assay solution. For example, $CO_2$ from the air may dissolve in the assay solution to provide carbonate and bicarbonate ions. For another example, sodium dihydrogen phosphate may be added to the assay solution to provide dihydrogen phosphate ions.

The concentration of this component in the assay solutions (for both assay under the first or normal physiological condition and assay under the second or aberrant condition) may be the same or substantially the same as the concentration of the same component that is typically found in a naturally-occurring bodily fluid of a mammal, such as a human. In other embodiments, the concentration of the component may be higher, especially when the component is an ion that can function to assist the binding between the mutant polypeptide and its binding partner, because it has been observed that higher concentration of such ion can form ionic bonds with the mutant polypeptide and its binding partner, practically facilitate the bindings and increase the probability of finding more hits or candidate conditionally active polypeptides.

In some embodiments, the concentration of the ion in the assay solutions may positively correlate with the probability of finding more hits using the assay, particularly when concentrations in excess of normal physiological concentrations are employed. For example, human serum has a concentration of about 15-30 mM of bicarbonate ion. In one example, as the concentration of bicarbonate ion in the assay solutions was increased from 3 mM to 10 mM, to 20 mM, to 30 mM, to 50 mM and to 100 mM, the number of hits in the assay also increased with each increase in bicarbonate concentration. In view of this, the assay solutions may employ concentrations of bicarbonate ranging from about 3 mM to about 200 mM, or from about 5 mM to about 150 mM or from about 5 mM to about 100 mM, or from about 10 mM to about 100 mM or from about 20 mM to about 100 mM or from about 25 mM to about 100 mM or from about 30 mM to about 100 mM or from about 35 mM to about 100 mM or from about 40 mM to about 100 mM or from about 50 mM to about 100 mM.

In another embodiment, the concentration of citrate in the assay solutions may be from about 30 μM to about 120 μM, or from about 40 μM to about 110 μM, or from about 50 μM to about 110 μM, or from about 60 μM to about 100 μM, or from about μM to about 90 μM, or about μM.

In one embodiment, the normal physiological condition is a normal physiological pH in the range of 7.2-7.6 and the aberrant condition is an aberrant pH in the range of 5.5-7.2, 6-7, or 6.2-6.8. The assay solution for the assay under the normal physiological condition has the normal physiological pH and 50 mM of bicarbonate ion. The assay solution for the assay under the aberrant condition has the aberrant pH and 50 mM of bicarbonate ion. Because the pKa of bicarbonate ion is at about 6.4, the bicarbonate ion can assist the binding between the mutant polypeptides and its binding partner at the aberrant pH of 6.0-6.4, such as pH 6.0 or 6.2.

In yet another embodiment, the normal physiological condition is a normal physiological pH in the range of 7.2-7.6 and the aberrant condition is an aberrant pH in the range of 5.5-7.2, 6-7, or 6.2-6.8. The assay solution for the assay under the normal physiological condition has the normal physiological pH and 80 μM of citrate ion. The assay solution for the assay under the aberrant condition has the aberrant pH and 80 μM of citrate ion. Because the citrate ion has a pKa of 6.4, the citrate ion can effectively assist the binding between the mutant polypeptides and the binding partner in the assay solution for aberrant condition with pH 6.0-6.4. Therefore more candidate conditionally active polypeptides may be identified that have higher binding activity under condition of pH 6.0-6.4 and lower activity under condition of pH at 7.2-7.8. The other ions, including acetate, histidine, bicarbonate, HATP and HADP, function in a similar way to enable an assay solution containing the ion to effectively screening for mutant polypeptides with a higher binding activity at a pH around the pKa of the ion and a lower binding activity at a pH that is different from the pKa of the ion (e.g., normal physiological pH).

In yet another embodiment, the normal physiological condition is a normal physiological temperature at 37° C. and the aberrant condition is an aberrant temperature at 38-39° C. (temperature in some tumor microenvironments). The assay solution for the assay under the normal physiological condition has the normal physiological temperature and 20 mM of bicarbonate ion. The assay solution for the assay under the aberrant condition has the aberrant temperature and 20 mM of bicarbonate ion.

In yet another embodiment, the normal physiological condition is a particular concentration of an electrolyte in normal human serum and the aberrant condition is the concentration of the same electrolyte in a different, aberrant concentration which may be present at a different location in the animal or human or may result from a condition of the animal or human that alters the normal physiological concentration of an electrolyte in human serum.

The binding between a mutant polypeptide and/or its binding partner can also be influenced in a number of other ways. Typically, this influence will be exerted by inclusion of one or more additional components in the assay solutions. These additional components may be designed to interact with either the mutant polypeptide, the binding partner or both. In addition, these additional components may use combinations of two or more interactions as well as combinations of two or more types of interactions to influence the binding.

In one embodiment, the binding interaction of interest is between an antibody and an antigen. In this embodiment, one or more additional components may be included in the assay solutions to exert influence on the antibody, antigen or both. In this manner, the desired binding interaction may be enhanced.

In addition to the ions that can form ionic bonds with a mutant polypeptide and/or its binding partner to assist the binding between the mutant polypeptide and the binding partner, the present invention also includes other components that may be employed assist binding between a mutant polypeptide and its binding partner. In one embodiment, molecules that can form hydrogen bonds with a mutant polypeptide and/or its binding partner are employed. In another embodiment, molecules that are capable of hydrophobic interaction with a mutant polypeptide and/or its binding partner may be used. In yet another embodiment, molecules that are capable of Van der Waals' interactions with a mutant polypeptide and/or its binding partner are contemplated.

As used herein, the term "hydrogen bond" refers to a relatively weak, noncovalent interaction between a hydrogen covalently bonded to an electronegative atom, such as carbon, nitrogen, oxygen, sulfur, chlorine, or fluorine (hydrogen bond donor), with an unshared electron pair of an electron donor atom, such as nitrogen, oxygen, sulfur, chlorine, or fluorine (hydrogen bond acceptor).

Components capable of forming a hydrogen bond with a mutant polypeptide and/or its binding partner include organic molecules as well as inorganic molecules with a polar bond. Mutant polypeptides and/or binding partners for mutant polypeptides typically contain amino acids that can form hydrogen bonds. Suitable amino acids have a side chain with a polar group that is capable of forming a hydrogen bond. Non-limiting examples of suitable amino acids include glutamine (Gln), glutamic acid (Glu), arginine (Arg) asparagines (Asn), aspartic acid (Asp), lysine (Lys), histidine (His), serine (Ser), threonine (Thr), tyrosine (Tyr), cysteine (Cys), methionine (Met), and tryptophan (Trp).

These amino acids can function as both hydrogen donors and hydrogen acceptors. For example, the oxygen atom in an —OH group such as may be found in Ser, Thr, and Tyr, the oxygen atom in a —C=O group such as may be found in Glu and Asp, the sulfur atom in an —SH group or —SC— such as may be found in Cys and Met, the nitrogen atom in a —NH$_3^+$ group such as may be found in Lys and Arg, and the nitrogen atom in an —NH— group such as may be found in Trp, His and Arg, may all function as a hydrogen acceptor. Also, groups in this list including a hydrogen atom (e.g. —OH, —SH, NH$_3^+$ and —NH—) may function as a hydrogen donor.

In some embodiments, the backbone of the mutant polypeptide and/or its binding partner may also participate in forming one or more hydrogen bonds. For example, the backbone may have a repeating structure of —(C=O)—NH— such as in peptide bonds. The oxygen and nitrogen atoms in this structure may function as hydrogen acceptors, while the hydrogen atom may participate in the hydrogen bond.

The inorganic compounds that have at least one polar bond involving a hydrogen or oxygen atom that may be used for hydrogen bonding may include, for example, H$_2$O, NH$_3$, H$_2$O$_2$, hydrazine, carbonates, sulfates and phosphates. Organic compounds such as alcohols; phenols; thiols; aliphatic, amines, amides; epoxides, carboxylic acids; ketones, aldehydes, ethers, esters, organochlorides, and organofluorides. Compounds that can form hydrogen bonds are well known in the chemical literature, such as those discussed in, for example, "The Nature of the Chemical Bond," by Linus Pauling, Cornell University Press, 1940, pages 284 to 334.

In some embodiments, the alcohols may include methanol, ethanol, propanol, isopropanol, butanol, pentanol, 1-hexanol, 2-octanol, 1-decanol, cyclohexanol, and the higher alcohols; diols such as ethylene glycol, propylene glycol, glycerol, diethylene glycol, and polyalkylene glycols. Suitable phenols include hydroquinone, resorcinol, catechol, phenol, o-, m-, and p-cresol, thymol, alpha and beta-naphthol, pyrogallol, guaiacol, and phloroglucinol. Suitable thiols include methanethiol, ethanethiol, 1-propanethiol, 2-propanethiol, butanethiol, tert-butyl mercaptan, pentanethiols, hexanethiol, thiophenol, dimercaptosuccinic acid, 2-mercaptoethanol, and 2-mercaptoindole. Suitable amines include methylamine, ethylamine, propylamine, isopropylamine, aniline, dimethylamine and methylethylamine, trimethylamine, aziridine, piperidine, N-methylpiperidine, benzidine, cyclohexyl amine, ethylene diamine, hexamethylene diamine, o-, m-, and p-toluidine and N-phenylpiperidine. Suitable amides include ethanamide, N,N-dimethylacetamide, N,N-dimethyl formamide, N,N-dimethyl methoxy acetamide and N-methyl-N-p-cyanoethyl formamide. The epoxides may include ethylene oxide, propylene oxide, tert-butyl hydroperoxide, styrene oxide, epoxide glycidol, cyclohexene oxide, di-tert-butyl peroxide, cumene hydroperoxide or ethylbenzene hydroperoxide, isobutylene oxide, and 1,2-epoxyoctane. The carboxylic acids may include terephthalic acid, isophthalic acid, phthalic acid, salicylic acid, benzoic acid, acetic acid, lauric acid, adipic acid, lactic acid, citric acid, acrylic acid, glycine, hexa-hydrobenzoic acid, o-, m-, and p-toluic acids, nicotinic acid, isonicotinic acid, and para-aminobenzoic acid. The ketones may include acetone, 3-propanone, butanone, pentanone, methylethyl ketone, diisobutyl ketone, ethyl butyl ketone, methyl isobutyl ketone, methyl tert-butyl ketone, cyclohexanone, acetone, methyl ethyl ketone, methyl propyl ketone, methyl butyl ketone, methyl amyl ketone, methyl hexyl ketone, diethyl ketone, ethyl butyl ketone, dipropyl ketone, diisobutyl ketone, diacetone alcohol, phorone, isophorone, cyclohexanone, methyl cyclohexanone, and acetophenone. The aldehydes may include formaldehyde, acetaldehyde, propionaldehyde, butyraldehyde, benzaldehyde, cinnamaldehyde, sobutyraldehyde, valeraldehyde, octaldehyde, benzaldehyde, cinnamaldehyde, cyclohexanone, salicylaldehyde, and furfural. The esters include ethyl acetate, methyl acetate, ethyl formate, butyl acetate, ethyl lactate, ethyl butyrate, propyl acetate, ethyl formate, propyl formate, butyl formate, amyl formate, methyl acetate, ethyl acetate, propyl acetate, butyl acetate, amyl acetate, methyl isoamyl acetate, methoxybutyl acetate, hexyl acetate, cyclohexyl acetate, benzyl acetate, methyl propionate, ethyl propionate, butyl propionate, amyl propionate, methyl butyrate, ethyl butyrate, butyl butyrate, amyl butyrate, methyl acetoacetate, and ethyl acetoacetate. Ethers that may be used in the present invention include dimethyl ether, methyl ethyl ether, diethyl ether, methyl propyl ether, and dimethoxyethane. The ethers may be cyclic, such as ethylene oxide, tetrahydrofuran, and dioxane.

The organochlorides include chloroform, pentachloroethane, dichloromethane, trichloromethane, carbon tetrachloride, tetrachloromethane, tetrachloroethane, pentachloroethane, trichloroethylene, tetrachloroethylene, and ethylene dichloride. The organofluorides may include fluoromethane, difluoromethane, trifluoromethane, trifluoroethane tetrafluoroethane, pentafluoroethane, difluoropropane, trifluoropropane, tetrafluoropropane, pentafluoropropane, hexafluoropropane, and heptafluoropropane, Hydrogen bonds may be divided by the strength of the bond: strong, moderate, or weak hydrogen bonds (Jeffrey, George A.; An introduction to hydrogen bonding, Oxford University Press, 1997). The strong hydrogen bonds have donor-acceptor distances of 2.2-2.5 Å and energies in the range of 14-40 kcal/mol. The moderate hydrogen bonds have donor-acceptor distances of 2.5-3.2 Å and energies in the range of 4-15 kcal/mol. The weak hydrogen bonds have donor-acceptor distances of 3.2-4.0 Å and energies in the range of <4 kcal/mol. Some examples of hydrogen bonds with energy levels are F—H . . . :F (38.6 kcal/mol), O—H . . . :N (6.9 kcal/mol), O—H . . . :O (5.0 kcal/mol), N—H . . . :N (3.1 kcal/mol) and N—H . . . :O (1.9 kcal/mol). See more in Perrin et al. "Strong" hydrogen bonds in chemistry and biology, *Annual Review of Physical Chemistry*, vol. 48, pages 511-544, 1997; Guthrie, "Short strong hydrogen bonds: can they explain enzymic catalysis?" *Chemistry & Biology* March 1996, 3:163-170.

In some embodiments, the components used in the present invention can form a strong hydrogen bond with the mutant polypeptide and/or its binding partner. These components tend to have an atom with a strong electronegativity. The atoms known to have the strongest electronegativity are F>O>Cl>N, in this order. Thus, the present invention preferably uses an organic compound that includes fluorine, a hydroxyl group or a carbonyl group, in forming the hydrogen bond. In one embodiment, organofluorines may be used in the present invention for forming a strong hydrogen bond.

In another embodiment, components capable of a hydrophobic interaction with a mutant polypeptide and/or its binding partner are employed. Such components include organic compounds with a hydrophobic group.

As used herein, the term "hydrophobic interaction" refers to reversible attractive interactions between a hydrophobic compound or a hydrophobic region of a compound and another hydrophobic compound or hydrophobic region of the other compound. This type of interaction has been described in "Hydrophobic Interactions," A. Ben-Nairn (1980), Plenum Press, New York.

Hydrophobic materials are repelled by water molecules because of their non-polar nature. When relatively nonpolar molecule or groups in aqueous solution associate with other nonpolar molecules rather than with water, it is termed a "hydrophobic interaction."

The mutant polypeptides and their binding partners typically include amino acids that are capable of hydrophobic interactions. These amino acids will typically be characterized by having at least one side chain with a nonpolar group that is capable of a hydrophobic interaction. Hydrophobic amino acids include, for example, alanine (Ala), isoleucine (Ile), leucine (Leu), phenylalanine (Phe), valine (Val), proline (Pro), glycine (Gly), to a lesser extent, methionine (Met), and tryptophan (Trp).

Components that are capable of hydrophobic interactions with a mutant polypeptide and/or its binding partner include organic compounds that are hydrophobic molecules or molecules containing at least one hydrophobic moiety. In some embodiments, these hydrophobic components may be hydrocarbons selected from aromatic hydrocarbons, substituted aromatic hydrocarbons, polyaromatic hydrocarbons, aromatic or non-aromatic heterocycles, cycloalkanes alkanes, alkenes, and alkynes. Hydrophobic groups may include aromatic groups, alkyl, cycloalkyl, alkenyl and alkynyl groups. The terms, "alkyl," "alkenyl" and "alkynyl" as used herein refer to unsaturated aliphatic groups having one to thirty carbon atoms, including straight-chain alkenyl/alkynyl groups, branched-chain alkenyl/alkynyl groups, cycloalkenyl (alicyclic) groups, alkyl substituted cycloalkyl groups, and cycloalkyl substituted alkenyl/alkynyl groups. Such hydrocarbon moieties may also be substituted on one or more carbon atoms.

It may be understood that the strength of the hydrophobic interaction is based upon the available amount of "hydrophobes" that may interact one another. Thus, the hydrophobic interaction may be adjusted by, for example, increasing the amount of and/or "hydrophobic" nature of the hydrophobic moiety in the molecules involved in the hydrophobic interaction. For instance, a hydrophobic moiety, which in its original form may include a hydrocarbon chain, may be modified to increase its hydrophobicity (ability to increase the strength of hydrophobic interaction involved by the moiety) by having a hydrophobic side chain attach to one of the carbons of its carbon backbone. In a preferred embodiment of the invention, this may include the attachment of various polycyclic compounds, including for instance various steroidal compounds and/or their derivatives such as sterol type compounds, more particularly cholesterol. In general, the side chains may be linear chains, aromatic, aliphatic, cyclic, polycyclic, or any various other types of hydrophobic side chains as contemplated by those skilled in the art.

The type of components that are capable of van der Waals interactions with a mutant polypeptide and/or its binding partner are usually, but not always compounds with a polar moiety. As used herein, "van der Waals interactions" refer to attractions between atoms, moieties, molecules, and surfaces that are caused by dipole-dipole interactions and/or correlations in the fluctuating polarizations of nearby atoms, moieties, or molecules as a consequence of quantum dynamics.

The van der Waals interactions in the present invention are attractive forces between the mutant polypeptides or the binding partner and the component. The van der Waals interactions may arise from three sources. First, some molecules/moieties, although electrically neutral, may be permanent electric dipoles. Because of fixed distortion in the distribution of electron charge in the structure of some molecules/moieties, one side of a molecule/moiety is always somewhat positive and the opposite side somewhat negative. The tendency of such permanent dipoles to align with each other results in a net attractive force. This is interaction between two permanent dipoles (Keesom force).

Second, the presence of molecules that are permanent dipoles may temporarily distort the electron charge in other nearby polar or nonpolar molecules, thereby inducing further polarization. An additional attractive force results from the interaction of a permanent dipole with the neighboring induced dipole. This is an interaction between a permanent dipole and a corresponding induced dipole may be referred to as a Debye force. Third, even though no molecules involved are permanent dipoles (e.g., the organic liquid benzene), a force of attraction exists between molecules with two instantaneously induced dipoles in the molecules. This is interaction between two instantaneously induced dipoles may be referred to as a London dispersion force.

There are many amino acids in a mutant polypeptide and/or the binding partner that are capable of van der Waals interactions. These amino acids may have polar side chains, including glutamine (Gln), asparagine (Asn), histidine (His), serine (Ser), threonine (Thr), tyrosine (Tyr), cysteine (Cys), methionine (Met), tryptophan (Trp). These amino acids may also have a side chain with a non-polar group, including alanine (Ala), isoleucine (Ile), leucine (Leu), phenylalanine (Phe), valine (Val), proline (Pro), glycine (Gly).

The components that are capable of van der Waals interactions with a mutant polypeptide and/or its binding partner include polar or non-polar inorganic compounds that are soluble in the assay solution. The assay solution is generally an aqueous solution and thus these polar or non-polar inorganic compounds are preferably soluble in water. Preferred materials for van der Waals interactions are those that are polar such that they are capable of dipole-dipole interactions. For example $AlF_3$ has polar Al—F bonds and is soluble in water (about 0.67 g/100 ml water at 20° C.). $HgCl_2$ has polar Hg—Cl bonds and is soluble in water at 7.4 g/100 ml at 20° C. $PrCl_2$ has polar Pr—Cl bonds and is soluble in water at about 1 g/100 ml at 20° C.

Suitable polar compounds that are capable of van der Waals interactions include alcohols, thiols, ketones, amines, amides, esters, ethers, and aldehydes. Suitable examples of these compounds have been described above in relation to hydrogen bonding. Suitable non-polar compounds that are capable of van der Waals interactions include aromatic hydrocarbons, substituted aromatic hydrocarbons, polyaromatic hydrocarbons, aromatic or non-aromatic heterocycles, cycloalkanes, alkanes, alkenes, alkynes.

The hydrogen bonding components, hydrophobic components and Van der Waals components can be employed to influence binding of a mutant polypeptide and its binding partner in a number of ways. In one embodiment the hydrogen bonding, hydrophobic interaction and/or Van der Waals interaction may form a bridge between the mutant polypeptide and its binding partner. Such a bridge may bring the mutant polypeptide and binding partner into closer proximity to one another to facilitate binding and/or position the mutant polypeptide and/or binding partner relative to one another in a way that facilitates binding.

In another embodiment, the hydrogen bonding and/or hydrophobic interaction may increase the probability of the mutant polypeptide binding to its binding partner by, for example, by causing the polypeptides and binding partners to group or associate with one another in a manner which increases the binding probability. Thus, one or more of these interactions may be used alone or in combination to group the mutant polypeptides and binding partners closer together or to arrange the mutant polypeptides and binding partners in a manner that facilitates binding by, for example, causing the binding sites to be drawn closer together or causing the non-binding portions of the molecules to arrange further away from one another thereby allowing the binding sites to locate closer to one another.

In still another embodiment, the hydrogen bonding and/or hydrophobic interaction may influence the conformation of a mutant polypeptide and/or its binding partner to provide a conformation that is more conducive to the binding of the mutant polypeptide with its binding partner. Specifically, binding to or interacting with one or more of the amino acids of the mutant polypeptide and/or binding partner may cause one or more conformational shifts in the mutant polypeptide or binding partner that favors the mutant polypeptide/binding partner binding reaction.

The present invention conducts two pairs of assays, one to seek a decrease in activity for a mutant polypeptide in the assay at the normal physiological condition when compared to the parent polypeptide from which the mutant polypeptide was derived at said normal physiological condition, and a second assay to seek an increase in activity of the mutant polypeptide in the assay under the aberrant condition when compared to the parent polypeptide from which the mutant polypeptide was derived at said aberrant condition. In some cases, the parent polypeptide from which the mutant polypeptide was derived is a wild-type polypeptide. In other cases, the parent polypeptide may itself be a mutant polypeptide that has been prepared using one or more of the mutation techniques described elsewhere herein.

The condition used in the pairs of assays of the present invention may be selected from temperature, pH, osmotic pressure, osmolality, oxidative stress, electrolyte concentration and the concentration of any other component of the assay solution or media. Thus, a particular component of the assay media may be used at substantially the same concentration in both pairs of assays. In such case, the component is typically present for the purpose of simulating a particular environment in a human or animal such as serum, a tumor microenvironment, a synovial environment, a neural environment or any other environment which may be encountered at the point of administration, may be traversed by the administered treatment or may be encountered at the point of treatment. One important aspect of selecting one or more components that simulate these environments is that it may improve the results of the selection process carried out using the pairs of assays. For example, simulating a particular environment allows various effects of particular components of that environment on the mutant polypeptides to be evaluated in the selection process. Components of a particular environment may, for example, alter or bind with the mutant polypeptide, inhibit the activity of the mutant polypeptide, inactivate the mutant polypeptide, etc.

In some embodiments, one or more components of the assay solutions are preferably small compounds, such as bisulfide, bicarbonate, histidine, histamine, citrate, lactate, and acetate. In one embodiment, the small molecule component is preferably present in the assay solution at a concentration of from about 100 μm to about 100 mM, or, more preferably from about 0.5 to about 50 mM, or from about 1 to about 10 mM.

The concentration of the component in the assay solutions may be the same or substantially the same as the concentration of the same component that is typically found in a naturally-occurring bodily fluid of a mammal, such as a human. This may be referred to as a normal physiological concentration of the component in the bodily fluid. In other embodiments, the concentration of a particular component in the assay solutions may be less than, or greater than the concentration of the same component that is typically found in a naturally-occurring bodily fluid of a mammal, such as a human.

In another embodiment, a component may be present at substantially different concentrations in each of the pairs of assays. In such case, the presence, absence or concentration of the component becomes the condition that is being assayed since it is the concentration of the component that is the condition that differentiates between the assay solutions for the assay under a normal physiological condition and the assay solution for the assay under an aberrant condition. Thus, the conditionally active polypeptide produced by this embodiment of the method of the present invention would be selected for an activity at least partially dependent on the concentration of the component.

In some embodiments, the component may be present in one pair of assay solutions but entirely absent from the other pair of assay solutions. For example, the concentration of lactate in the assay solution for the aberrant condition may be set to a level simulating a lactate concentration in the tumor microenvironment. Lactate may be absent from the pair of assay solutions for the normal physiological condition.

In one embodiment, the normal physiological condition is a first lactate concentration representative of a normal physiological condition and the aberrant condition is a second lactate concentration representative of an aberrant condition that exists in a particular location in the body.

In another example, glucose may be absent in the assay solution for the aberrant condition to simulate the absence of glucose that may be found in a tumor microenvironment, while glucose may be set to a level that simulates a blood plasma glucose concentration in the pair of assay solutions for the normal physiological condition. This feature may be used for preferential delivery of the conditionally active polypeptide to the location or environment without no or minimal activity in transit, and activation of the conditionally active polypeptide when it reaches the environment where the concentration of the component in the assay solution for the aberrant condition is present.

For example, a tumor microenvironment typically has both a lower glucose concentration and a higher lactate concentration in comparison with human serum. The normal physiological concentration of glucose is in the range of about 2.5 mM to about 10 mM in serum. On the other hand, the glucose concentration is typically very low in the range of 0.05 mM to 0.5 mM in the tumor microenvironment. In one embodiment, the assay solution for the assay under the normal physiological condition has a glucose concentration in the range of about 2.5 mM to about 10 mM and the assay solution for the assay under the aberrant condition has a glucose concentration in the range of about 0.05 mM to about 0.5 mM. The conditionally active polypeptide thus produced has a higher activity in a low glucose environment (in tumor microenvironment) than in a higher glucose environment (in normal tissues or blood). This conditionally active polypeptide will be functional in the tumor microenvironment but have a low activity in transit in the blood stream.

The normal physiological concentration of lactate in serum is in the range of about 1 mM to about 2 mM. On the other hand, lactate concentration is typically in the range of 10 mM to 20 mM in the tumor microenvironment. In one embodiment, the assay solution for the assay under the normal physiological condition has a lactate concentration in the range of about 1 mM to about 2 mM and the assay solution for the assay under the aberrant condition has a lactate concentration in the range of about 10 mM to about 20 mM. The conditionally active polypeptide thus produced has higher activity in a high lactate concentration environment (in tumor microenvironment) than in a lower lactate environment (in normal tissues or blood). This conditionally active polypeptide will thus be functional in the tumor microenvironment but have a low activity in transit in the blood stream.

Similarly, it is known that sore muscles have a higher (aberrant) concentration of lactate than normal. Thus, when seeking a mutant polypeptide that will be active in a sore muscle environment, the pair of assays at the aberrant condition can be conducted in the presence of a higher concentration of lactate to simulate the sore muscle environment, while the pair of assays at the normal physiological condition can be conducted with a lower concentration of, or in the absence of, lactate. In this manner, the mutant polypeptide can be selected for enhanced activity in a sore muscle environment with an increased lactate concentration. Such a conditionally active polypeptide may be useful as an anti-inflammatory agent, for example.

In another embodiment, two or more components may be used in both pairs of the assay solutions. In this type of assay, the conditionally active polypeptide may be selected using characteristics of both of the two types of assays described above. Alternatively, the selectivity of the conditionally active polypeptide can be increased using two or more components. For example, returning to the tumor microenvironment, the pair of assays at the aberrant condition can be conducted in assay media with both a high lactate concentration and a low glucose concentration while the corresponding pair of assays at the normal physiological condition can be conducted in an assay media with both a relatively lower lactate concentration and a relatively higher glucose concentration.

The present invention contemplates that each component selected from the inorganic compounds, ions, and organic molecules may be used alone or in combination to select a conditionally active polypeptide that is more active at one concentration of the component than at a different concentration of the same component.

Assays relying on different concentrations of one or more metabolites as the differentiating condition(s) between the normal environment (normal physiological condition) and the aberrant environment (aberrant condition) may be particularly suitable for selecting a conditionally active polypeptide that is more active in the tumor microenvironment than in blood plasma, because the tumor microenvironment typically has a significant number of metabolites that have different concentrations in comparison with the concentrations of the same metabolites in blood plasma.

Kinoshita et al., "Absolute Concentrations of Metabolites in Human Brain Tumors Using In Vitro Proton Magnetic Resonance Spectroscopy," *NMR IN BIOMEDICINE*, vol. 10, pp. 2-12, 1997, compared the metabolites in a normal brain and brain tumors. This group discovered that N-acetyl aspartate has a concentration of 5000-6000 µM in normal brain but the concentration is only 300-400 µM in glioblastoma, 1500-2000 µM in astrocytoma, and 600-1500 µM in anaplastic astrocytoma. Further, inositol has a concentration of 1500-2000 µM in a normal brain but the concentration is 2500-4000 µM in glioblastoma, 2700-4500 µM in astrocytoma, and 3800-5800 µM in anaplastic astrocytoma. Phosphorylethanolamine has a concentration of 900-1200 µM in a normal brain but the concentration is 2000-2800 µM in glioblastoma, 1170-1370 µM in astrocytoma, and 1500-2500 µM in anaplastic astrocytoma. Glycine has a concentration of 600-1100 µM in a normal brain but the concentration is 4500-5500 µM in glioblastoma, 750-1100 µM in astrocytoma, and 1900-3500 µM in anaplastic astrocytoma. Alanine has a concentration of 700-1150 µM in a normal brain but the concentration is 2900-3600 µM in glioblastoma, 800-1200 µM in astrocytoma, and 300-700 µM in anaplastic astrocytoma. These metabolites may also have different concentration in blood, for example, N-acetyl aspartate has a concentration of about 85000 µM in blood; inositol has a concentration of about 21700 µM in blood; glycine has a concentration of about 220-400 µM in blood; alanine has a concentration of about 220-300 µM in blood.

Therefore, these metabolites, including at least N-acetyl aspartate, inositol, glycine and alanine, may be used at different concentrations in the assay solutions to select conditionally active polypeptides that are active in brain tumors but not active in blood or normal brain tissue. For example, an assay solution with a concentration of 85000 µM of N-acetyl aspartate may be used for the pair of assays under a normal physiological condition and an assay solution with a concentration of 350 µM of N-acetyl aspartate may be used for the pair of assays under an aberrant condition to select conditionally active polypeptides that are active in the tumor microenvironment of glioblastoma, but not active or at least less active in blood or normal brain tissue.

Mayers et al., "Elevated circulating branched chain amino acids are an early event in pancreatic adenocarcinoma development," *Nature Medicine*, vol. 20, pp. 1193-1198, 2014, studied the concentrations of a variety of different metabolites including branched chain amino acids in prediagnostic blood plasma of pancreatic patients. It was found that in pancreatic tumor patients, there are several metabolites that are present in the bloodstream at different concentrations relative to the concentrations of the same metabolites in the blood of a human without pancreatic cancer. Mayers et al. also found that pancreatic cancer patients have significantly elevated branched amino acids in their blood plasma, in comparison with normal subjects. The branched amino acids that are present at elevated concentrations include isoleucine, leucine and valine (Table 1 of Mayers et al.). There are other metabolites shown in FIG. 1 of Mayers that are present at significantly different concentrations in the blood plasma of pancreatic cancer patients than in normal healthy humans. These metabolites include at least acetylglycine, glycine, phenylalanine, tyrosine, 2-aminoadipate, taurodeoxycholate/taurochenodeoxycholate, aconitate, isocitrate, lactate, a-glycerophosphate and urate. Thus, based on the findings that certain metabolites are present at different concentrations in the blood plasma of pancreatic cancer patients and normal healthy patients, it can be predicted that the tumor microenvironment of pancreatic cancer will also have different concentrations for these metabolites than would be present in the pancreatic microenvironment of a healthy patient.

Thus, in one embodiment, one or more of these metabolites may be used in the assay solution for the normal physiological condition in amounts that approximate the concentrations of these metabolites in the blood plasma in a healthy individual (i.e., normal physiological concentrations of the metabolites). For example, the known normal physiological concentrations in blood plasma of a healthy individual are about 1.60±0.31 mg/dL for isoleucine, about 1.91±0.34 mg/dL for leucine, and about 2.83±0.34 mg/dL for valine. The assay solution for the normal physiological condition may have normal physiological concentrations within these ranges of one or more of these branched amino acids. The assay solution for the aberrant condition may have the same branched amino acids at concentrations that are about 5 fold, or about 10 fold, or about 20 fold, or about 50 fold, or about 70 fold, or about 100 fold, or about 150 fold, or about 200 fold, or about 500 fold higher than the normal physiological concentrations in a healthy individual of the corresponding branched amino acids. This would reflect the fact that the pancreatic tumor microenvironment would be expected to have significantly elevated concentrations of these branched amino acids based on the findings of Mayers et al. since the higher concentrations of these branched amino acids found in the blood plasma detected by Mayers et al. originate from the tumor microenvironment and are diluted in the blood stream. Similarly, the assay under the aberrant condition may reflect the concentrations of other metabolites in the blood of a pancreatic cancer patient even if the concentrations of particular metabolites are significantly lower in the cancer patient than in the normal individual. In this manner, the screening can simulate the actual environment and thereby ensure the highest activity mutants for that particular environment are selected.

In some other embodiments, the assay solution for the normal physiological condition may comprise one or more branched amino acids at concentrations simulating concentrations in the blood plasma of pancreatic cancer patients to simulate the actual blood plasma environment for these patients. In such embodiments, the assay solution for the aberrant condition may have the same branched amino acids at concentrations that are about 2 fold, or about 3 fold, or about 4 fold, or about 5 fold, or about 7 fold, or about 8 fold, or about 10 fold, or about 15 fold, or about 20 fold, or about 50 fold higher than the concentrations of the corresponding branched amino acids in the blood plasma of pancreatic cancer patients to reflect the fact that these higher concentrations are originating in the tumor microenvironment and the concentrations in the blood stream represent a dilution of the actual concentrations of the tumor microenvironment. Similarly, other metabolites may also have different concentrations in the assay solutions for the normal physiological condition and aberrant condition to reflect actual differences expected from the data collected for the blood stream. In some instances, a deficiency of a particular metabolite may be noted in the blood stream of a pancreatic patient in which case a concentration reflecting the measured concentration in the blood stream can be used in the assay for the normal physiological condition, and an even lower concentration can be used in the assay for the aberrant condition to account for the expectation that said metabolite is likely being consumed in the tumor microenvironment. The conditionally active polypeptides thus selected using the assay solutions will be more active in the pancreatic cancer microenvironment than in the blood plasma of pancreatic cancer patients.

In some embodiments, the entire blood plasma of pancreatic cancer patients may be used in the present invention. For example, in one embodiment, a simulation of one or more components of the blood plasma of pancreatic cancer patient may be used in the assay solutions for one or both of assays under the normal physiological condition and the aberrant condition. In an exemplary embodiment, the assay solution for the normal physiological condition has a pH in the range of 7.2-7.6 and with 30 wt. % of blood plasma of a pancreatic cancer patient added and the assay solution for the aberrant condition has a pH in the range of 6.2-6.8 and with 30 wt. % of blood plasma of pancreatic cancer patient added. In this embodiment, the blood plasma of the pancreatic cancer patient is present to both (1) ensure that the conditionally active polypeptide is not activated in the blood at pH 7.2-7.6, and (2) also ensure that the conditionally active polypeptide can be activated by the pH 5.5-7.2, 6-7, or 6.2-6.8 in the tumor microenvironment even in the presence of this composition of metabolites that is found in the blood of the pancreatic cancer patient. This will tailor the treatment for a pancreatic cancer patient.

In another exemplary embodiment, the assay solution for the normal physiological condition has a pH in the range of 7.2-7.6 and with 30 wt. % of blood plasma of pancreatic cancer patient added and the assay solution for the aberrant condition has a pH in the range of 5.5-7.2 or 6.2-6.8 and without any blood plasma of pancreatic cancer patient added.

The same component selected from the inorganic compounds, ions, and organic molecules may be used in each of the several types of assays discussed above. For example, in the case of lactate the lactate may be used at substantially the same concentration in the pairs of assay solutions for both normal physiological condition and aberrant condition. The normal physiological condition and aberrant condition will then differ in one or more other aspects, such as temperature, pH, concentration of another component, etc. In a different embodiment, the lactate may be used as one of the differentiating factors between the normal physiological condition and aberrant condition to reflect the fact that the lactate has a higher concentration in an aberrant tumor microenvironment than in a normal physiological condition (a non-tumor microenvironment).

In some embodiments, the two or more components are added at substantially the same concentration to both assay solutions for normal physiological condition and aberrant condition. For example, both citrate and bovine serum albumin (BSA) are added to the assay solutions. The citrate concentration may be about 80 $\mu$M and the BSA concentration may be about 10-20% in both assay solutions. More specifically, the assay solution for the pair of assays under the normal physiological condition may have a pH in the range of 7.2-7.6, with citrate at a concentration of about 80 $\mu$M and BSA at a concentration about 10-20%. The assay solution for the pair of assays under the aberrant condition may have a pH in the range of 6.2-6.8, with citrate at a concentration of about 80 $\mu$M and BSA at a concentration about 10-20%.

In one embodiment, serum may be added to both assay solutions for normal physiological condition and aberrant condition at substantially the same concentration. Because the serum has a large number of inorganic compounds, ions, organic molecules (including polypeptides), the assay solutions will have multiple and large number of components selected from inorganic compounds, ions, organic molecules presented at substantially the same concentrations between the two assay solutions. The assay solutions may have 5 to 30 vol. %, or 7 to 25 vol. %, or 10 to 20 vol. %, or 10 to 15 vol. %, of serum. In some other embodiments, the assay solutions for both normal physiological condition and aberrant condition are free of serum. The serum may be human serum, bovine serum, or serum from any other mammals In some other embodiments, the assay solutions are free of serum.

The assay solutions for the normal physiological condition and aberrant condition may have different pHs. The pH of such assay solutions may be adjusted using $CO_2$ and $O_2$ levels in the buffer through use of bicarbonate.

In some other embodiments, at least one of the two or more components is added to the assay solutions for normal physiological condition and aberrant condition at different concentrations. For example, both lactate and bovine serum albumin (BSA) are added to the assay solutions. The lactate concentration may be different between the assay solutions for the normal physiological condition and aberrant condition, while the BSA may have the same concentration in both assay solutions. The lactate may have a concentration in the range of from 30 to 50 mg/dL in the assay solution for the aberrant condition and concentration in the range of from 8-15 mg/dL in the assay solution for the normal physiological condition. On the other hand, the BSA has the same concentration in both assay solutions, such as about 10-20%. The conditionally active polypeptide thus selected from using these assay solutions is more active at high lactate concentration at 30-50 mg/dL than at low lactate concentration at 8-15 mg/dL in the presence of BSA.

In some embodiments, the assay solutions may be designed for selecting conditionally active polypeptides with an activity dependent on two or more conditions. In one exemplary embodiment, the conditionally active polypeptide may have activity dependent on both pH and lactate. The assay solutions for selecting such a conditionally active polypeptide may be an assay solution for the normal physiological condition with pH at 7.2-7.6, lactate at a concentration in the range of from 8 to 15 mg/dL. The assay solution for the aberrant condition may have a pH at 6.2-6.8, lactate at a concentration in the range of from 30 to 50 mg/dL. Optionally the assay solutions for both normal physiological condition and aberrant condition may also comprise an ion to assist the binding between the mutant polypeptide and its binding partner, thus to increase the number of hits for candidate biologic active polypeptide.

In yet another exemplary embodiment, the conditionally active polypeptide may have activity dependent on pH, glucose and lactate. The assay solutions for selecting such a conditionally active polypeptide may be an assay solution for the normal physiological condition with pH at 7.2-7.6, glucose at a concentration in the range of 2.5-10 mM, lactate at a concentration in the range of from 8 to 15 mg/dL. The assay solution for the aberrant condition may be with pH at 6.2-6.8, glucose at a concentration in the range of 0.05 to 0.5 mM, lactate at a concentration in the range of from 30 to 50 mg/dL. Optionally the assay solutions for both normal physiological condition and aberrant condition may also comprise an ion to assist the binding between the mutant polypeptides and their binding partner, thus to increase the number of candidate biological active polypeptide binding to the binding partner at pH 6.2-6.8. The selected conditionally active polypeptide using such assay solutions is more active in an environment with pH 6.2-6.8, glucose concentration of 0.05 to 0.5 mM and lactate concentration of 30 to 50 mg/dL than in an environment with pH 7.2-7.6, glucose concentration of 2.5-10 mM and lactate concentration of 8 to 15 mg/dL.

The two or more components selected from inorganic compounds, ions, and organic molecules are for making an assay solution for the aberrant condition that simulates the environment at the location/site to which the selected conditionally active polypeptide will be delivered (i.e., targeted site). In some embodiments, at least three components presented in the environment at the targeted site may be added to the assay solution, or at least four components presented in the environment at the targeted site may be added to the assay solution, or at least five components presented in the environment at the targeted site may be added to the assay solution, or at least six components presented in the environment at the targeted site may be added to the assay solution.

In one embodiment, a fluid retrieved from the targeted site (where the conditionally active polypeptide will be more active) may be directly used as the assay solution for the assay under the aberrant condition. For example, synovial fluid may be retrieved from a subject, preferably from a subject with joint disease in need of treatment. The retrieved synovial fluid, optionally diluted, may be used as an assay solution in the pair of assays at the aberrant condition to select the conditionally active polypeptide. By using the retrieved synovial fluid, optionally diluted, as the assay solution for the assay under the aberrant condition, and an assay solution that simulates human blood plasma for the assay under the normal physiological condition, the conditionally active polypeptide (e.g., TNF-alpha) that is selected will be more active at the joint than at other locations or organs. For example, subjects with inflammatory joints (such as arthritis) may be treated with TNF-alpha. However, TNF-alpha typically has severe side effects of damaging other tissues and organs. A conditionally active TNF-alpha that is more active in the synovial fluid but not active or less active in blood will deliver the activity of TNF-alpha to the joints while reducing or potentially eliminating the side effects of the TNF-alpha on the rest of the body.

The development of conditionally active polypeptide that has an activity dependent on multiple conditions will result in improved selectivity of the conditionally active polypeptide to a target site in the body of a subject. Ideally, at other locations with only some of the conditions present the conditionally active polypeptide is not active or at least significantly less active. In one embodiment, the conditionally active polypeptide that is active at pH 6.2-6.8, glucose concentration of 0.05 to 0.5 mM and lactate concentration of 30 to 50 mg/dL can be specifically delivered to a tumor microenvironment because these conditions are all present in the tumor microenvironment. Other tissues or organs may have one or two of these conditions present but not all three, thus not be sufficient to fully activate the conditionally active polypeptide in the other tissues or organs. For example, the exercised muscle may have a low pH in the range of 6.2-6.8. However, it may not have another assayed condition. Thus the conditionally active polypeptide is not active or at least less active in the exercised muscle.

In some embodiments, steps may be taken to confirm that the activity of the conditionally active polypeptide is truly dependent on the conditions used to select the conditionally active polypeptide. For example, the conditionally active polypeptide is selected to be dependent on three conditions: pH 6.2-6.8, glucose concentration of 0.05 to 0.5 mM and lactate concentration of 30 to 50 mg/dL. The selected conditionally active polypeptide may then be tested at each of the three conditions individually and in environments with pairs of the three conditions to confirm that the conditionally active polypeptide is not active or less active in these test conditions or environments.

In some embodiments, certain components of serum may be purposely minimized or omitted from the assay media. For example, when screening antibodies, components of serum that bind with or adsorb antibodies can be minimized in or omitted from the assay media. Such bound antibodies may give false positives thereby including bound mutant antibodies that are not conditionally active but rather are merely bound to a component present in serum under a variety of different conditions. Thus, careful selection of assay components to minimize or omit components that can potentially bind with mutants in the assay can be used to reduce the number of non-functional mutants that may be inadvertently identified as positive for conditional activity due to binding to a component in the assay other than the desired binding partner. For example, in some embodiments where mutant polypeptides with a propensity to bond with components in human serum are being screened, BSA may be used in the assay solution in order to reduce or eliminate the possibility of false positives caused by mutant polypeptides bonding to components of human serum. Other similar replacements can also be made in particular cases to achieve the same goal.

In some embodiments, the assay conditions simulate the environment in the vicinity of a cell membrane such as inside, at or outside the cell membrane, or the environment in a joint. Some factors that may affect binding activities when screening in a cell membrane environment include expression of receptors, internalization, antibody drug complex (ADC) potency, etc.

The format of assays may be any suitable assays known to a person skilled in the art. Examples include ELISA, enzymatic activity assay, real tissue screening in vitro (organs, etc), tissue slides, whole animal, cell lines and use of 3D systems. For example, suitable cell-based assays are described in WO 2013/040445, tissue based assays are described in U.S. Pat. No. 7,993,271, whole animal based screening methods are described in US 2010/0263599, 3D system based screening methods are described in US 2011/0143960.

In some embodiments, the evolving step may produce mutant polypeptides that may simultaneously have other desired properties besides the conditionally active characteristics discussed above. Suitable other desired properties that may be evolved may include binding activity, expression, humanization, etc. Therefore, the present invention may be employed to produce a conditionally active polypeptide that also has an improvement in at least one or more of these other desired properties. Selection step(s) can be employed to select for both the conditional activity and for one or more other desired properties of the mutant polypeptides.

In some embodiments, the present invention produces the conditionally active polypeptide. The selected conditionally active polypeptide may be further mutated using one of the mutagenesis techniques disclosed herein in, for example, a second evolving step, to improve another property of the selected conditionally active polypeptide such as binding activity, expression, humanization, etc. After the second evolving step, the mutant polypeptides may be screened for both the conditional activity and the improved property.

In some embodiments, after evolving the parent polypeptide to produce mutant polypeptides, a first conditionally active polypeptide is selected, which exhibits both: (a) a decrease in a first activity in an assay under the normal physiological condition compared to the parent polypeptide, and (b) an increase in the first activity in the assay under an aberrant condition compared to the parent polypeptide. The first conditionally active polypeptide may then be further subjected to one or more additional evolving, expressing and selecting steps to select at least a second conditionally active polypeptide that (1) exhibits both: (a) a decrease in a second activity in an assay under the normal physiological condition compared to the parent, and (b) an increase in the second activity in the assay under an aberrant condition compared to the parent polypeptide, or (2) a larger ratio between the first activity at the aberrant condition and the first activity at the normal physiological condition, in comparison with the first conditionally active polypeptide and/or the parent polypeptide. Note that the second conditionally active polypeptide may have both of the first activity and second activity higher under the aberrant condition in comparison with the parent polypeptide, as well as the first activity and second activity lower under the normal physiological condition in comparison with the parent polypeptide.

In some aspects, the expression step is performed in a eukaryotic cell production host. The host may be 3T3 mouse fibroblast cells; BHK21 Syrian hamster fibroblast cells; MDCK, dog epithelial cells; Hela human epithelial cells; PtK1 rat kangaroo epithelial cells; SP2/0 mouse plasma cells; and NS0 mouse plasma cells; HEK 293 human embryonic kidney cells; COS monkey kidney cells; CHO, CHO-S Chinese hamster ovary cells; R1 mouse embryonic cells; E14.1 mouse embryonic cells; H1 human embryonic cells; H9 human embryonic cells; PER C.6, human embryonic cells; *S. cerevisiae* yeast cells; and pichia yeast cells. The selected conditionally active polypeptide may then be produced in large quantity in the same eukaryotic cell production host. By using the same eukaryotic cell production host in both expressing step and for the final production, higher expression level may be achieved for the conditionally active polypeptide.

In certain embodiments, the present invention is aimed at producing conditionally active polypeptides with a large activity ratio of the activity at the aberrant condition (or the second condition) and the activity at the normal physiological condition (or the first condition) (e.g., a larger selectivity between the aberrant and normal physiological conditions). The ratio, or selectivity, of the activity at the aberrant condition (or the second condition) and the activity at the normal physiological condition (or the first condition) may be at least about 2:1, or at least about 3:1, or at least about 4:1, or at least about 5:1, or at least about 6:1, or at least about 7:1, or at least about 8:1, or at least about 9:1, or at least about 10:1, or at least about 11:1, or at least about 12:1, or at least about 13:1, or at least about 14:1, or at least about 15:1, or at least about 16:1, or at least about 17:1, or at least about 18:1, or at least about 19:1, or at least about 20:1, or at least about 30:1, or at least about 40:1, or at least about 50:1, or at least about 60:1, or at least about 70:1, or at least about 80:1, or at least about 90:1, or at least about 100:1.

In one embodiment, conditionally active polypeptide is an antibody, which may have a ratio between the activity at the aberrant condition and the activity at the normal physiological condition of at least about 5:1, or at least about 6:1, or at least about 7:1, or at least about 8:1, or at least about 9:1, or at least about 10:1, or at least about 15:1, or at least about 20:1, or at least about 40:1, or at least about 80:1. In one embodiment, the conditionally active polypeptide is used to target a tumor site where the conditionally active polypeptide is active at the tumor site (in tumor microenvironment) and significantly less active or inactive at a non-tumor site (normal physiological condition).

In one embodiment, the conditionally active polypeptide is an antibody that is intended to be conjugated with another agent such as those disclosed elsewhere herein. The conditionally active antibody may have a higher ratio of the activity at the aberrant condition and the activity at the normal physiological condition. For example, the conditionally active antibody that is to be conjugated with another agent may have a ratio of the activity at the aberrant condition to the activity at the normal physiological condition of at least about 10:1, or at least about 11:1, or at least about 12:1, or at least about 13:1, or at least about 14:1, or at least about 15:1, or at least about 16:1, or at least about 17:1, or at least about 18:1, or at least about 19:1, or at least about 20:1. This may be particularly important when the conjugated agent is, for example, toxic or radioactive, since such a conjugated agent is desirably concentrated at the disease or treatment site (where the aberrant condition is present).

E. Production of the Conditionally Active Polypeptides

The selected conditionally active polypeptides, with reversible or irreversible activity, may be produced for therapeutic, diagnostic, research and related purposes, and/or can be subjected to one or more additional cycles of evolving and selecting.

The conditionally active polypeptides may be produced using a polypeptide expression cell production host or an organism. To make the production process more efficient, the DNA encoding the conditionally active polypeptide may undergo codon optimization for the cell production host or organism. Codon optimization has been described previously, such as Narum et al., "Codon optimization of gene fragments encoding Plasmodium falciparum merozoite proteins enhances DNA vaccine protein expression and immunogenicity in mice," *Infect. Immun.* 2001 December, 69(12): 7250-3, which describes codon-optimization in the mouse system; Outchkourov et al., "Optimization of the expression of Equistatin in *Pichia pastoris*, protein expression and purification," *Protein Expr. Purif.* 2002 February; 24(1): 18-24, which describes codon-optimization in the yeast system; Feng et al., "High level expression and mutagenesis of recombinant human phosphatidylcholine transfer protein using a synthetic gene: evidence for a C-terminal membrane binding domain" *Biochemistry* 2000 Dec. 19, 39(50): 15399-409, which describes codon-optimization in *E. coli*; Humphreys et al., "High-level periplasmic expression in *Escherichia coli* using a eukaryotic signal peptide: importance of codon usage at the 5' end of the coding sequence", *Protein Expr. Purif.* 2000 Nov. 20(2):252-64, which describes how codon usage affects protein secretion in *E. coli*.

The cell production host may be a mammalian system selected from one of the group consisting of CHO, HEK293, IM9, DS-I, THP-I, Hep G2, COS, NIH 3T3, C33a, A549, A375, SK-MEL-28, DU 145, PC-3, HCT 116, Mia PACA-2, ACHN, Jurkat, MM1, Ovcar 3, HT 1080, Panc-1, U266, 769P, BT-474, Caco-2, HCC 1954, MDA-MB-468, LnCAP, NRK-49F, and SP2/0 cell lines; and mouse splenocytes and rabbit PBMC. In one embodiment, the mammalian system is selected from a CHO or HEK293 cell line. In one specific aspect, the mammalian system is a CHO-S cell line. In another embodiment, the mammalian system is a HEK293 cell line.

In some embodiments, the cell production host is a yeast cell system, for example *S. cerevisiae* yeast cells or pichia yeast cells. In some embodiments, the cell production host is prokaryotic cells such as *E. coli* (Owens R J and Young R J, *J. Immunol. Meth.*, vol. 168, p. 149, 1994; Johnson S and Bird R E, *Methods Enzymol.*, vol. 203, p. 88, 1991). The conditionally active polypeptide may also be produced in plants (Firek et al. *Plant Mol. Biol.*, vol. 23, p. 861, 1993).

The conditionally active polypeptides may also be produced by synthetic methods, using chemical methods well known in the art. See e.g., Caruthers, "New chemical methods for synthesizing polynucleotides," *Nucleic Acids Res. Symp. Ser.* 215-223, 1980; Horn, "Synthesis of oligonucleotides on cellulose. Part II: design and synthetic strategy to the synthesis of 22 oligodeoxynucleotides coding for Gastric Inhibitory Polypeptide (GIP)," *Nucleic Acids Res. Symp. Ser.* 225-232, 1980; Banga, A. K., Therapeutic Peptides and Proteins, Formulation, Processing and Delivery Systems, Technomic Publishing Co., Lancaster, Pa., 1995. For example, peptide synthesis can be performed using various solid-phase techniques (see e.g., Roberge, "A strategy for a convergent synthesis of N-linked glycopeptides on a solid support", *Science* 269:202, 1995; Merrifield, "Concept and early development of solid-phase peptide synthesis", *Methods Enzymol.* 289:3-13, 1997) and automated synthesis may be achieved, e.g., using the ABI 43 IA Peptide Synthesizer (Perkin Elmer) in accordance with the instructions provided by the manufacturer.

Solid-phase chemical peptide synthesis methods have been known in the art since the early 1960's (Merrifield, R. B., "Solid-phase synthesis I. The synthesis of a tetrapeptide", *J. Am. Chem. Soc,* 85:2149-2154, 1963) (See also Stewart, J. M. and Young, J. D., Solid Phase Peptide Synthesis, 2nd Ed., Pierce Chemical Co., Rockford, 111., pp. 11-12)) and have recently been employed in commercially available laboratory peptide design and synthesis kits (Cambridge Research Biochemicals). Such commercially available laboratory kits have generally utilized the teachings of H. M. Geysen et al., "Use of peptide synthesis to probe viral antigens for epitopes to a resolution of a single amino acid," *Proc. Natl. Acad. Sci., USA,* 81:3998, 1984 and provide for synthesizing peptides upon the tips of a multitude of "rods" or "pins" all of which are connected to a single plate. When such a system is utilized, a plate of rods or pins is inverted and inserted into a second plate of corresponding wells or reservoirs, which contain solutions for attaching or anchoring an appropriate amino acid to the pin's or rod's tips. By repeating such a process step, i.e., inverting and inserting the rod's and pin's tips into appropriate solutions, amino acids are built into desired peptides. In addition, a number of available FMOC peptide synthesis systems are available. For example, assembly of a polypeptide or fragment can be carried out on a solid support using an Applied Biosystems, Inc. Model 431 A™ automated peptide synthesizer. Such equipment provides ready access to the peptides of the disclosure, either by direct synthesis or by synthesis of a series of fragments that can be coupled using other known techniques.

The conditionally active polypeptides can also be glycosylated. The glycosylation can be added post-translationally, either chemically or by cellular biosynthetic mechanisms, wherein the latter incorporates the use of known glycosylation motifs, which can be native to the sequence or can be added as a peptide or added in the nucleic acid coding sequence. The glycosylation can be O-linked or N-linked.

The conditionally active polypeptides include all "mimetic" and "peptidomimetic" forms. The terms "mimetic" and "peptidomimetic" refer to a synthetic chemical compound which has substantially the same structural and/or functional characteristics of the polypeptides of the disclosure. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. As with polypeptides of the disclosure which are conservative variants, routine experimentation will determine whether a mimetic is within the scope of the disclosure, i.e., that its structure and/or function is not substantially altered.

Polypeptide mimetic compositions of the disclosure can contain any combination of non-natural structural components. In alternative aspect, mimetic compositions of the disclosure include one or all of the following three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. For example, a polypeptide of the disclosure can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —(C=O)CH$_2$— for —(C=O)—NH—), aminomethylene (CH$_2$—NH), ethylene, olefin (CH=CH), ether (CH$_2$—O), thioether (CH$_2$—S), tetrazole (CN$_4$—), thiazole, retroamide, thioamide, or ester (see, e.g., Spatola (1983) in Chemistry and Biochemistry of Amino Acids, Peptides and Proteins, Vol. 7, pp 267-357, "Peptide Backbone Modifications," Marcell Dekker, N. Y.).

A polypeptide of the disclosure can also be characterized as a mimetic by containing all or some non-natural residues in place of naturally occurring amino acid residues. Non-natural residues are well described in the scientific and patent literature; a few exemplary non-natural compositions useful as mimetics of natural amino acid residues and guidelines are described below. Mimetics of aromatic amino acids can be generated by replacing by, e.g., D- or L-naphylalanine; D- or L-phenylglycine; D- or L-2 thieneylalanine; D- or L-1,-2, 3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluorophenylalanine; D- or L-p-biphenylphenylalanine; D- or L-p-methoxy-biphenylphenylalanine; D- or L-2-indole(alkyl) alanines; and, D- or L-alkylanines, where alkyl can be substituted or unsubstituted methyl, ethyl, propyl, hexyl, butyl, pentyl, isopropyl, iso-butyl, sec-isotyl, iso-pentyl, or a non-acidic amino acids. Aromatic rings of a non-natural amino acid include, e.g., thiazolyl, thiophenyl, pyrazolyl, benzimidazolyl, naphthyl, furanyl, pyrrolyl, and pyridyl aromatic rings.

Mimetics of acidic amino acids can be generated by substitution by, e.g., non-carboxylate amino acids while maintaining a negative charge; (phosphono) alanine; sulfated threonine. Carboxyl side groups (e.g., aspartyl or glutamyl) can also be selectively modified by reaction with carbodiimides (R'~N—C—N—R') such as, e.g., 1-cyclohexyl-3(2-moφpholinyl-(4-ethyl) carbodiimide or 1-ethyl3 (4-azonia-4, 4-dimetholpentyl) carbodiimide Aspartyl or glutamyl can also be converted to asparaginyl and glutaminyl residues by reaction with ammonium ions. Mimetics of basic amino acids can be generated by substitution with, e.g., (in addition to lysine and arginine) the amino acids ornithine, citrulline, or (guanidino)-acetic acid, or (guanidino)alkyl-acetic acid, where alkyl is defined above. Nitrile derivative (e.g., containing the CN-moiety in place of COOH) can be substituted for asparagine or glutamine. Asparaginyl and glutaminyl residues can be deaminated to the corresponding aspartyl or glutamyl residues. Arginine residue mimetics can be generated by reacting arginyl with, e.g., one or more conventional reagents, including, e.g., phenylglyoxal, 2,3-butanedione, 1,2-cyclo-hexanedione, or ninhydrin, preferably under alkaline conditions. Tyrosine residue mimetics can be generated by reacting tyrosyl with, e.g., aromatic diazonium compounds or tetranitromethane. N-acetylimidizol and tetranitromethane can be used to form O-acetyl tyrosyl species and 3-nitro derivatives, respectively. Cysteine residue mimetics can be generated by reacting cysteinyl residues with, e.g., alpha-haloacetates such as 2-chloroacetic acid or chloroacetamide and corresponding amines; to give carboxymethyl or carboxyamidomethyl derivatives. Cysteine residue mimetics can also be generated by reacting cysteinyl residues with, e.g., bromo-trifluoroacetone, alpha-bromo-beta-(5-imidozoyl) propionic acid; chloroacetyl phosphate, N-alkylmaleimides, 3-nitro-2-pyridyl disulfide; methyl 2-pyridyl disulfide; p-chloromercuribenzoate; 2-chloromercuri-4 nitrophenol; or, chloro-7-nitrobenzo-oxa-1,3-diazole. Lysine mimetics can be generated (and amino terminal residues can be altered) by reacting lysinyl with, e.g., succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitrobenzenesulfonic acid, O-methylisourea, 2,4, pentanedione, and transamidase-catalyzed reactions with glyoxylate. Mimetics of methionine can be generated by reaction with, e.g., methionine sulfoxide. Mimetics of proline include, e.g., pipecolic acid, thiazolidine carboxylic acid, 3- or 4-hydroxy proline, dehydroproline, 3- or 4-methylproline, or 3,3,-dimethylproline. Histidine residue mimetics can be generated by reacting histidyl with, e.g., diethylprocarbonate or para-bromophenacyl bromide. Other mimetics include, e.g., those generated by hydroxylation of proline and lysine; phosphorylation of the hydroxyl groups of seryl or threonyl residues; methylation of the alpha-amino groups of lysine, arginine and histidine; acetylation of the N-terminal amine; methylation of main chain amide residues or substitution with N-methyl amino acids; or amidation of C-terminal carboxyl groups.

A residue, e.g., an amino acid, of a polypeptide of the disclosure can also be replaced by an amino acid (or peptidomimetic residue) of the opposite chirality. Thus, any amino acid naturally occurring in the L-configuration (which can also be referred to as the R or S, depending upon the structure of the chemical entity) can be replaced with the amino acid of the same chemical structural type or a peptidomimetic, but of the opposite chirality, referred to as the D-amino acid, but also can be referred to as the R- or S-form.

The disclosure also provides methods for modifying the conditionally active polypeptides by either natural processes, such as post-translational processing (e.g., phosphorylation, acylation, etc.), or by chemical modification techniques. Modifications can occur anywhere in the polypeptide, including the peptide backbone, the amino acid side-chains and the amino or carboxyl termini. It will be appreciated that the same type of modification may be present in the same or varying degrees at several sites in a given polypeptide. Also a given polypeptide may have many types of modifications. Modifications include acetylation, acylation, PEGylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of a phosphatidylinositol, cross-linking cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristolyation, oxidation, pegylation, proteolytic processing, phosphorylation, prenylation, racemization, selenoylation, sulfation, and transfer-RNA mediated addition of amino acids to a protein such as arginylation. See, e.g., Creighton, T. E., a s-Structure and Molecular Properties 2nd Ed., W. H. Freeman and Company, New York (1993); Posttranslational Covalent Modification of Proteins, B. C. Johnson, Ed., Academic Press, New York, pp. 1-12 (1983).

F. Pharmaceutical Compositions

The selected conditionally active polypeptides, or the products engineered from the conditionally active polypeptides, may be used in pharmaceutical compositions. In one aspect, these conditionally active polypeptides or engineered conditionally active polypeptides are commercially produced using one of the methods disclosed herein. Some suitable pharmaceutical compositions are described in U.S. Pat. No. 8,709,755 B2.

The pharmaceutical compositions may be used to treat various types of cancers including carcinoma, blastoma, and sarcoma, and certain leukemia or lymphoid malignancies, benign and malignant tumors, and malignancies e.g., sarcomas, carcinomas, and melanomas. The cancers may be non-solid tumors (such as hematological tumors) or solid tumors. Adult tumors/cancers and pediatric tumors/cancers are also included.

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors that may be treated include sarcomas and carcinomas, including fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

The conditionally active polypeptide may also be used to remove senescent cells from a subject. Senescent cells include cells that are characterized by having an essentially permanent growth arrest. Senescent cells are essentially unresponsive to proliferation-cues. The phenomenon of senescence can occur at the end of the proliferative lifespan of normal cells or in normal or tumor cells in response to, for example, chemotherapeutic agents, radiation, DNA damage or other cellular insults. It is described in the art that senescent cells are withdrawn from the cell cycle through independent activity of p53-p21ciP1 or p 16ink4a, each of which is described as individually sufficient for inducing and maintaining the non-proliferative state (Rodier et al., *J Cell Biol* 192:547-556 (2011)).

There are many diseases or conditions wherein the removal of senescent cells is beneficial. Such diseases or conditions may include cancer, preferably melanoma, more preferably metastatic melanoma, chronic inflammatory diseases or neurological diseases such as Alzheimer's disease or Parkinson's disease. Other diseases include atherosclerosis, chronic inflammatory diseases such as arthritis or athrosis, cancer, osteoarthritis, diabetes, diabetic ulcers, kyphosis, scoleosis, hepatic insufficiency, cirrhosis, Hutchinson-Gilford progeria syndrome (HGPS), laminopaties, osteoporosis, dementia, (cardio)vascular diseases, obesity, metabolic syndrome, acute myocardial infarction, emphysema, insulin sensitivity, boutonneuse fever, sarcopenia, neurodegenerative diseases such as Alzheimer's, Huntington's or Parkinson's disease, cataracts, anemia, hypertension, fibrosis, age-related macular degeneration, COPD, asthma, renal insufficiency, incontinence, hearing loss such as deafness, vision loss such as blindness, sleeping disturbances, pain such as joint pain or leg pain, imbalance, fear, depression, breathlessness, weight loss, hair loss, muscle loss, loss of bone density, frailty and/or reduced fitness.

The pharmaceutical compositions including the conditionally active polypeptides, or the products engineered from the conditionally active polypeptides, can be formulated according to known methods for preparing pharmaceutical compositions. In such methods, the conditionally active polypeptides are typically combined with a mixture, solution or composition containing a pharmaceutically acceptable carrier.

A pharmaceutically acceptable carrier is a material that can be tolerated by a recipient patient. Sterile phosphate-buffered saline is one example of a pharmaceutically acceptable carrier. Other suitable pharmaceutically acceptable carriers are well-known to those in the art. (See, e.g., Gennaro (ed.), Remington's Pharmaceutical Sciences (Mack Publishing Company, 19th ed. 1995)) Formulations may further include one or more excipients, preservatives, solubilizers, buffering agents, albumin to prevent protein loss on vial surfaces, etc.

The form of the pharmaceutical compositions, the route of administration, the dosage and the regimen naturally depend upon the condition to be treated, the severity of the illness, the age, weight, and sex of the patient, etc. These considerations can be taken into account by a skilled person to formulate suitable pharmaceutical compositions. The pharmaceutical compositions of the invention can be formulated for topical, oral, parenteral, intranasal, intravenous, intramuscular, subcutaneous or intraocular administration and the like.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition of, for example, sterilized water or physiological saline, permit the constitution of injectable solutions.

In some embodiments, tonicity agents, sometimes known as "stabilizers" are present to adjust or maintain the tonicity of a liquid in a composition. When used with large, charged biomolecules such as proteins and antibodies, they are often termed "stabilizers" because they can interact with the charged groups of the amino acid side chains, thereby lessening the potential for inter- and intra-molecular interactions. Tonicity agents can be present in any amount of from 0.1% to 25% by weight, preferably 1 to 5% of the pharmaceutical composition. Preferred tonicity agents include polyhydric sugar alcohols, preferably trihydric or higher sugar alcohols, such as glycerin, erythritol, arabitol, xylitol, sorbitol and mannitol.

Additional excipients include agents which can serve as one or more of the following: (1) bulking agents, (2) solubility enhancers, (3) stabilizers and (4) and agents preventing denaturation or adherence to the container wall. Such excipients may include: polyhydric sugar alcohols (enumerated above); amino acids such as alanine, glycine, glutamine, asparagine, histidine, arginine, lysine, ornithine, leucine, 2-phenylalanine, glutamic acid, threonine, etc.; organic sugars or sugar alcohols such as sucrose, lactose, lactitol, trehalose, stachyose, mannose, sorbose, xylose, ribose, ribitol, myoinisitose, myoinisitol, galactose, galactitol, glycerol, cyclitols (e.g., inositol), polyethylene glycol; sulfur containing reducing agents, such as urea, glutathione, thioctic acid, sodium thioglycolate, thioglycerol, α-monothioglycerol and sodium thio sulfate; low molecular weight proteins such as human serum albumin, bovine serum albumin, gelatin or other immunoglobulins; hydrophilic polymers such as polyvinylpyrrolidone; monosaccharides (e.g., xylose, mannose, fructose, glucose; disaccharides (e.g., lactose, maltose, sucrose); trisaccharides such as raffinose; and polysaccharides such as dextrin or dextran.

Non-ionic surfactants or detergents (also known as "wetting agents") may be employed to help solubilize the therapeutic agent as well as to protect the therapeutic protein against agitation-induced aggregation, which also permits the formulation to be exposed to shear surface stress without causing denaturation of the active therapeutic protein or antibody. Non-ionic surfactants may be present in a concentration range of about 0.05 mg/ml to about 1.0 mg/ml, preferably about 0.07 mg/ml to about 0.2 mg/ml.

Suitable non-ionic surfactants include polysorbates (20, 40, 60, 65, 80, etc.), polyoxamers (184, 188, etc.), PLURONIC® polyols, TRITON®, polyoxyethylene sorbitan monoethers (TWEEN®-20, TWEEN®-80, etc.), lauromacrogol 400, polyoxyl 40 stearate, polyoxyethylene hydrogenated castor oil 10, 50 and 60, glycerol monostearate, sucrose fatty acid ester, methyl celluose and carboxymethyl cellulose. Anionic detergents that can be used include sodium lauryl sulfate, dioctyle sodium sulfosuccinate and dioctyl sodium sulfonate. Cationic detergents include benzalkonium chloride or benzethonium chloride.

In one aspect, the conditionally active polypeptide may be used in a pharmaceutical composition with one or more anti-cancer agents for the treatment of cancers. For example, the anti-cancer agents may be a chemotherapeutic agent, a radiation therapeutic agent, a hormonal therapeutic agent, a toxin, or an immunotherapeutic agent. The anti-cancer agent may be selected from any known anti-cancer agent including, but not limited to, a taxane, a maytansinoid, an auristatin, a duocarmycin, monomethyl auristatin E MMAE), a soporific agent, a duomycin, a calicheamicin, an anthracycline, a CC-1065 analog, docetaxel, a cathepsin, ricin, gelonin, Pseudomonas exotoxin, diphtheria toxin, RNase, and a toxic radioisotope.

In another aspect, the conditionally active polypeptide may be conjugated to the anti-cancer agent. The conjugation may be covalently link the anti-cancer agent with the conditionally active polypeptide. In some cases, the conjugation may be non-covalent, such as ionic bonds between the anti-cancer agent and the conditionally active polypeptide.

The ratio of the molecules of the anti-cancer agent conjugated to the molecules conditionally active polypeptide of up to 3:1, or 4:1, or 5:1, or 6:1. In one example the ratio of anti-cancer agent to the conditionally active polypeptide is about 4:1.

The doses used for the administration can be adapted as a function of various parameters, and in particular as a function of the mode of administration used, of the relevant pathology, or alternatively of the desired duration of treatment. To prepare pharmaceutical compositions, an effective amount of the conditionally active polypeptides, or the products further engineered from the conditionally active polypeptides, may be dissolved or dispersed in a pharmaceutically acceptable carrier or aqueous medium.

The pharmaceutical formulations suitable for injectable use include sterile aqueous solutions or dispersions; carriers such as sesame oil, peanut oil or aqueous propylene glycol; and sterile powders for the extemporaneous preparation of sterile injectable solutions or dispersions. In all cases, the formulations must be sterile and must be fluid to the extent that easy syringability exists. It must be stable under the conditions of manufacture and storage and must be preserved against the contaminating action of microorganisms, such as bacteria and fungi.

Solutions of the conditionally active polypeptides as free base or pharmacologically acceptable salts can be prepared in a water suitably mixed with a surfactant. Dispersions can also be prepared in glycerol, liquid polyethylene glycols, and mixtures thereof and in oils. Under ordinary conditions of storage and use, these preparations contain a preservative to prevent the growth of microorganisms.

The conditionally active polypeptides and the products engineered from the conditionally active polypeptides can be formulated into a composition in a salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the conditionally active polypeptides in the required amount in the appropriate solvent with one or more of the other ingredients enumerated above, as may be required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly concentrated solutions for direct injection is also contemplated, where the use of dimethyl sulfoxide (DMSO) as solvent is envisioned to result in extremely rapid penetration, delivering high concentrations of the active agents to a small tumor area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

The conditionally active polypeptides and the products engineered from the conditionally active polypeptides may be formulated within a therapeutic mixture to deliver about 0.0001 to 10.0 milligrams, or about 0.001 to 5 milligrams, or about 0.001 to 1 milligrams, or about 0.001 to 0.1 milligrams, or about 0.1 to 1.0 or even about 10 milligrams per dose. Multiple doses can also be administered at selected time intervals.

In some embodiments, the upper limit for the dosage of the conditionally active polypeptide for treating the diseases and conditions disclosed in this application is 2.0 µg/ml of body fluid, or, more preferably, 1.11 µg/ml of body fluid of the subject.

In addition to the compounds formulated for parenteral administration, such as intravenous or intramuscular injection, other pharmaceutically acceptable forms include, e.g. tablets or other solids for oral administration; time release capsules; and any other form currently used.

In certain embodiments, the use of liposomes and/or nanoparticles is contemplated for the introduction of the conditionally active polypeptides, or the products further engineered from the conditionally active polypeptides, into host cells. The formation and use of liposomes and/or nanoparticles are known to those of skill in the art.

Nanocapsules can generally entrap compounds in a stable and reproducible way. To avoid side effects due to intracellular polymeric overloading, such ultrafine particles (sized around 0.1 µm) are generally designed using polymers able to degrade in vivo. Biodegradable polyalkyl-cyanoacrylate nanoparticles that meet these requirements are contemplated for use in the present invention.

Liposomes are formed from phospholipids that are dispersed in an aqueous medium and spontaneously form multilamellar concentric bilayer vesicles (also termed multilamellar vesicles (MLVs)). MLVs generally have diameters of from 25 nm to 4 µm. Sonication of MLVs results in the formation of small unilamellar vesicles (SUVs) with diameters in the range of 200 to 500 Å, containing an aqueous solution in the core. The physical characteristics of liposomes depend on pH, ionic strength and the presence of divalent cations Pharmaceutical formulations containing the conditionally active polypeptides, or the products engineered from the conditionally active polypeptides, as described herein are prepared by mixing with one or more optional pharmaceutically acceptable carriers (Remington's Pharmaceutical Sciences 16th edition, Osol, A. Ed. (1980)), in the form of lyophilized formulations or aqueous solutions. Pharmaceutically acceptable carriers include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171, 586 and WO2006/044908, the latter formulations including a histidine-acetate buffer.

The formulation herein may also contain more than one active ingredient as necessary for the particular indication being treated. Preferably, ingredients with complementary activities that do not adversely affect each other may be combined into a single formulation. For example, it may be desirable to provide an EGFR antagonist (such as erlotinib), an anti-angiogenic agent (such as a VEGF antagonist which may be an anti-VEGF antibody) or a chemotherapeutic agent (such as a taxoid or a platinum agent) in addition to the conditionally active antibody, antibody fragment or immunoconjugate of the present invention. Such active ingredients are suitably present in combination in amounts that are effective for the purpose intended.

Active ingredients may be encapsulated in microcapsules prepared, for example, by coacervation techniques or by interfacial polymerization. For example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions may be employed. Such techniques are disclosed in Remington's Pharmaceutical Sciences 16th edition, Osol, A. Ed. (1980).

Sustained-release preparations may also be prepared. Suitable examples of sustained-release preparations include semipermeable matrices of solid hydrophobic polymers containing the antibody or antibody fragment, which matrices may be in the form of shaped articles, e.g. films, or microcapsules.

In one aspect, two or more conditionally active polypeptides of the disclosure may be used simultaneously or sequentially in treatment of subject. Such treatment method may dramatically reduce toxicity.

In another aspect, the conditionally active polypeptide has an immunomodulatory activity that is suitable for combinatory therapies. For example, such conditionally active polypeptide may be used in combination with a prodrug.

In another aspect, the conditionally active polypeptide may itself have prodrug activity.

In yet another aspect, the conditionally active polypeptide may be used in diagnosing of cancer in a subject. The conditionally active polypeptide may be exposed to cells or tissue of the subject, where the conditionally active polypeptide binds to a target on cancer cells. The binding of the conditionally active polypeptide to the cancer cells can be determined when the conditionally active polypeptide is labeled. The labels may be a radioactive agent or a fluorophore, such as phycoerythrin or fluorescein isothiocyanate (also known as fluoroisothiocyanate or FITC). The contacting of the cells or tissue with the conditionally active polypeptide occurs in vitro or in side of the body of the subject.

In some embodiments, the conditionally active polypeptides, or the products engineered from the conditionally active polypeptides, may be used to produce an article of manufacture containing materials useful for the treatment, prevention and/or diagnosis of the disorders described. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is the conditionally active polypeptides, or the products further engineered from the conditionally active polypeptides, of the invention. The label or package insert indicates that the composition is used for treating the condition of choice. Moreover, the article of manufacture may comprise (a) a first container with a composition contained therein, wherein the composition comprises a conditionally active polypeptides, or a product engineered from the conditionally active polypeptide; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The article of manufacture can optionally comprise the container as a component of a parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal delivery device or system.

The conditionally active polypeptides, or the products engineered from the conditionally active polypeptides, may be included in a medical device, wherein the device is suitable to contacting or administering the conditionally active polypeptides, or the products further engineered from the conditionally active polypeptides, by at least one mode selected from parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal.

In some further embodiments, the conditionally active polypeptides, or the products engineered from the conditionally active polypeptides, may be included in a kit in lyophilized form in a first container, and an optional second container comprising sterile water, sterile buffered water, or at least one preservative selected from the group consisting of phenol, m-cresol, p-cresol, o-cresol, chlorocresol, benzyl alcohol, phenylmercuric nitrite, phenoxyethanol, formaldehyde, chlorobutanol, magnesium chloride, alkylparaben, benzalkonium chloride, benzethonium chloride, sodium dehydroacetate and thimerosal, or mixtures thereof in an aqueous diluent. In one aspect, in the kit, the concentration of the conditionally active polypeptides, or the products engineered from the conditionally active polypeptides, in the first container is reconstituted to a concentration of about 0.1 mg/ml to about 500 mg/ml with the contents of the second container, In another aspect, the second container further comprises an isotonicity agent. In another aspect, the second container further comprises a physiologically acceptable buffer. In one aspect, the disclosure provides a method of treating at least one parent-protein-mediated condition, comprising administering to a patient in need thereof a formulation provided in a kit and reconstituted prior to administration.

The following examples are illustrative, but not limiting, of the present disclosure. Other suitable modifications and adaptations of the variety of conditions and parameters normally encountered in the field, and which are obvious to those skilled in the art, are within the scope of the disclosure.

EXAMPLES

Examples 1-5 for making conditionally active polypeptides have been described in U.S. Pat. No. 8,709,755 B2, which are hereby incorporated by reference herein.

Example 6: Evolving a Light Chain or a Heavy Chain of an Antibody

The heavy chain and light chain of an antibody F1-10F10 were separately evolved using CPE. The light chain mutants were screened to discover 26 light chain mutants with conditional activity, in this case the mutants were more active at pH 6.0 than the wild-type and the mutants less active at pH 7.4 than the wild-type. The 26 light chain mutants had their mutations at 8 different positions in the light chain 3 of the 8 positions appeared in more than 5 of the 26 light chain mutants. These 3 positions were deemed to be hot spots in the light chain. The heavy chain mutants were screened to discover 28 heavy chain mutants with conditional activity. The 28 heavy chain mutants had their mutations at 8 different positions in the heavy chain 3 of the 8 positions appeared in more than 5 of the 28 heavy chain mutants. These 3 positions were deemed to be hot spots in the heavy chain. The conditional activity of the light chain mutants and heavy chain mutants was confirmed by an ELISA assay.

The best conditionally active antibody generated by this example had a 17-fold difference in its activity at pH 6.0 to its activity at pH 7.4. In addition, many of the conditionally active antibodies had an activity that was reversible at a pH between the normal physiologic pH of 7.4 and the aberrant pH of 6.0. Interestingly, most of the conditionally active antibodies generated from this example exhibited optimal binding activity at a pH of about 5.5 to 6.5, when the activity of the conditionally active antibodies was tested in the pH range of 5.0 to 7.4 by the ELISA assay.

The activity of the conditionally active antibodies generated by this example was also confirmed by a FACS (Fluorescence-activated cell sorting) assay using whole cells, where CHO cells were used to express the antigen of the antibodies at pH 6.0 and pH 7.4. The conditionally active antibodies were added to CHO cells in order to measure the binding activity. The FACS assay confirmed the general trend in the results of the ELISA assay for the selectivity of the conditionally active antibodies at pH 6.0 relative to pH 7.4.

Example 7: Selecting Conditionally Active Antibodies in a Special Buffer

Mutant antibodies generated by an evolving step in accordance with the present invention were subjected to an assay at a normal physiologic pH of 7.4 and to an assay at an aberrant pH of 6.0. Both assays were performed using a phosphate buffered saline (PBS) solution including a bicarbonate found in human serum. The concentration of Bicarbonate in the solution was a typical concentration of Bicarbonate in a human serum, i.e. a physiological concentration. A comparative test was done using the same PBS solution without bicarbonate.

The assay for measuring the binding activity for the mutant antibodies or conditionally active antibodies in this example was an ELISA assay, which was carried out as follows:
1. The pre-day of ELISA: the wells were coated with 100 ul of antibody Ab-A ECD his tag (2.08 mg/ml) antigen at 1 ug/ml with PBS,
3. The buffer solution was flicked off from the 96 well plate coated with Antibody Ab-A-His antigen, and blotted dry on paper towels.
4. The plates were washed 3× with buffer N or PBS,
5. The plates were blocked with 200 ul of designated buffer at room temperature for 1 hour,
6. The selected CPE/CPS mutants and the wild type protein were diluted to 75 ng/ml in designated buffer solutions according to the layout. The pH of the buffer solution was set to either 6.0 or 7.4 (hereinafter "the designated buffer solution"),
6. The buffer was flicked off and 100 ul of 75 ng/ml sample was added to each well according to the plate layout,
7. The plates were incubated at room temperature for 1 hour,
8. The buffer was flicked off from the 96 well plate, and blotted dry on paper towels,
9. The plate was washed with 200 ul of the designated buffer solution for a total of 3 times according to the layout,
10. Anti-Flag HRP was prepared in the designated buffer solution at a 1:5000 dilution and 100 ul of the Anti-Flag horseradish peroxidase (HRP) was added to each well according to the layout,
11. The plate was incubated at room temperature for 1 hour,
13. The plate was washed with 200 ul of the designated buffer solution a total of 3 times,
14. The plate was developed with 50 ul of 3,3', 5,5;-tetramethylbenzidine (TMB) for 1.5 min.

It was found that the assays in the PBS buffer solution containing bicarbonate resulted in a significantly higher success rate for the selection of conditionally active antibodies. In addition, the conditionally active antibodies selected using the PBS buffer solution containing bicarbonate tended to have much higher ratio of their activity at pH 6.0 to the activity at pH 7.4 thereby providing a significantly higher selectivity.

It was further observed that when the selected conditionally active antibodies (using PBS buffer solution with bicarbonate were tested in the PBS buffer solution without bicarbonate, the selectivity of the conditionally active antibodies at pH 6.0 relative to pH 7.0 was significantly reduced. However, when bicarbonate was added to this PBS buffer solution in a physiological amount, the selectivity of the same conditionally active antibodies was restored.

In another assay, the selected conditionally active antibodies were tested in a Krebs buffer solution with added bicarbonate. The higher ratio of the activity at pH 6.0 to the activity at pH 7.4 was also observed in this Krebs buffer solution with added bicarbonate. It appears that this may have been at least partly due to the presence of bicarbonate in the Krebs buffer solution.

When the concentration of bicarbonate was reduced in the PBS buffer solution to concentrations below its physiological concentration, it was observed that the activity of the conditionally active antibody at the normal physiological pH of 7.4 was increased. The increase in the activity of the conditionally active antibody at pH 7.4 was observed to be related to the decrease in the concentration of bicarbonate in the PBS buffer solution.

The wild-type antibody was not affected by the different amounts of bicarbonate in the PBS buffer solution when assayed at pH 7.4 as its activity remained the same at all the same concentrations of bicarbonate in the PBS buffer solution that were tested for the conditionally active antibody.

Example 8: Selecting Conditionally Active Antibodies in Different Buffers

The mutant antibodies generated by an evolving step according to the present invention were subjected to an ELISA assay at a normal physiologic pH (7.4) and an ELISA assay at an aberrant pH (6.0). Both ELISA assays were performed using different buffers, including buffers based on Krebs buffer with bovine serum albumin (BSA), and buffers based on PBS buffer with bicarbonate and BSA.

The ELISA assay was carried out as follows:
1. The pre-day of ELISA: wells were coated with 100 ul of Antibody Ab-A ECD his tag (2.08 mg/ml) antigen at 1 ug/ml with coating buffer (Carbonate-Bicarbonate buffer).
2. The buffer solution was flicked off from the 96 well plate coated with Antibody Ab-A-His antigen, and blotted dry on paper towels.
3. The plates were washed 3× with 200 ul of 20 buffers.
4. The plates were blocked with 200 ul of 20 buffers at room temperature for 1 hour.
5. The mutants and chimera were diluted to 75 ng/ml in 20 buffers according to the layout.
6. The buffer was flicked off and 100 ul of diluted sample was added to each well according to the plate layout.
7. The plates were incubated at room temperature for 1 hour.
8. The buffer from the 96 well plate was flicked off, and the plate was blotted dry using paper towels.
9. The plates were washed with 200 ul of 20 buffers a total of 3 times.
10. An anti-flag IgG HRP was prepared in 20 buffers at 1:5000 dilution. 100 μl of the anti-flag IgG HRP solution was added to each well.
11. The plates were incubated at room temperature for 1 hour.
12. The plates were washed with 200 ul of 20 buffers a total of 3 times.
13. The plates were developed with 50 ul 3,3', 5,5;-tetramethylbenzidine for 30 seconds.

The conditionally active antibodies selected using assays in the PBS buffer solution with bicarbonate exhibited a much higher ratio of the activity at pH 6.0 to the activity at pH 7.4, in comparison with those selected using an assay in PBS buffer solution without bicarbonate. In addition, the Krebs buffer solution with added bicarbonate also provided a higher ratio of the activity at pH 6.0 to the activity at pH 7.4 when comparison with the assay in PBS buffer solution without bicarbonate. It appears the bicarbonate is important to the selection of desirable conditionally active antibodies.

Example 9: Selecting Conditionally Active Antibodies in Different Buffers

Conditionally active antibodies to an antigen that are more active at pH 6.0 than the wild type antibody and less active at pH 7.4 than the wild type antibody were screened in this example. The screening steps were conducted using the buffers in Tables 2 and 3 below. The buffers in Table 2 were based on Krebs buffer, with additional components added as shown in column 1 of Table 2.

TABLE 2

| Krebs Buffer Based Assay Buffers | | | | | | | | |
|---|---|---|---|---|---|---|---|---|
| Additional comopents in pH of the | Buffer 1 | | Buffer 2 | | Buffer 3 | | Buffer 4 | |
| buffers | pH 6.0 | pH 7.4 | pH 6.0 | pH 7.4 | pH 6.0 | pH 7.4 | pH 6.0 | pH 7.4 |
| D-Glucose | 0 | 0 | 1.8 | 1.8 | 1.8 | 1.8 | 1.8 | 1.8 |
| Magnesium Chloride | 0.0468 | 0.0468 | 0 | 0 | 0.0468 | 0.0468 | 0.0468 | 0.0468 |
| Potassium Chloride | 0.34 | 0.34 | 0.34 | 0.34 | 0 | 0 | 0.34 | 0.34 |
| Sodium Chloride | 7 | 7 | 7 | 7 | 7 | 7 | 0 | 0 |
| Sodium Phosphate Dibasic | 0.1 | 0.1 | 0.1 | 0.1 | 0.1 | 0.1 | 0.1 | 0.1 |
| Sodium Phosphate Monobasic | 0.18 | 0.18 | 0.18 | 0.18 | 0.18 | 0.18 | 0.18 | 0.18 |
| Sodium Bicarbonate | 1.26 | 1.26 | 1.26 | 1.26 | 1.26 | 1.26 | 1.26 | 1.26 |
| Lactic acid | 16 mM | 1 mM | 16 mM | 1 mM | 16 mM | 1 mM | 16 mM | 1 mM |
| BSA | 10 | 10 | 10 | 10 | 10 | 10 | 10 | 10 |
| Additional comopents in pH of the | Buffer 5 | | Buffer 6 | | Buffer 7 | | Buffer 8 (KREBS) | |
| buffers | pH 6.0 | pH 7.4 | pH 6.0 | pH 7.4 | pH 6.0 | pH 7.4 | pH 6.0 | pH 7.4 |
| D-Glucose | 1.8 | 1.8 | 1.8 | 1.8 | 1.8 | 1.8 | 1.8 | 1.8 |
| Magnesium Chloride | 0.0468 | 0.0468 | 0.0468 | 0.0468 | 0.0468 | 0.0468 | 0.0468 | 0.0468 |

TABLE 2-continued

Krebs Buffer Based Assay Buffers

| | | | | | | | | |
|---|---|---|---|---|---|---|---|---|
| Potassium Chloride | 0.34 | 0.34 | 0.34 | 0.34 | 0.34 | 0.34 | 0.34 | 0.34 |
| Sodium Chloride | 7 | 7 | 7 | 7 | 7 | 7 | 7 | 7 |
| Sodium Phosphate Dibasic | 0 | 0 | 0.1 | 0.1 | 0.1 | 0.1 | 0.1 | 0.1 |
| Sodium Phosphate Monobasic | 0.18 | 0.18 | 0 | 0 | 0.18 | 0.18 | 0.18 | 0.18 |
| Sodium Bicarbonate | 1.26 | 1.26 | 1.26 | 1.26 | 0 | 0 | 1.26 | 1.26 |
| Lactic acid | 16 mM | 1 mM | 16 mM | 1 mM | 16 mM | 1 mM | 16 mM | 1 mM |
| BSA | 10 | 10 | 10 | 10 | 10 | 10 | 10 | 10 |

Some assay buffers based on PBS buffer with additional components are shown in Table 3 below. The components in the buffers of Tables 3 and 4 are presented as amount in grams added in one liter of buffer. But the concentration of human serum is 10 wt. % of the buffer.

TABLE 3

PBS Buffer Based Assay Buffers

| | Additional Component | | | |
|---|---|---|---|---|
| | Buffer 9 (PBS, commercial) | | Buffer 10 (PBS + NaHCO3) | |
| | pH of buffers | | | |
| | pH 6.0 | pH 7.4 | pH 6.0 | pH 7.4 |
| KH2PO4 | 0.144 | 0.144 | 0.144 | 0.144 |
| NaCl | 9 | 9 | 9 | 9 |
| Na2HPO4 | 0.795 | 0.795 | 0.795 | 0.795 |
| Lactic acid | 16 mM | 1 mM | 16 mM | 1 mM |
| Sodium Bicarbonate | NA | NA | 1.26 | 1.26 |
| BSA | 10 | 10 | 10 | 10 |

The screening was carried out using an ELISA assay with these assay buffers. The ELISA assay was carried out as described in Examples 7-8. The selected conditionally active antibodies for each of the 10 assay buffers were presented in Table 4 below. The OD 450 absorbance is reversely correlated with the binding activity in the ELISA assay.

TABLE 4

Selected Conditionally Active Antibodies (Mutants) Using Different Assay Buffers

| | OD 450 | Selected mutants | wild type |
|---|---|---|---|
| Buffer 1 | pH 6.0 | 0.859 | 1.6414 |
| | pH 7.4 | 0.0883 | 1.2474 |
| Buffer 2 | pH 6.0 | 0.6599 | 1.1708 |
| | pH 7.4 | 0.0717 | 1.1839 |
| Buffer 3 | pH 6.0 | 0.4806 | 0.7765 |
| | pH 7.4 | 0.0723 | 1.3497 |
| Buffer 4 | pH 6.0 | 1.7364 | 1.7777 |
| | pH 7.4 | 0.4457 | 1.6173 |
| Buffer 5 | pH 6.0 | 0.6776 | 1.6905 |
| | pH 7.4 | 0.0747 | 1.3987 |
| Buffer 6 | pH 6.0 | 0.7244 | 1.4123 |
| | pH 7.4 | 0.0731 | 1.3439 |
| Buffer 7 | pH 6.0 | 0.6212 | 1.348 |
| | pH 7.4 | 0.8044 | 1.7381 |
| Buffer 8 | pH 6.0 | 0.7977 | 1.3893 |
| | pH 7.4 | 0.1042 | 1.5535 |
| Buffer 9 | pH 6.0 | 0.468 | 1.5087 |
| | pH 7.4 | 0.4455 | 1.347 |
| Buffer 10 | pH 6.0 | 0.5626 | 1.3439 |
| | pH 7.4 | 0.0727 | 1.2547 |

The selectivity of some of the selected conditionally active antibodies was confirmed using buffers 8 and 9 and it was found that they do have the desired selectivity in pH 6.0 over pH 7.4, as presented in FIG. 1. Note that using different buffers affected the selectivity of the conditionally active antibodies.

Example 10: Activity of Conditionally Active Antibodies in Different Buffers

Figure 2:
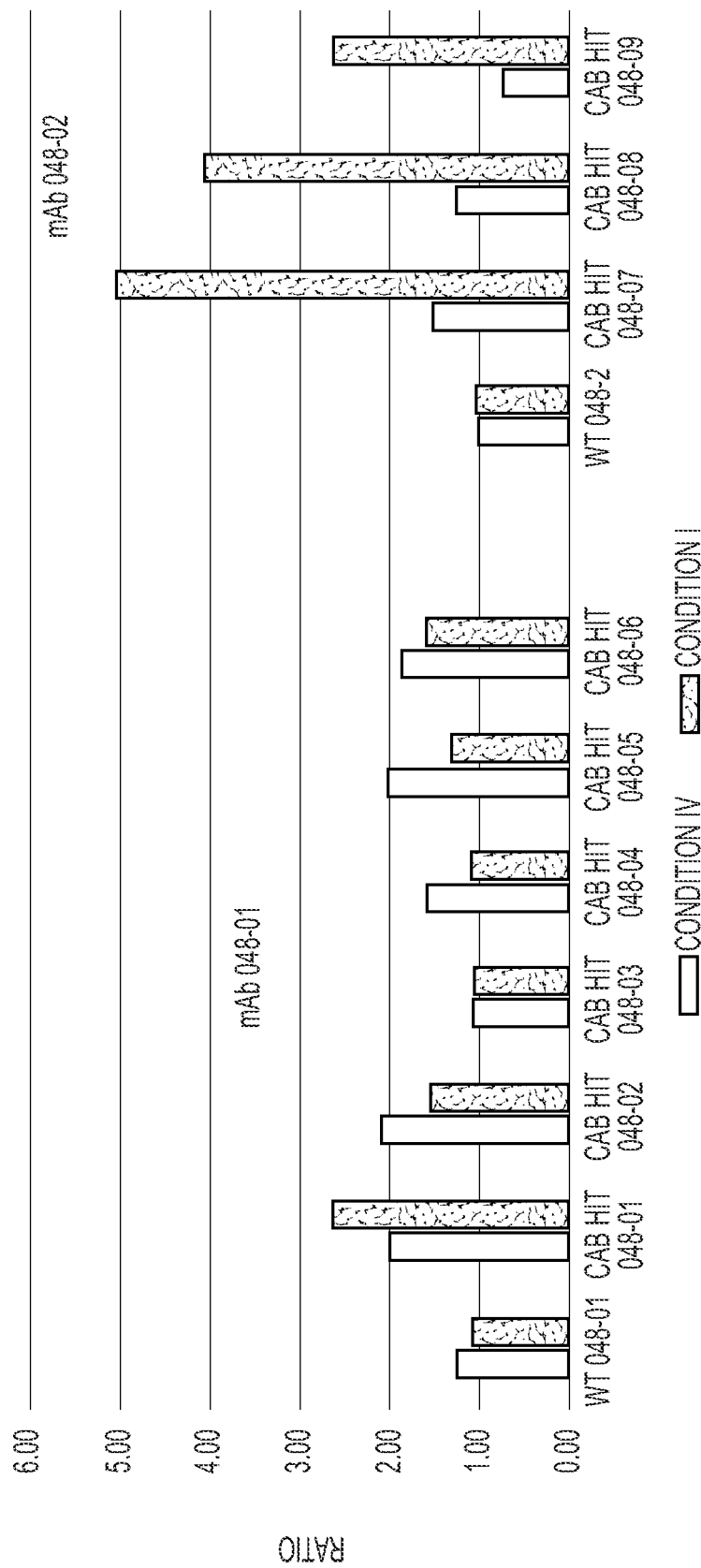
FIG. 2 shows the binding activities assayed in different buffer solutions of several different conditionally active antibodies to an antigen.

The Activity of conditionally active antibodies evolved from two monoclonal antibodies (mAb 048-01 and mAb 048-02 as parent antibodies) respectively were measured in two different buffers (FIG. 2). The two buffers were phosphate buffer (Condition IV) and Krebs buffer (Condition I). Six conditionally active antibodies were evolved from mAb 048-01: CAB Hit 048-01, CAB Hit 048-02, CAB Hit 048-03, CAB Hit 048-04, CAB Hit 048-05, and CAB Hit 048-06. Three conditionally active antibodies were evolved from mAb 048-02: CAB Hit 048-07, CAB Hit 048-08, and CAB Hit 048-09.

This study showed that the selectivity (the ratio of the activity in the assay at pH 6.0 to the activity in the assay at pH/7.4) of the conditionally active antibodies was affected by the buffer used in the assay. The conditionally active antibodies evolved from wild-type mAb 048-02 showed a significantly higher selectivity in the Krebs buffer than in the phosphate buffer (FIG. 2).

Example 11: Selectivity of Conditionally Active Antibodies and Bicarbonate

Figure 3:
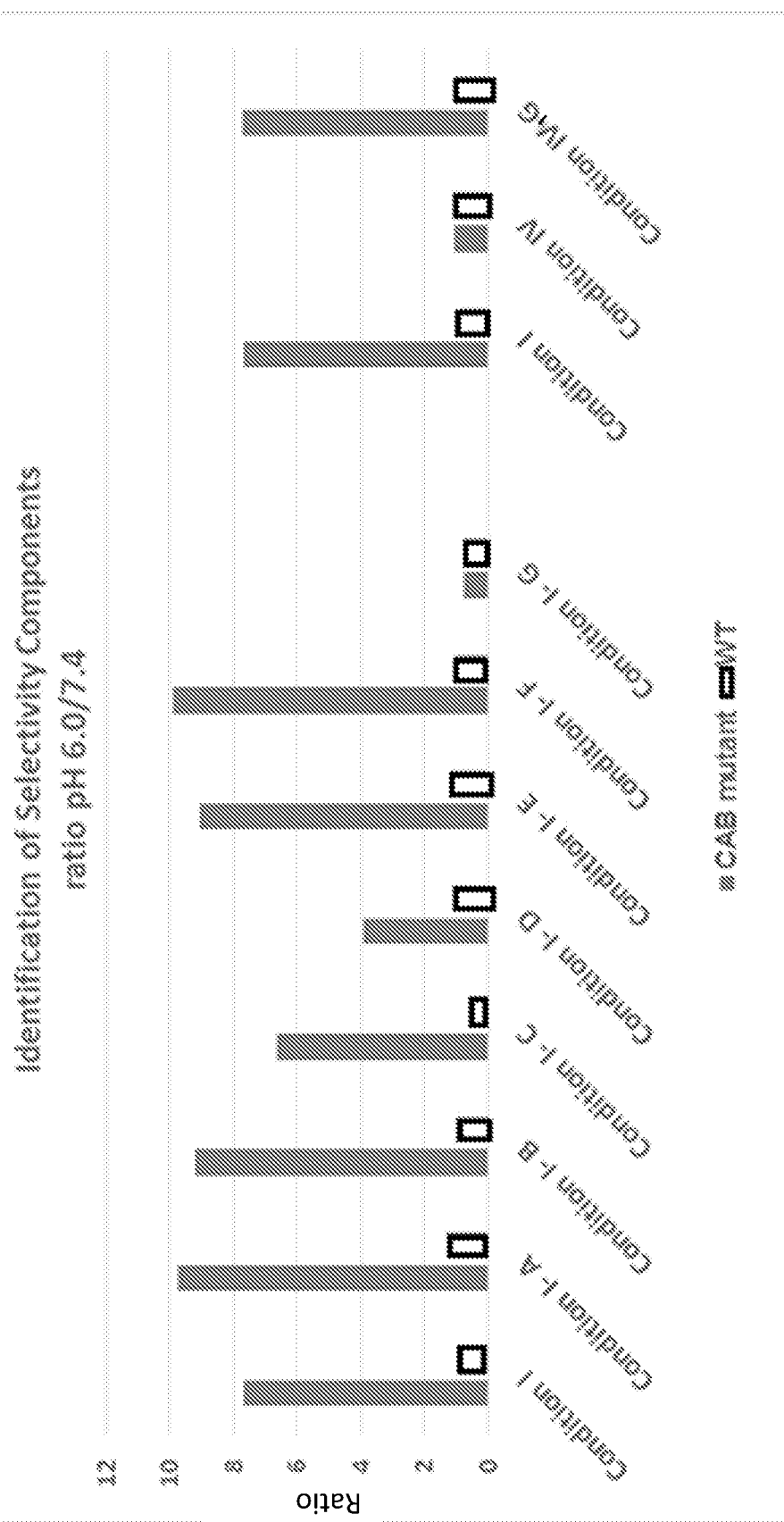
FIG. 3 shows the effects of changing the composition of Krebs buffer on the binding activity of a conditionally active antibody.

In Example 10 higher selectivity of the conditionally active antibodies was observed in Krebs buffer (Condition I) than in phosphate buffer (Condition IV). This was directed to identification of the component in the Krebs buffer that made the most significant contribution to the higher selectivity observed in Example 10. The selectivity of one conditionally active antibody was retested in buffers that were derived from Krebs buffer with various components subtracted therefrom one at a time (FIG. 3, left group of bars). When the complete Krebs buffer was used, the selectivity of the conditionally active antibody is high with an activity ratio of pH 6.0/7.4 of about 8. As components A-F were each subtracted from the Krebs buffer, the selectivity of the conditionally active antibody was not lost, though the conditionally active antibody became less selective when each of components C and D was subtracted. However, when component G (bicarbonate) was subtracted from Krebs buffer, the selectivity of the conditionally active antibody was completely lost. See FIG. 3. This indicates that bicarbonate is at least partially responsible for the high selectivity of the conditionally active antibodies in the Krebs buffer.

The selectivity of the same conditionally active antibody was then measured in phosphate buffer (Condition IV), which does not have bicarbonate and it was observed that the selectivity of the conditionally active antibody was completely lost in the phosphate buffer. When bicarbonate was added to the phosphate buffer, the selectivity of the conditionally active antibody was restored to the level observed in the Krebs buffer. This confirmed that bicarbonate was required for the selectivity of this conditionally active antibody.

Example 12: Bicarbonate Suppresses Binding at pH 7.4

Figure 4:
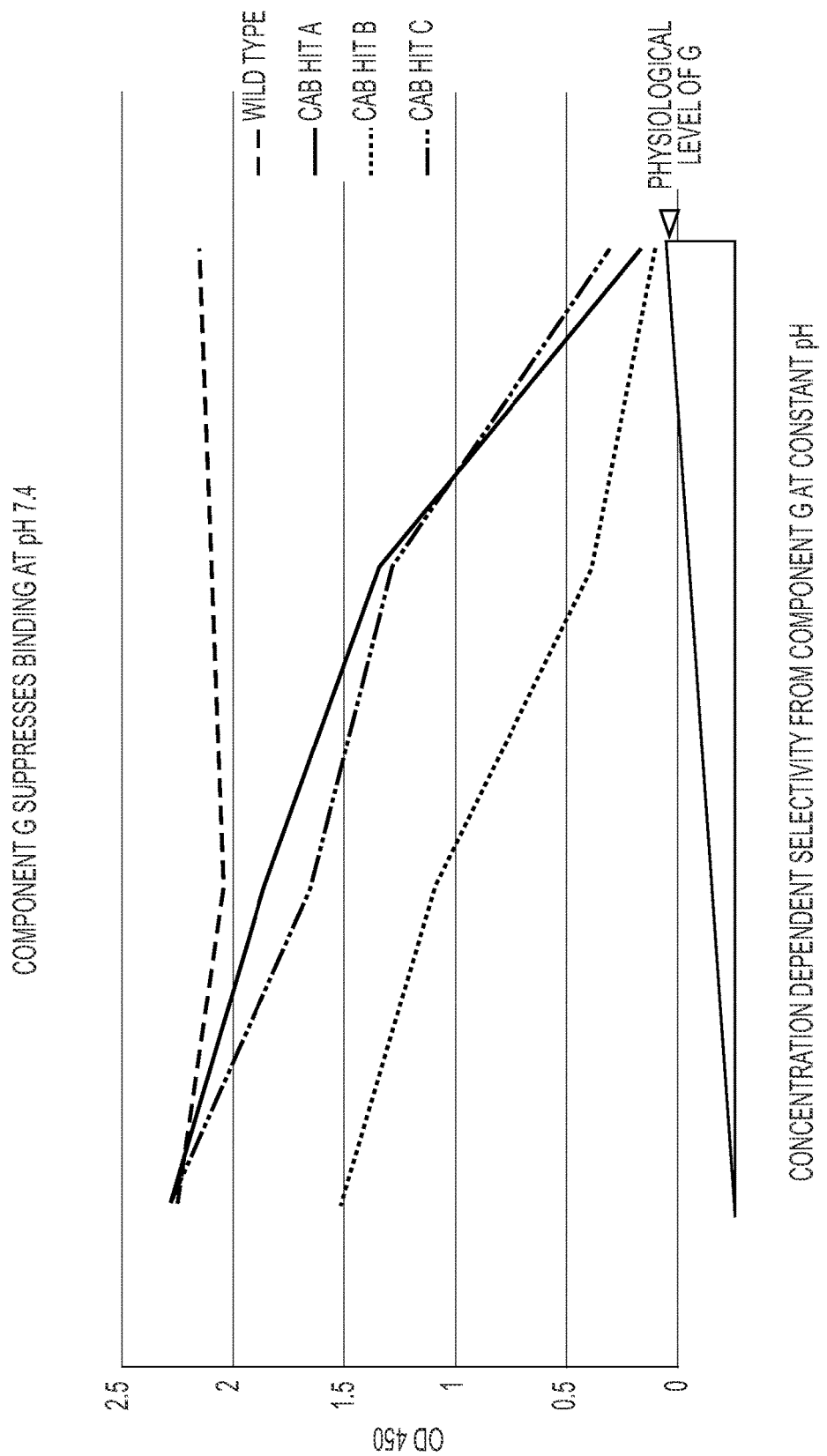
FIG. 4 shows that the binding activities of three different conditionally active antibodies were dependent on the presence and concentration of bicarbonate at pH 7.4, as described in Example 12.

This example measured the binding activity at pH 7.4 for three conditionally active antibodies (CAB Hit A, CAB Hit B, and CAB Hit C) in buffers having different concentrations of bicarbonate ranging from 0 to the physiological concentration of bicarbonate (about 20 mM, FIG. 4). It was observed that the binding activity of all three conditionally active antibodies at pH 7.4 decreased in a dose-dependent manner as the concentration of bicarbonate increased from 0 to the physiological concentration (FIG. 4). On the other hand, the binding activity of the wild-type antibody was not affected by the bicarbonate. This study showed that the selectivity of the conditionally active antibodies in the presence of bicarbonate was likely due at least in part to loss of binding activity for the conditionally active antibodies at pH 7.4 due to interaction with the bicarbonate.

Example 13: Activity of Conditionally Active Antibodies Against ROR2 in Different Buffers Conditionally active antibodies against ROR2 that were selected using assay solutions containing sodium bicarbonate (as described in Example 9) were tested in different buffers: CAB-P was a standard phosphate saline buffer (PBS buffer) used at a pH of 6.0 or 7.4; CAB-PSB was a PBS buffer supplemented with 15 mM of sodium bicarbonate at a pH off 6.0 or 7.4; and CAB-PSS was a PBS buffer supplemented with 10 mM of sodium sulfide nonahydrate at a pH off 6.0 or 7.4.

The activity of these conditionally active antibodies was measured according to the following ELISA protocol:
1. One day before ELISA: the plate was coated with 100 ul of 1 ug/ml antigen overnight in PBS at 4° C.
2. Wash plates twice with 200 ul of CAB-P, CAB-PSB, or CAB-PSS buffer according to the plate layout.
3. Block plates with 200 ul of CAB-P, CAB-PSB, or CAB-PSS buffer according to plate layout at room temperature for 1 hour.
4. Dilute antibody sample and positive control in of CAB-P, CAB-PSB, or CAB-PSS buffer as indicated in the plate layout.
5. Flicked off blocking buffer from 96 well plate, blot dry on paper towels.
6. Add 100 ul of diluted antibody samples, positive control or negative control to each well according to the plate layout.
6. Incubate the plates at room temperature for 1 hour.
7. Prepare Secondary antibody in of CAB-P, CAB-PSB, or CAB-PSS buffer according to the plate layout.
8. Flicked off buffer from 96 well plate, blot dry on paper towels.
9. Wash the plates for a total of 3 times with 200 ul of CAB-P, CAB-PSB, or CAB-PSS buffer according to the plate layout.
10. Add diluted secondary antibody in of CAB-P, CAB-PSB, or CAB-PSS buffer to each well according to the plate layout.
11. Incubate the plate at room temperature for 1 hour.
12. Flicked off buffer from 96 well plates, blot dry on paper towels.
13. Wash the plates for a total of 3 times with of CAB-P, CAB-PSB, or CAB-PSS buffer.
14. Bring 3,3', 5,5'-tetramethylbenzidine (TMB) substrate to room temperature.
15. Flick off buffers from plate, blot dry on paper towels.
16. Add 50 ul of TMB substrate.
17. Stop development with 50 ul 1N HCl. Development time was 3 min.
18. Read at OD450 nm using a plate reader.

Figure 7:
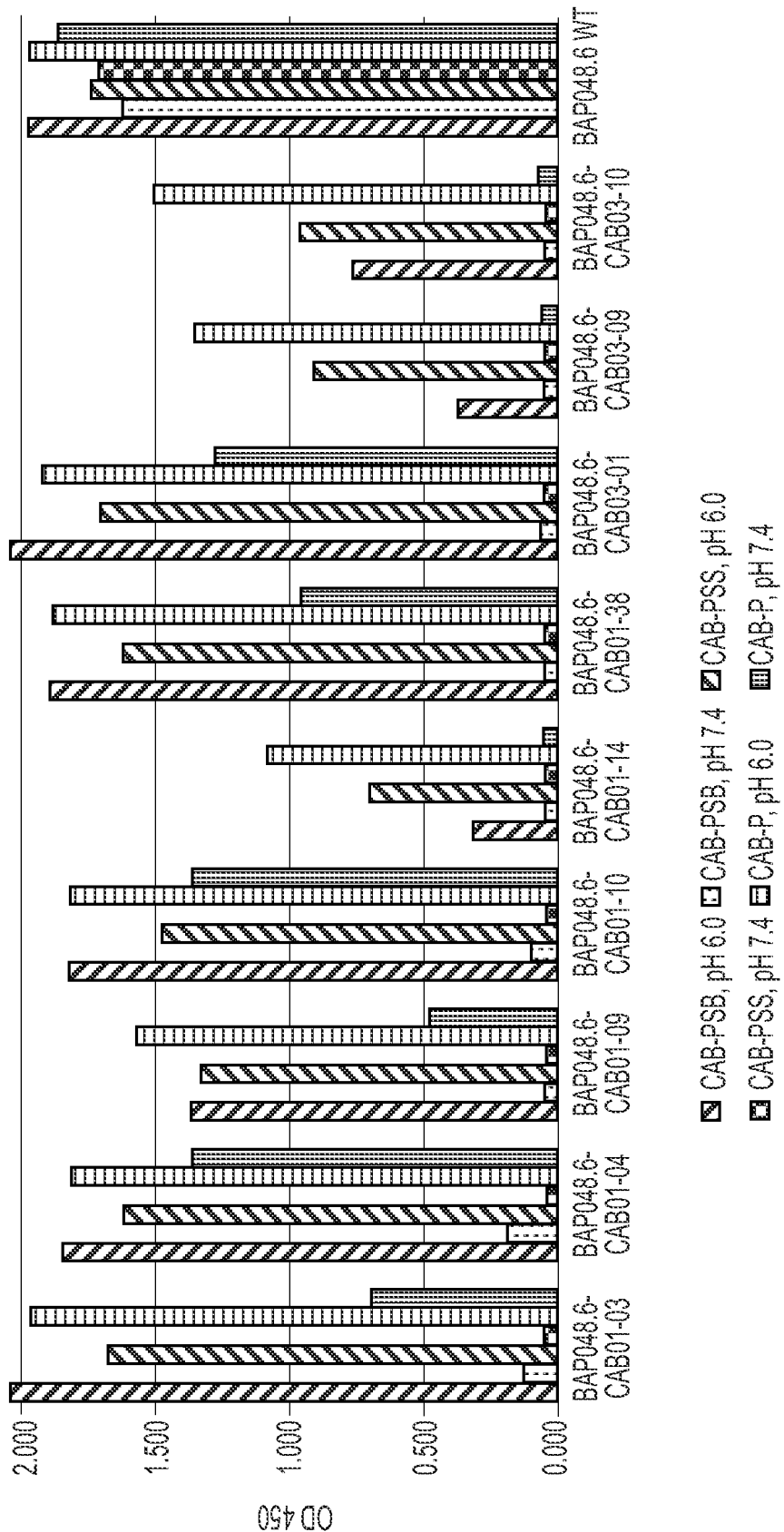
FIG. 7 shows the activities of conditionally active antibodies against ROR2 in different buffer solutions.

The activity of these conditionally active antibodies against ROR2 is presented in FIG. 7. The conditionally active antibodies showed higher activity in CAB-PSB buffer at pH 6.0 than at pH 7.4, i.e., selectivity at pH 6.0 over pH 7.4. This selectivity was lost or significantly reduced in CAB-P buffers for several conditionally active antibodies. But this selectivity was also observed in CAB-PSS buffers at pH 6.0 over pH 7.4. On the contrary, the wild-type antibody showed relatively minimal or no selectivity in any of the buffers.

This example demonstrates that bisulfide has similar function as the bicarbonate for mediating the conditional binding for the tested conditionally active antibodies against ROR2.

Figure 8:
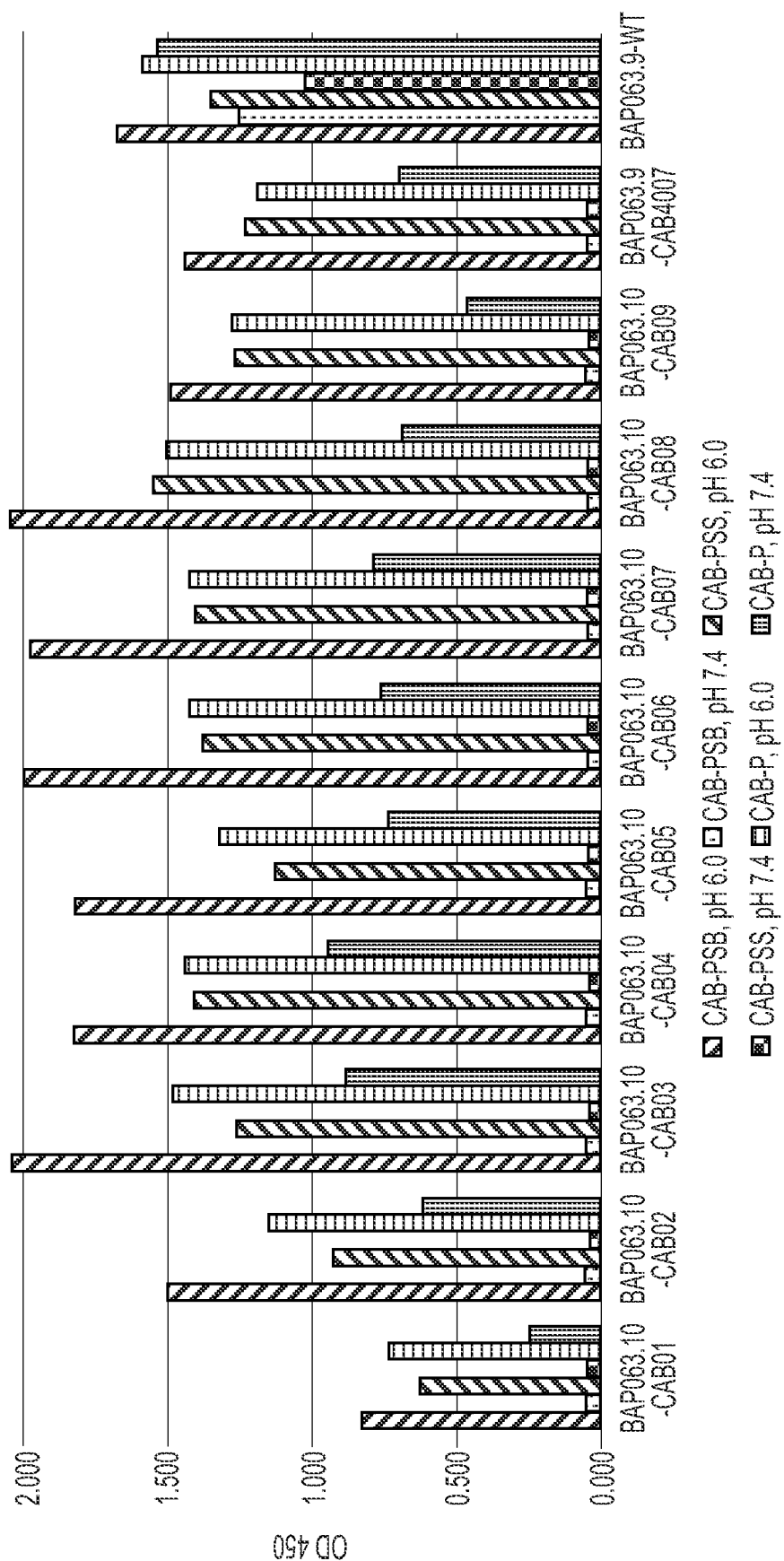
FIG. 8 shows the activities of conditionally active antibodies against Ax1 in different buffer solutions.

Example 14: Activity of Conditionally Active Antibodies Against Ax1 in Different Buffers Conditionally active antibodies against Ax1 that were selected using assay solutions containing sodium bicarbonate (as described in Example 9) were tested in different buffers: CAB-P, CAB-PSB, and CAB-PSS, as described in Example 13. The activities of these conditionally active antibodies against Ax1 were measured using the same ELISA protocol as described in Example 13 and is presented in FIG. 8. The conditionally active antibodies showed higher activity in CAB-PSB buffer at pH 6.0 than at pH 7.4, i.e., selectivity at pH 6.0 over pH 7.4. This selectivity was lost or significantly reduced in CAB-P buffers for these conditionally active antibodies. The selectivity was also observed in CAB-PSS buffers at pH 6.0 over pH 7.4. On the contrary, the wild-type antibody showed essentially no selectivity in any of the buffers.

This example also demonstrates that bisulfide had a similar function as the bicarbonate for mediating the conditional binding for the tested conditionally active antibodies against Ax1.

Example 15: Cell Killing by the Anti-Ax1 Antibodies

The cell killing activities of several conditionally active anti-Ax1 antibodies were tested using A549 cells. The cell killing activities were measured at two pH levels: 6.0 and 7.4, representing a pH in tumor microenvironment and a normal physiological pH, respectively. The percentage of cell killing at various antibody concentrations is shown in FIGS. 9A-9E.

Figure 9A:
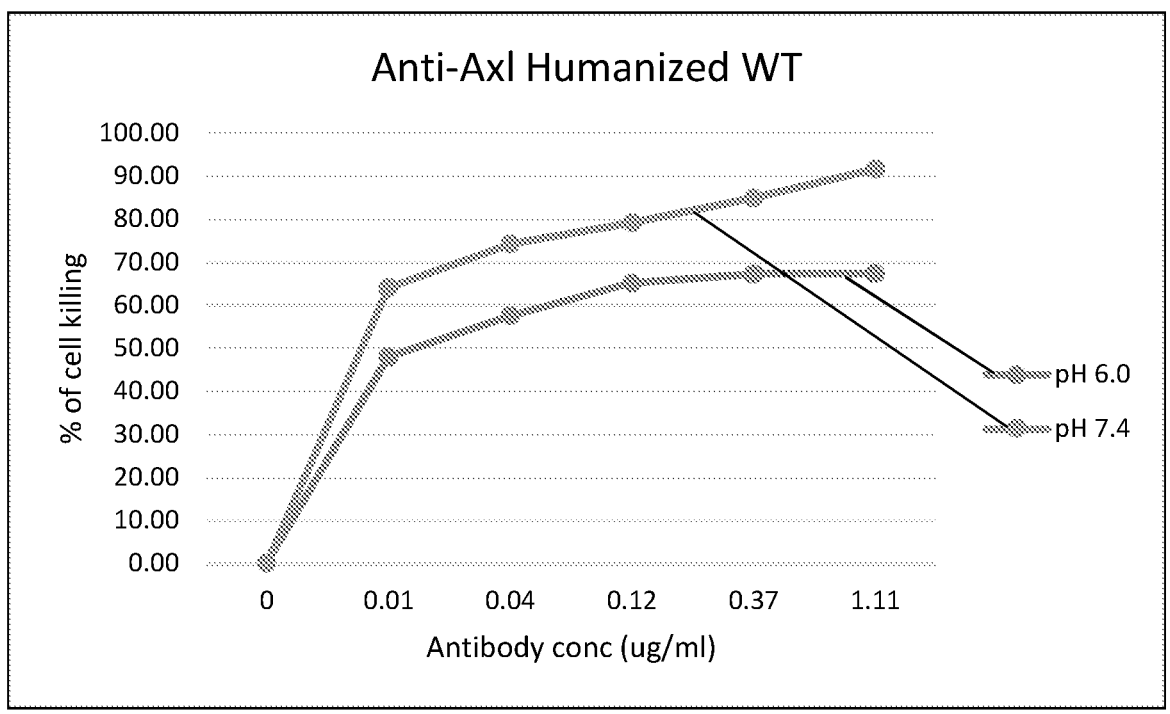
FIGS. 9A-9E show results of a cell killing of A549 cells using a wild-type anti-Ax1 antibody and conditionally active anti-Ax1 antibodies at pH 6.0 and pH 7.4 at different antibody concentrations.
Figure 9B:
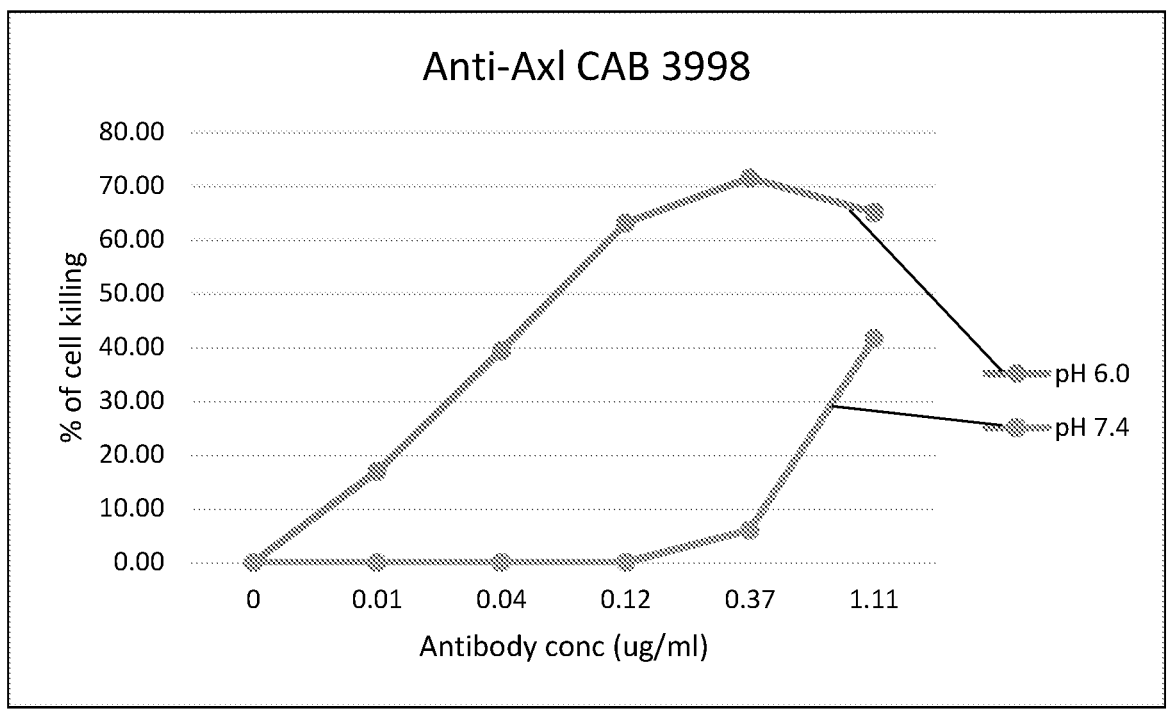
Figure 9C:
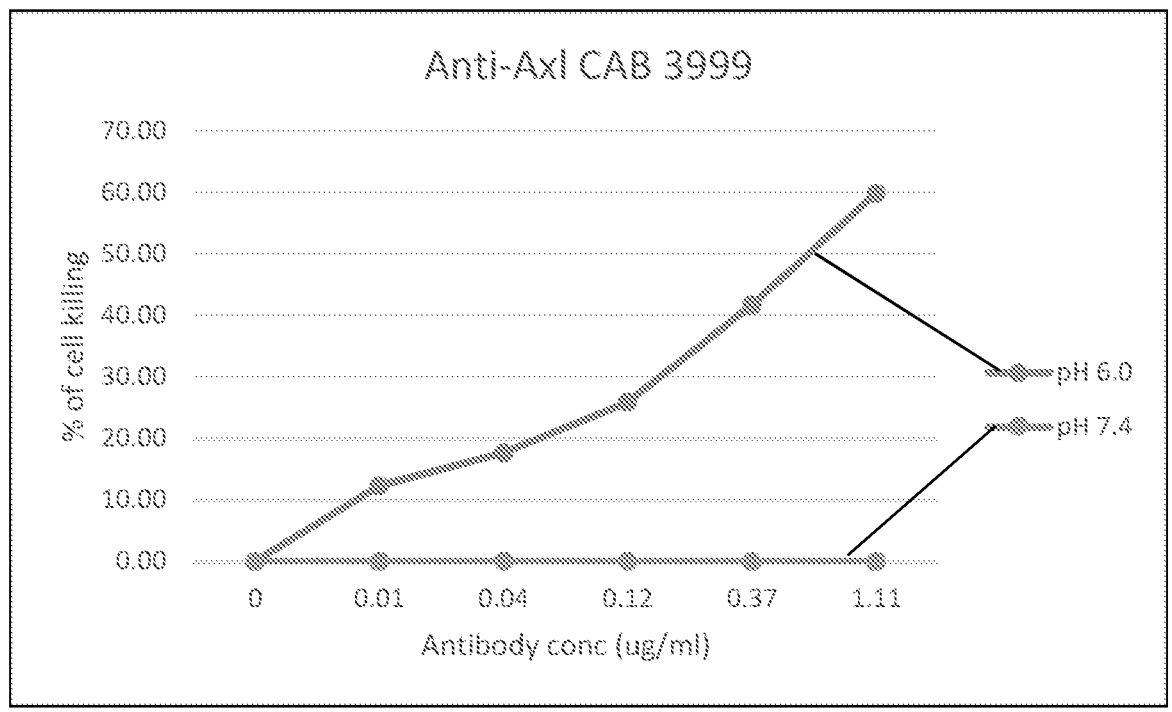
Figure 9D:
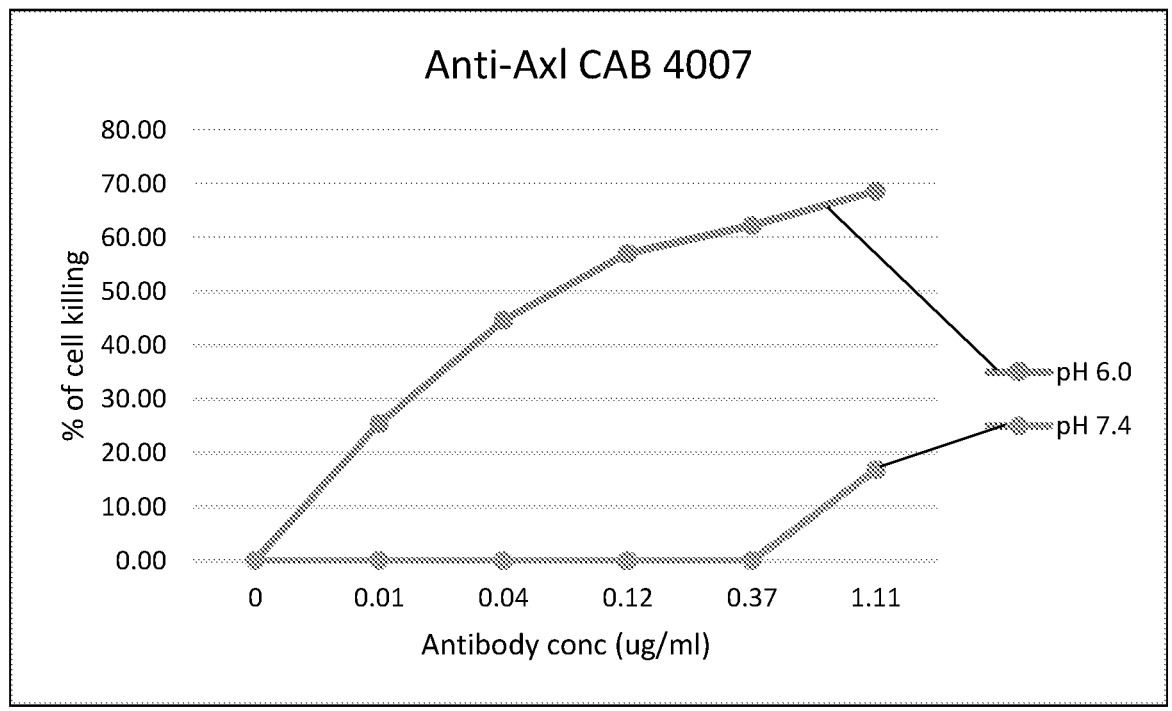
Figure 9E:
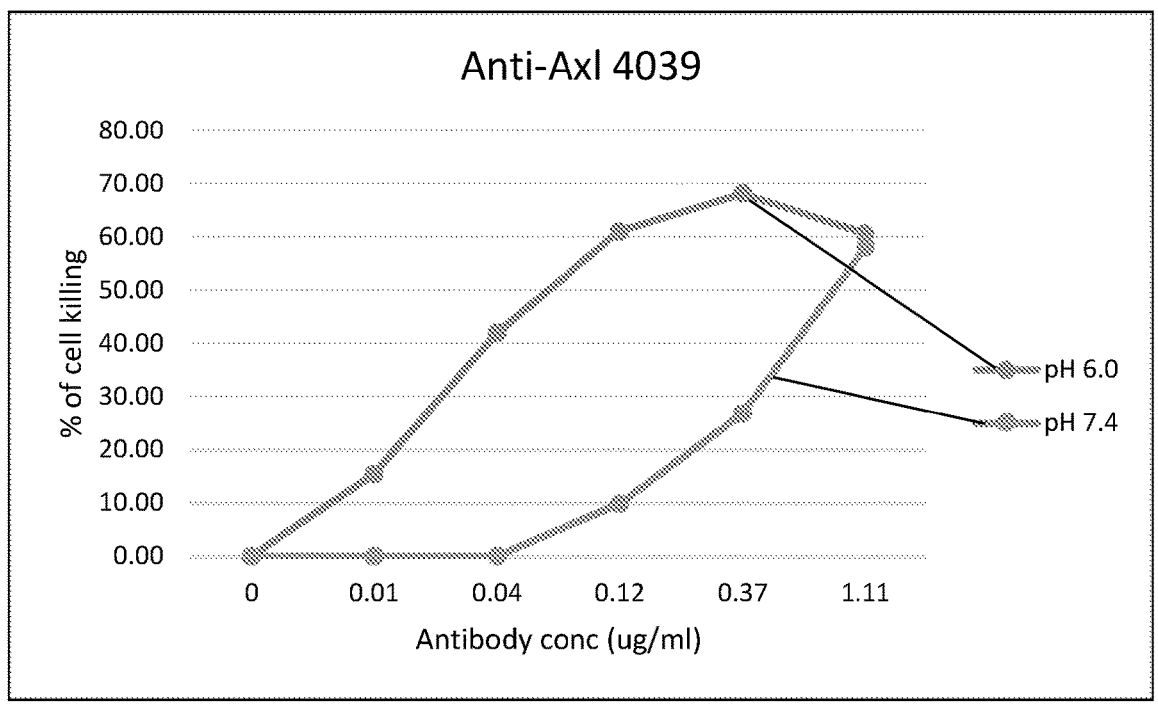

The two tests gave consistent results. The negative control (anti-Ax1 humanized WT) showed similar cell killing activities at both pH 6.0 and pH 7.4 for the A549 cells (FIG. 9A). In contrast, the conditionally active anti-Ax1 antibodies showed significantly higher cell killing activity at pH 6.0 in comparison with the cell killing activity at pH 7.4, especially at low antibody concentrations at which the antibodies did not saturate the A549 cells (FIGS. 9B-9E).

Example 16: Binding Affinity to Cyno-Ax1 by the Anti-Ax1 Antibodies

The binding affinity to cyno-Ax1 by the conditionally active anti-Ax1 antibodies was measured and compared with the binding affinity to human Ax1 (hAx1) in PBS and KREBS buffers at pHs of 6.0 and 7.4 (FIGS. 10A-10D). The cyno-Ax1 is an Ax1 protein from a non-human primate, namely, the cynomolgus macaques monkey.

Figure 10A:
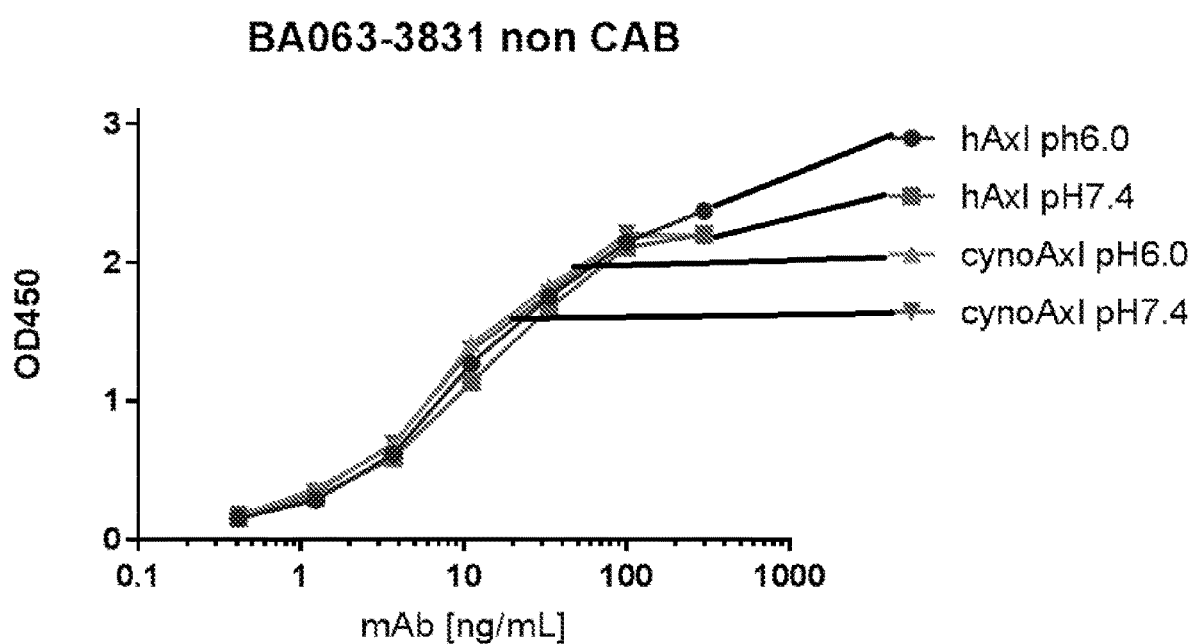
FIGS. 10A-10D show binding affinity to human Ax1 and cynomolgus Ax1 of conditionally active anti-Ax1 antibodies in different buffers and at different pH levels.
Figure 10B:
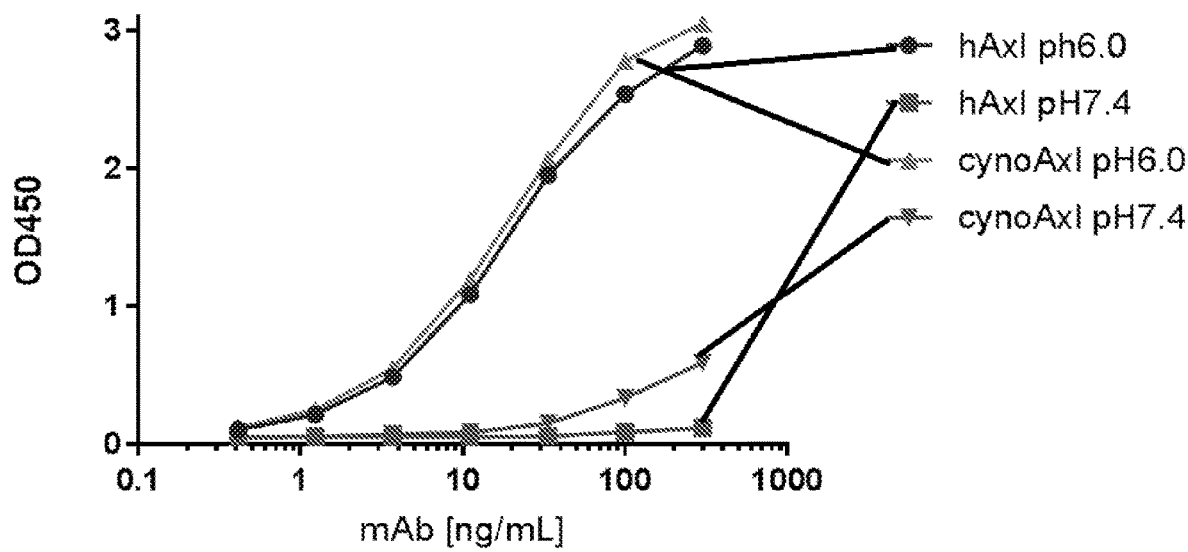
Figure 10C:
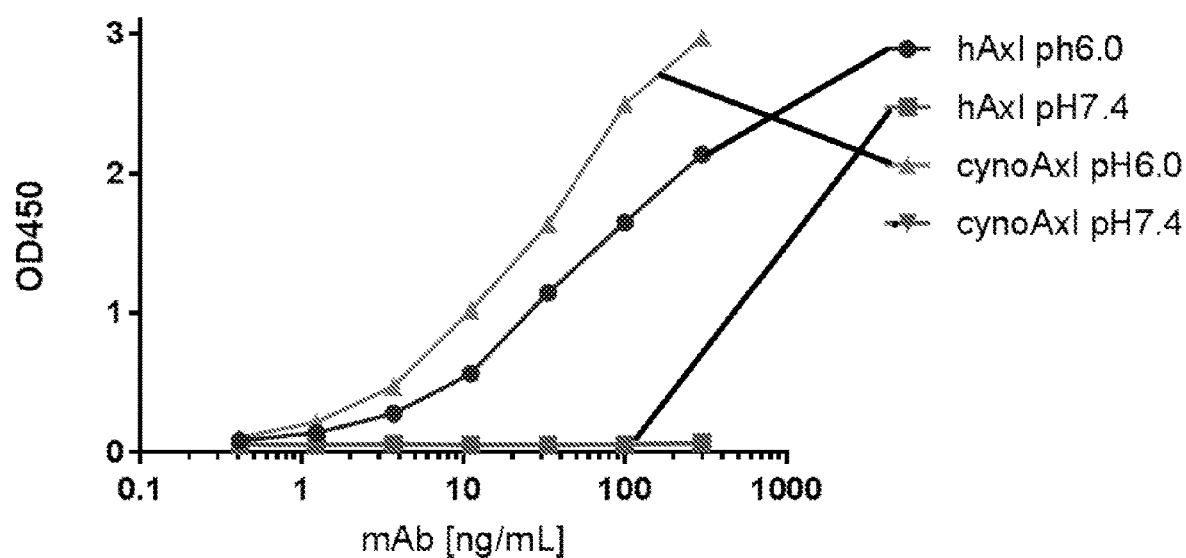
Figure 10D:
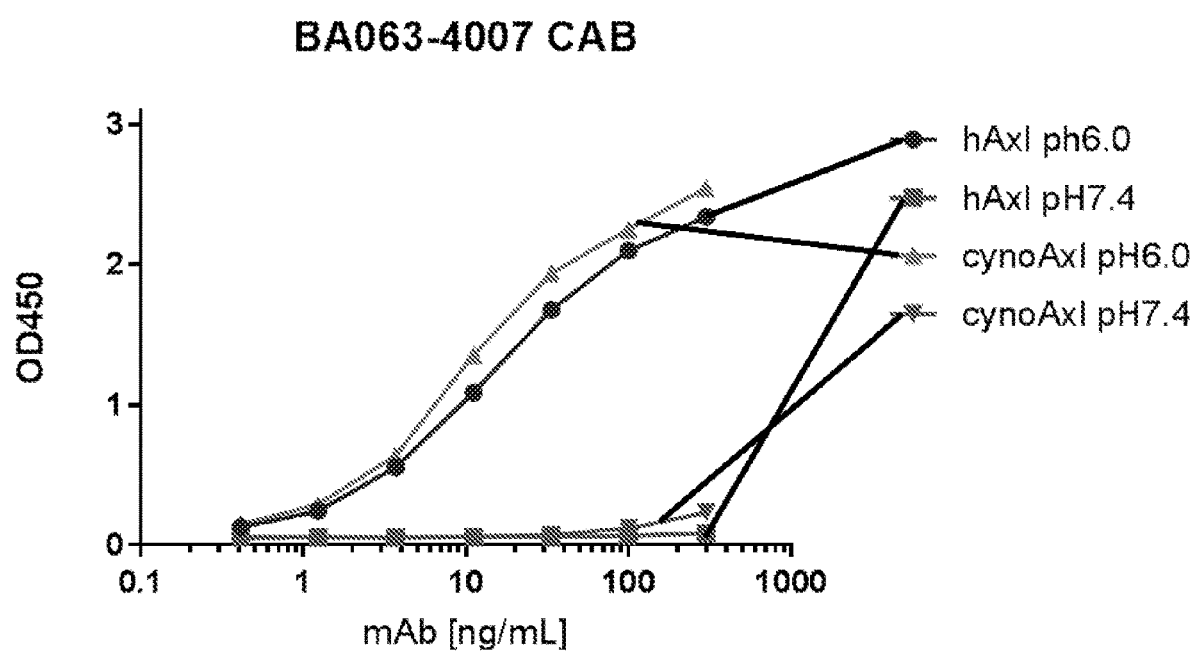
Figure 11A:
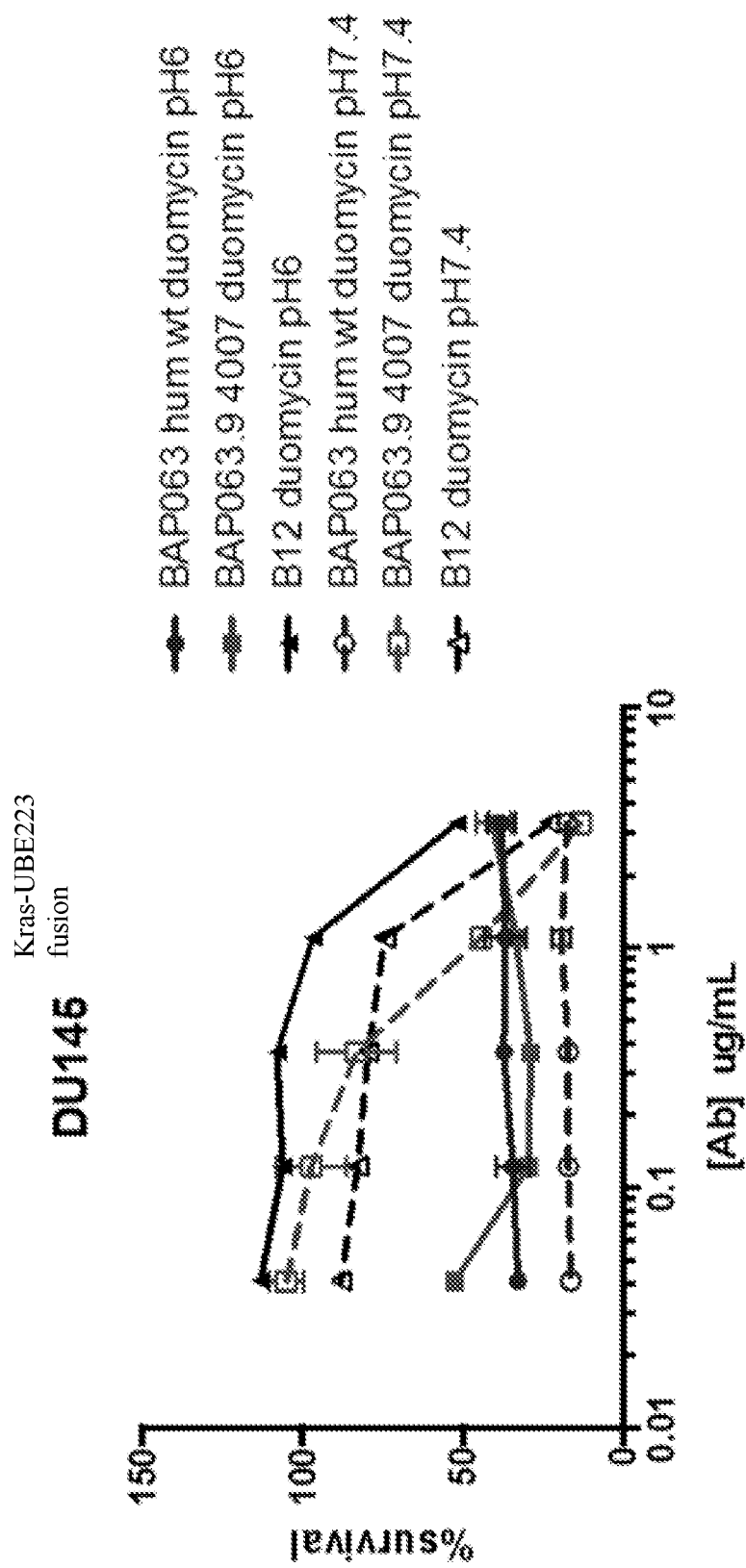
FIGS. 11A-11H show cell killing of different cell lines at different pH levels by conditionally active anti-Ax1 antibodies conjugated to duomycin.
Figure 11B:
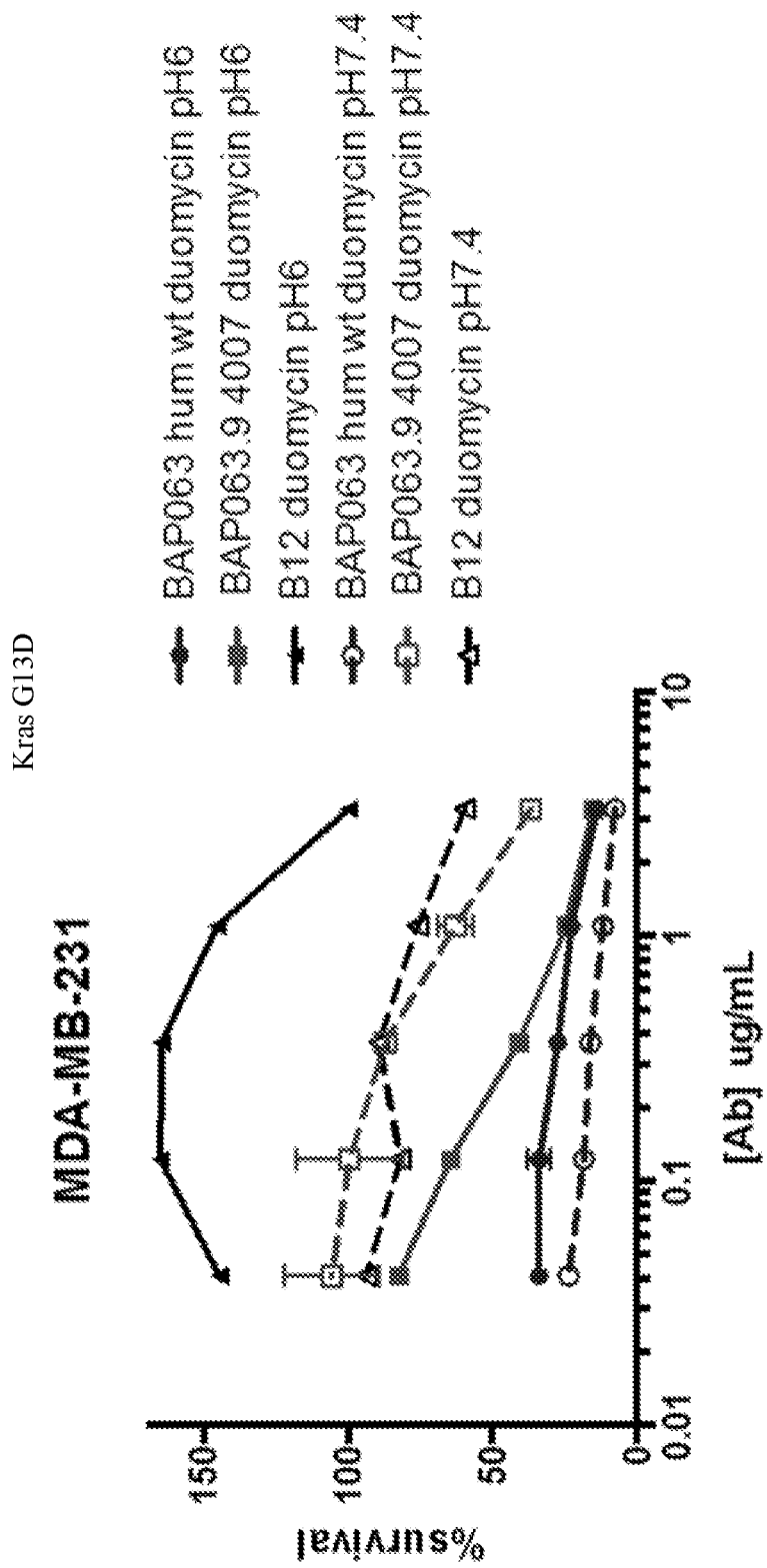
Figure 11C:
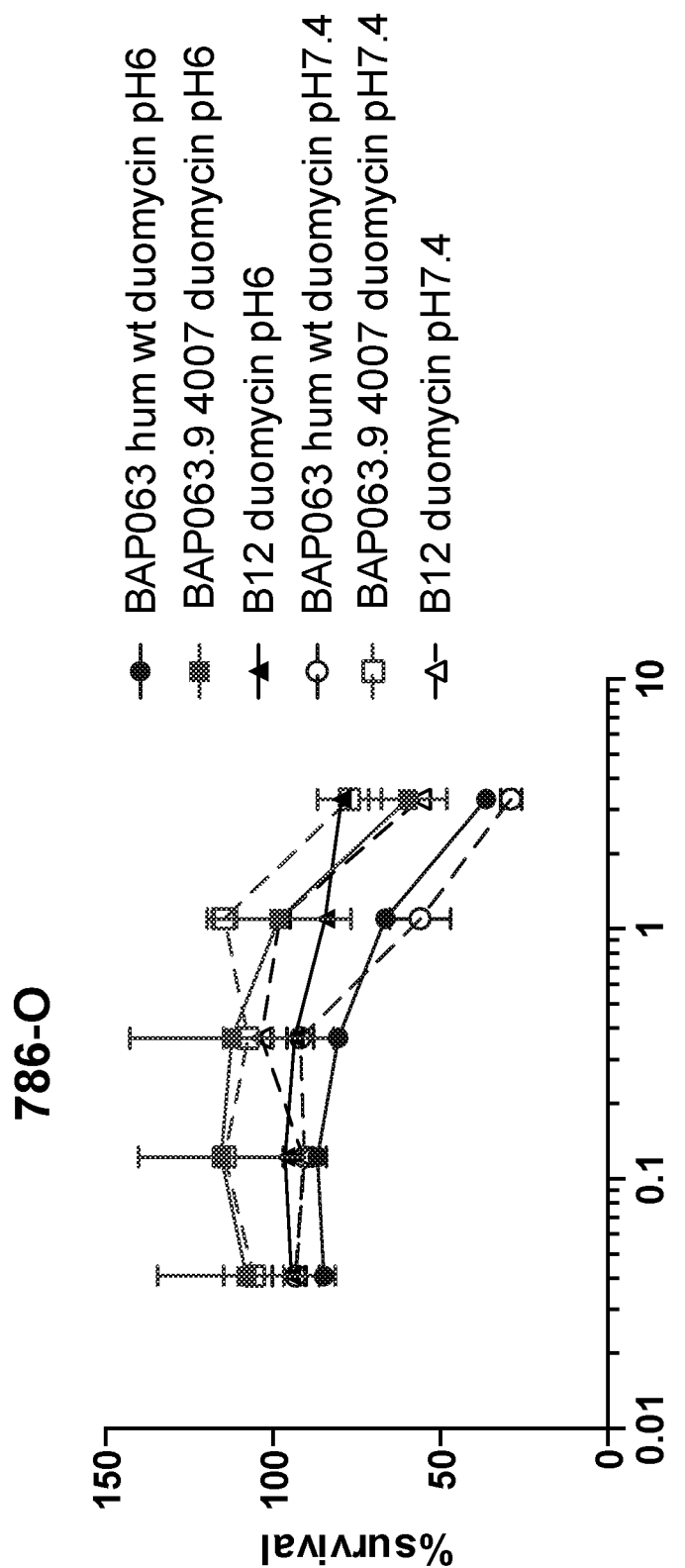
Figure 11D:
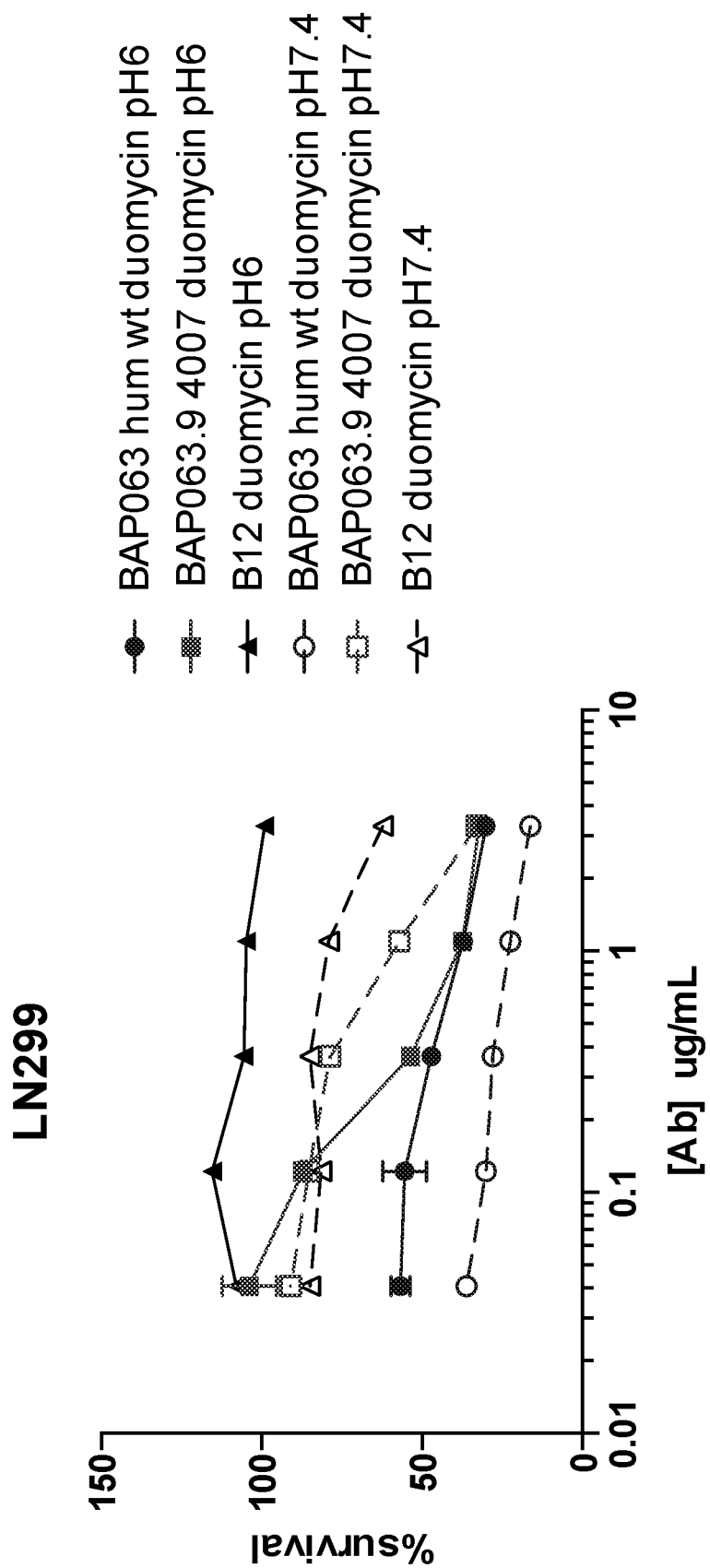
Figure 11E:
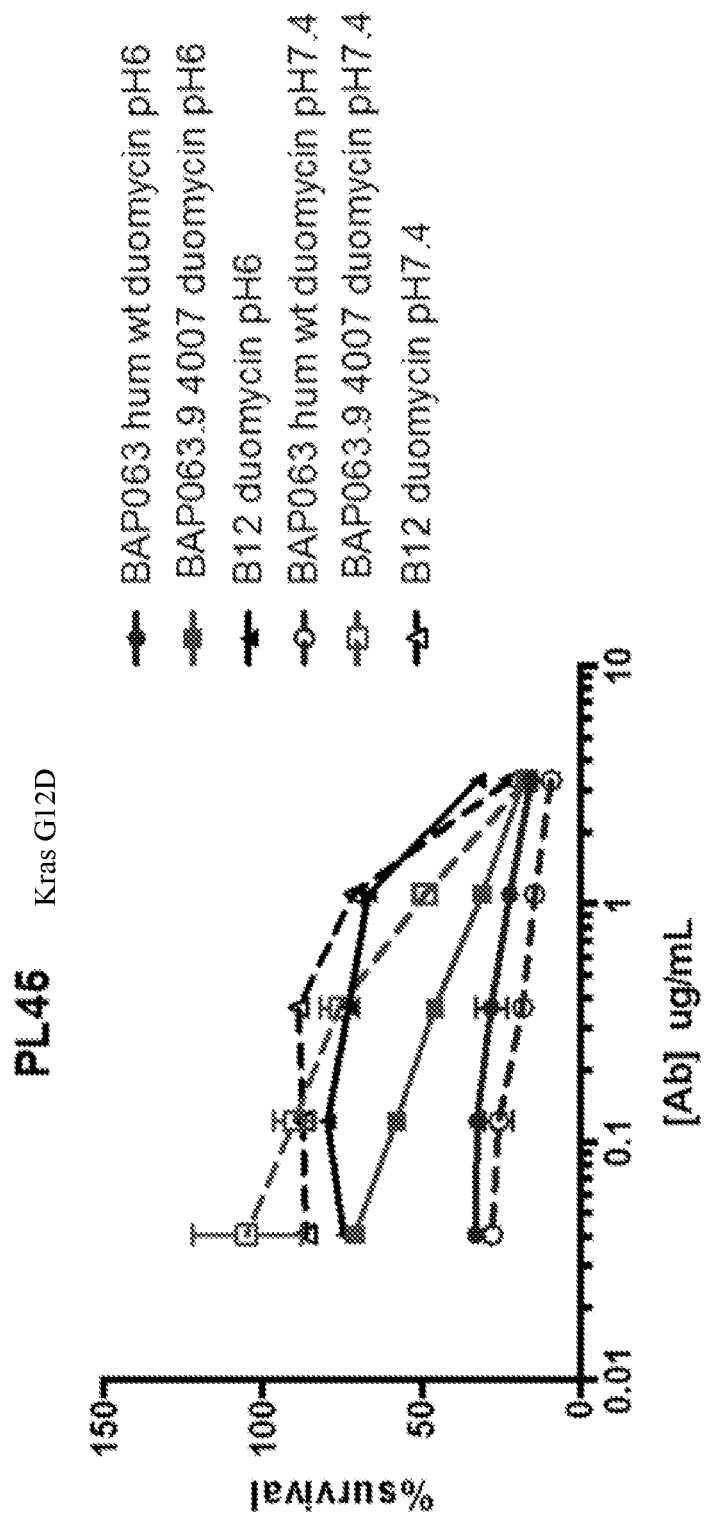
Figure 11F:
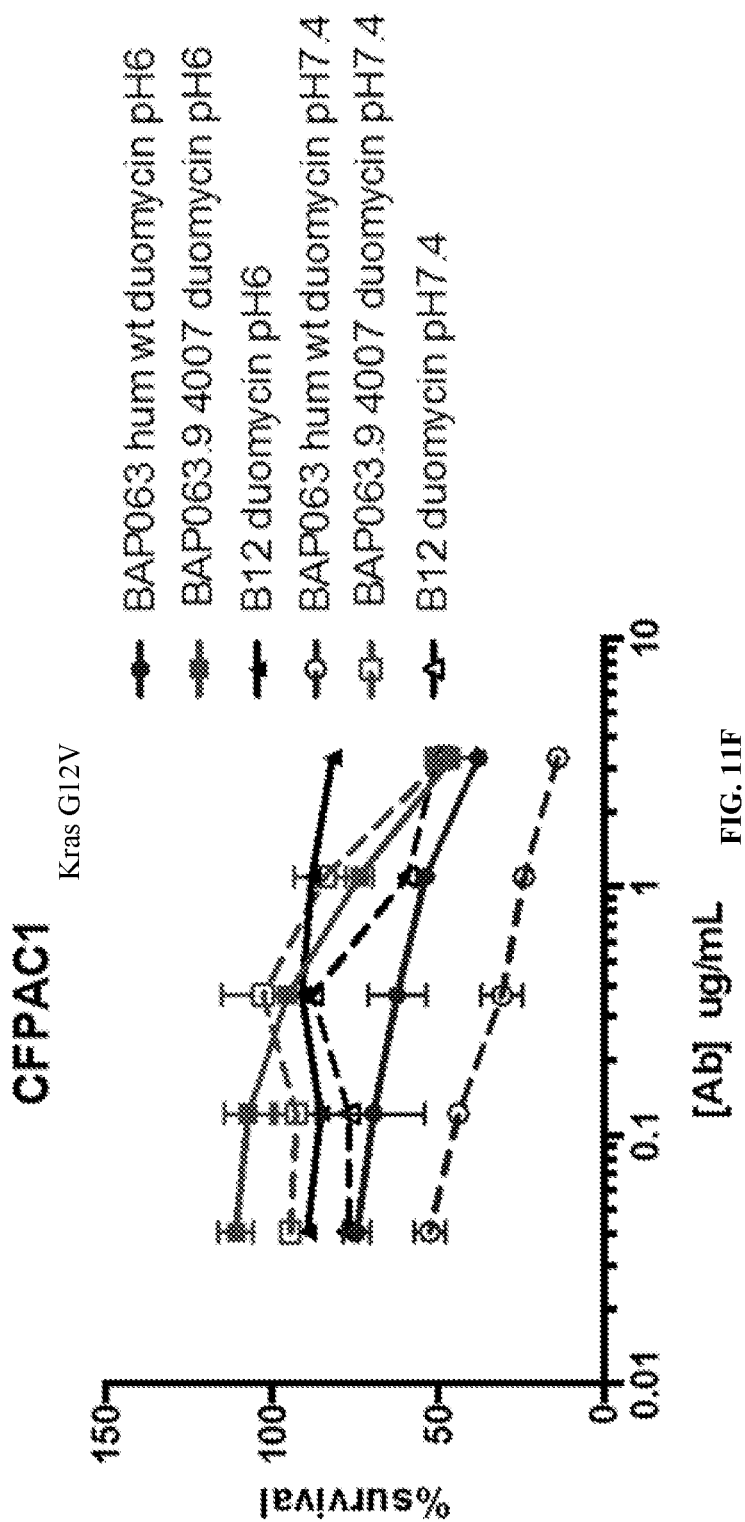
Figure 11G:
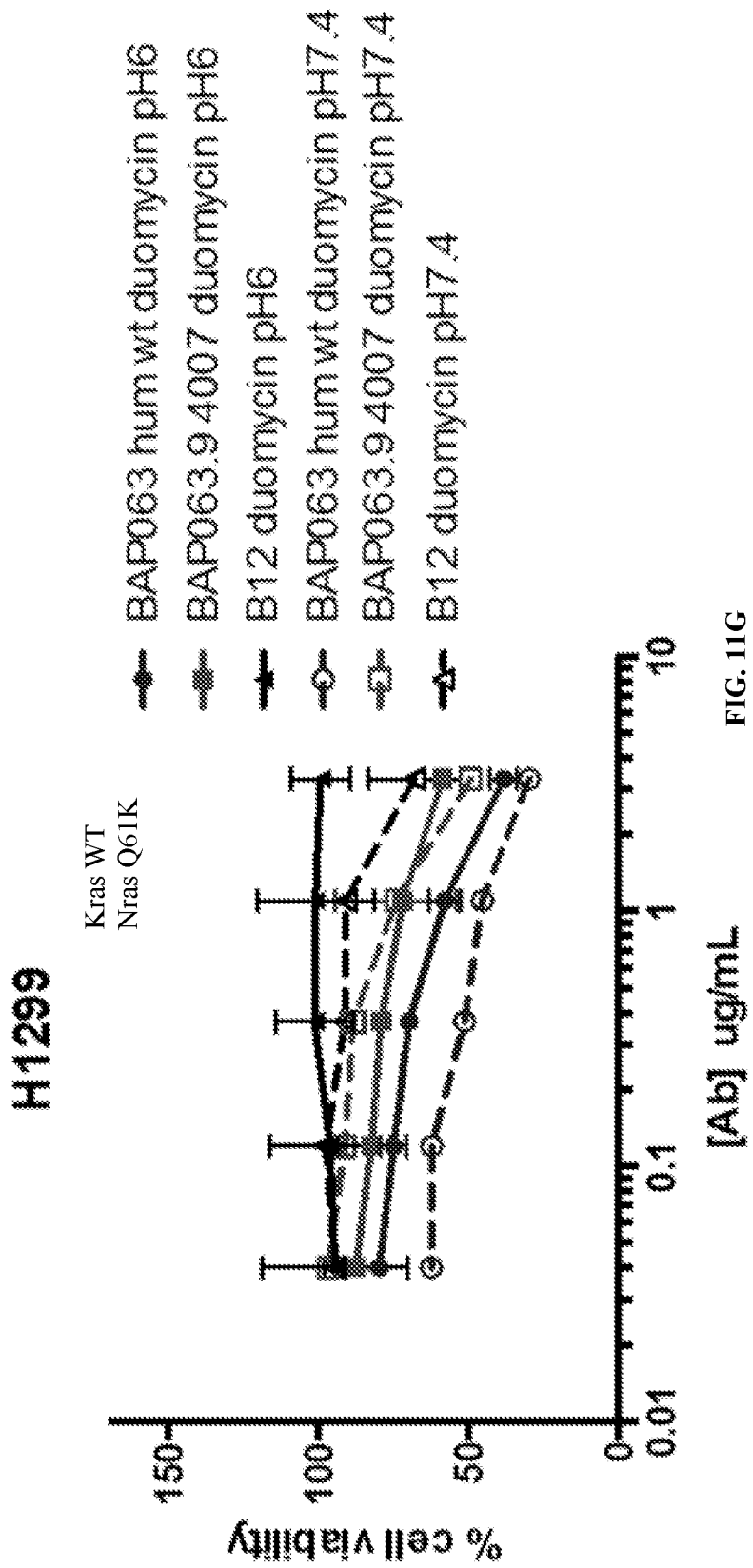
Figure 11H:
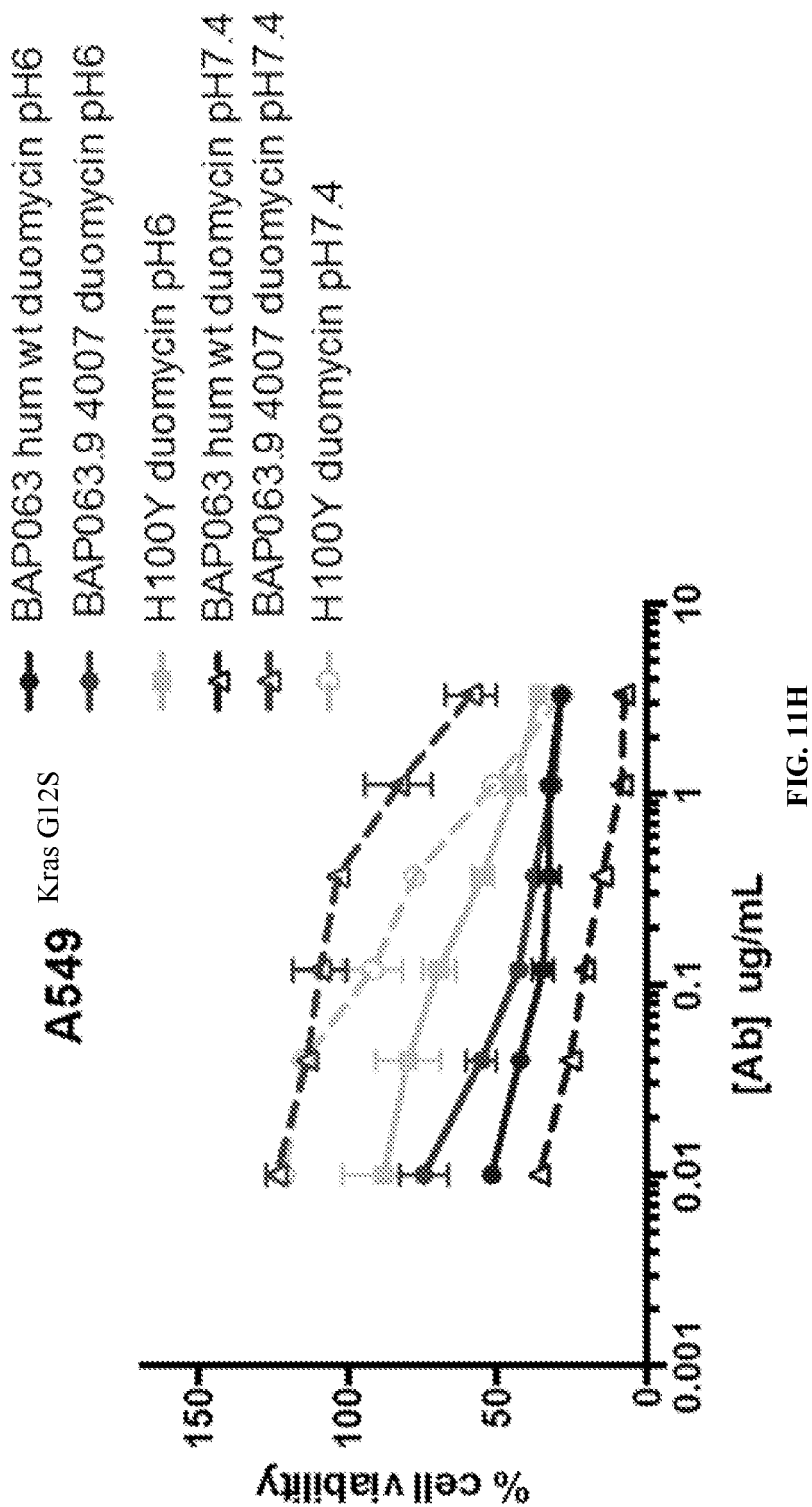

The negative control (BA-3831-WT) showed a similar binding affinity to both human Ax1 (hAx1) and cynomolgus Ax1 (cyno-Ax1) at both pH 6.0 and 7.4 in PBS and KREBS buffers (FIG. 10A). The conditionally active anti-Ax1 antibodies showed lower binding affinity to cyno-Ax1 at pH 7.4, in comparison with the binding affinity to cyno-Ax1 at pH 6.0 (FIGS. 10B-10D). The difference between the binding affinities at pH 6.0 and pH 7.0 in PBS buffer was not significant, due to the absence of bicarbonate ion in the PBS buffer.

Example 17: Cytotoxicity of Anti-Ax1 Antibodies Conjugated to Duomycin

Duomycin is cytotoxic since it inhibits cell growth by stopping protein synthesis. One of the conditionally active anti-Ax1 antibodies, BAP063.9 4007, was conjugated to duomycin. Two negative controls were used in this test, BAP063 hum WT (the wild-type anti-Ax1 antibody from which BAP063.9 4007 was derived) and B12 (an anti-B12 antibody), both were also conjugated duomycin.

Several cell lines were treated with the three duomycin-conjugated antibodies (BAP063.9 4007, BAP063 hum WT, and B12) at pHs of 6.0 and 7.4 (FIGS. 11A-11H). The duomycin-conjugated antibody BAP063.9 4007 showed significantly higher cytotoxicity to cell lines DU145 (prostate cancer cells), MDA-MD-231 (breast cancer cells), PL45 (pancreatic cancer cells), and A549 (adenocarcinoma cells) at pH 6.0 in comparison with the cytotoxicity to the same cells at pH 7.4. On the other hand, the negative controls did not show a difference in cytotoxicity between pH 6.0 and pH 7.4.

Example 18: Anti-Ax1 Antibodies Conjugated to a Model Toxin

Figure 12:
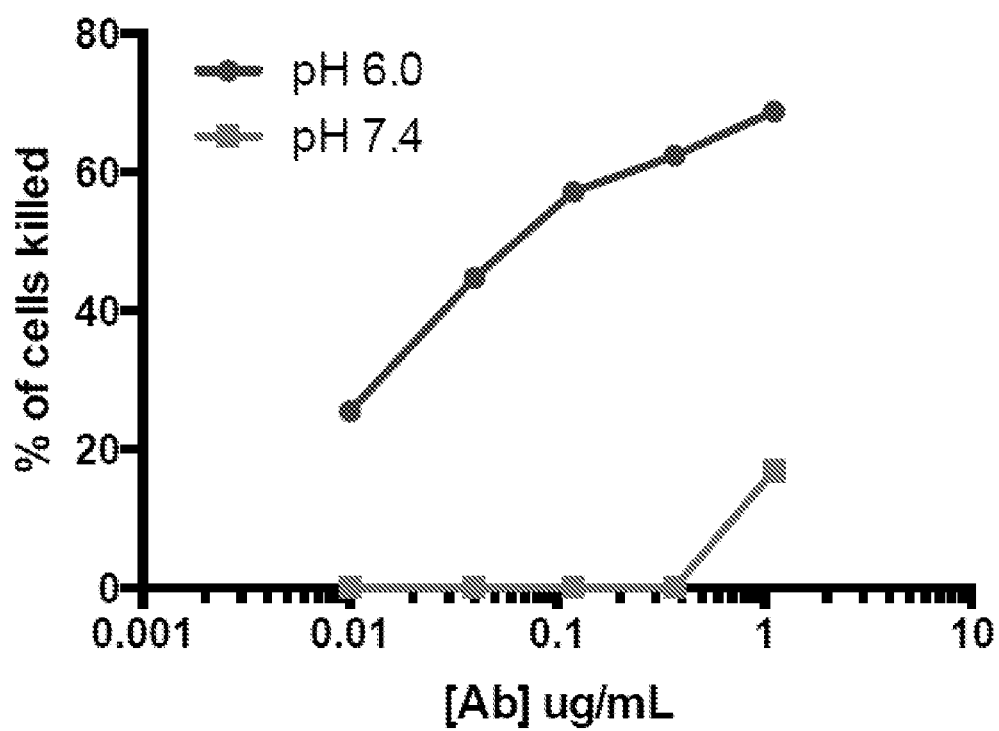
FIG. 12 shows cell killing of A549 cells at different pH levels by a conditionally active anti-Ax1 antibody conjugated to Duomycin.

The conditionally active anti-Ax1 antibody was conjugated to a model toxin (e.g., duomycin) to produce a conditionally active antibody-drug conjugate (CAB-Ax1-ADC). The CAB-Ax1-ADC was first tested to confirm that the conditional cell killing activity was not altered by the drug conjugation process. This test showed that the CAB-Ax1-ADC killed significantly more cells at pH 6.0 than at pH 7.4 (FIG. 12).

Figure 13:
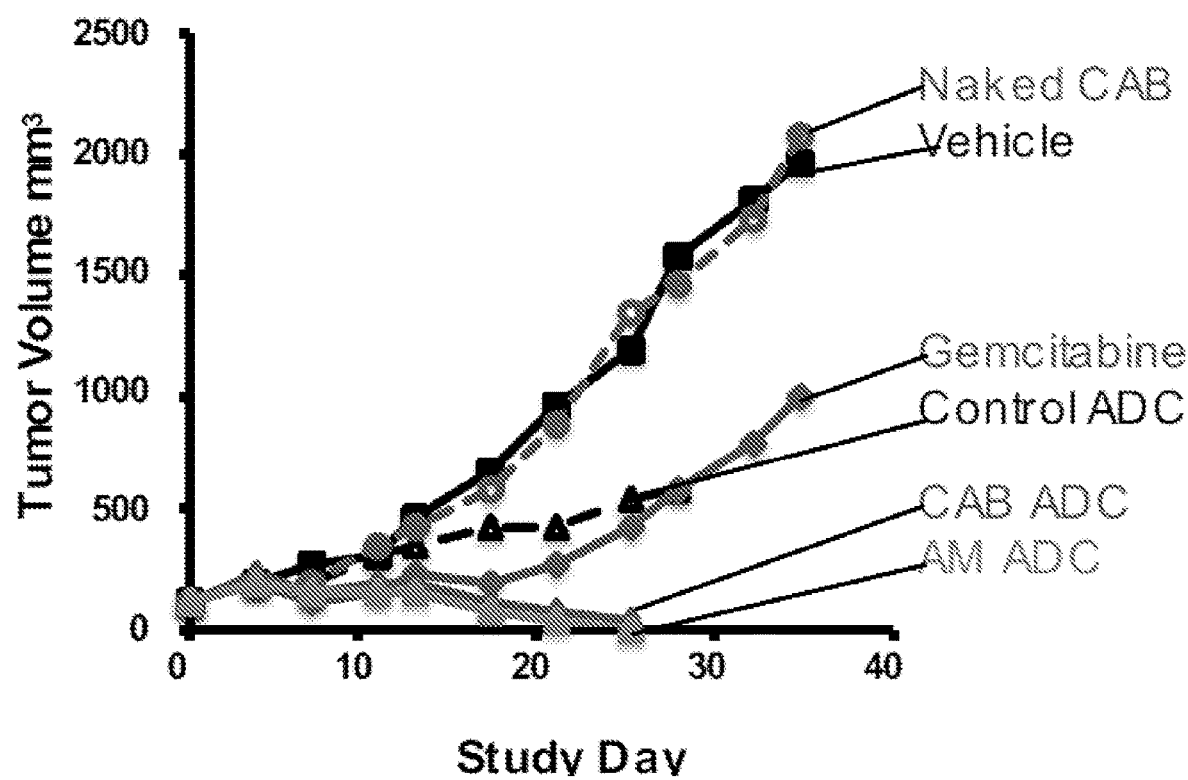
FIG. 13 shows effects on tumor volume in xenografted mice of treatment with a duomycin-conjugated conditionally active anti-Ax1 antibody.

The CAB-Ax1-ADC was then injected into mice bearing MiaPaCa2 xenograft tumors at a dose of 1 mg/kg twice weekly for 3 weeks. Several controls were used in this study, including naked CAB (the same anti-Ax1 antibody with no conjugation), vehicle, the toxin alone (gemcitabine), a control ADC (duomycin conjugated to an antibody that does not bind to the tumor cells), and an affinity matching anti-Ax1 ADC (AM-ADC) with duomycin. The study showed that the CAB-Ax1-ADC (CAB-ADC) with duomycin and AM-ADC with duomycin provided a significantly greater reduction in the size of the tumor, in comparison with the controls (FIG. 13). Neither the toxin alone or vehicle alone, reduced the size of tumors. This study shows that the conditionally active anti-Ax1 antibody conjugated with toxin is as effective in reducing tumor size as an affinity matching antibody (AM-ADC).

Figure 14A:
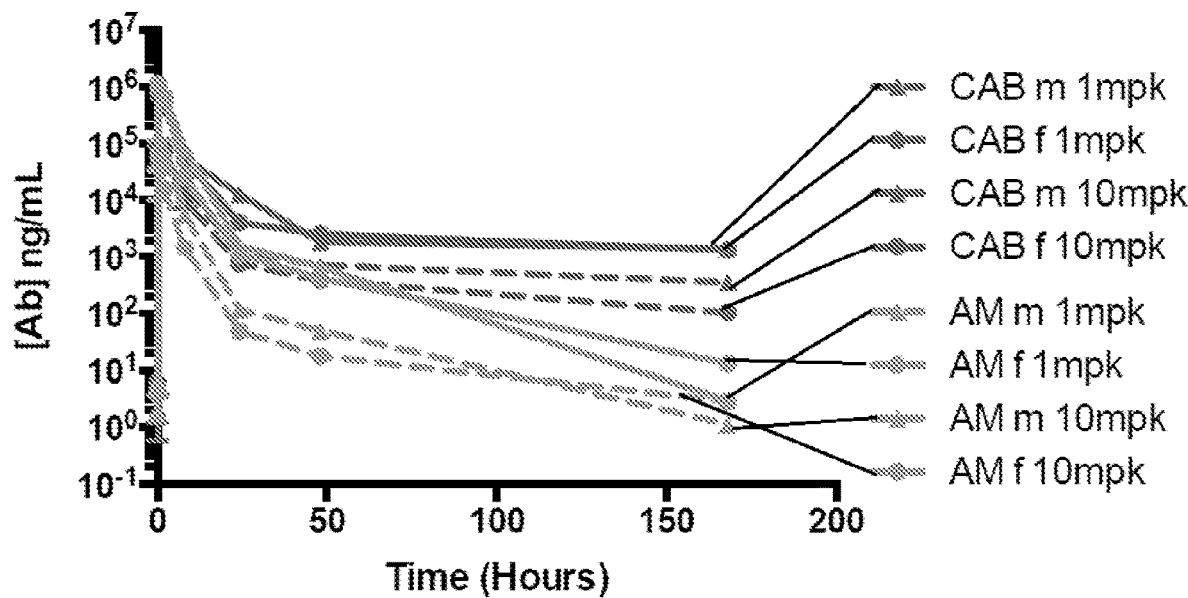
FIGS. 14A-14B show the detected presence of the duomycin-conjugated conditionally active anti-Ax1 antibody in the blood of cynomolgus monkeys over time after injection of the anti-Ax1 antibody/duomycin conjugate.
Figure 14B:
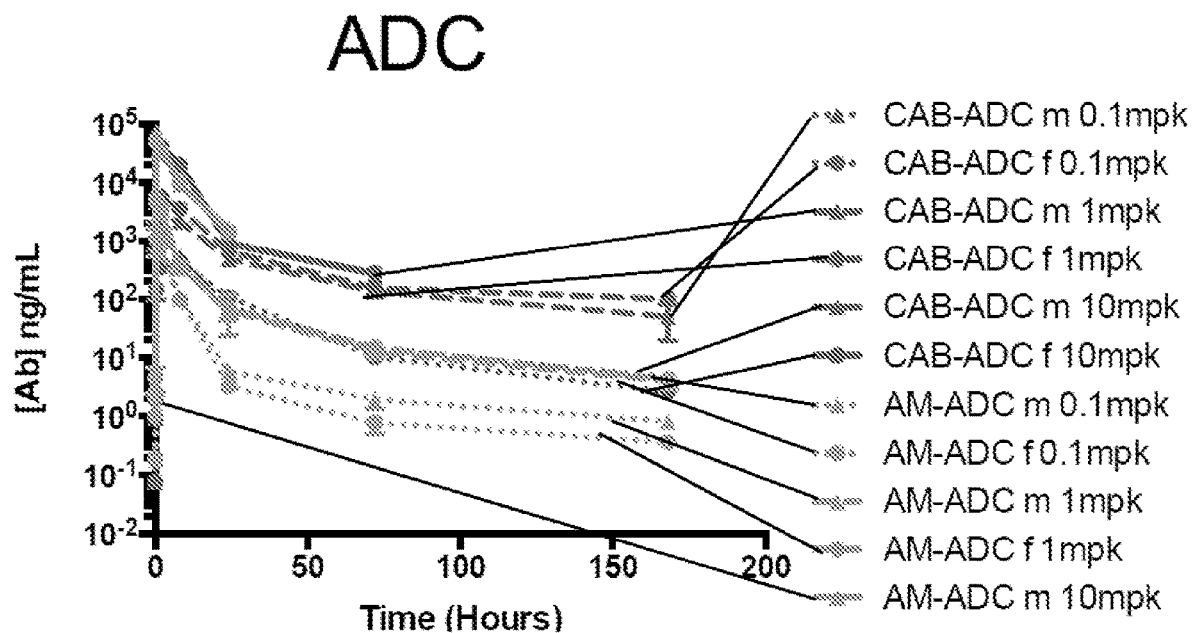

Example 19: Serum Concentrations of Anti-Ax1 Antibody Drug Conjugates in Cynomolgus Macaques Monkeys The drug (duomycin) conjugate of the conditionally active anti-Ax1 antibody (CAB-ADC) was injected into male and female cynomolgus macaques monkeys at three doses: 0.1, 1, and 10 mg/kg. Unconjugated anti-Ax1 antibody was used as a control. The affinity matching antibody drug conjugate (AM-ADC) was also used as a control. The serum concentrations of the (CAB-ADC) were measured over a period of one week (168 hours, see FIGS. 14A-14B). The CAB-ADC persisted in the monkey serum longer than the AM-ADC control (FIG. 14B). There was no significant difference between the male and female monkeys (FIGS. 14A-14B).

Figure 15A:
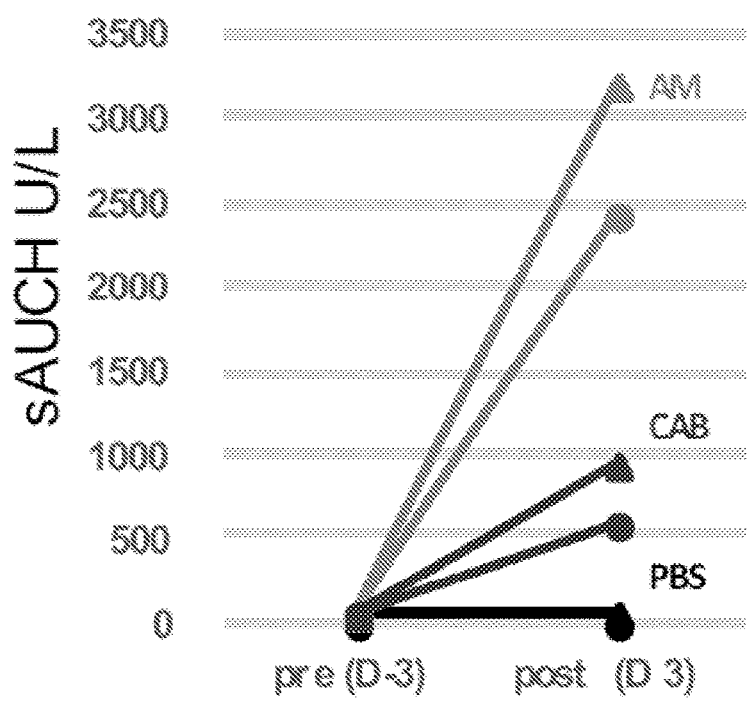
FIG. 15A shows the detected presence of Aspartate transaminase (AST) in the blood of cynomolgus monkeys over time starting just prior to injection (pre (D-3)) until 3 days after injection (post (D-3)) of duomycin conjugated conditionally active anti-Ax1 antibodies.
Figure 15B:
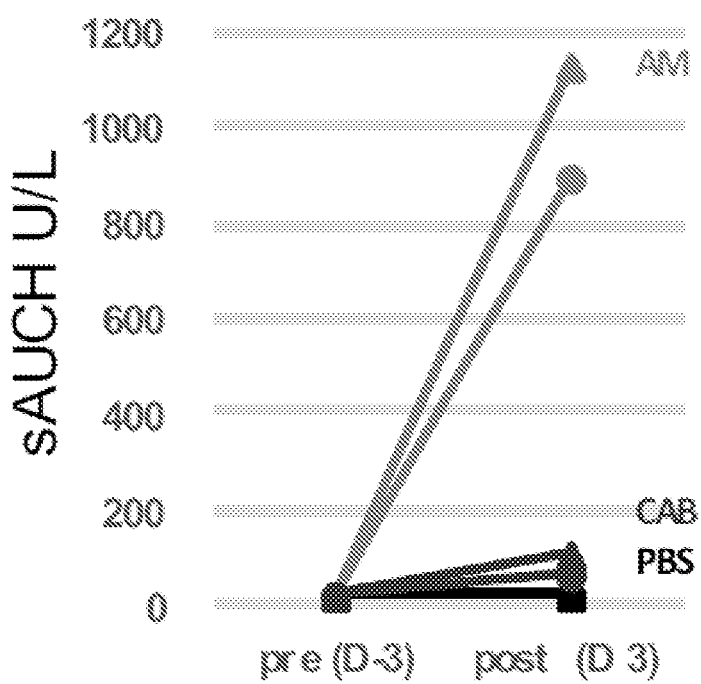
FIG. 15B shows the detected presence of Alanine Aspartate transaminase (ALT) in the blood of cynomolgus monkeys over time starting just prior to injection (pre (D-3)) until 3 days after injection (post (D-3)) of duomycin conjugated conditionally active anti-Ax1 antibodies.

Example 20: Toxicity of Anti-Ax1 Antibody Drug Conjugates in Cynomolgus Macaques Monkeys The toxicity of the CAB-ADC was tested in cynomolgus macaques monkeys. Aspartate transaminase (AST) and alanine transaminase (ALT) have been used as indicators of liver toxicity of drugs by the Food and Drug Administration (FDA). The serum AST and ALT levels were measured in both the male and female monkey (FIGS. 15A-15B). The vehicle (PBS) caused no AST or ALT level alteration in the serum, while the matching antibody drug conjugate (AM-ADC) with duomycin showed very high AST and ALT levels. The CAB-ADC showed significantly reduced AST and ALT levels, in comparison with the AM-ADC control. This indicates that the anti-Ax1 antibody drug conjugates of the present invention have significantly reduced liver toxicity relative to the matching antibody drug conjugate AM-ADC.

Figure 16:
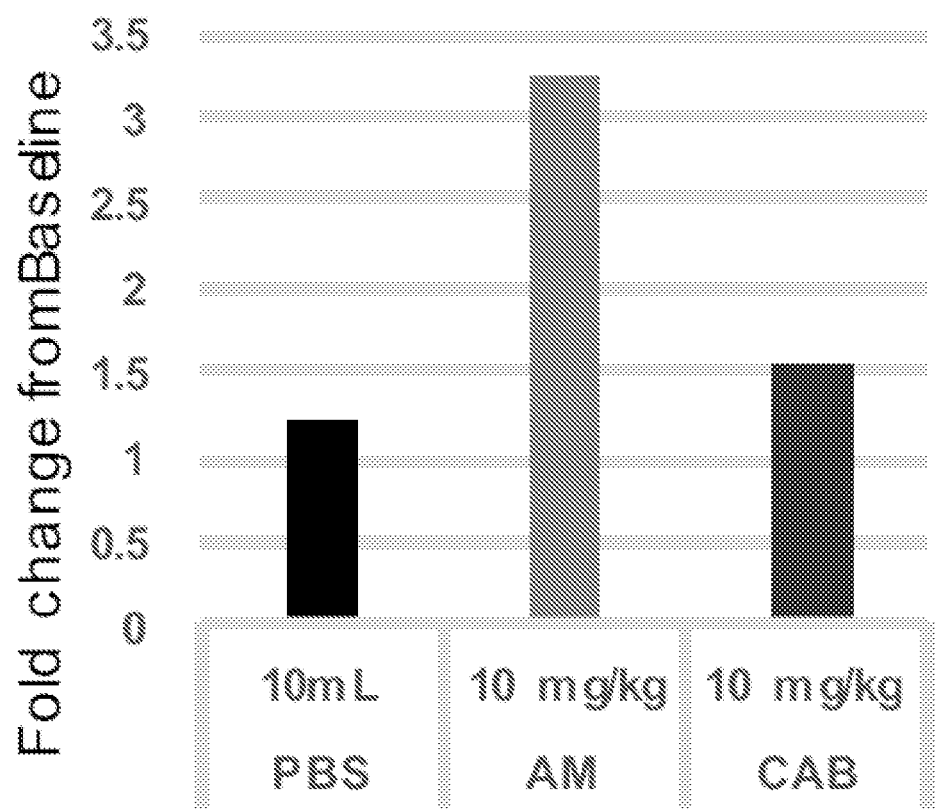
FIG. 16 shows the lymphocyte count over time in the blood of cynomolgus monkeys after injection of duomycin conjugated conditionally active anti-Ax1 antibodies.

The CAB-ADC with duomycin was also found to cause less inflammation in the monkeys (FIG. 16). The counts of lymphocytes in the blood of the monkeys after injections of CAB-ADC, AM-ADC and PBS were collected. In comparison with AM-ADC which caused significant inflammation, the CAB-ADC caused only mild inflammation in the monkeys.

Example 21: Anti-Ror2 Antibodies Conjugated to a Model Toxin

The conditionally active anti-Ror2 antibody was conjugated to a model toxin (e.g., paclitaxel) to produce a conditionally active antibody-drug conjugate (Ror2-CAB-ADC).

Figure 17A:
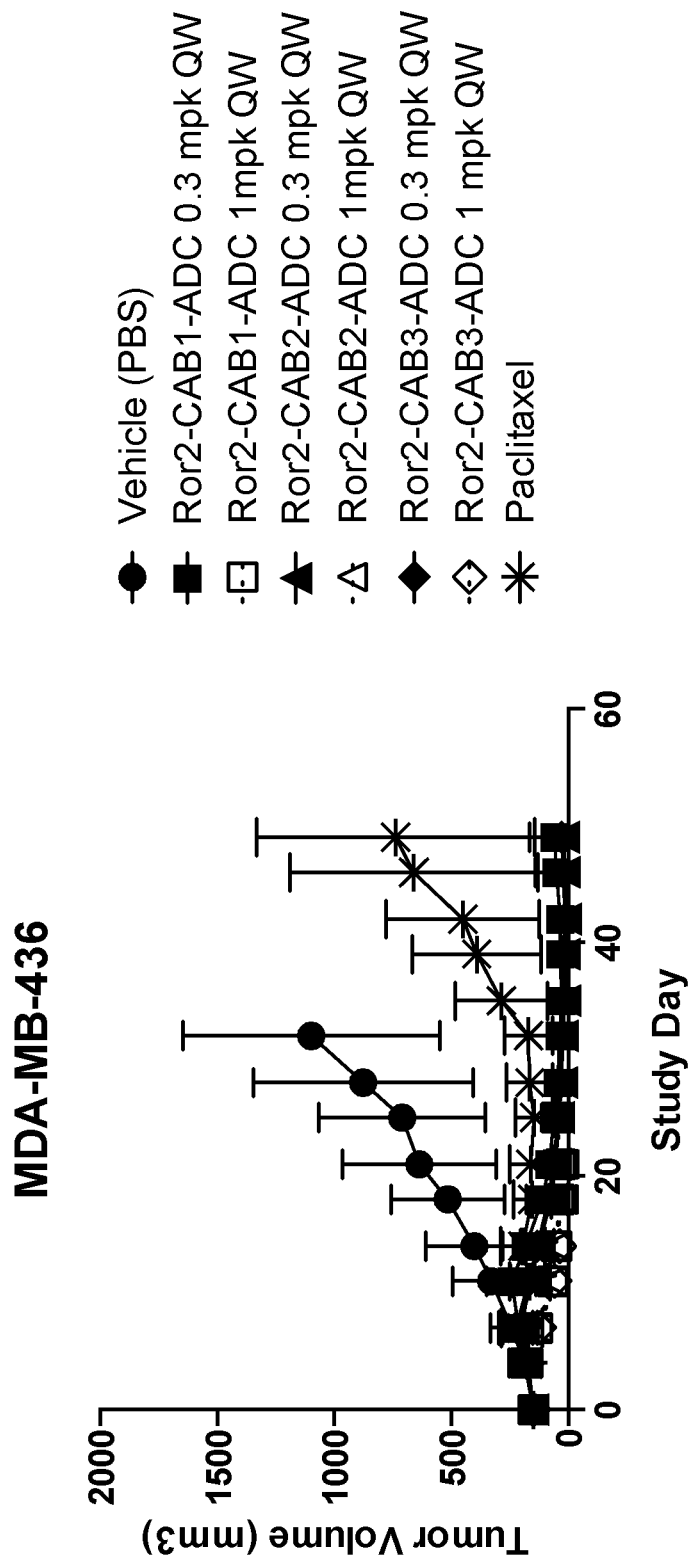
FIGS. 17A, 17B and 17C show effects on tumor volume in xenografted mice after treatment with a paclitaxel-conjugated conditionally active anti-Ror2 antibody, as described in Example 21.
Figure 17B:
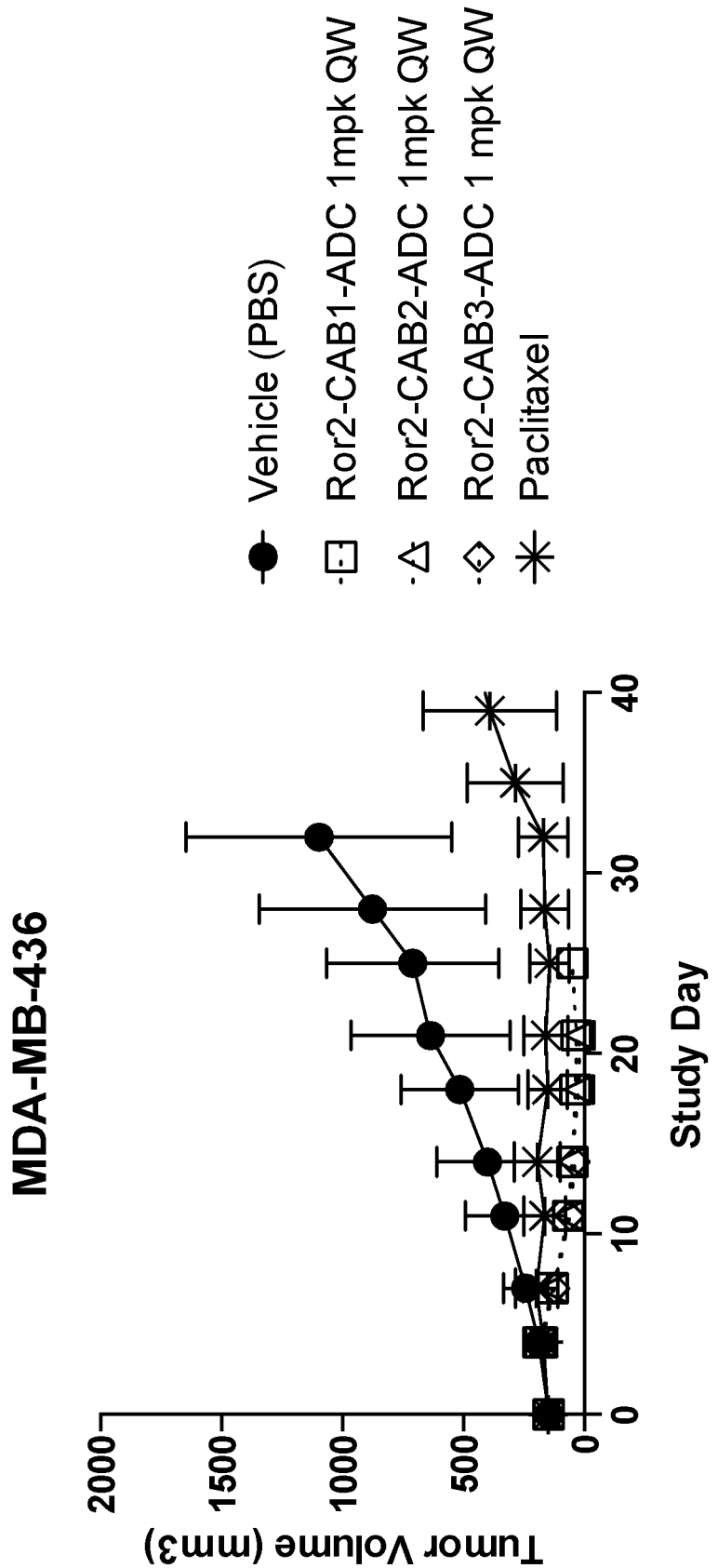
Figure 17C:
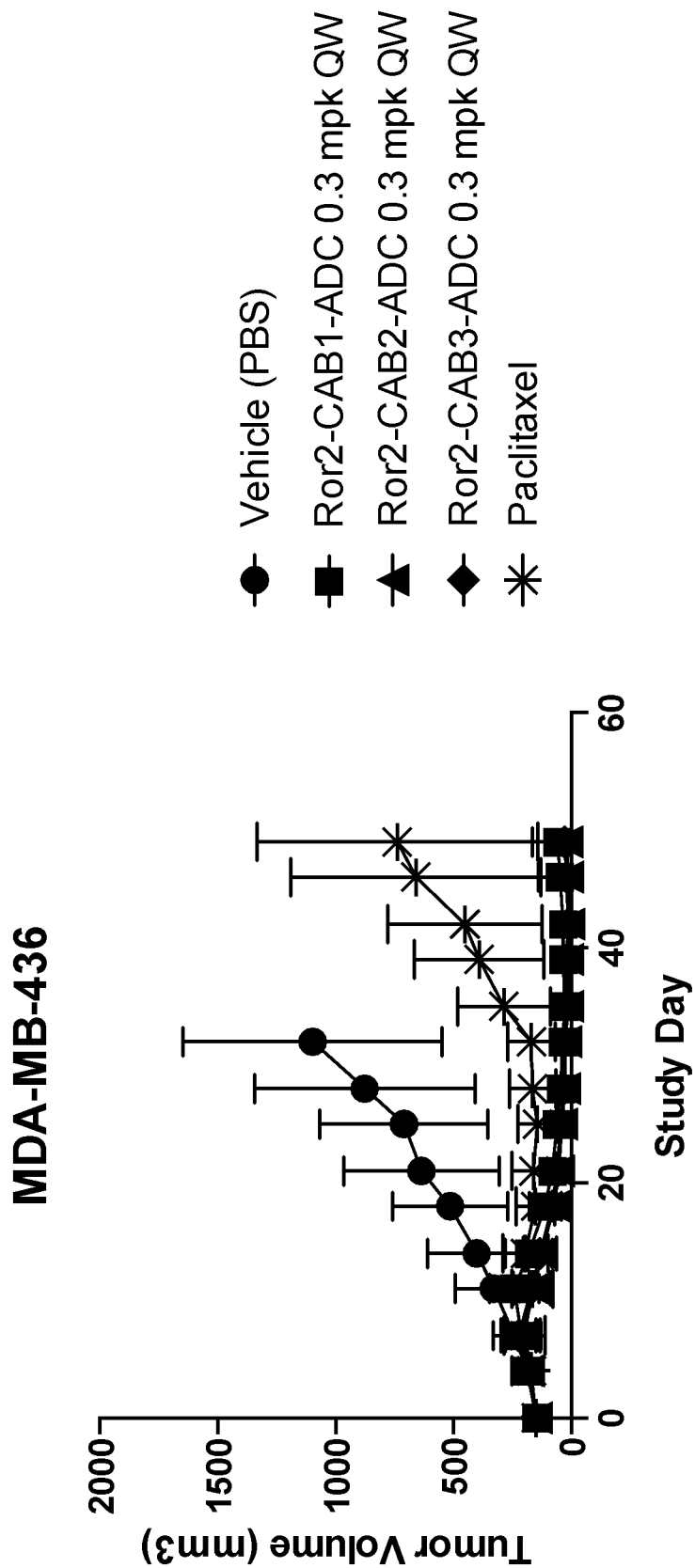

Tumors were induced in mice by injection of MDA-MB-436 tumor cells to produce xenografted mice. The Ror2-CAB-ADC was then injected into the xenografted mice at a dose of 0.3 or 1 mg/kg once a week for 2 weeks. The controls used in this study included PBS buffer as vehicle and the toxin alone (paclitaxel). The study showed that the Ror2-CAB-ADC provided a significantly greater reduction in the size of the tumor, in comparison with the controls (FIGS. 17A-17C). The results for the 0.3 mg/kg dosage group are presented in FIG. 17B and the results for the 1 mg/kg dosage group are presented in FIG. 17C. This study showed that the conditionally active anti-Ror2 antibody conjugated with toxin is effective in reducing tumor size in mice.

It must be noted that as used herein and in the appended claims, the singular forms "a", "an", and "the" include plural references unless the context clearly dictates otherwise. Furthermore, the terms "a" (or "an"), "one or more," and "at least one" can be used interchangeably herein. The terms "comprising," "including," "having," and "constructed from" can also be used interchangeably.

Unless otherwise indicated, all numbers expressing quantities of ingredients, properties such as molecular weight, percent, ratio, reaction conditions, and so forth used in the specification and claims are to be understood as being modified in all instances by the term "about," whether or not the term "about" is present. Accordingly, unless indicated to the contrary, the numerical parameters set forth in the specification and claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

It is to be understood that each component, compound, substituent or parameter disclosed herein is to be interpreted as being disclosed for use alone or in combination with one or more of each and every other component, compound, substituent or parameter disclosed herein.

It is also to be understood that each amount/value or range of amounts/values for each component, compound, substituent or parameter disclosed herein is to be interpreted as also being disclosed in combination with each amount/value or range of amounts/values disclosed for any other component(s), compounds(s), substituent(s) or parameter(s) disclosed herein and that any combination of amounts/values or ranges of amounts/values for two or more component(s), compounds(s), substituent(s) or parameters disclosed herein are thus also disclosed in combination with each other for the purposes of this description.

It is further understood that each range disclosed herein is to be interpreted as a disclosure of each specific value within the disclosed range that has the same number of significant digits. Thus, a range of from 1-4 is to be interpreted as an express disclosure of the values 1, 2, 3 and 4. It is further understood that each lower limit of each range disclosed herein is to be interpreted as disclosed in combination with each upper limit of each range and each specific value within each range disclosed herein for the same component, compounds, substituent or parameter. Thus, this disclosure to be interpreted as a disclosure of all ranges derived by combining each lower limit of each range with each upper limit of each range or with each specific value within each range, or by combining each upper limit of each range with each specific value within each range.

Furthermore, specific amounts/values of a component, compound, substituent or parameter disclosed in the description or an example is to be interpreted as a disclosure of either a lower or an upper limit of a range and thus can be combined with any other lower or upper limit of a range or specific amount/value for the same component, compound, substituent or parameter disclosed elsewhere in the application to form a range for that component, compound, substituent or parameter, All documents mentioned herein are hereby incorporated by reference in their entirety or alternatively to provide the disclosure for which they were specifically relied upon. The applicant(s) do not intend to dedicate any disclosed embodiments to the public, and to the extent any disclosed modifications or alterations may not literally fall within the scope of the claims, they are considered to be part hereof under the doctrine of equivalents.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meanings of the terms in which the appended claims are expressed.

What is claimed is:

1. A method of preparing a conditionally active antibody or antibody fragment from a parent antibody, single chain antibody or antibody fragment, said method comprising steps of:
   i. evolving a DNA encoding the parent antibody, single chain antibody or antibody fragment to increase the net charge of the parent antibody, single chain antibody or antibody fragment using one or more techniques selected from increasing a total number of codons of charged amino acid residues in the DNA, decreasing a total number of codons of uncharged amino acid residues in the DNA and a combination thereof, to create mutant DNAs;
   ii. expressing the mutant DNAs to obtain mutant antibodies or antibody fragments; and
   iii. selecting the conditionally active antibody or antibody fragment from the mutant antibodies or antibody fragments which is reversibly inactivated in a first assay at a first value of a condition and exhibits a decrease in activity in the first assay at the first value of the condition compared to the same activity in a second assay at a second value of the same condition, and
   the charged amino acid residues are selected from Aspartic acid, Glutamic acid, Arginine, Lysine, and Histidine.

2. The method of claim 1, wherein the evolving step employs site directed mutagenesis selected from oligonucleotide-mediated mutagenesis, PCR mutagenesis, and cassette mutagenesis.

3. The method of claim 1, wherein the evolving step comprising introducing one or more codons of charged amino acid residues into the DNA.

4. The method of claim 1, wherein the evolving step comprising codon substitution, codon deletion, or codon insertion.

5. The method of claim 1, wherein the charged amino acid residues are selected from Aspartic acid and Glutamic acid.

6. The method of claim 3, wherein the one or more codons are introduced into a region of the DNA that encodes an active site of the parent antibody, single chain antibody or antibody fragment.

7. The method of claim 3, wherein the one or more charged amino residues are introduced into a region outside of an active site of the parent antibody, single chain antibody or antibody fragment.

8. The method of claim 1, wherein the evolving step comprises evolving the DNA to introduce one or more codons of charged amino acid residues into complementarity determining regions of the parent antibody, single chain antibody or antibody fragment.

9. The method of claim 1, wherein the condition is selected from pH, temperature, osmotic pressure, osmolality, oxidative stress, electrolyte concentration, and concentration of a protein.

10. The method of claim 1, wherein the first and second assays are performed in assay solutions comprising a protein found in blood.

11. The method of claim 10, wherein the blood protein is albumin.

12. The method of claim 1, wherein the first and second assays are performed in assay solutions in the absence of serum.

13. The method of claim 1, wherein the value of the first condition is a value of a normal physiological condition that is within a normal range of the physiological condition at a site of administration of the conditionally active antibody or antibody fragment to a subject, or at a tissue or organ at a site of action of the conditionally active antibody or antibody fragment of a subject, and the value of the second condition is a value of an aberrant condition that deviates from the normal range of the physiological condition at the site of administration of the conditionally active antibody or antibody fragment, or at the tissue or organ at the site of action of the conditionally active antibody or antibody fragment.

14. The method of claim 9, wherein the condition is pH and the first and second assays are performed in assay media including at least one species having a molecular weight of less than 900 a.m.u. and a pKa up to 3 units away from the first value of pH.

15. The method of claim 9, wherein the condition is pH and the first and second assays are performed in assay media including at least one species having a molecular weight of less than 900 a.m.u. and a pKa between the second value of pH and the first value of pH.

16. The method of claim 10, wherein the first and second assays are performed in assay media including a species selected from histidine, histamine, hydrogenated adenosine diphosphate, hydrogenate adenosine triphosphate, citrate, acetate, lactate, hydrogen sulfide, bisulfide, ammonium, bicarbonate, dihydrogen phosphate and a combination thereof.

17. The method of claim 1, wherein the parent antibody, single chain antibody or antibody fragment is selected from an antibody, a single chain antibody, and an antibody fragment and the activity is a binding activity to an antigen.

18. The method of claim 1, wherein the selecting step further comprises selecting the conditionally active antibody or antibody fragment based on a property selected from affinity, expression level, and humanization.

19. The method of claim 1, wherein the expression step employs phage display or a eukaryotic cell production host.

20. The method of claim 19, wherein expression step is performed in the eukaryotic cell production host and the selected conditionally active antibody or antibody fragment is expressed in the same eukaryotic cell production host.

21. The method of claim 1, wherein the charged amino acid residues are selected from Aspartic acid, Glutamic acid, Arginine and Lysine.

* * * * *

UNITED STATES PATENT AND TRADEMARK OFFICE
CERTIFICATE OF CORRECTION

| | |
|---|---|
| PATENT NO. | : 11,279,924 B2 |
| APPLICATION NO. | : 16/324453 |
| DATED | : March 22, 2022 |
| INVENTOR(S) | : Short et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 48 days.

Signed and Sealed this
Twenty-ninth Day of November, 2022

Katherine Kelly Vidal
*Director of the United States Patent and Trademark Office*

SEQUENCE LISTING

<160> NUMBER OF SEQ ID NOS: 18

<210> SEQ ID NO 1
<211> LENGTH: 107
<212> TYPE: PRT
<213> ORGANISM: human

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ser Ala
            20                  25                  30

Val Ala Trp Tyr Gln Gln Lys Pro Gly Gln Ala Pro Arg Leu Leu Ile
           35                  40                  45

Tyr Trp Ala Ser Thr Arg His Thr Gly Val Pro Ser Arg Phe Ser Gly
       50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Glu His Phe Ser Thr Pro Leu
               85                  90                  95

Thr Phe Gly Gln Gly Thr Lys Val Glu Ile Lys
               100                 105

<210> SEQ ID NO 2
<211> LENGTH: 107
<212> TYPE: PRT
<213> ORGANISM: Artificial
<220> FEATURE:
<223> OTHER INFORMATION: Synthetic sequence

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Val Ser Ala
               20                  25                  30

Val Ala Trp Tyr Gln Gln Lys Pro Gly Gln Ala Pro Arg Leu Leu Ile
           35                  40                  45

Tyr Trp Gln Asp Thr Arg His Thr Gly Val Pro Ser Arg Phe Ser Gly
       50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Glu His Phe Ser Thr Pro Leu
               85                  90                  95

Thr Phe Gly Gln Gly Thr Lys Val Glu Ile Lys
               100                 105

<210> SEQ ID NO 3
<211> LENGTH: 107
<212> TYPE: PRT
<213> ORGANISM: Artificial
<220> FEATURE:
<223> OTHER INFORMATION: Synthetic sequence

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ser Ala
               20                  25                  30

Val Ala Trp Tyr Gln Gln Lys Pro Gly Gln Ala Pro Arg Leu Leu Ile
           35                  40                  45

Tyr Trp Gln Asp Thr Arg His Thr Gly Val Pro Ser Arg Phe Ser Gly
       50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Glu His Phe Ser Pro Pro Leu
               85                  90                  95

Thr Phe Gly Gln Gly Thr Lys Val Glu Ile Lys
               100                 105

<210> SEQ ID NO 4

```
<211> LENGTH: 107
<212> TYPE: PRT
<213> ORGANISM: Artificial
<220> FEATURE:
<223> OTHER INFORMATION: synthetic sequence

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Val Ser Ala
            20                  25                  30

Val Ala Trp Tyr Gln Gln Lys Pro Gly Gln Ala Pro Arg Leu Leu Ile
        35                  40                  45

Tyr Trp Gln Asp Thr Arg His Thr Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Glu His Phe Ser Pro Pro Leu
                85                  90                  95

Thr Phe Gly Gln Gly Thr Lys Val Glu Ile Lys
            100                 105

<210> SEQ ID NO 5
<211> LENGTH: 107
<212> TYPE: PRT
<213> ORGANISM: Artificial
<220> FEATURE:
<223> OTHER INFORMATION: Synthetic sequence

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Val Ser Ala
            20                  25                  30

Val Ala Trp Tyr Gln Gln Lys Pro Gly Gln Ala Pro Arg Leu Leu Ile
        35                  40                  45

Tyr Trp Gln Asp Thr Arg His Thr Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Glu His Phe Ser Pro Pro Leu
                85                  90                  95

Arg Phe Gly Gln Gly Thr Lys Val Glu Ile Lys
            100                 105

<210> SEQ ID NO 6
<211> LENGTH: 120
<212> TYPE: PRT
<213> ORGANISM: Human

<400> SEQUENCE: 6

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Ser Phe Thr Gly His
            20                  25                  30

Thr Met Asn Trp Ile Arg Gln Pro Pro Gly Lys Gly Leu Glu Trp Ile
        35                  40                  45

Gly Leu Ile Lys Pro Ser Asn Gly Gly Thr Ser Tyr Asn Gln Lys Phe
50                  55                  60
```

Lys Gly Arg Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala His Gly His Tyr Glu Ser Tyr Phe Ala Met Asp Tyr Trp Gly Gln
                100                 105                 110

Gly Thr Leu Val Thr Val Ser Ser
            115                 120

<210> SEQ ID NO 7
<211> LENGTH: 120
<212> TYPE: PRT
<213> ORGANISM: Artificial
<220> FEATURE:
<223> OTHER INFORMATION: Synthetic sequence

<400> SEQUENCE: 7

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Ser Phe Thr Gly Ala
                20                  25                  30

Thr Met Asn Trp Ile Arg Gln Pro Pro Gly Lys Gly Leu Glu Trp Ile
            35                  40                  45

Gly Leu Ile Lys Pro Ser Asn Gly Gly Thr Ser Tyr Asn Gln Lys Phe
        50                  55                  60

Lys Gly Arg Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala His Gly His Tyr Glu Ser Tyr Glu Ala Met Asp Tyr Trp Gly Gln
                100                 105                 110

Gly Thr Leu Val Thr Val Ser Ser
            115                 120

<210> SEQ ID NO 8
<211> LENGTH: 119
<212> TYPE: PRT
<213> ORGANISM: Artificial
<220> FEATURE:
<223> OTHER INFORMATION: Synthetic sequence

<400> SEQUENCE: 8

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Ser Phe Trp Gly Ala
                20                  25                  30

Thr Met Asn Trp Ile Arg Gln Pro Pro Gly Lys Gly Leu Glu Trp Ile
            35                  40                  45

Gly Leu Ile Lys Pro Ser Asn Gly Gly Thr Ser Tyr Asn Gln Lys Phe
        50                  55                  60

Lys Gly Arg Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala His Gly His Tyr Glu Ser Tyr Glu Ala Met Asp Tyr Trp Gly Gln
                100                 105                 110

Gly Thr Leu Val Thr Val Ser

-continued

115

<210> SEQ ID NO 9
<211> LENGTH: 120
<212> TYPE: PRT
<213> ORGANISM: Artificial
<220> FEATURE:
<223> OTHER INFORMATION: Synthetic sequence

<400> SEQUENCE: 9

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Ser Phe Thr Gly His
            20                  25                  30

Thr Met Asn Trp Ile Arg Gln Pro Pro Gly Lys Gly Leu Glu Trp Ile
        35                  40                  45

Gly Leu Ile Lys Pro Ser Asn Gly Gly Thr Ser Tyr Asn Gln Lys Phe
    50                  55                  60

Lys Gly Arg Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala His Gly His Tyr Glu Ser Tyr Glu Ala Met Asp Tyr Trp Gly Gln
            100                 105                 110

Gly Thr Leu Val Thr Val Ser Ser
        115                 120

<210> SEQ ID NO 10
<211> LENGTH: 106
<212> TYPE: PRT
<213> ORGANISM: Mouse

<400> SEQUENCE: 10

Gln Ile Val Leu Thr Gln Ser Pro Ala Ile Met Ser Ala Ser Pro Gly
1               5                   10                  15

Glu Lys Val Thr Ile Thr Cys Ser Ala Thr Ser Ser Val Ser Tyr Met
            20                  25                  30

His Trp Phe Gln Gln Lys Pro Gly Thr Ser Pro Lys Leu Trp Ile Tyr
        35                  40                  45

Gly Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Phe Thr
                85                  90                  95

Phe Gly Gln Gly Thr Lys Val Glu Ile Lys
            100                 105

<210> SEQ ID NO 11
<211> LENGTH: 106
<212> TYPE: PRT
<213> ORGANISM: Artificial
<220> FEATURE:
<223> OTHER INFORMATION: Synthetic sequence

<400> SEQUENCE: 11

Gln Ile Val Leu Thr Gln Ser Pro Ala Ile Met Ser Ala Ser Pro Gly
1               5                   10                  15

Glu Lys Val Thr Ile Thr Cys Ser Ala Thr Ser Ser Glu Ser Tyr Met

```
                20                  25                  30

His Trp Phe Gln Gln Lys Pro Gly Thr Ser Pro Lys Leu Trp Ile Tyr
            35                  40                  45

His Thr Ser Asn Leu Ala Ser Gly Val Pro Ala Arg Phe Ser Gly Ser
        50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Phe Thr
                85                  90                  95

Phe Gly Gln Gly Thr Lys Val Glu Ile Lys
            100                 105

<210> SEQ ID NO 12
<211> LENGTH: 106
<212> TYPE: PRT
<213> ORGANISM: Artificial
<220> FEATURE:
<223> OTHER INFORMATION: Synthetic sequence

<400> SEQUENCE: 12

Ala Ile Gln Leu Thr Gln Ser Pro Ser Ser Leu Ser Ala Ser Val Gly
1               5                   10                  15

Asp Arg Val Thr Ile Thr Cys Ser Ala Thr Ser Ser Val Ser Tyr Met
            20                  25                  30

His Trp Tyr Gln Gln Lys Pro Gly Gln Ala Pro Arg Leu Leu Ile Tyr
            35                  40                  45

Gly Thr Ser Asn Leu Ala Ser Gly Val Pro Asp Arg Phe Ser Gly Ser
        50                  55                  60

Gly Ser Gly Thr Asp Phe Thr Leu Lys Ile Ser Arg Val Glu Ala Glu
65                  70                  75                  80

Asp Val Gly Val Tyr Tyr Cys Gln Gln Arg Ser Ser Tyr Pro Phe Thr
                85                  90                  95

Phe Gly Gln Gly Thr Lys Val Glu Ile Lys
            100                 105

<210> SEQ ID NO 13
<211> LENGTH: 106
<212> TYPE: PRT
<213> ORGANISM: Artificial
<220> FEATURE:
<223> OTHER INFORMATION: Synthetic sequence

<400> SEQUENCE: 13

Ala Ile Gln Leu Thr Gln Ser Pro Ser Ser Leu Ser Ala Ser Val Gly
1               5                   10                  15

Asp Arg Val Thr Ile Thr Cys Ser Ala Thr Ser Ser Val Ser Tyr Met
            20                  25                  30

His Trp Tyr Leu Gln Lys Pro Gly Gln Ser Pro Gln Leu Leu Ile Tyr
            35                  40                  45

Gly Thr Ser Asn Leu Ala Ser Gly Val Pro Asp Arg Phe Ser Gly Ser
        50                  55                  60

Gly Ser Gly Thr Asp Phe Thr Leu Lys Ile Ser Arg Val Glu Ala Glu
65                  70                  75                  80

Asp Val Gly Val Tyr Tyr Cys Gln Gln Arg Ser Ser Tyr Pro Phe Thr
                85                  90                  95

Phe Gly Gln Gly Thr Lys Val Glu Ile Lys
            100                 105
```

<210> SEQ ID NO 14
<211> LENGTH: 122
<212> TYPE: PRT
<213> ORGANISM: Mouse

<400> SEQUENCE: 14

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
                20                  25                  30

Thr Met His Trp Met Lys Gln Ser His Arg Lys Ser Leu Glu Trp Ile
            35                  40                  45

Gly Gly Ile Asn Thr Asn Asn Gly Gly Thr Gly Tyr Asn Gln Lys Phe
        50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Gly Ser Leu Tyr Ser Tyr Gly Asn Ser Tyr Phe Asp Tyr Trp
                100                 105                 110

Gly Gln Gly Thr Leu Val Thr Val Ser Ser
            115                 120

<210> SEQ ID NO 15
<211> LENGTH: 122
<212> TYPE: PRT
<213> ORGANISM: Artificial
<220> FEATURE:
<223> OTHER INFORMATION: Synthetic sequence

<400> SEQUENCE: 15

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Glu Thr Glu Asp
                20                  25                  30

Thr Asp His Trp Met Lys Gln Ser His Arg Lys Ser Leu Glu Trp Ile
            35                  40                  45

Gly Gly Glu Asn Asp Asn Asn Gly Gly Thr Gly Tyr Asn Gln Lys Phe
        50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Phe Cys
                85                  90                  95

Ala His Gly Ser Leu Tyr Ser Tyr Gly Asn Ser Tyr Phe Asp Tyr Trp
                100                 105                 110

Gly Gln Gly Thr Leu Val Thr Val Ser Ser
            115                 120

<210> SEQ ID NO 16
<211> LENGTH: 122
<212> TYPE: PRT
<213> ORGANISM: Artificial
<220> FEATURE:
<223> OTHER INFORMATION: Synthetic sequence

<400> SEQUENCE: 16

Gln Val Gln Leu Val Gln Ser Gly Ala Glu Val Lys Lys Pro Gly Ala
1               5                   10                  15

```
Ser Val Lys Val Ser Cys Lys Ala Ser Gly Tyr Thr Phe Thr Glu Tyr
            20                  25                  30

Thr Met His Trp Val Arg Gln Ala Arg Gly Gln Arg Leu Glu Trp Ile
            35                  40                  45

Gly Gly Ile Asn Thr Asn Asn Gly Gly Thr Gly Tyr Asn Gln Lys Phe
        50                  55                  60

Lys Gly Arg Val Thr Ile Ser Ala Asp Lys Ser Ile Ser Thr Ala Tyr
 65                 70                  75                  80

Leu Gln Trp Ser Ser Leu Lys Ala Ser Asp Thr Ala Met Tyr Tyr Cys
                85                  90                  95

Ala His Gly Ser Leu Tyr Ser Tyr Gly Asn Ser Tyr Phe Asp Tyr Trp
            100                 105                 110

Gly Gln Gly Thr Leu Val Thr Val Ser Ser
            115                 120

<210> SEQ ID NO 17
<211> LENGTH: 122
<212> TYPE: PRT
<213> ORGANISM: Artificial
<220> FEATURE:
<223> OTHER INFORMATION: Synthetic sequence

<400> SEQUENCE: 17

Glu Val Gln Leu Val Gln Ser Gly Ala Glu Val Lys Lys Pro Gly Glu
 1               5                  10                  15

Ser Leu Arg Ile Ser Cys Lys Gly Ser Gly Tyr Thr Phe Thr Glu Tyr
            20                  25                  30

Thr Met His Trp Val Arg Gln Ala Pro Gly Gln Gly Leu Glu Trp Met
            35                  40                  45

Gly Gly Ile Asn Thr Asn Asn Gly Gly Thr Gly Tyr Asn Gln Lys Phe
        50                  55                  60

Lys Gly Arg Val Thr Ile Ser Ala Asp Lys Ser Ile Ser Thr Ala Tyr
 65                 70                  75                  80

Leu Gln Trp Ser Ser Leu Lys Ala Ser Asp Thr Ala Met Tyr Tyr Cys
                85                  90                  95

Ala His Gly Ser Leu Tyr Ser Tyr Gly Asn Ser Tyr Phe Asp Tyr Trp
            100                 105                 110

Gly Gln Gly Thr Leu Val Thr Val Ser Ser
            115                 120

<210> SEQ ID NO 18
<211> LENGTH: 122
<212> TYPE: PRT
<213> ORGANISM: Artificial
<220> FEATURE:
<223> OTHER INFORMATION: Synthetic sequence

<400> SEQUENCE: 18

Glu Val Gln Leu Val Gln Ser Gly Ala Glu Val Lys Lys Pro Gly Glu
 1               5                  10                  15

Ser Leu Arg Ile Ser Cys Lys Gly Ser Gly Tyr Thr Phe Thr Glu Tyr
            20                  25                  30

Thr Met His Trp Ile Arg Gln Ser Pro Ser Arg Gly Leu Glu Trp Leu
            35                  40                  45

Gly Gly Ile Asn Thr Asn Asn Gly Gly Thr Gly Tyr Asn Gln Lys Phe
        50                  55                  60

Lys Gly Arg Val Thr Ile Ser Ala Asp Lys Ser Ile Ser Thr Ala Tyr
 65                 70                  75                  80
```

```
Leu Gln Trp Ser Ser Leu Lys Ala Ser Asp Thr Ala Met Tyr Tyr Cys
                85              90              95

Ala His Gly Ser Leu Tyr Ser Tyr Gly Asn Ser Tyr Phe Asp Tyr Trp
            100             105             110

Gly Gln Gly Thr Leu Val Thr Val Ser Ser
        115             120
```